US011900604B2

(12) United States Patent
Tan et al.

(10) Patent No.: US 11,900,604 B2
(45) Date of Patent: Feb. 13, 2024

(54) ADAPTIVE EXPERT SYSTEM FOR ANALYSIS AND CLASSIFICATION OF DNA SAMPLE DATA

(71) Applicant: ANDE CORPORATION, Waltham, MA (US)

(72) Inventors: Eugene Tan, Lexington, MA (US); Hua Jiang, Chelmsford, MA (US); Richard F. Selden, Lincoln, MA (US)

(73) Assignee: ANDE Corporation, Waltham, MA (US)

( * ) Notice: Subject to any disclaimer, the term of this patent is extended or adjusted under 35 U.S.C. 154(b) by 1283 days.

(21) Appl. No.: 16/034,058

(22) Filed: Jul. 12, 2018

(65) Prior Publication Data

US 2019/0019290 A1 Jan. 17, 2019

Related U.S. Application Data

(60) Provisional application No. 62/542,099, filed on Aug. 7, 2017, provisional application No. 62/531,711, filed on Jul. 12, 2017.

(51) Int. Cl.
*G06T 7/00* (2017.01)
*G16B 15/00* (2019.01)
*G16B 20/00* (2019.01)
*G16B 20/20* (2019.01)

(52) U.S. Cl.
CPC ............ *G06T 7/0014* (2013.01); *G16B 15/00* (2019.02); *G16B 20/00* (2019.02); *G16B 20/20* (2019.02); *G06T 2207/10056* (2013.01); *G06T 2207/30072* (2013.01)

(58) Field of Classification Search
None
See application file for complete search history.

(56) References Cited

U.S. PATENT DOCUMENTS

| | | | |
|---|---|---|---|
| 6,236,944 B1 | 5/2001 | Miller et al. | |
| 6,442,491 B1 * | 8/2002 | Miller ................... | G16B 40/30 702/19 |
| 8,018,593 B2 | 9/2011 | Tan et al. | |
| 8,173,417 B2 | 5/2012 | Tan et al. | |
| 8,206,974 B2 | 6/2012 | Tan et al. | |
| 8,425,861 B2 | 4/2013 | Selden et al. | |
| 8,720,036 B2 | 5/2014 | Selden et al. | |
| 8,858,770 B2 | 10/2014 | Tan et al. | |
| 8,961,765 B2 | 2/2015 | Tan et al. | |
| 9,012,208 B2 | 4/2015 | Selden et al. | |
| 9,174,210 B2 | 11/2015 | Selden et al. | |
| 9,310,304 B2 | 4/2016 | Schumm et al. | |
| 9,314,795 B2 | 4/2016 | Selden et al. | |
| 9,354,199 B2 | 5/2016 | Selden et al. | |
| 9,366,631 B2 | 6/2016 | Tan et al. | |
| 9,494,519 B2 | 11/2016 | Selden et al. | |
| 9,523,656 B2 | 12/2016 | Tan et al. | |
| 9,550,985 B2 | 1/2017 | Tan et al. | |
| 9,606,083 B2 | 3/2017 | Tan et al. | |
| 9,797,841 B2 | 10/2017 | Schumm et al. | |
| 9,889,449 B2 | 2/2018 | Tan et al. | |
| 9,994,895 B2 | 6/2018 | Tan et al. | |
| 2003/0028916 A1 | 2/2003 | Moyer et al. | |
| 2018/0169660 A1 | 6/2018 | Tan et al. | |

FOREIGN PATENT DOCUMENTS

WO   WO-2017/082034 A1   5/2017

OTHER PUBLICATIONS

Pabinger, Stephan, et al. "A survey of tools for variant analysis of next-generation genome sequencing data." Briefings in bioinformatics 15.2 (2014): 256-278.*
Anonymous, "STR analysis—Wikipedia", URL:https://en.wikipedia.org/w/index.php?title=STR_analysis&oldid=742695494 XP055501131 [Retrieved from the Internet on Nov. 5, 2019].
Bieber, Frederick R. et al., "Evaluation of forensic DNA mixture evidence: protocol for evaluation, interpretation, and statistical calculations using the combined probability of inclusion", BMC Genetics, vol. 17, No. 1, Aug. 31, 2016.
Bille, T.W. et al., "Comparison of the performance of different models for the interpretation of low level mixed DNA profiles", Electrophoresis, 2014. 35:3125-33.
Bright, J. A., "A series of recommended tests when validating probabilistic DNA profile interpretation software", Forensic Science International: Genetics, 2015. 14:125-131.
Callaghan, T. Rapid DNA instrument update & enhancement plans for codis. http://docplayer.net/4802515-Rapid-dna-instrument-update-enhancement-plans-for-codis.html. (2013).
Carney, C. et al., "Developmental validation of the ANDE rapid DNA system with FlexPlex assay for arrestee and reference buccal swab processing and database searching," Forensic Science International: Genetics. (2019). vol. 40, pp. 120-130.
Cooper, S. J. et al., Investigating a common approach to DNA profile interpretation using probabilistic software. Forensic Science International: Genetics, 2015. 16:121-131.
Donn, Steven M. et al., "Manual of Neonatal Respiratory Care", DE ISBN: 9781461421542 Jan. 1, 2012 (Jan. 1, 2012), URL:https://www.ohioattorneygeneral.gov/Files/Law-Enforcement/BCI/Laboratory-Division/LM-DNA-Methods-030118-Rev20.aspx XP055539729 ISBN: 9781461421542 [Retrieved from the Internet on Jan. 9, 2019].

(Continued)

*Primary Examiner* — G. Steven Vanni
(74) *Attorney, Agent, or Firm* — Cesari & McKenna, LLP

(57) ABSTRACT

Described herein is an adaptive expert system comprising a computing device having a memory that stores programmatic instructions and a processor that executes the programmatic instructions. The adaptive expert system receives sample data comprising at least one of raw data, optical data, and electropherogram data from a DNA analysis device, said data generated from a sample containing DNA. The adaptive expert system determines at least one characteristic of the sample data. The adaptive expert system utilizes the at least one characteristic to classify the sample data and apply a predefined parameter set to the said sample data to generate an output.

9 Claims, 85 Drawing Sheets
(67 of 85 Drawing Sheet(s) Filed in Color)

(56) References Cited

OTHER PUBLICATIONS

Frequently Asked Questions on CODIS and NDIS, https://www.fbi.gov/services/laboratory/biometric-analysis/codis/codis-and-ndis-fact-sheet. [Retrieved from the Internet on Nov. 6, 2019].

Gill, P. et al., Interpreting simple STR mixtures using allelic peak areas.: Forensic Sci. Int. 1998; 91: pp. 41-53.

Grover, R. et al., "FlexPlex27-highly multiplexed rapid DNA identification for law enforcement, kinship, and military applications", Int. J. Legal Med. (2017), 131:1489-1501.

International Search Report for PCT/US2018/041838 dated Mar. 28, 2019, 7 pages.

Lynch, Kevin J., Development of Integrated Criminal Justice Expert System Applications, 2002, Artificial Intelligence Group Management Information Systems Department, University of Arizona Laboratory Bureau, Phoenix Police Department, (2005), 10 pages.

Manna, Angelo Della et al., "Developmental validation of the DNAscan Rapid DNA, Analysis instrument and expert system for reference sample processing", Forensic Science International, Genetics 25 (2016) 145-156.

Modified Rapid DNA processing https://www.fbi.gov/services/laboratory/biometricanalysis/codis/rapid-dna. [Retrieved from the Internet Nov. 6, 2019].

Moretti, T. R. et al., "Internal validation of STRmix™ for the interpretation of single source and mixed DNA profiles", Forensic Science International: Genetics, 2017. 29:126-144.

Nicklas, Janice A., "Quantification of DNA in forensic samples", Anal Bioanal Chem, (2003) 376: 1160-1167 DOI 10.1007/s00216-003-1924-z.

Riley, B., "U.S. Department of Defense Biometric and Forensic Technology Forum. Center for Strategic and International Studies", https://www.csis.org/events/us-department-defensebiometricand-forensic-technology-forum. (2012).

Scherer, J. et al., "Design and operation of a portable scanner for high performance microchip capillary array electrophoresis," *Review of Scientific Instruments.* (2020). vol. 81, pp. 113105-1-113105-7.

Selden, Richard F. et al., "Rapid DNA Identification: Changing The Paradigm", FBI National Academy Associates Magazine, Jan./Feb. 2018.

Tan, E. et al., Fully integrated, fully automated generation of short tandem repeat profiles, *Investigative Genetics* (2013), 4: 16.

Taylor, D. A. et al., "The interpretation of single source and mixed DNA profiles", Forensic Science International: Genetics. 7(5) (2013) 516-528.

Thakur M. et al., "Functional validation of human-specific PowerPlex21 System (Promega, USA) in chimpanzee (Pan troglodytes)," BMC Res Notes, (2018). 11:695.

Turingan, R. S. et al., "Rapid DNA analysis for automated processing and interpretation of low DNA content samples", Investigative Genetics, (2016), 7:2.

U.S. House of Representatives and Senate of the U.S. Federal Rapid DNA Act of 2017, https://www.govtrack.us/congress/bills/115/hr510/text.

"Frequently Asked Questions on CODIS and NDIS," Federal Bureau of Investigation (FBI) Laboratory Services, Biometric Analysis website, available at https://www.fbi.gov/services/laboratory/biometric-analysis/codis/codis-and-ndis-fact-sheet, accessed May 10, 2022, 13 pages.

"Quality Assurance Standards for DNA Databasing Laboratories," Federal Bureau of Investigation (FBI), effective date Sep. 1, 2011, 29 pages.

Callaghan, Thomas, "Rapid DNA Instrument Update & Enhancement Plans for CODIS," Biometrics Consortium Conference 2013, Tampa, Florida, Sep. 19, 2013, 34 pages.

"Rapid DNA General Information," Federal Bureau of Investigation (FBI) Laboratory Services, Biometric Analysis website, available at https://www.fbi.gov/services/laboratory/biometric-analysis/codis/rapid-dna, accessed May 10, 2022, 5 pages.

U.S. Department of Justice Office of Justice Programs "Using DNA to Solve Cold Cases" 2002.

* cited by examiner

```xml
<?xml version="1.0" encoding="UTF-8"?>
<CODISImportFile xmlns="urn:CODISImportFile-schema">
  <HEADERVERSION>3.2</HEADERVERSION>
  <MESSAGETYPE>Import</MESSAGETYPE>
  <DESTINATIONORI>I7001</DESTINATIONORI>
  <SOURCELAB>I7001</SOURCELAB>
  <SUBMITBYUSERID>NBservice7001</SUBMITBYUSERID>
  <SUBMITDATETIME>2017-07-05T14:59:52</SUBMITDATETIME>
  <BATCHID>c734fbdd758f4585970e5e607f694577</BATCHID>
  <KIT>NetBio.1.0</KIT>
  <SPECIMEN CASEID="BGV">
    <SPECIMENID>E007C12854A56681</SPECIMENID>
    <SPECIMENCATEGORY>Other</SPECIMENCATEGORY>
    <SPECIMENCOMMENT>Automated Allele calling</SPECIMENCOMMENT>
    <LOCUS>
      <LOCUSNAME>D8S1179</LOCUSNAME>
      <READINGBY>NBservice7001</READINGBY>
      <READINGDATETIME>2017-07-05T14:59:52</READINGDATETIME>
      <ALLELE>
        <ALLELEVALUE>10</ALLELEVALUE>
      </ALLELE>
      <ALLELE>
        <ALLELEVALUE>13</ALLELEVALUE>
      </ALLELE>
    </LOCUS>
    <LOCUS>
      <LOCUSNAME>D21S11</LOCUSNAME>
      <READINGBY>NBservice7001</READINGBY>
      <READINGDATETIME>2017-07-05T14:59:52</READINGDATETIME>
      <ALLELE>
        <ALLELEVALUE>30</ALLELEVALUE>
      </ALLELE>
      <ALLELE>
        <ALLELEVALUE>31.2</ALLELEVALUE>
      </ALLELE>
    </LOCUS>
    <LOCUS>
      <LOCUSNAME>D7S820</LOCUSNAME>
      <READINGBY>NBservice7001</READINGBY>
      <READINGDATETIME>2017-07-05T14:59:52</READINGDATETIME>
      <ALLELE>
        <ALLELEVALUE>10</ALLELEVALUE>
      </ALLELE>
    </LOCUS>
    <LOCUS>
      <LOCUSNAME>CSF1PO</LOCUSNAME>
      <READINGBY>NBservice7001</READINGBY>
      <READINGDATETIME>2017-07-05T14:59:52</READINGDATETIME>
      <ALLELE>
        <ALLELEVALUE>10</ALLELEVALUE>
      </ALLELE>
    </LOCUS>
```

FIG. 12

| | Parameter | Profile Phenotype | | | | | |
|---|---|---|---|---|---|---|---|
| | | Intermediate signal strength samples | High Signal Strength Samples with wide peaks and iNTA | Intermediate signal strength samples with low peak height ratios | Low signal strength samples with low peak heights and low peak height ratios | Very Low Signal Content Samples | Failed samples |
| 1 | ILS condition | Pass | Pass | Pass | Pass | Pass | Fail |
| 2 | Number of CODIS 20 Loci called | 20 | <20 | <20 | <20 | <20 | N/A |
| 3 | Signal Strength | Intermediate | High | Intermediate | Low | Low | N/A |
| 4 | Number of Loci with alleles with PH less than the PH threshold | 0 | 0 | 0 | >0 | >0 | N/A |
| 5 | Number of Loci with alleles with PH greater than PH min | ≥6 (≥20) | ≥6 (≥20) | ≥6 (≥20) | ≥6 | <6 | N/A |
| 6 | Number of Loci with PHR of less than PHR threshold | 0 | 0 | >0 | ≥0 | ≥0 | N/A |
| 7 | Number of loci with wide peaks and iNTAp | 0 | >0 | 0 | 0 | 0 | N/A |

FIG. 38

| Position# | Blue | Green | Yellow | Red | Purple | Orange |
|---|---|---|---|---|---|---|
| 1 | 3527 | 2492 | 1876 | 1709 | 1560 | 1435 |
| 2 | 3577 | 2543 | 1919 | 1756 | 1614 | 1448 |
| 3 | 3587 | 2555 | 1919 | 1772 | 1590 | 1445 |
| 4 | 3576 | 2558 | 1918 | 1769 | 1617 | 1453 |
| 5 | 3596 | 2570 | 1926 | 1786 | 1637 | 1453 |
| 6 | 3582 | 2556 | 1918 | 1767 | 1624 | 1438 |
| 7 | 3586 | 2556 | 1917 | 1768 | 1608 | 1447 |
| 8 | 3592 | 2568 | 1937 | 1787 | 1628 | 1450 |
| 9 | 3571 | 2561 | 1924 | 1788 | 1627 | 1454 |
| 10 | 3581 | 2562 | 1929 | 1785 | 1628 | 1458 |
| 11 | 3597 | 2574 | 1932 | 1789 | 1618 | 1450 |
| 12 | 3577 | 2561 | 1917 | 1788 | 1626 | 1452 |
| 13 | 3575 | 2557 | 1926 | 1779 | 1618 | 1445 |
| 14 | 3576 | 2538 | 1908 | 1765 | 1611 | 1440 |
| 15 | 3577 | 2558 | 1922 | 1778 | 1616 | 1445 |
| 16 | 3575 | 2560 | 1916 | 1788 | 1632 | 1451 |
| 17 | 3582 | 2564 | 1929 | 1785 | 1626 | 1449 |
| 18 | 3576 | 2574 | 1929 | 1798 | 1637 | 1453 |
| 19 | 3575 | 2550 | 1924 | 1778 | 1626 | 1453 |
| 20 | 3581 | 2559 | 1920 | 1789 | 1629 | 1456 |
| 21 | 3573 | 2544 | 1910 | 1781 | 1634 | 1454 |
| 22 | 3589 | 2563 | 1912 | 1786 | 1644 | 1456 |
| 23 | 3570 | 2560 | 1921 | 1771 | 1636 | 1451 |
| 24 | 3572 | 2553 | 1914 | 1782 | 1629 | 1451 |
| 25 | 3569 | 2559 | 1923 | 1791 | 1627 | 1449 |
| 26 | 3590 | 2565 | 1921 | 1787 | 1635 | 1455 |
| 27 | 3573 | 2562 | 1920 | 1780 | 1641 | 1454 |
| 28 | 3579 | 2567 | 1930 | 1790 | 1627 | 1464 |
| 29 | 3574 | 2557 | 1914 | 1785 | 1624 | 1456 |
| 30 | 3579 | 2562 | 1913 | 1787 | 1637 | 1461 |

FIG. 64a

| | | | | | |
|---|---|---|---|---|---|
| 4001 | 4362 | 4537 | 4375 | 7459 | 7261 | 2110 |
| 4002 | 4350 | 4467 | 4294 | 7310 | 7142 | 2077 |
| 4003 | 4324 | 4452 | 4226 | 7213 | 7062 | 2082 |
| 4004 | 4285 | 4404 | 4187 | 7207 | 7067 | 2090 |
| 4005 | 4244 | 4371 | 4148 | 7123 | 6951 | 2056 |
| 4006 | 4216 | 4358 | 4148 | 7160 | 6984 | 2067 |
| 4007 | 4204 | 4380 | 4189 | 7216 | 6996 | 2050 |
| 4008 | 4210 | 4461 | 4257 | 7326 | 7062 | 2061 |
| 4009 | 4248 | 4542 | 4380 | 7460 | 7131 | 2063 |
| 4010 | 4273 | 4601 | 4506 | 7601 | 7193 | 2075 |
| 4011 | 4306 | 4710 | 4682 | 7789 | 7296 | 2096 |
| 4012 | 4354 | 4776 | 4843 | 7916 | 7340 | 2101 |
| 4013 | 4389 | 4841 | 5011 | 8096 | 7366 | 2095 |
| 4014 | 4421 | 4901 | 5182 | 8296 | 7493 | 2115 |
| 4015 | 4489 | 5001 | 5443 | 8667 | 7761 | 2150 |
| 4016 | 4574 | 5195 | 5867 | 9274 | 8166 | 2197 |
| 4017 | 4675 | 5447 | 6467 | 10191 | 8889 | 2266 |
| 4018 | 4853 | 5851 | 7251 | 11461 | 9791 | 2360 |
| 4019 | 5052 | 6353 | 8120 | 12818 | 10791 | 2477 |
| 4020 | 5289 | 6922 | 9084 | 14343 | 11925 | 2597 |
| 4021 | 5526 | 7507 | 10074 | 15939 | 13065 | 2729 |
| 4022 | 5782 | 8141 | 11141 | 17605 | 14325 | 2871 |
| 4023 | 6015 | 8724 | 12363 | 19518 | 15761 | 3012 |
| 4024 | 6280 | 9431 | 13842 | 21826 | 17384 | 3202 |
| 4025 | 6541 | 10068 | 15298 | 24221 | 19212 | 3414 |
| 4026 | 6906 | 11038 | 17200 | 27188 | 21414 | 3659 |
| 4027 | 7265 | 11883 | 19129 | 30241 | 23697 | 3905 |
| 4028 | 7747 | 13048 | 21193 | 33480 | 26083 | 4173 |
| 4029 | 8269 | 14292 | 23224 | 36681 | 28578 | 4421 |
| 4030 | 8848 | 15597 | 25260 | 39929 | 30877 | 4693 |

FIG. 64b

| | | | | | |
|---|---|---|---|---|---|
| 8071 | 3398 | 2276 | 1956 | 2142 | 2020 | 1466 |
| 8072 | 3400 | 2279 | 1965 | 2163 | 2031 | 1457 |
| 8073 | 3390 | 2274 | 1962 | 2149 | 1991 | 1469 |
| 8074 | 3388 | 2281 | 1961 | 2141 | 2033 | 1469 |
| 8075 | 3396 | 2273 | 1946 | 2141 | 2009 | 1470 |
| 8076 | 3391 | 2286 | 1970 | 2158 | 2046 | 1471 |
| 8077 | 3396 | 2273 | 1953 | 2151 | 2027 | 1475 |
| 8078 | 3394 | 2273 | 1948 | 2145 | 2037 | 1468 |
| 8079 | 3398 | 2273 | 1966 | 2151 | 2058 | 1476 |
| 8080 | 3403 | 2283 | 1974 | 2174 | 2050 | 1472 |
| 8081 | 3404 | 2278 | 1963 | 2147 | 2033 | 1482 |
| 8082 | 3399 | 2283 | 1971 | 2156 | 2026 | 1471 |
| 8083 | 3409 | 2282 | 1966 | 2151 | 2024 | 1475 |
| 8084 | 3408 | 2283 | 1965 | 2164 | 2028 | 1477 |
| 8085 | 3412 | 2289 | 1972 | 2149 | 2043 | 1474 |
| 8086 | 3400 | 2276 | 1959 | 2151 | 2012 | 1474 |
| 8087 | 3410 | 2282 | 1960 | 2150 | 2026 | 1481 |
| 8088 | 3400 | 2281 | 1965 | 2144 | 2023 | 1476 |
| 8089 | 3401 | 2274 | 1965 | 2146 | 2047 | 1469 |
| 8090 | 3394 | 2273 | 1951 | 2127 | 1993 | 1484 |
| 8091 | 3394 | 2283 | 1961 | 2146 | 2024 | 1472 |
| 8092 | 3396 | 2279 | 1966 | 2167 | 2034 | 1467 |
| 8093 | 3402 | 2276 | 1970 | 2178 | 2040 | 1474 |
| 8094 | 3396 | 2278 | 1965 | 2157 | 2037 | 1477 |
| 8095 | 3393 | 2280 | 1965 | 2150 | 2000 | 1480 |
| 8096 | 3397 | 2276 | 1966 | 2170 | 2036 | 1479 |
| 8097 | 3403 | 2275 | 1949 | 2144 | 2023 | 1479 |
| 8098 | 3379 | 2274 | 1952 | 2143 | 2006 | 1471 |
| 8099 | 3394 | 2270 | 1971 | 2137 | 2027 | 1472 |
| 8100 | 3399 | 2287 | 1951 | 2143 | 2025 | 1464 |

FIG. 64c

| Peak | Position | Color | Locus | Allele Number | Fragment Size (b) | Peak Height | Width | Asymmetry | Width Dev | Shape Dev |
|---|---|---|---|---|---|---|---|---|---|---|
| 1 | 2546 | Blue | AMEL | X | 90.71 | 9531 | 4.351 | 0.019 | -0.086 | 0.385 |
| 2 | 2556 | Blue | AMEL | X | 91.77 | 10916 | 4.437 | 0.004 | -0.076 | 0.383 |
| 3 | 2602 | Blue | AMEL | Y | 96.52 | 8166 | 4.492 | 0.038 | -0.05 | 0.371 |
| 4 | 2613 | Blue | AMEL | Y | 97.66 | 9526 | 4.244 | 0.005 | -0.073 | 0.398 |
| 5 | 2641 | Blue | | | 100.52 | 185 | 3.12 | 0.01 | -0.012 | 0.084 |
| 6 | 2668 | Blue | D3S1358 | 8 | 103.32 | 160 | 4.3 | 0.01 | -0.031 | 0.042 |
| 7 | 2685 | Blue | D3S1358 | 8.2 | 105 | 379 | 3.844 | 0.122 | -0.001 | 0.109 |
| 8 | 2697 | Blue | D3S1358 | 8.3 | 106.28 | 84 | 2.953 | 0.01 | -0.034 | 0.039 |
| 9 | 2709 | Blue | D3S1358 | 9 | 107.56 | 274 | 8.055 | 0.259 | 0.64 | 0.408 |
| 10 | 2721 | Blue | D3S1358 | 9.1 | 108.71 | 444 | 4.319 | 0.148 | 0.463 | 0.075 |
| 11 | 2775 | Blue | D3S1358 | 10.2 | 114.16 | 1624 | 3.316 | 0.049 | -0.324 | 0.618 |
| 12 | 2809 | Blue | D3S1358 | 11.1 | 117.59 | 74 | 2.125 | 0.006 | -0.043 | 0.043 |
| 13 | 2818 | Blue | D3S1358 | 11.2 | 118.47 | 184 | 2.689 | 0.002 | -0.089 | 0.096 |
| 14 | 2829 | Blue | D3S1358 | 11.3 | 119.61 | 163 | 3.312 | 0.075 | -0.06 | 0.068 |
| 15 | 2838 | Blue | D3S1358 | 12 | 120.41 | 533 | 3.641 | 0.014 | -0.153 | 0.176 |
| 16 | 2848 | Blue | D3S1358 | 12.1 | 121.44 | 252 | 3.511 | 0.033 | -0.045 | 0.095 |
| 17 | 2875 | Blue | D3S1358 | 12.3 | 123.94 | 77 | 2.509 | 0.04 | -0.041 | 0.045 |
| 18 | 2889 | Blue | D3S1358 | 13.1 | 125.34 | 232 | 3.195 | 0.024 | -0.091 | 0.102 |
| 19 | 2896 | Blue | D3S1358 | 13.1 | 125.99 | 52 | 2.444 | 0.009 | -0.027 | 0.031 |
| 20 | 2913 | Blue | D3S1358 | 13.3 | 127.53 | 107 | 2.438 | 0.014 | -0.054 | 0.058 |
| 21 | 2939 | Blue | D3S1358 | 14.1 | 130.04 | 201 | 6.474 | 0.003 | 0.026 | 0.085 |
| 22 | 2959 | Blue | D3S1358 | 14.3 | 131.92 | 116 | 3.745 | 0.035 | -0.035 | 0.04 |
| 23 | 2969 | Blue | D3S1358 | 15 | 132.81 | 226 | 5.055 | 0 | -0.018 | 0.056 |
| 24 | 2982 | Blue | D3S1358 | 15.1 | 134.05 | 251 | 4.183 | 0.058 | -0.008 | 0.063 |
| 25 | 3004 | Blue | D3S1358 | 15.3 | 136.07 | 656 | 4.242 | 0.014 | -0.135 | 0.17 |
| 26 | 3016 | Blue | D3S1358 | 16 | 137.1 | 1781 | 4.727 | 0.046 | -0.111 | 0.362 |
| 27 | 3049 | Blue | D3S1358 | 16.3 | 140.13 | 3776 | 4.821 | 0.22 | -0.07 | 0.445 |
| 28 | 3060 | Blue | D3S1358 | 17 | 141.16 | 9791 | 4.711 | 0.032 | -0.11 | 0.379 |
| 29 | 3095 | Blue | D3S1358 | 17.3 | 144.41 | 3211 | 4.149 | 0.887 | 1.935 | 0.835 |
| 30 | 3106 | Blue | D3S1358 | 18 | 145.36 | 7681 | 4.607 | 0.087 | -0.126 | 0.443 |

FIG. 65a

| | | | | | | | |
|---|---|---|---|---|---|---|---|
| 251 | 2890 | Yellow | | | | | |
| 252 | 2900 | Yellow | | 125.41 | 668 | 5.6 | 0.034 | -0.017 | 0.196 |
| 253 | 2912 | Yellow | | 126.37 | 518 | 4.475 | 0.04 | -0.098 | 0.137 |
| 254 | 2922 | Yellow | | 127.47 | 343 | 2.824 | 0.042 | -0.158 | 0.168 |
| 255 | 2934 | Yellow | | 128.41 | 222 | 1.993 | 0.004 | -0.138 | 0.151 |
| 256 | 2945 | Yellow | | 129.54 | 693 | 3.071 | 0.066 | -0.288 | 0.326 |
| 257 | 2955 | Yellow | | 130.62 | 673 | 4.177 | 0.011 | -0.128 | 0.179 |
| 258 | 2966 | Yellow | vWA | 131.48 | 293 | 2.962 | 0.006 | -0.136 | 0.153 |
| 259 | 2977 | Yellow | vWA | 10 | 132.51 | 468 | 3.371 | 0.07 | -0.179 | 0.206 |
| 260 | 2999 | Yellow | vWA | 10.1 | 133.57 | 872 | 3.741 | 0.036 | -0.268 | 0.316 |
| 261 | 3012 | Yellow | vWA | 10.3 | 135.58 | 217 | 2.183 | 0.002 | -0.133 | 0.144 |
| 262 | 3025 | Yellow | vWA | 11 | 136.77 | 182 | 3.42 | 0.029 | -0.068 | 0.078 |
| 263 | 3035 | Yellow | vWA | 11.1 | 137.96 | 237 | 6.192 | 0.124 | 0.055 | 0.091 |
| 264 | 3046 | Yellow | vWA | 11.2 | 138.89 | 1037 | 6.049 | 0.015 | 0.088 | 0.246 |
| 265 | 3057 | Yellow | vWA | 11.3 | 139.86 | 137 | 3.364 | 0.019 | -0.057 | 0.064 |
| 266 | 3067 | Yellow | vWA | 12 | 140.9 | 272 | 2.534 | 0.005 | -0.153 | 0.166 |
| 267 | 3100 | Yellow | vWA | 12.1 | 141.82 | 442 | 3.606 | 0.023 | -0.161 | 0.184 |
| 268 | 3110 | Yellow | vWA | 13 | 144.82 | 493 | 4.319 | 0.051 | -0.151 | 0.184 |
| 269 | 3130 | Yellow | vWA | 13.1 | 145.78 | 378 | 2.835 | 0.017 | -0.187 | 0.205 |
| 270 | 3141 | Yellow | vWA | 13.3 | 147.54 | 1819 | 5.19 | 0.222 | -0.051 | 0.428 |
| 271 | 3154 | Yellow | vWA | 14 | 148.59 | 4914 | 4.982 | 0.124 | -0.068 | 0.376 |
| 272 | 3163 | Yellow | vWA | 14.1 | 149.73 | 519 | 2.582 | 0.022 | -0.301 | 0.324 |
| 273 | 3176 | Yellow | vWA | 14.2 | 150.58 | 309 | 2.791 | 0.309 | 44.174 | 0.247 |
| 274 | 3187 | Yellow | vWA | 14.3 | 151.73 | 14769 | 4.079 | 0.256 | -0.237 | 0.659 |
| 275 | 3199 | Yellow | vWA | 15 | 152.72 | 35894 | 4.699 | 0.034 | -0.131 | 0.457 |
| 276 | 3213 | Yellow | vWA | 15.1 | 153.8 | 353 | 5.695 | 0.352 | 43.245 | 0.051 |
| 277 | 3258 | Yellow | vWA | 15.2 | 155.01 | 264 | 3.278 | 0.034 | -0.11 | 0.131 |
| 278 | 3277 | Yellow | vWA | 16.2 | 159.03 | 398 | 3.228 | 0.029 | -0.188 | 0.211 |
| 279 | 3304 | Yellow | vWA | 17 | 160.68 | 4209 | 4.389 | 0.014 | -0.225 | 0.62 |
| 280 | 3312 | Yellow | vWA | 17.2 | 163.02 | 493 | 4.049 | 0.07 | -0.164 | 0.187 |
| | | | vWA | 17.3 | 163.75 | 1003 | 3.339 | 0.107 | -0.465 | 0.514 |

FIG. 65b

| | | | | | | | | |
|---|---|---|---|---|---|---|---|---|
| 536 | 3247 | Purple | FGA | 15.1 | 158.04 | 82 | 3.85 | -0.03 | 0.037 |
| 537 | 3267 | Purple | FGA | 15.3 | 159.81 | 165 | 3.988 | -0.047 | 0.063 |
| 538 | 3290 | Purple | FGA | 16.1 | 161.86 | 77 | 3.458 | -0.032 | 0.035 |
| 539 | 3335 | Purple | FGA | 17 | 165.72 | 181 | 4.741 | -0.057 | 0.071 |
| 540 | 3348 | Purple | FGA | 17.1 | 166.81 | 104 | 3.676 | -0.045 | 0.054 |
| 541 | 3379 | Purple | FGA | 18 | 169.53 | 127 | 4.559 | -0.037 | 0.046 |
| 542 | 3391 | Purple | FGA | 18.1 | 170.51 | 69 | 2.743 | -0.039 | 0.043 |
| 543 | 3416 | Purple | FGA | 18.3 | 172.63 | 156 | 3.582 | -0.06 | 0.076 |
| 544 | 3427 | Purple | FGA | 19 | 173.59 | 1497 | 4.062 | -0.349 | 0.631 |
| 545 | 3462 | Purple | FGA | 19.3 | 176.57 | 2214 | 5.024 | 3.909 | 1.262 |
| 546 | 3476 | Purple | FGA | 20 | 177.72 | 9354 | 6.035 | -0.057 | 0.429 |
| 547 | 3526 | Purple | FGA | 21 | 181.98 | 190 | 7.043 | -0.014 | 0.055 |
| 548 | 3573 | Purple | FGA | 22 | 185.9 | 1205 | 5.765 | -0.098 | 0.281 |
| 549 | 3622 | Purple | FGA | 23 | 190.01 | 7260 | 5.823 | -0.13 | 0.514 |
| 550 | 3673 | Purple | FGA | 24 | 194.31 | 69 | 4.767 | -0.024 | 0.029 |
| 551 | 3720 | Purple | FGA | 25 | 198.18 | 107 | 11.109 | 0.04 | 0.062 |
| 552 | 3804 | Purple | FGA | 26.3 | 205.09 | 96 | 7.42 | -0.013 | 0.029 |
| 553 | 4082 | Purple | FGA | 32.1 | 227.66 | 99 | 5.615 | 0.006 | 0.037 |
| 554 | 4102 | Purple | FGA | 32.3 | 229.25 | 64 | 6.7 | -0.012 | 0.019 |
| 555 | 4234 | Purple | FGA | 35.1 | 239.91 | 129 | 7.2 | -0.005 | 0.04 |
| 556 | 4749 | Purple | FGA | 45.1 | 281.05 | 97 | 17.575 | 0.038 | 0.092 |
| 557 | 4829 | Purple | FGA | 46.3 | 287.3 | 59 | 2.188 | -0.022 | 0.047 |
| 558 | 5393 | Purple | DYS576 | 15.3 | 331.75 | 762 | 17.973 | 0.193 | 0.354 |
| 559 | 5445 | Purple | DYS576 | 17 | 335.89 | 7022 | 23.222 | 0.663 | 1.612 |
| 560 | 5535 | Purple | DYS576 | 18.3 | 343.14 | 52 | 7.8 | -0.02 | 0.025 |
| 561 | 5583 | Purple | DYS576 | 20 | 347.03 | 112 | 19.825 | 0.022 | 0.073 |
| 562 | 5624 | Purple | DYS576 | 20.3 | 350.3 | 63 | 8.224 | -0.005 | 0.034 |
| 563 | 6417 | Purple | DYS570 | 16 | 417.64 | 65 | 11.6 | -0.02 | 0.025 |
| 564 | 6458 | Purple | DYS570 | 17 | 421.32 | 665 | 11.968 | -0.142 | 0.199 |
| 565 | 6500 | Purple | DYS570 | 18 | 425.05 | 5629 | 17.141 | 0.077 | 0.534 |

FIG. 65c

ADAPTIVE EXPERT SYSTEM FOR ANALYSIS AND CLASSIFICATION OF DNA SAMPLE DATA

RELATED APPLICATIONS

This application claims priority to U.S. Provisional Patent Application No. 62/531,711, filed on Jul. 12, 2017, and U.S. Provisional Patent Application No. 62/542,099, filed on Aug. 7, 2017.

BACKGROUND

The human genome includes stretches of DNA composed of short tandem repeats (STRs). There are several hundred thousand STR loci in the human genome. The analysis of such STR loci is an important tool for genetic linkage studies, forensics, and clinical diagnostics. For example, over the past quarter century, DNA fingerprinting (the generation of STR profiles for identification) has become invaluable in criminal justice investigations. Rapid DNA Identification enables generation of STR profiles in approximately two hours or less. Furthermore, certain approaches to Rapid DNA Identification allow the analysis to be performed outside controlled laboratory environment, by non-technical operators. Accordingly, the advent of Rapid DNA Identification promises to further expand the utility of DNA fingerprinting worldwide and is now beginning to play an important role in military, intelligence, disaster victim identification, national identity, corporate security, immigration, and border and port applications, among others. Identification of criminals and terrorists, identification of unidentified individuals and remains, exoneration of the innocent, and familial reunification are but a few applications of Rapid DNA technology.

The process of generating a DNA ID (also referred to as an STR profile, DNA profile, and DNA fingerprint) typically comprises three steps. First, DNA is extracted and purified from the sample of interest (this step may be eliminated, in so-called "direct PCR" protocols). Second, the STR loci of interest are amplified, typically in a multiplex reaction containing sets of primer pairs, one of each pair being fluorescently-labelled. Third, amplification is generally followed by separation of the fluorescently labeled amplicons by electrophoresis. When a sufficient number of loci is interrogated, a DNA ID is generated providing the discriminating power needed for human identification.

In forensic laboratories, DNA is often quantified following purification. In fact, human-specific DNA quantification has been required by the FBI in order to permit the resulting DNA Fingerprints to be searched against Federal and State DNA databases [The FBI Director's Databasing Quality Assurance Standards for DNA Databasing Laboratories—Effective Sep. 1, 2011].

The major rationale for the quantitation requirement is to determine the amount of human DNA in a given sample to prevent utilizing too little or too much human DNA in an amplification reaction [Janice A. Nicklas • Eric Buel Quantification of DNA in forensic samples Anal Bioanal Chem (2003) 376: 1160-1167 DOI 10.1007/s00216-003-1924-z]. If too little human DNA is used in the amplification, artifacts including allele peak height imbalance, allele drop-out, and allele drop-in, can occur. If too much sample DNA is used, artifacts including increased stutter, increased incomplete non-template addition, allele drop-ins, pull-up (or bleed-through) peaks resulting from incomplete color separation, peak "flat-topping" caused by a high signal peak being cut-off at the upper limit of dynamic range of the electrophoretic detection system, and extra-wide peaks resulting from too much signal at a given peak during separation, can occur.

These artifacts can lead to difficulties in interpretation of a DNA ID by conventional Expert Systems that are utilized to interpret electropherograms following STR processing. [Development of Integrated Criminal Justice Expert System Applications, 2002, Artificial Intelligence Group Management Information Systems Department, University of Arizona Laboratory Bureau, Phoenix Police Department]. Many conventional Expert Systems have been developed, including GeneMapper®ID, GeneMapper®ID-X, GeneMarker® HID, i-Cubed™, OSIRIS, and TrueAllele™. [Frequently Asked Questions on CODIS and NDIS, available at the FBI Laboratory Services, Biometric Analysis website]. Conventional Expert Systems typically have standard (or baseline) rules and standard (or baseline) parameter sets defined by users, and these rules and parameters are either fixed or require manual manipulation to change; in any case, they are highly subjective. In addition to requiring substantial time, these problematic DNA IDs may cause calling errors in conventional Expert Systems (which may lead to misidentifications and errors in database search and match protocols) and the need to reprocess the sample (whether repeating the process from the purification, amplification, or separation step). Repeats add to the time and cost of DNA fingerprinting and may not always be possible dues to sample or intermediate product constraints. Accordingly, for evaluation of crime scene samples, the DNA Advisory Board to the FBI recommends the use of human-specific quantification rather than total DNA quantification, which can ensure that an appropriate amount of human DNA is subjected to amplification even if bacterial, fungal, or other non-human DNA is present is the sample. However, human-specific DNA quantification may be expensive and time-consuming—another contributing factor in the DNA backlog problem in forensic DNA laboratories. And human-specific DNA quantitation itself may be inaccurate, leading to the myriad of artifacts and interpretation problems discussed above.

With or without DNA quantitation, conventional Expert Systems have serious limitations. In fact, the FBI has only approved Expert systems for use with reference samples (e.g. buccal swabs or blood obtained directly from an individual) and stated that "(t)here are no Expert Systems approved for use on casework (forensic unknown) samples." [Frequently Asked Questions on CODIS and NDIS, ibid.]. The conventional Expert System and trained forensic analyst typically work together as follows:

The Expert System applies its standard (or baseline) rules and standard (or baseline) parameter sets to raw data to generate a baseline DNA ID.

The Expert System highlights some of the anomalies in the DNA ID.

The Analyst reviews the output DNA ID.

The Analyst makes a manual change to the one or more Expert System rules and parameters in an attempt to optimize the result.

The Analyst reviews the results of each change and continues the cycle of change and review.

The Analyst may override Expert System results for any given peak (for example, the Analyst may manually mark a peak in red to indicate that he or she is uncomfortable with or disagrees with an Expert System determination). The Analyst may also accept a peak that the Expert System has been failed by the Expert System. In addition, the Analyst may reject a DNA ID in which the Expert System has identified no anomalous peaks or accept a DNA ID in which the Expert System has identified one or multiple problems. The conventional Expert System does not Pass or Fail a DNA ID—that function is performed by the Analyst after manual editing and review of the DNA ID.

Other Analysts are typically required to review this process to obtain a confirmed result.

Often, the initial Analyst decides to reprocess the sample to generate a more suitable input to the conventional Expert System. Reprocessing may take many forms, including either extracting of purifying DNA from another portion of the sample (e.g. a cutting of a swab) or from another sample entirely (e.g. a nearby blood spatter stain), repurifying or concentrating or otherwise manipulating a solution derived from the sample containing DNA, re-amplifying, or re-separating amplified DNA by re-injecting the same or a different amount of amplified DNA in the electrophoresis system). This reprocessing may also be performed if the other analyst (s) cannot confirm the interpretation of the results of each other or the initial Analyst.

Whenever reprocessing is performed, the above steps are repeated. Reprocessing is quite common, and, for certain samples, may occur 2, 3, 5, 10 or more times.

Conventional Expert Systems rely on human interpretation, which is highly subjective and can vary from analysts to analyst and, for a given analyst, from day to day. Analysts may judge a peak or DNA ID based on a "sense" of the data as opposed to application of a formal algorithm—this can lead to mistakes or indeterminate results (which leads to repeats as above). Conventional Expert Systems are also limited by sample processing (whether due to poor sample collection, too much sample processed, too little sample processed, or other causes) and by instrumentation (which, for example, may saturate and show bleedthrough peaks). Even the requirement for an analyst is itself an Expert System limitation. In many settings—such as the battlefield, disaster sites, the crime scene, immigration offices, and borders and ports for example—the number of analysts skilled at working with conventional Expert Systems is limited.

Accordingly, there is a long-felt need for an improved Expert System that effectively expands the dynamic range of DNA fingerprinting (i.e. DNA ID-generating) processes, including extraction, purification, amplification, separation and detection, and corresponding analysis. Such improved Expert Systems may eliminate the need for DNA quantitation or, in cases in which it is mandated, enhance its effectiveness. This long-felt need applies to conventional laboratory processing, automated or semi-automated laboratory processing, and to Rapid DNA Identification.

SUMMARY OF THE INVENTION

A major problem faced during complex macromolecular analytic processes is that many sample types, including but not limited to biological sample types, have significant variability of their component analytes. Detection and measurement systems have defined dynamic ranges within which the analytes may be detected, but often, analyte quantities or concentrations fall outside these dynamic ranges. When this occurs, the user may decide to re-run a given sample, adjusting the mass or volume or dilution of input sample. The re-run may allow the analytes of interest to fall within the dynamic range, or further re-runs may be required. In addition to requiring addition time and cost of multiple runs, there are cases in which sample is limiting and is unavailable for re-runs. Another approach when the analytes of interest fall outside the dynamic range is for the user to adjust the instrument or software to allow the analyte to fall within the dynamic range of the system. This may be effective in very simple systems (illustratively, manually changing the coarse focus control of a microscope to enable a specimen to be visualized), but this type of adjustment is much more difficult in a complex system. In addition to requiring time and expense, this approach requires a sophisticated operator—in biological analytic processes, such operators are typically laboratory-based.

Furthermore, current interpretation of DNA IDs by forensic analysts, with or without the use on an Expert System, is highly subjective. Day-to-day variation in interpretation by an individual, individual-to-individual variation, and lab to lab variation all may result in variability of result for a given DNA ID and repeated runs of samples with features that fall on the edge of a subjectively (and sometimes sub-consciously) defined aspect of the data.

Accordingly, we have addressed these problems by creating an automated Expert System that appropriately adapts to variable samples and processes data on analytes falling within an effectively expanded dynamic range and clearly defines precise algorithms to handle such samples. The teachings of the instant invention yield "Adaptive Expert Systems" (AES) that accelerate sample analysis, limit sample requirements, reduce re-runs, make the DNA quantitation step optional, provide more useful data per sample, and allow complex analyses to be performed, inside or outside of the laboratory and by technical or non-technical operators without a requirement for technical reviewers or review. The AES of the invention are applicable to sample data that falls outside the conventional dynamic range of a system or within that dynamic range, and allows analysis of single source, mixture, clinical, environmental, veterinary, wildlife, and a variety of other samples. This solution has been accomplished by identifying certain patterns and characteristics of sample analyte data, changing data handling and analysis operations from what a computer and expert system software would typically do. This substantial analytic improvement is applicable in a wide range of settings and applications.

The inventions disclosed herein may be practiced with a wide variety of instruments, systems and methods, and on a wide variety of sample types, including the following microfluidic electrophoresis patents and patent applications, and sample treatment patents and patent applications, each of which is hereby incorporated by reference in its entirety: U.S. Pat. Nos. 8,018,593; 8,173,417; 8,206,974; 8,425,861 8,720,036; 8,858,770; 8,961,765; 9,012,208; 9,174,210; 9,310,304; 9,314,795; 9,354,199; 9,366,631; 9,494,519; 9,523,656; 9,550,985; 9,606,083; 9,797,841; 9,889,449 and 9.994,895 and U.S. patent application Ser. No. 15/894,630.

Forensic samples are highly variable and must have their value maximized. For example, in criminal law enforcement, DNA evidence from crime scene samples has the potential to generate investigative leads, identify suspects, and exonerate the innocent. In military activities, DNA data generated from samples collected during sensitive site exploitation activities may protect civilians and warfighters and the value of the data gained from those samples must be commensurate with the sacrifices made to obtain them. Rapid DNA Identification has the potential to expand the intelligence leads garnered from crime scene evaluation and SSE missions and shorten the timeliness in which those leads can be pursued, denying criminals and terrorists their anonymity, their freedom of movement, and stifling their ability to operate undetected. In short, DNA evidence from forensic samples has the potential to dramatically improve societal safety by identifying criminals and terrorists and exonerating the innocent.

Rapid DNA identification is the fully automated generation and interpretation of DNA IDs, preferably in less than two hours. The impact of rapid DNA technology is evidenced by the fact that the Department of Defense, the Federal Bureau of Investigation (FBI), and the Department of Homeland Security have collaborated to develop a series of requirements for rapid DNA Identification systems [Ben Riley (2012) U.S. Department of Defense Biometric and Forensic Technology Forum. Center for Strategic and International Studies.].

Furthermore, the FBI's establishment of the Rapid DNA Index System (RDIS) [Callaghan, T. (2013) Rapid DNA instrument update & enhancement plans for CODIS. Biometrics Consortium Conference, Sep. 19, 2013, Tampa, Florida], and the unanimous passage by the U.S. House of Representatives and Senate of the U.S. Federal Rapid DNA Act of 2017 suggest that DNA ID generation outside the laboratory will become routine.

The ANDE 6C Rapid DNA system [Eugene Tan, Rosemary S Turingan, Catherine Hogan, Sameer Vasantgadkar, Luke Palombo, James W Schumm, Richard F. Selden. Fully integrated, fully automated generation of short tandem repeat profiles, *Investigative Genetics* (2013), 4:16; Rosemary S. Turingan, Sameer Vasantgadkar, Luke Palombo, Catherine Hogan, Hua Jiang, Eugene Tan and Richard F. Selden. Rapid DNA analysis for automated processing and interpretation of low DNA content samples. *Investigative Genetics* (2016) 7:2; Angelo Della Manna, Jeffrey V. Nye, Christopher Carney, Jennifer S. Hammons, Michael Mann, Farida Al Shamali, PhD, Peter M. Vallone, PhD, Erica L. Romsos, PhD, Beth Ann Marne, Eugene Tan, PhD, Rosemary S. Turingan, PhD, Catherine Hogan, Richard F. Selden, M D PhD, Julie L. French. Developmental validation of the DNAscan Rapid DNA Analysis instrument and expert system for reference sample processing. *Forensic Science International: Genetics* 25 (2016) 145-156; Richard F. Selden, M D, PhD, James H. Davis. Rapid DNA Identification: Changing The Paradigm. *FBI National Academy Associates Magazine*, January/February 2018] is a fully integrated, ruggedized system capable of field-forward operation by a nontechnical operator following minimal training. The system employs a reagent-containing, single disposable microfluidic chip and a fully integrated instrument to generate DNA IDs. The system as presented in several of the Examples employs the FlexPlex assay [Ranjana Grover, Hua Jiang, Rosemary S. Turingan, Julie L. French, Eugene Tan, and Richard F. Selden, FlexPlex27—highly multiplexed rapid DNA identification for law enforcement, kinship, and military applications, *Int. J. Legal Med.* (2017), 131:1489-1501]. FlexPlex is a multiplex assay which interrogates 27 loci. The assay contains 23 autosomal loci (D1S1656, D2S1338, D2S441, D3S1358, D5S81, D6S1043, D7S820, D8S1179, D1051248, D125391, D135317, D165539, D18551, D195433, D21S11, D22S1045, FGA, CSF1PO, Penta E, TH01, vWA, TPDX, and SE33), three Y-chromosomal loci (DYS391, DYS576, and DYS570), and Amelogenin. In addition to the STR loci of the FBI's expanded CODIS core loci, FlexPlex27 generates data compatible with the ENFSI/EDNAP Expanded European Standard set and a wide range of national DNA databases including Australia's National Criminal Investigation DNA Database, Canada's National DNA Data Bank, China's National DNA Database, Germany's DNA-Analyze-Datei, New Zealand's National DNA profile databank, and the United Kingdom's National DNA Database. Note that the teachings of the invention can be applied to any STR assay, whether singleplex or multiplex. A large number of commercial STR assays are available.

Following insertion of samples into a chip and of the chip into the instrument, the system performs all required processes for DNA ID generation for each sample including DNA extraction and purification, PCR amplification, electrophoretic separation, fluorescence detection, and data analysis by the on-board expert system [Grover et al., ibid.]. In May 2018, the ANDE 6C Rapid DNA system became the first to receive the FBI's National DNA Index System approval under the CODIS 20 standard [FBI Rapid DNA General Information, available at the FBI Laboratory Services, Biometric Analysis website]. The ANDE system incorporates privileges for a tiered group of users, including: Operator (typically a non-technical user that does not have access to DNA ID yet may be informed of process results and suggested next steps); Admin typically a forensic analysts that is given access to DNA ID data); and SuperAdmin (typically a more senior individual that is given privileges to adjust user-configurable settings to reflect jurisdictional policies). Other tiers are added (or removed) based on jurisdictional requirements.

The system described herein is capable of analyzing essentially any biological or forensic sample, for example, ranging from those typically with high DNA content (e.g. buccal swabs, fresh human tissue such as muscle, liver, blood, and bone) to samples typically with low DNA content (e.g. samples collected from handled objects (epithelial touch), very small amounts of human tissue, bone, teeth or blood, and degraded samples). To be clear, any sample type may have high or low content of DNA—the quantity of the sample collected and the conditions under which the samples were stored directly impact the quantity of DNA for the sample. As such, the instant invention is appropriate for the analysis of essentially any forensic sample, including but not limited to liquid blood or bloodstains, liquid saliva or saliva stains, and liquid semen or dried semen stains (including from vasectomized males) deposited on virtually any surface; genital/vaginal/cervical samples collected on swabs or gauze, or as aspirates; rectal/anal swabs; penile swabs; pieces of tissue/skin; fingernails; plucked and shed hairs (e.g., head, pubic, body); skin cells on drinking vessels, oral epithelial cells on drinking vessels (e.g. cups, bottles, straws, glasses, cans), clothing (e.g., neck collars, waistbands, hat linings); slides containing tissue, semen, urine and urine stains, buccal swabs, hairs, bone, teeth, fingernails, tissues from internal organs (including brain, heart, lung, kidney, bladder, muscle, liver, and skin), bone, vaginal swabs, cervical swabs, body swabs, anal swabs, genital swabs, clothing where biological fluids may be deposited (e.g., women's panty crotches or blood-, saliva-, or semen-stained items) and other clothing in close contact with the body where skin cells may have rubbed off (e.g., collars, waistbands, hats), bedding (with vaginal/semen stains or rubbed off skin cells), fingernail clippings, cigarette butts, toothbrushes, hairs in razors and hairbrushes, discarded facial tissues or handkerchiefs with nasal secretions, condoms, gum, feminine products, pathology paraffin blocks or slides from previous surgery or from autopsy. The system is also directly applicable to mixture samples.

Furthermore, the instant invention is applicable to human and non-human sample types. The system can be utilized in the evaluation of samples containing viruses, bacteria, and fungi, for example. These may be found in clinical sample in the presence of human DNA, in a veterinary sample (in the presence of host animal DNA), in a food sample, in an environmental sample, in a fuel sample, or other sample types. The invention is also applicable to STRs and other genetic features is mammals (e.g. horse, cattle, goat, sheep, pig, cat, dog, mouse, lion, elephant, rhinoceros, zebra), bird, fish, amphibian, reptile, plant (e.g. corn, soy, coffee, wheat, rice, cannabis).

The Adaptive Expert System (AES) of the Invention allows DNA IDs to be processed using an enhanced Expert System that automatically and intelligently adapts calling parameters based on characteristics of sample data detected following the physical manipulation of DNA (sample data and sample analyte data are defined as raw data, optical data, electropherogram data, or other types of data) in order to maximize the allelic information extracted from forensic samples. The AES output optimizes DNA ID calling to generate the maximum number of correct allele calls while minimizing or eliminating miscalls due to allelic dropins or dropouts for each sample.

In a DNA ID, an allele is one copy of a DNA fragment present at a specific spot on a chromosomal locus. A given locus may be heterozygous (two alleles of different sizes), homozygous (both alleles the same size), or hemizygous (a single allele because only one copy of the locus is present—such as the X or Y chromosome of a male). Tri-alleles are occasional present (three alleles in a locus), and 1, 2, 3, 4 or, many more alleles may be present in a locus from a DNA ID generated from a mixture (a sample containing DNA from more than one contributor). An allelic dropin is an allele observed in the DNA ID that is artifactual and an allelic dropout is the absence or a true allele in the DNA ID that is actually present in the source genome. Both dropins and dropouts can lead to incorrect DNA IDs, although using relaxed DNA database searching criteria (e.g. allowing for one or more mismatches during the search) can routinely compensate for these events.

In addition to maximizing the value of STR-based DNA IDs, the Adaptive Expert System of the present invention may also be applied to the analysis of other analytes. For example, the analyte may be a proteins, peptides, messenger RNAs, antisense RNAs, transfer RNAs, ribosomal RNAs, other RNAs, nucleic acids, oligonucleotides, DNA or RNA fragments containing Single Nucleotide Polymorphisms, lipids, carbohydrates, metabolites, steroids, synthetic polymers, other macromolecules, inorganic or other organic chemicals, or combinations of these analytes. The invention allows the analysis of samples containing these analytes to be much more efficient that currently possible by enabling the Expert System to modify parameter during analysis, harvesting as much useful information as possible from the sample.

As can be appreciated, an Expert System typically comprises a minimum of two components, a knowledge base (e.g., a set of data elements comprising facts and rules that are stored in a database) and an inference engine (e.g., programmatic instructions executing on a processor of a computing device coupled to the database). The inference engine retrieves facts from the database and analyzes the facts using the rules to, e.g., draw conclusions and/or infer additional facts. For example, facts can comprise raw data, or optical data, or electropherogram data or any other data input, and of anything inferred from this input by the Expert System. For example, inferred facts or characteristics may include:

Signal to noise ratio of each dye channel
Peak position
Peak base assignments
Peak fragment size
Peak color
Peak locus
Peak Allele #
Peak height
Peak width
Peak shape
Peak morphology
Peak asymmetry
Peak width deviation
Peak shape deviation
Base confidences
Heterozygote peak height
Heterozygote peak height ratio
Average heterozygote peak height by color
Homozygote peak height
Average homozygote peak height by color
Relative signal strength of alleles within loci
Relative signal strength of alleles as compared to allele size (e.g. bases)
iNTA peak height
iNTA peak height ratio
Stutter peak height
Stutter ratio
ILS success
Number of peaks in the locus
Number of called alleles
Number of alleles labeled in red warning boxes
Number of alleles unlabeled
Number of loci with alleles with PH less than the PH threshold
Number of loci with alleles with PH greater than PH threshold
Number of loci with PHR less than PHR threshold
Number of loci with PHR greater than PHR threshold
Number of loci with wide peaks
Number of loci with iNTA greater than iNTA threshold
Number of loci with three or more peaks that are labeled in red warning boxes.
Number of loci with four or more peaks that are labeled in red warning boxes.
Number of heterozygote loci labeled in red warning boxes
Number of homozygote loci labeled in red warning boxes
Number of Bleed-through peaks
Number of CODIS20 loci called
Number of CODIS 18 loci called
Number of Autosomal loci called
Number of flex plex loci called"
DNA ID Success
Base assignments
Dye spectra
Processed dye traces As described herein, the AES may be used as an integrated module in an Expert System or as a standalone module. Furthermore, the AES may be used as part of or integrated within a Rapid DNA system, modified Rapid DNA system, or conventional STR analysis system. The principles described herein can also be applied to SNPs, autosomal STRs, Y-STRs, X-STRs, samples with inhibition and degradation (e.g. in which the inhibitor or degradation affects the DNA ID and the AES corrects for this), samples with contaminants (e.g. in which the contaminant peaks are detected and purposefully ignored by the Expert System), samples with mixtures, or essentially any other measurement of a genome that is impacted by nucleic acid (DNA or RNA) quantity in the sample.

Forensic samples vary significantly in their DNA content and DNA condition, and the AES is configured to adapt to DNA content and condition to maximize the information that may be derived from a given sample. In other words, if a small quantity of somewhat degraded DNA is generated from a high value piece of evidence, (e.g. wire twist from an improvised explosive device), the AES should not be limited to evaluating the raw data (or optical data, color-corrected electropherogram data, or other data) based on the same Expert System parameter set that would be employed to evaluate data generated from a buccal swab from a detainee. The reason is straightforward and practical—it is relatively easy to go back to a detainee to collect another sample, but it may be difficult or impossible to get another sample from an IED. Furthermore, even with large or readily obtainable quantities of a sample available, the quantity or condition of the DNA within or on the sample may be such that generation of an ideal DNA ID may not be possible. For example, a DNA ID from a wire twist from an exploded IED (improvised explosive device) using an AES parameter set adapted for low DNA content samples may result in an output DNA ID containing only 10 of 27 possible STR loci (this is a "partial DNA ID," (one that contains only a subset of the STR loci present in the assay; a full DNA ID is one that contains all or nearly all of the STR loci present in the assay). Nevertheless, this partial DNA ID would have significant operational value and will allow effective matching against US Department of Defense (DoD) databases (random match probability would likely be approximately 1 in hundreds of millions). It would make no sense to evaluate such a sample solely using a parameter set requiring characteristics expected from amplified STRs derived from a cheek swab.

The operational value of a sample is established by the collection agency or user, and the agency or user will determine if sample data will be processed automatically either using standard expert system parameters, AES parameters, or both. One or more AES parameter options, with increasing degrees of aggressiveness in calling, can be provided and be selected based on the operational value of the sample. Samples with the highest operational value, perhaps ones that are difficult or impossible to obtain or otherwise limited, may be processed with an aggressive parameter sets (e.g. designed to derive as much information as possible from a sample while accepting the possibility of dropins or dropouts) and conservative parameter sets (e.g. designed to minimize allelic dropins and dropouts with the potential cost of reduced information from a given sample). Readily available samples and those in large quantity may be processed with a more conservative parameter set. However, these are only generalized guidelines—ultimately, a series of parameter sets may be utilized and corresponding results presented to the user. This presentation may be via a computer-generated file or using a graphic user interface (GUI). For example, the GUI may present the type of parameter set (perhaps numbered based on aggressiveness) and the number of alleles called. By clicking on each paired data set, the user can visualize the electropherogram or allele table itself.

DNA IDs may be defined to pass or fail based on the number of loci that are called by the AES. This definition is typically based on the minimum number of called loci that are required to search a DNA database, or perform a kinship, mixture, or other analysis. The number of loci is defined by the agency or user (preferably using a GUI-based configuration screen) and this value is passed to the AES. XML files contain metadata on the sample, locus and allele data and are output in a format that is compatible for searching of databases (e.g. CODIS software and the databases including the US National DNA Index System, Rapid DNA Index System, State DNA Index Systems, Local DNA Index Systems, and International DNA index systems). XML files are generated for all samples, however, the AES may be configured to allow or disallow the transfer of the .XML file to the user based on whether the sample passes or fails.

In general, there are five major classes of forensic samples and corresponding DNA IDs:

Single-source samples (i.e. containing genomic DNA from a single contributor) with low quantities of DNA relative to the typical dynamic range of the Rapid DNA or Conventional Laboratory DNA Identification System Single-source samples with high quantities of DNA relative to the typical dynamic range of the Rapid DNA or Conventional Laboratory DNA Identification System Single-source samples with quantities of DNA within the typical dynamic range of the Rapid DNA or Conventional Laboratory DNA Identification System Mixture samples, consisting of DNA from 2 or more individuals; each individual contributor with DNA falling into one of the first three categories. In these samples, the peaks from each of the donors will be present in the DNA ID with relative signal strength corresponding to the relative amount of DNA from each of the donors. Mixture samples may be due to the presence of multiple donor genomes in the evidence or may be due to contamination by genomes from the sample collector, individuals handling the sample, or by manufacturers of reagents and materials used to process the sample. Contamination can also be caused by the presence of non-human genomes present in the original sample or inadvertently added to the sample (e.g. certain bacterial species will generate peaks under certain amplification conditions).

Inhibited/degraded samples with unbalanced characteristics. For example, the peak heights may slope from high to low as peak molecular weight increases (sloping), from low to high as peak molecular weight increases (reverse sloping), or regional sloping, or allele-specific effects. This class may overlap with any of the previous four classes.

Other classes of DNA IDs are possible based on a wide range of factors including sample types, processing approaches, instrumentation, reagents, and consumables. For example, DNA IDs with excessive bleedthrough peaks (even in the absence of high signal, perhaps due to a suboptimal color correction matrix) may be a class when certain optical systems are utilized. "Typical dynamic range" refers to the dynamic range of a system in the absence of the AES of the invention. For example, the typical dynamic range of a conventional DNA Identification system may fall between 0.1 ng to 3 ng of purified DNA introduced into the PCR reaction.

The DNA content of most sample types, even in samples from the same source material, can be highly variable. Whether a swab from a cup or bottle, bloodstain, tissue sample (e.g. muscle, brain, liver, kidney, bladder) a vaginal swab from a Sexual Assault Kit (SAK), cigarette butt, cell phone, keyboard, wire twist, door knob, or a bone fragment, sample-to-sample variation is commonplace. The source of the variation could be the tissue type itself (e.g. tissue regions with greater or lesser cell density—and concomitant DNA content); the shedding process (e.g. someone with a moist mouth may leave more cells of a cigarette butt than someone with a dry mouth); the collection process (e.g. a thorough collection of fingerprint on a cell phone battery may yield more DNA than a less thorough collection); inhibitors present with the DNA (e.g. heme and denim are two of many chemicals known to inhibit the amplification process under certain circumstances); and the condition of the DNA itself (DNA exposed to fire or explosion may be more degraded than DNA from a sample stored under less demanding environmental conditions). DNA IDs from degraded and inhibited samples typically show a reduction in signal strength with increasing fragment sizes. In these cases, the signal strengths of the large fragments may be below the calling requirements of the standard parameters. To accommodate for this variability, the AES described herein has been designed and programmed to recognize DNA IDs with low or high DNA content or degraded DNA or inhibited DNA or combinations of these and automatically adapt calling and interpretation rules and parameter sets accordingly.

This AES is particularly useful in that it allows a nontechnical field operator to run essentially any sample type without needing to know anything about DNA content or condition—effectively replacing the judgment and experimental capabilities of a forensic scientist in the lab. In fact, the AES is superior to the lab scientist in that it automatically adjusts Expert System parameter sets and rules in a standardized manner as opposed to the person-to-person variability that occurs across laboratories today.

The invention, in one aspect, features an adaptive expert system comprising a computing device having a memory that stores programmatic instructions and a processor that executes the programmatic instructions. The adaptive expert system receives sample data comprising at least one of raw data, optical data, or electropherogram data from a DNA analysis device, said data generated from a sample containing DNA. The adaptive expert system generate a baseline DNA ID from said sample data. The adaptive expert system determines at least one characteristic of the baseline DNA ID. The adaptive expert system utilizes the at least one characteristic to classify the baseline DNA ID and apply a pre-defined parameter set to said sample data to generate an output.

The above aspect can include one or more of the following features. In some embodiments, the output comprises one or more of: an .xml file, an .fsa file, a .bmp file, or an allele table. In some embodiments, the at least one characteristic is signal strength. In some embodiments, the at least one characteristic is one or more of: signal to noise ratio of each dye channel, peak position, peak base assignments, peak fragment size, peak color, peak locus, peak allele #, peak height, peak width, peak shape, peak morphology, peak asymmetry, peak width deviation, peak shape deviation, base confidences, heterozygote peak height, heterozygote peak height ratio, average heterozygote peak height by color, homozygote peak height, average homozygote peak height by color, relative signal strength of alleles within loci, relative signal strength of alleles as compared to allele size (e.g. bases), iNTA peak height, iNTA peak height ratio, stutter peak height, stutter ratio, ILS success, number of peaks in the locus, number of called alleles, number of alleles labeled in red warning boxes, number of alleles unlabeled, number of loci with alleles with PH less than the PH threshold, number of loci with alleles with PH greater than PH threshold, number of loci with PHR less than PHR threshold, number of loci with PHR greater than PHR threshold, number of loci with wide peaks, number of loci with iNTA greater than iNTA threshold, number of loci with three or more peaks that are labeled in red warning boxes, number of loci with four or more peaks that are labeled in red warning boxes, number of heterozygote loci labeled in red warning boxes, number of homozygote loci labeled in red warning boxes, number of bleed-through peaks, number of CODIS20 loci called, number of CODIS 18 loci called, number of autosomal loci called, number of flex plex loci called, DNA ID success, base assignments, dye spectra, or processed dye traces.

In some embodiments, the output is utilized to search a database of DNA IDs. In some embodiments, the output is utilized to compare two or more DNA IDs to assess kinship.

In some embodiments, when the characteristic classifies the sample data as having high DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the optical data as having low DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the sample data as a mixture, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold. In some embodiments, the applied pre-defined parameter set generates a first set of called alleles, and said called alleles are extracted from the sample data generating modified sample data, and the adaptive expert system utilizes the at least one characteristic to classify the modified sample data and apply a pre-defined parameter set to said modified sample data to generate a second set of called alleles.

In some embodiments, when the characteristic classifies the sample data as inhibited and/or degraded, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, based upon classifying the baseline DNA ID and applying a pre-defined parameter set, the computing device modifies a value of one or more characteristics utilized to classify a DNA ID and apply a pre-defined parameter set. In some embodiments, based upon classifying the baseline DNA ID and applying a pre-defined parameter set, the computing device modifies one or more pre-defined parameter sets utilized to generate an output when applied to a DNA ID. In some embodiments, the computing device generates a visualization of the output for presentation on a display device. In some embodiments, the visualization comprises a number of alleles called for each of one or more parameter sets.

The invention, in another aspect, features an adaptive expert system comprising a computing device having a memory that stores programmatic instructions and a processor that executes the programmatic instructions. The adaptive expert system receives sample data comprising at least one of raw data, optical data, and electropherogram data from a DNA analysis device, said data generated from a sample containing DNA. The adaptive expert system determines at least one characteristic of the sample data. The adaptive expert system utilizes the at least one characteristic to classify the sample data and apply a predefined parameter set to the said sample data to generate an output.

The above aspect can include one or more of the following features. In some embodiments, the output comprises one or more of: an .xml file, an .fsa file, a .bmp file, or an allele table. In some embodiments, the at least one characteristic is signal strength. In some embodiments, the at least one characteristic is one or more of: signal to noise ratio of each dye channel, peak position, peak base assignments, peak fragment size, peak color, peak locus, peak allele #, peak height, peak width, peak shape, peak morphology, peak asymmetry, peak width deviation, peak shape deviation, base confidences, heterozygote peak height, heterozygote peak height ratio, average heterozygote peak height by color, homozygote peak height, average homozygote peak height by color, relative signal strength of alleles within loci, relative signal strength of alleles as compared to allele size (e.g. bases), iNTA peak height, iNTA peak height ratio, stutter peak height, stutter ratio, ILS success, number of peaks in the locus, number of called alleles, number of alleles labeled in red warning boxes, number of alleles unlabeled, number of loci with alleles with PH less than the PH threshold, number of loci with alleles with PH greater than PH threshold, number of loci with PHR less than PHR threshold, number of loci with PHR greater than PHR threshold, number of loci with wide peaks, number of loci with iNTA greater than iNTA threshold, number of loci with three or more peaks that are labeled in red warning boxes, number of loci with four or more peaks that are labeled in red warning boxes, number of heterozygote loci labeled in red warning boxes, number of homozygote loci labeled in red warning boxes, number of bleed-through peaks, number of CODIS20 loci called, number of CODIS 18 loci called, number of autosomal loci called, number of flex plex loci called, DNA ID success, base assignments, dye spectra, or processed dye traces.

In some embodiments, the output is utilized to search a database of DNA IDs. In some embodiments, the output is utilized to compare two or more DNA IDs to assess kinship.

In some embodiments, when the characteristic classifies the sample data as having high DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the sample data as having low DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the sample data as a mixture, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold. In some embodiments, the applied pre-defined parameter set generates a first set of called alleles, and said called alleles are extracted from the sample data generating modified sample data, and the adaptive expert system utilizes the at least one characteristic to classify the modified sample data and apply a pre-defined parameter set to said modified sample data to generate a second set of called alleles.

In some embodiments, when the characteristic classifies the sample data as inhibited and/or degraded, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, based upon classifying the sample data and applying a pre-defined parameter set, the computing device modifies a value of one or more characteristics utilized to classify the sample data and apply a pre-defined parameter set. In some embodiments, based upon classifying the sample data and applying a pre-defined parameter set, the computing device modifies one or more pre-defined parameter sets utilized to generate an output when applied to a DNA ID. In some embodiments, the computing device generates a visualization of the output for presentation on a display device. In some embodiments, the visualization comprises a number of alleles called for each of one or more parameter sets.

The invention, in another aspect, features an adaptive expert system comprising a computing device having a memory that stores programmatic instructions and a processor that executes the programmatic instructions. The adaptive expert system receives data from an analysis device, said data generated from a sample containing an analyte. The adaptive expert system determines, using the data, at least one characteristic of the analyte. The adaptive expert system utilizes the at least one characteristic to classify the data and apply a predefined parameter set to the data to generate an output.

The above aspect can include one or more of the following features. In some embodiments, the analyte is one or more of: proteins, peptides, messenger RNAs, antisense RNAs, transfer RNAs, ribosomal RNAs, other RNAs, nucleic acids, oligonucleotides, DNA or RNA fragments containing Single Nucleotide Polymorphisms, lipids, carbohydrates, metabolites, steroids, synthetic polymers, other macromolecules, inorganic or other organic chemicals, or combinations of these analytes.

The invention, in another aspect, features an adaptive expert system comprising a computing device having a memory that stores programmatic instructions and a processor that executes the programmatic instructions. The adaptive expert system receives data from a DNA analysis device, said data generated from a sample containing a plurality of genomic DNA from at least one major contributor and at least one minor contributor. The adaptive expert system determines, using the data, at least one characteristic of a first DNA ID corresponding to a major contributor. The adaptive expert system utilizes the characteristic to classify the first DNA ID and apply a predefined parameter set to the data. The adaptive expert system subtracts one or more characteristics from the first DNA ID to determine at least one characteristic of a second DNA ID corresponding to a minor contributor.

The invention in another aspect, features an adaptive expert system comprising a computing device having a set of decision making nodes, said nodes capable of self-learning when presented with a set of sample data with known outputs, said computing device having a memory that stores programmatic instructions and a processor that executes the programmatic instructions. The adaptive expert system receives sample data comprising at least one of raw data, optical data, and electropherogram data from a DNA analysis device, said data generated from a sample containing DNA. The adaptive expert system determines at least one characteristic of the sample data. The adaptive expert system applies said set of decision making nodes to generate an optimal set of expert system parameters for a given set of characteristics from the sample data; and apply the optimal set of expert system parameters to the said sample data to generate an output.

The above aspect can include one or more of the following features. In some embodiments, the output comprises one or more of: an .xml file, an .fsa file, a .bmp file, or an allele table. In some embodiments, the at least one characteristic is signal strength. In some embodiments, the at least one characteristic is one or more of: signal to noise ratio of each dye channel, peak position, peak base assignments, peak fragment size, peak color, peak locus, peak allele #, peak height, peak width, peak shape, peak morphology, peak asymmetry, peak width deviation, peak shape deviation, base confidences, heterozygote peak height, heterozygote peak height ratio, average heterozygote peak height by color, homozygote peak height, average homozygote peak height by color, relative signal strength of alleles within loci, relative signal strength of alleles as compared to allele size (e.g. bases), iNTA peak height, iNTA peak height ratio, stutter peak height, stutter ratio, ILS success, number of peaks in the locus, number of called alleles, number of alleles labeled in red warning boxes, number of alleles unlabeled, number of loci with alleles with PH less than the PH threshold, number of loci with alleles with PH greater than PH threshold, number of loci with PHR less than PHR threshold, number of loci with PHR greater than PHR threshold, number of loci with wide peaks, number of loci with iNTA greater than iNTA threshold, number of loci with three or more peaks that are labeled in red warning boxes, number of loci with four or more peaks that are labeled in red warning boxes, number of heterozygote loci labeled in red warning boxes, number of homozygote loci labeled in red warning boxes, number of bleed-through peaks, number of CODIS20 loci called, number of CODIS 18 loci called, number of autosomal loci called, number of flex plex loci called, DNA ID success, base assignments, dye spectra, or processed dye traces.

In some embodiments, the output is utilized to search a database of DNA IDs. In some embodiments, the output is utilized to compare two or more DNA IDs to assess kinship.

In some embodiments, when the characteristic classifies the sample data as having high DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the sample data as having low DNA content, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, when the characteristic classifies the sample data as a mixture, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold. In some embodiments, the applied pre-defined parameter set generates a first set of called alleles, and said called alleles are extracted from the sample data generating modified sample data, and the adaptive expert system utilizes the at least one characteristic to classify the modified sample data and apply a pre-defined parameter set to said modified sample data to generate a second set of called alleles.

In some embodiments, wherein when the characteristic classifies the sample data as inhibited and/or degraded, the pre-defined parameter set applied modifies at least one of: heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of Bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, or Quality of search and match threshold.

In some embodiments, based upon classifying the sample data and applying a pre-defined parameter set, the computing device modifies a value of one or more characteristics utilized to classify the sample data and apply a pre-defined parameter set. In some embodiments, based upon classifying the sample data and applying a pre-defined parameter set, the computing device modifies one or more pre-defined parameter sets utilized to generate an output when applied to a DNA ID. In some embodiments, the computing device generates a visualization of the output for presentation on a display device. In some embodiments, the visualization comprises a number of alleles called for each of one or more parameter sets.

The invention, in another aspect, features an adaptive expert system comprising a computing device having a memory that stores programmatic instructions and a processor that executes the programmatic instructions. The adaptive expert system receives sample data from an optical detection system comprising at least two detectors or detector elements, said detectors or detector elements configured to collect fluorescence from dye-labelled DNA to generate an optical signal. The adaptive expert system subtracts a baseline of the optical signal. For at least one peak in the data, the adaptive expert system saturates the optical signal of at least one of the detectors or detector elements, and the adaptive expert system does not saturate the optical signal of at least one of the detectors or detector elements. The adaptive expert system calculates signal strength ratios of the detector or detector element optical signal of each of the saturated detectors or detector elements to each of the unsaturated detectors or detector elements in a portion of the peak where both detectors or detector elements are not saturated. The adaptive expert system calculates signal strength of the saturated detectors or detector elements in the saturated portion of the peak by multiplying the signal strength of the unsaturated detectors or detector elements by the corresponding signal strength ratio.

The above aspect can include one or more of the following features. In some embodiments, the optical detection system comprises at least 4 detectors or detector elements. In some embodiments, the optical detection system comprises at least 5 detectors or detector elements. In some embodiments, the optical detection system comprises at least 6 detectors or detector elements. In some embodiments, the optical detection system comprises at least 8 detectors or detector elements. In some embodiments, the optical detection system comprises at least 12 detectors or detector elements. In some embodiments, the optical detection system comprises at least 16 detectors or detector elements. In some embodiments, the optical detection system comprises at least 32 detectors or detector elements. In some embodiments, the optical detection system comprises at least 64 detectors or detector elements. In some embodiments, the optical detection system comprises at least 128 detectors or detector elements. In some embodiments, the optical detection system comprises at least 256 detectors or detector elements.

The invention, in another aspect, features an adaptive expert system comprising a computing device having a memory that stores programmatic instructions and a processor that executes the programmatic instructions. The adaptive expert system receives sample data comprising at least one of raw data, optical data, and electropherogram data from a DNA analysis device, said data generated from a sample containing DNA. The adaptive expert system determines at least one criteria for maximizing results of an iteration. The adaptive expert system modifies at least one parameter by iteratively varying the parameter value in order to maximize the criteria, and generate an output.

The above aspect can include one or more of the following features. In some embodiments, the parameter set applied modifies at least one of: Heterozygote Peak Height Threshold, Heterozygote Peak Height Ratio Threshold, Homozygote Peak Height Threshold, Heterozygote Peak Height Threshold for 2nd peak, Homozygote Peak Height Ratio threshold, Hemizygote Peak Height Minimum threshold, Allele PH/PA threshold in Zone 1, Allele PH/PA threshold in Zone 2, Allele PH/PA threshold in Zone 3, Allele PH/PA threshold in Zone 4, Maximum Number of dropins, Maximum Number of dropouts, Signal to noise ratio threshold of each dye channel, Peak base assignment limits, Peak fragment size threshold, Peak height threshold, Peak width threshold, Peak shape threshold, Peak morphology threshold, Peak asymmetry threshold, Peak width deviation limit, Peak shape deviation limit, Base confidences threshold, Heterozygote peak height threshold, Heterozygote peak height ratio threshold, Average heterozygote peak height by color threshold, Homozygote peak height threshold, Average homozygote peak height by color threshold, Relative signal strength of alleles within loci threshold, Relative signal strength of alleles as compared to allele size threshold, iNTA peaks height threshold, iNTA peak height ratio threshold, Stutter peak height threshold, Stutter ratio threshold, triallate peak height threshold, triallele peak height ratio threshold, mixture peak height threshold, ILS success limits, High iNTA rule state, Mixture sample protection rule state, Low signal protection rule state, Maximum Number of peaks in the locus, Maximum Number of called alleles, Maximum Number of alleles labeled in red warning boxes threshold, Maximum Number of alleles unlabeled threshold, Maximum Number of loci with alleles with PH less than the PH threshold, Maximum Number of loci with alleles with PH greater than PH threshold, Maximum Number of loci with PHR less than PHR threshold, Maximum Number of loci with PHR greater than PHR threshold, Maximum Number of loci with wide peaks, Maximum Number of loci with iNTA greater than iNTA threshold, Maximum Number of loci with three or more peaks that are labeled in red warning boxes, Maximum Number of loci with four or more peaks that are labeled in red warning boxes, Maximum Number of heterozygote loci labeled in red warning boxes, Maximum Number of homozygote loci labeled in red warning boxes, Maximum Number of bleed-through peaks, Minimum Number of CODIS20 loci called, Minimum Number of CODIS 18 loci called, Minimum Number of Autosomal loci called, Minimum Number of flex plex loci called, Minimum number of called loci to generate a CMF file, Quality of DNA ID threshold, Quality of search and match threshold, or Search stringency.

In some embodiments, the criteria for iteration is defined by at least one of: Number of called loci CODIS20, Number of called loci CODIS18, Number of called loci FlexPlex, Number of loci that change from homozygote to heterozygote, Number of dropins, Number of dropouts, Number of alleles labeled in red warning boxes, Quality of DNA ID threshold, or Quality of search and match threshold. In some embodiments, the steps for the iteration are not fixed and can vary depending on rate of change in the criteria.

Other aspects and advantages of the invention will become apparent from the following detailed description, taken in conjunction with the accompanying drawings, illustrating the principles of the invention by way of example only.

BRIEF DESCRIPTION OF THE DRAWINGS

The patent or application file contains at least one drawing executed in color. Copies of this patent or patent application publication with color drawings will be provided by the Office upon request and payment of the necessary fee.

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 12 shows a portion of an .xml file.

FIG. 38 shows a summary table of DNA classification.

FIGS. 64a to 64c show a segment of the optical data that is generated for a sample by the ANDE instrument.

FIGS. 65a to 65c show a snapshot of the peak characteristics for all the peaks in the sample data.

DETAILED DESCRIPTION

Figure 1:
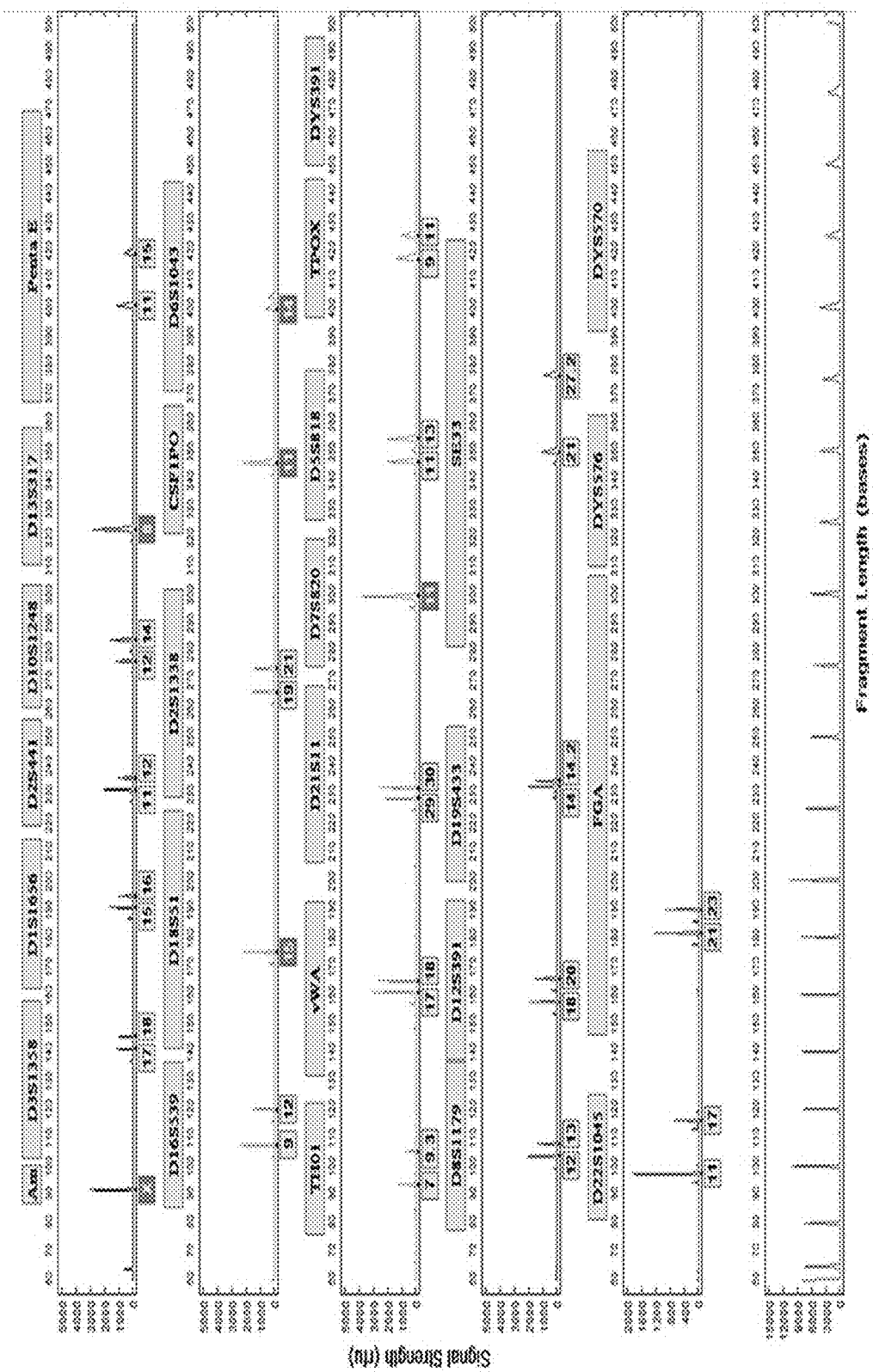
FIG. 1 shows a representative DNA ID from a sample with DNA content below the dynamic range of the Rapid DNA system using a standard expert system parameter set.

There are several approaches to generating a DNA ID:

Laboratory-based conventional processing (typically with separate equipment for DNA extraction/purification, PCR amplification, and electrophoretic separation and detection) with the use of a DNA quantitation step. Laboratory-based conventional processing may also utilize automated equipment and robotics to perform individual processing steps.

Laboratory-based conventional processing without the use of a DNA quantitation step.

Rapid DNA processing using a single chip and processing protocol (regardless of DNA quantity in the sample).

Rapid DNA processing using a single chip and multiple processing protocols based on the presumed DNA quantity in a sample. In cases in which low DNA content in a sample is presumed, the processing protocol might include, for example, a longer time for DNA binding to occur to a bead or another substrate, the use of additional cycles of PCR amplification, modification of electrophoresis injection conditions, or a combination of these and other modifications.

Rapid DNA processing using a chip that quantifies DNA content during processing.

Rapid DNA processing of a cell extract purified and DNA-quantified prior to insertion and processing in the Rapid DNA chip and instrument.

Rapid DNA processing using one or more of a selection of chips, said chips used based on the expected DNA content of a given sample. For example, in the instant invention, two types of chips are utilized: 1) A chip termed HDC, HDC FP, HDC PP16, or A-Chip that is optimal for samples that are presumed to contain high DNA content (e.g. a buccal swab, a typical bloodstain, or a fragment of fresh tissue); 2) A chip termed LDC, LDC FP, LDC PP16, or I-Chip that is optimal for samples that are presumed to contain low quantities of DNA (e.g. a swab of a cup, can or bottle, a small bloodstain, a human hair, fingerprints on a shell casing gun handle, or IED component, or clothing such as the brim of a cap or the collar of a shirt).

Rapid DNA processing using more than a single chip (e.g. several cartridges per run) with the various types of processing described above.

Modified Rapid DNA processing [FBI Rapid DNA General Information, ibid.] in which some or all of the DNA processing steps occur using a Rapid DNA device but the resulting data must be subjected to human review or manipulation.

In these approaches, the DNA ID is generated by an instrument to separate and detect the DNA. Examples of instruments that can generate sample data are described in Example 1. In these cases, a detection system in the instrument is in communication with the processor. The detection system provides the processor with optical data to use as input for generating the DNA ID.

Using these approaches, it is often possible to generate a DNA ID with peaks that fall within the dynamic range of the detection system being applied based on the use of a standard expert system parameter set. However, in each of the above cases (conventional or Rapid DNA, even when DNA content is quantified), it is possible that—following PCR amplification, electrophoretic separation, and detection (often but not always by laser-induced fluorescence based on the covalent attachment of dyes on at least one primer of each primer pair utilized for amplification)—the sample data (including signal strength) generated by the resulting STR peaks fall outside of the dynamic range of the overall system. Several basic classes of DNA IDs may be generated as a result.

A. Samples with DNA Content Below the Dynamic Range of a Given Chip Type or System First, some forensic samples with relatively low DNA content (i.e. low relative to the DNA analysis system used), degraded DNA, inhibitors, or suboptimal nucleic acid purification, amplification, separation, or detection will result in DNA IDs with relatively low signal. For example, samples such as a cigarette butt with limited saliva or a single conventional fingerprint may have low DNA content, even with respect to an I-Chip. Similarly, samples such as liver, large bloodstains, or bone may be expected to contain a large quantity of DNA per sample yet may generate low signal using an A-Chip. Regardless of their genesis, Low Signal DNA IDs present one or more of the following characteristics:

Average heterozygote peak height (RFU) less than a defined quantity in the detection system. For example, 3,000 RFU is a value that may be selected for certain applications using the ANDE system.

Loci with peak heights below a standard (buccal) Expert System calling threshold that are not labeled.

Loci with heterozygote peak height ratios that are too low and are labeled—but in red warning boxes to indicate an issue. Note that, in the ANDE system, red warning boxes on the electropherogram (often presented as a picture and stored as a file with .bmp, or .png, or .pdf format) mark the position and size of a particular STR allele but indicate that some aspect of that allele is problematic. In the ANDE system, alleles labelled in red warning boxes are typically not included in the final .XML files or allele table. In contrast, "called alleles" are labeled in gray boxes and are included in the final .XML file and allele table.

Homozygote loci labeled in red warning boxes.

Multiple homozygote loci that are labeled in red warning boxes.

Alleles with iNTA levels that are within the standard levels. For example, iNTA peaks are nominally 0.2 that of the primary peaks in the ANDE system. The standard AES parameter set considers peaks that are 1 base smaller than the primary peak and less than 0.2× of the height of the primary peak, as an iNTA peak. The iNTA peak will not be labeled by the expert system.

Alleles with peak widths that are within the standard levels.

All peaks in the sample being labeled in red warning boxes.

Although characteristics such as signal strength, peak height ratios, and peak widths will necessarily vary based on the type of DNA analysis system (or different settings on individual, nominally identical instruments), the concept is generally applicable to any such system. Furthermore, additional characteristics can be derived from the sample data detected following the physical manipulation of DNA (raw data, optical data, electropherogram data, or other types of data) to further classify the sample data. Furthermore, although the sample data is broadly classified as Low DNA content, the sample data within this classification can also be further delineated into subcategories. The work presented herein is focused on the ANDE Rapid DNA system using A-Chips and I-Chips.

In addition to eliminating the need for a forensic scientist (or another individual with expertise in the interpretation of DNA IDs), the AES does not require input from a user. The AES automatically processes the DNA ID, with no human interaction, analysis, or review required.

FIG. 1 shows a representative DNA ID from a sample with DNA content below the dynamic range of the Rapid DNA system using a standard expert system parameter set (in this case developed for buccal swabs using an A-Chip), with several of the features noted above. The specific features observed in this sample are:

Average heterozygote peak height (RFU) less 3000 RFU.

Loci with peak heights below a standard (buccal) Expert System calling threshold that are not labeled. See D6S1043.

Multiple homozygote loci labeled in red warning boxes. See Am, D13S317, D18S51, CSF1PO, D7S820.

All iNTA peaks are at levels that are within the standard levels and are not labeled by the expert system.

All Alleles have peak widths that are within the standard levels.

It is critical to note that the loci labeled in red contain useful data—the standard "buccal" expert system rules are too conservative for samples which have low DNA content (as frequently occurs in bone, muscle, teeth, casework, and SSE samples). In fact, this 27plex DNA ID contains sufficient information to allow establishment of identity with a random match probability of less than one in one sextillion ($10^{23}$, almost a trillion trillion)! The AES of the present invention can extract essentially all of this useful data.

In FIG. 1, sample data from a Low DNA content sample was analyzed with a standard set of (e.g. buccal) Expert System calling parameters. In this example of a sample with very low DNA content, the D6 locus was not called because one allele fell below the peak height calling threshold. As a result, the standard Expert System protected against dropouts by labeling homozygous loci with peaks less than 6000 rfu in red warning boxes. If at least seven loci are labeled in red warning boxes as a result, the standard Expert System utilized labels the entire DNA ID in red warning boxes (not the case in this DNA ID). Note that these rules are appropriate for buccal samples but are too conservative for SSE, casework, DVI, or other samples. Note that all of the red warning boxes are designating correct peaks. For a buccal sample, some agencies would choose to repeat the run on a new sample (or start with quantified DNA and run a new amplification reaction) in order to get a full DNA ID. The desire for a "perfect" DNA ID drives the use of the conservative parameters of the standard expert system settings.

When low DNA content samples are identified by the AES software, the calling parameter set is modified to increase the number of loci that are called. Parameter changes include:

Establish a peak height threshold based on the heterozygote signal strengths of called loci. This will effectively reduce the peak height threshold of the standard expert system parameter set. This reduced peak height threshold can be applied generally to all loci (e.g. threshold for all loci will be set to the same value) or independently to some specific or all loci (e.g. the peak height threshold within the Th01 locus is different than that in the TPDX locus) or to specific alleles (e.g. the Th01 8 allele peak height threshold is different than that of the Th01 10 allele and the vWA 11 allele).

Reduce the peak height ratio (PHR) threshold. The reduction in the PHR can be applied generally to all loci (e.g. the reduced PHR threshold for all loci will be set to the same value) or independently to some specific or all loci (e.g. the reduction of the PHR threshold within the Th01 locus is different than that in the TPDX locus) or to specific alleles (e.g. PHR's are established specifically for each STR allele in a given locus).

Disable low signal protection rules. In the standard Expert system, the low signal protection rule may be applied, and homozygous loci are labeled in red warning boxes when they have peak heights less than the protection peak height threshold. In the AES low DNA content parameter set, this rule is disabled, enabling these low signal homozygous peaks to be called.

Reduce the number of called loci required to pass a sample and generate an XML file, allele table, and BMP file.

Figure 2:
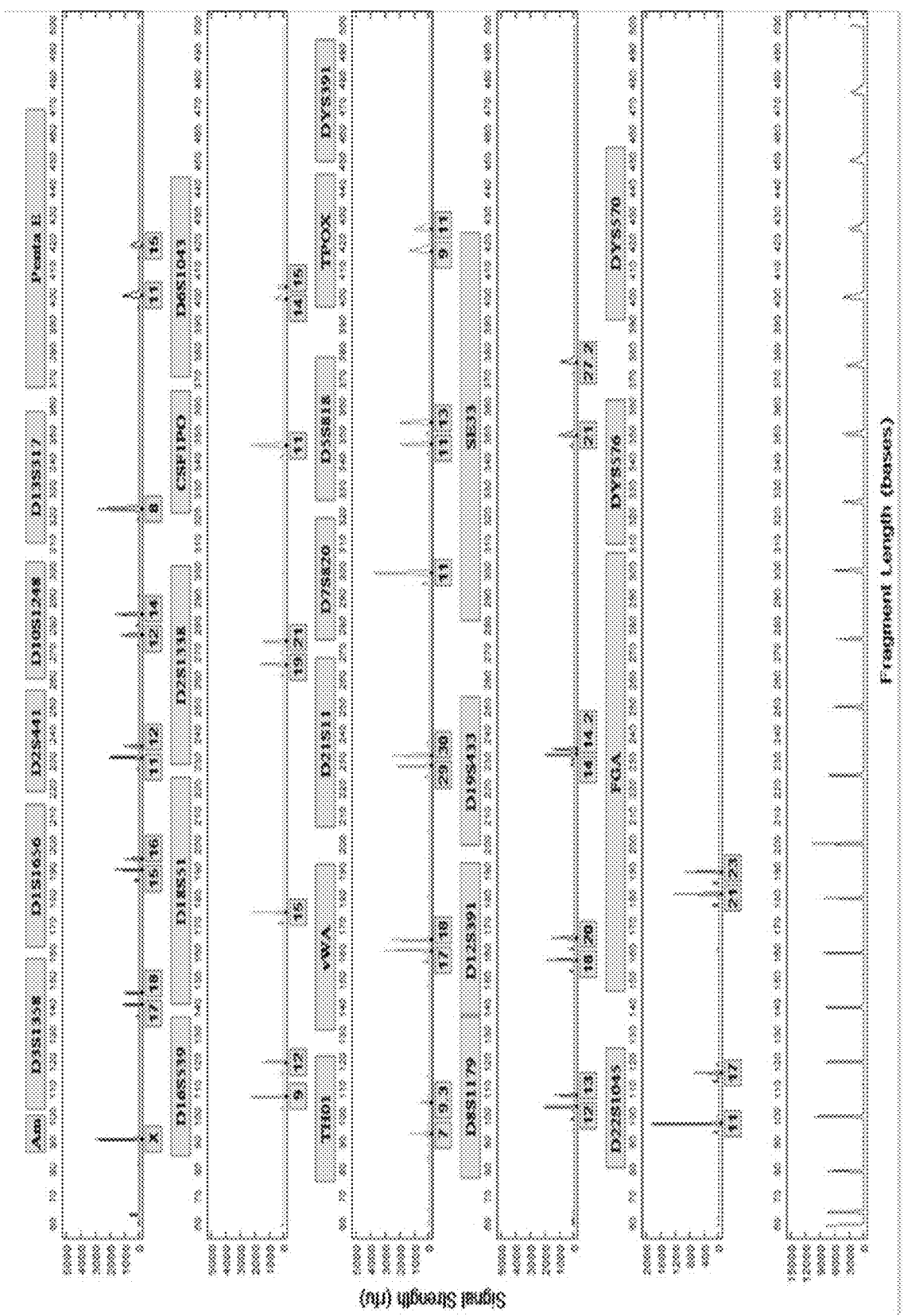
FIG. 2 shows the same DNA ID as FIG. 1, with the ANDE 6C raw data processed using the AES with parameters modified.

FIG. 2 shows the same DNA ID as FIG. 1, with the ANDE 6C raw data processed using the AES with parameters modified as noted above. The ANDE expert system can take as input of optical data (outputs of the detectors of the optical system—in .csv format) and raw electropherogram data (optical data that is color corrected by data processing—including .csv, .dat, ANDE proprietary format .nbo, .FSA and .HID formats) and generate outputs consisting of a DNA ID in .PNG format, XML format and .FSA format.

FIG. 2 shows the Low DNA input sample data of FIG. 1 recalled with the Adaptive Expert System. The D6 locus is now called based on a lower peak height threshold. As a result, the AES does not invoke the low signal protection rules to protect the sample against dropouts. In particular, homozygous loci with relatively low signal strength had been labelled in red warning boxes with the Standard Expert System parameters—this approach protects those loci from a dropout. But the Adaptive Expert System recognizes the low DNA content sample pattern and all loci are called, with no red warning boxes.

B. Samples with DNA Content Above the Dynamic Range of a Given Chip Type

Samples with DNA signal above the dynamic range of a given chip type may include certain SSE samples such as a cigarette butt, chewing gum, a bloodstain, or a drinking glass. Many such samples will generate full DNA IDs in the I-Chip, but some will result in DNA IDs with relatively high signal. Similarly, samples such as muscle, liver, blood, or bone, may generate high signal even using an A-Chip.

Samples with DNA content above the dynamic range of a given chip type generate DNA IDs that are characterized by one or more of the following:

Average heterozygote peak height (RFU) that are greater than 10,000 RFU.

Peaks that are saturated and have squared tops.

Occasional wide peaks that are above the acceptable width thresholds. These peaks are not labeled.

iNTA peaks with peak heights and peak height ratios that are above standard levels, and are sometimes labeled as true alleles. In particular, the iNTA peak height ratios of the amelogenin locus are above standard levels.

Samples with multiple loci with three labeled alleles, and all alleles in the sample being labeled in red.

Samples with at least one loci with four labeled alleles, and all alleles in the sample being labeled in red.

Figure 3:
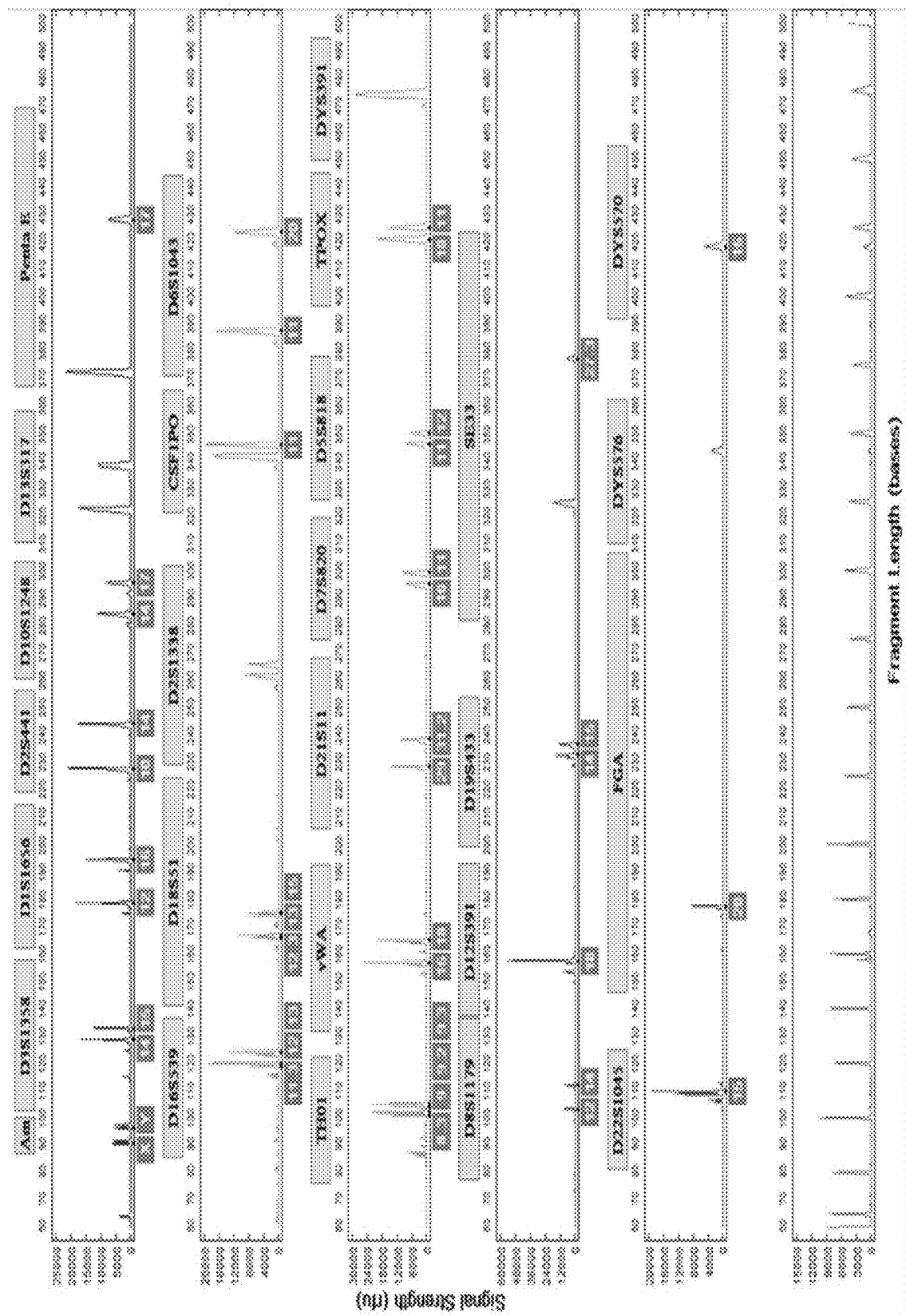
FIG. 3 shows a representative DNA ID of a sample with DNA content above the dynamic range of the chip type.

FIG. 3 shows a representative DNA ID of a sample with DNA content above the dynamic range of the chip type, with several of the features noted above. The specific features present in this figure are:

Average heterozygote peak height (RFU) that are greater than 10,000 RFU

Occasional wide peaks that are above the acceptable width thresholds. These peaks are not labeled. See D135317, Penta E, D2S1338, CSF1PO, DYS391, SE33 DYS376.

iNTA peaks with peak heights and peak height ratios that are above standard levels. See Am, D165539, D18551, Th01.

Samples with multiple loci with three labeled alleles, with all alleles in the sample being labeled in red. See D165539, D18551.

Samples with at least one loci with four labeled alleles, with all alleles in the sample being labeled in red. See Th01.

It is critical to note that the loci labeled in red contain useful data—the standard "buccal" expert system rules are too conservative for many sample types, including tissue samples such as bone, muscle, liver, and teeth. In fact, if called with an appropriate AES parameter set this 27plex DNA ID contains sufficient information to allow establishment of identity with a random match probability of less than one in one sextillion ($10^{23}$, almost a trillion trillion)! The AES of the present invention can extract essentially all of this useful data. Yet the standard Expert System failed the sample entirely. Accordingly, one of the major features of this invention is the ability of the Adaptive Expert System to assess the sample data to enable casework, DVI, and other samples to be processed differently than that of buccal swabs.

FIG. 3 shows a high DNA input sample analyzed with the standard Expert System. In this example of a sample with high DNA content, allele peaks have elevated signal. The iNTA peak of AM, D165539, D1851, Th01, vWA and D22S1045 are disproportionally higher than for samples within the DNA content dynamic range. This phenomenon causes the iNTA peak to appear proportionately higher and above the iNTA threshold. The standard Expert System no longer classifies it as an iNTA peak (an iNTA peak should not be labeled). In some cases (not observed in this example) the major allele peak saturates, but the iNTA (−1) peak is much lower and does not saturate. This phenomenon causes the iNTA peak to artificially appear proportionately higher than it is, and the standard Expert System no longer classifies it as an iNTA peak (an iNTA peak should not be labeled).

Instead, the standard Expert System labels the iNTA peak as an allele. For example, in the D16 locus, the 12 allele is labeled, but the iNTA peak is also labeled—as an 11.3 allele. Furthermore, in the standard Expert System employed here, the presence of two loci with three alleles each caused the Standard Expert System to consider the sample a mixture, labelling all the alleles in the DNA ID in red warning boxes (this Standard Expert System was designed to alert the user to the presence of a mixture). FIG. 3 also shows that for a sample with high DNA content, allele peaks in D13, D2 Penta E, DYS391, SE33, and DYS576 have wider peaks that are above the peak width threshold. As a result, the Standard Expert System peak width parameters fail the peaks, and these peaks are not labelled. Note that the Standard Expert System parameter set and rules are appropriate for most buccal samples (meaning that the vast majority of buccal samples have DNA content within the dynamic range of the system) but are too conservative for casework, SSE, DVI, or many other samples with high DNA content. This point is best illustrated by FIG. 3, in which all of the red warning boxes are designating correct peaks.

When high DNA samples are noted using the Standard Expert System, the Expert System can be modified to increase the number of loci that are called:

Establish a peak height calling threshold based on the heterozygote signal strengths of peaks within each locus. This will effectively increase the peak height threshold as compared to that of the standard expert system parameter set. This increased peak height threshold can be applied generally to all loci (e.g. threshold for all loci will be set to the same value) or independently to some specific or all loci (e.g. the peak height threshold within the Th01 locus is different than that in the TPDX locus) or to specific alleles (e.g. the Th01 8 allele peak height threshold is different than that of the Th01 10 allele and the vWA 11 allele).

Increase peak width thresholds. Peak widths will typically increase as the amount of DNA in the sample increases. This increase in the peak widths is further exacerbated for peaks with larger fragment sizes. When the width of a peak exceeds the standard parameters, the ES ignores the peak as an allele and does not label the peak or considers the peak in latter calculations.

Accommodate higher levels of iNTA and stutter. As the DNA content increases, the peak heights of the iNTA peaks tend to increase disproportionately to the primary allelic peak. When the Peak Height Threshold of the iNTA peak exceeds the standard parameters, the ES considers the iNTA peak an allele. The AES accommodates for higher iNTA by first identifying a sample as one with high potential for high iNTA. In this case, the iNTA PHR ratio for AM was used as an indicator for high iNTA. Note that other measures including iNTA within other loci and/or the presence of other characteristics (e.g. peak morphology) can be used to identify a potentially high iNTA sample. When a potentially high iNTA sample is identified, then iNTA calling rules are applied. The iNTA rules are described in detail in the section "High iNTA module".

Apply locus specific iNTA calling rules based on number of alleles in the locus. See iNTA rules are described in detail in the section "High iNTA module".

Reduce the number of called loci required to pass a sample. The expert system will fail a sample based on the number of called loci and reducing this threshold will allow more samples with called alleles to pass.

Figure 4:
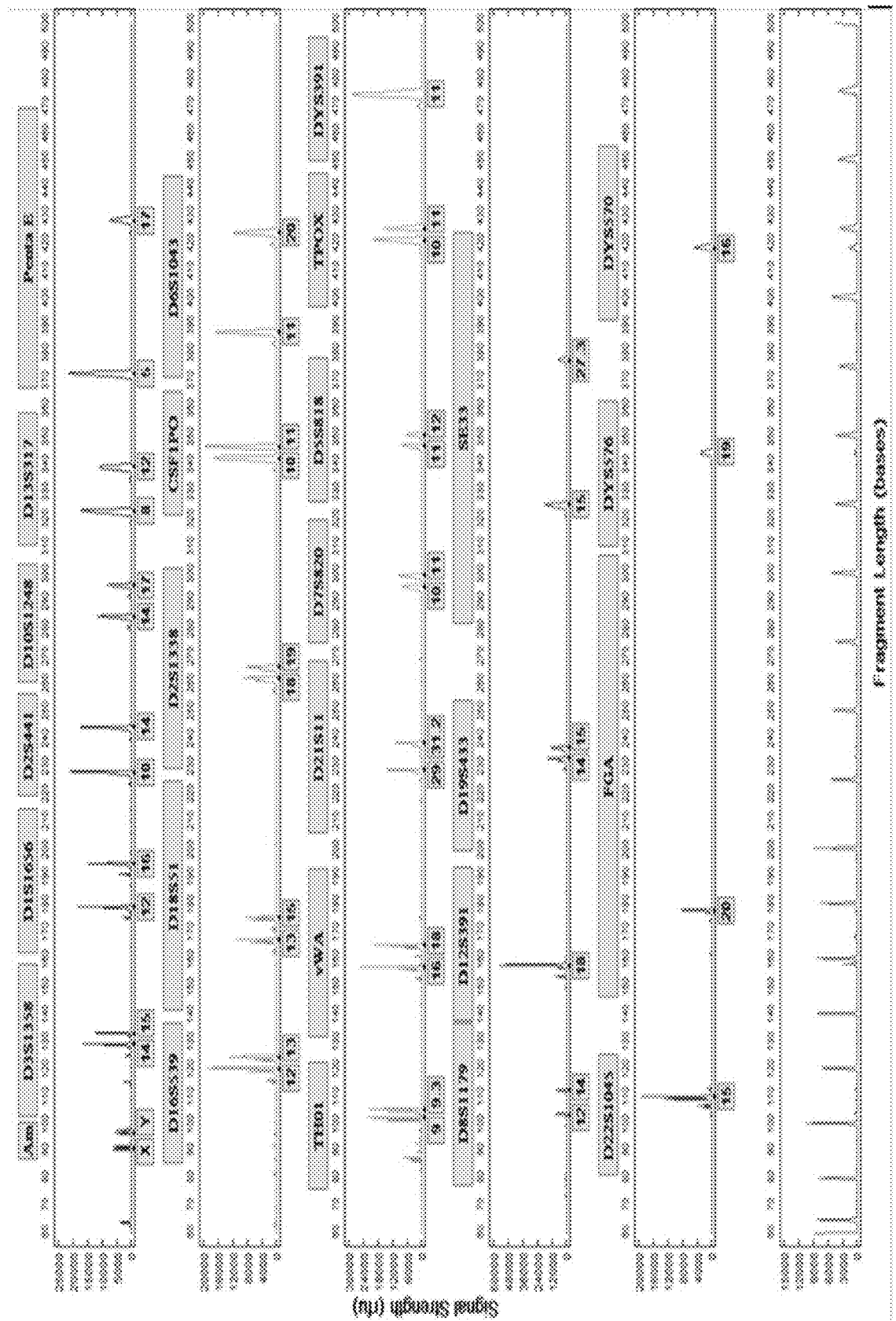
FIG. 4 shows the same DNA ID from FIG. 3, with the ANDE 6C sample data recalled using an Adaptive Expert System with parameter set modified with iNTA rules adjusted, the iNTA peaks are not called, and with the weak width parameter adjusted, the wide peaks are called.

FIG. 4 shows the same DNA ID from FIG. 3, with the ANDE 6C sample data recalled using an Adaptive Expert System with parameter set modified with iNTA rules adjusted, the iNTA peaks are not called, and with the peak width parameter adjusted, the wide peaks are called. Accordingly, a full DNA ID with no red warning boxes is the result. As discussed above, the Adaptive Expert System allows the nontechnical field operator to run essentially any sample type without needing to know anything about DNA content or condition. Again, it is critical to note that the loci labeled in red by the Standard Expert System contain useful data— the standard "buccal" expert system parameter set and rules are too conservative for tissue samples with high DNA content. Accordingly, one of the major features of this invention is the ability of the Adaptive Expert System to treat casework, SSE, DVI, and other samples differently than buccal swabs.

C. Mixture Samples

Samples with DNA originating from multiple donors may include certain SSE samples such as the swab of a door knob or steering wheel (e.g. handled by two or more people) or a sexual assault sample (e.g. a vaginal or cervical swab containing DNA from both the female and male). The ANDE Expert System, using standard parameters, would likely fail the DNA IDs of such a mixture sample. This is because standard parameters would typically be utilized to evaluate a single source sample.

Samples with contamination from two (or more) donors can be subclassified into one of at least three subclasses:

A—Sample with contamination having low DNA contents are characterized by one or more of the following:

Average heterozygote peak height (RFU) less 3000 RFU.

Loci with peak heights below a standard (buccal) Expert System calling threshold that are not labeled. See D6S1043.

Multiple homozygote loci labeled in red warning boxes. See Am, D13S317, D18S51, CSF1PO, D7S820.

All iNTA peaks are at levels that are within the standard levels and are not labeled by the expert system.

All Alleles have peak widths that are within the standard levels.

Two or more loci with three or more peaks that are labeled in red warning boxes.

One or more loci with four or more peaks that are labeled in red warning boxes.

All alleles in the sample are labeled in red.

Average heterozygote peak height (RFU) of the alleles are used to classify the samples as low DNA content (less than 3,000 RFU), Intermediate DNA content (between 3,000 and 10,000 RFU) and high DNA Content (greater than 10,000 RFU).

B—Sample with contamination having intermediate DNA contents are characterized by one or more of the following:

Average heterozygote peak height (RFU) of the alleles are between 3,000 and 10,000 RFU.

All iNTA peaks are at levels that are within the standard levels and are not labeled by the expert system.

All Alleles have peak widths that are within the standard levels.

Two or more loci with three or more peaks that are labeled in red warning boxes.

One or more loci with four or more peaks that are labeled in red warning boxes.

All alleles in the sample are labeled in red.

Note that mixture samples can also be subclassified as Low DNA content mixture samples and as High DNA content mixture samples.

C—Sample with contamination having high DNA contents are characterized by one or more of the following:

Average heterozygote peak height (RFU) that are greater than 10,000 RFU.

Peaks that are saturated and have squared tops.

Occasional wide peaks that are above the acceptable width thresholds. These peaks are not labeled.

iNTA peaks with peak heights and peak height ratios that are above standard levels, and are sometimes labeled as true alleles. In particular, the iNTA peak height ratios of the amelogenin locus are above standard levels.

Samples with multiple loci with three labeled alleles, and all alleles in the sample being labeled in red.

Samples with at least one loci with four labeled alleles, and all alleles in the sample being labeled in red.

Two or more loci with three or more peaks that are labeled in red warning boxes and the additional peaks are more than 1b from an adjacent allele (e.g. not iNTA peak).

One or more loci with four or more peaks that are labeled in red warning boxes and the additional peaks are more than 1b from an adjacent allele (e.g. not iNTA peak).

All alleles in the sample are labeled in red.

Figure 5:
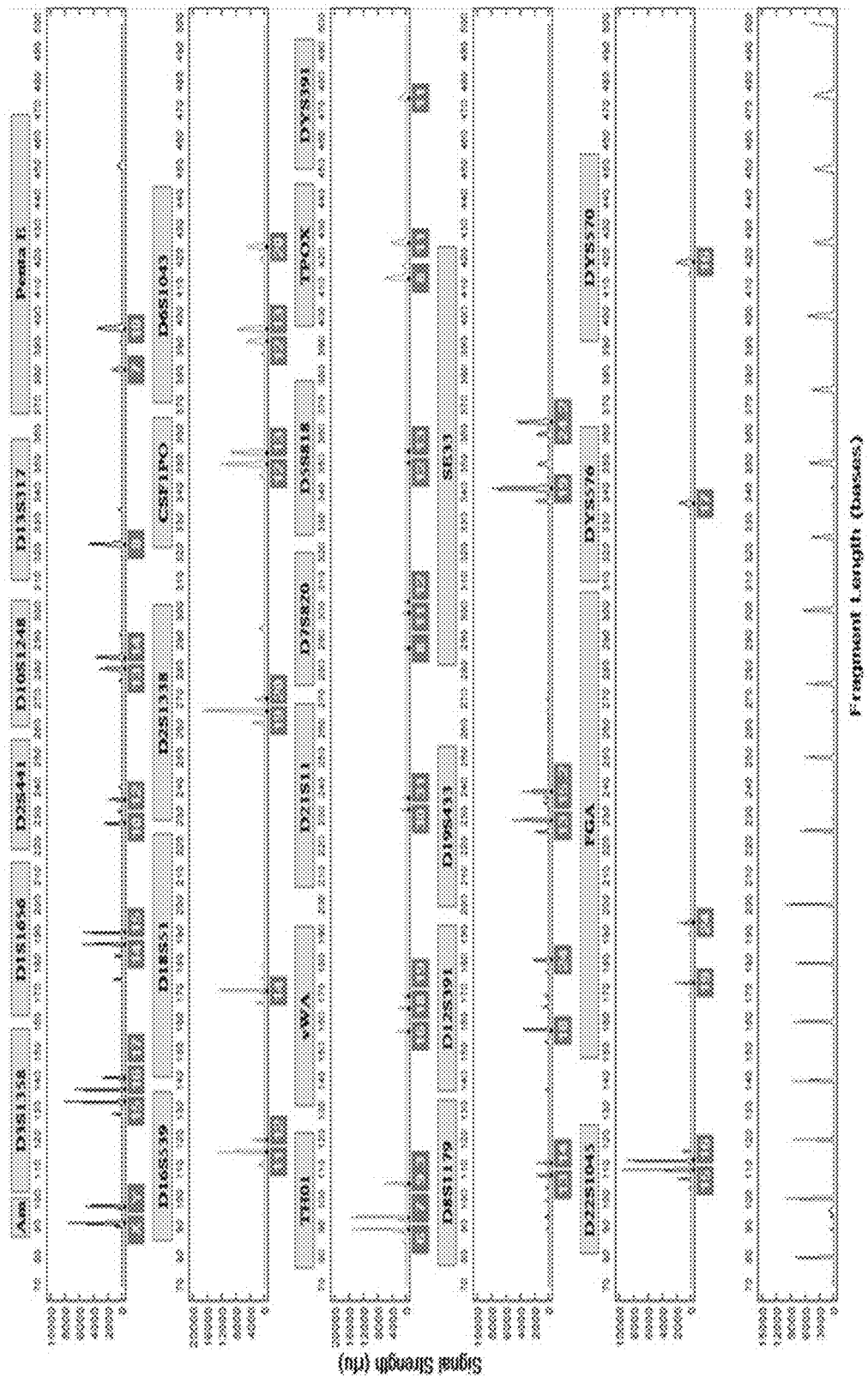
FIG. 5 shows a representative DNA ID of a contaminated sample (consisting of two donors) with intermediate DNA content above the dynamic range.

FIG. 5 shows a representative DNA ID of a contaminated sample (consisting of two donors) with intermediate DNA content above the dynamic range. The specific features present in this figure are:

Average heterozygote peak height (RFU) that are between 3,000 to 10,000 RFU.

All iNTA peaks are at levels that are within the standard levels and are not labeled by the expert system.

All Alleles have peak widths that are within the standard levels.

Two or more loci with three or more peaks that are labeled in red warning boxes. See locus D3S1358, Th01, vWA, and D7S820.

One or more loci with four or more peaks that are labeled in red warning boxes

All alleles in the sample are labeled in red.

Figure 6:
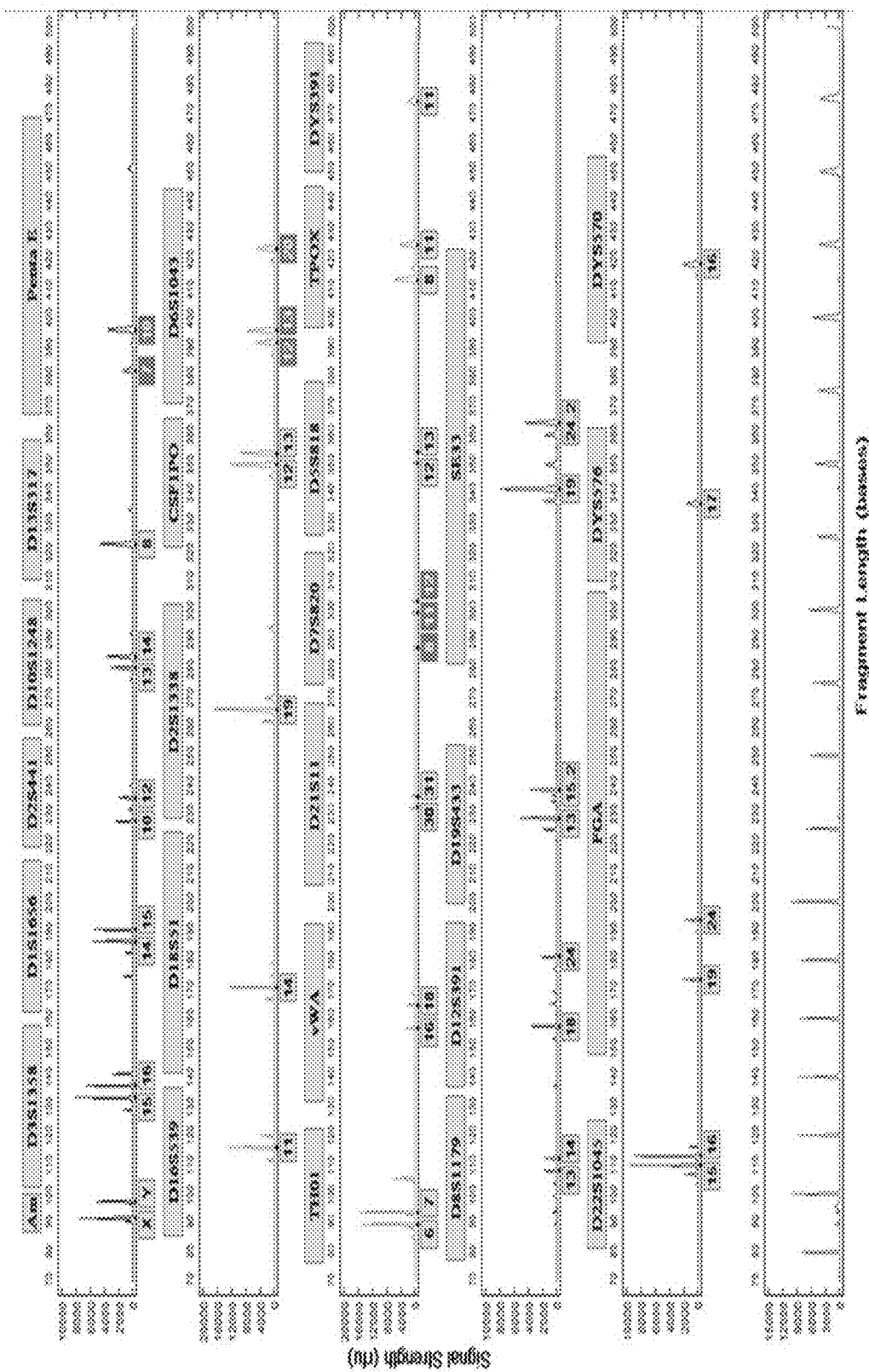
FIGS. 6 and 7 show the resultant DNA ID of the primary donor and of the secondary donor respectively, when the sample data is processed with the Adaptive Expert System.
Figure 7:
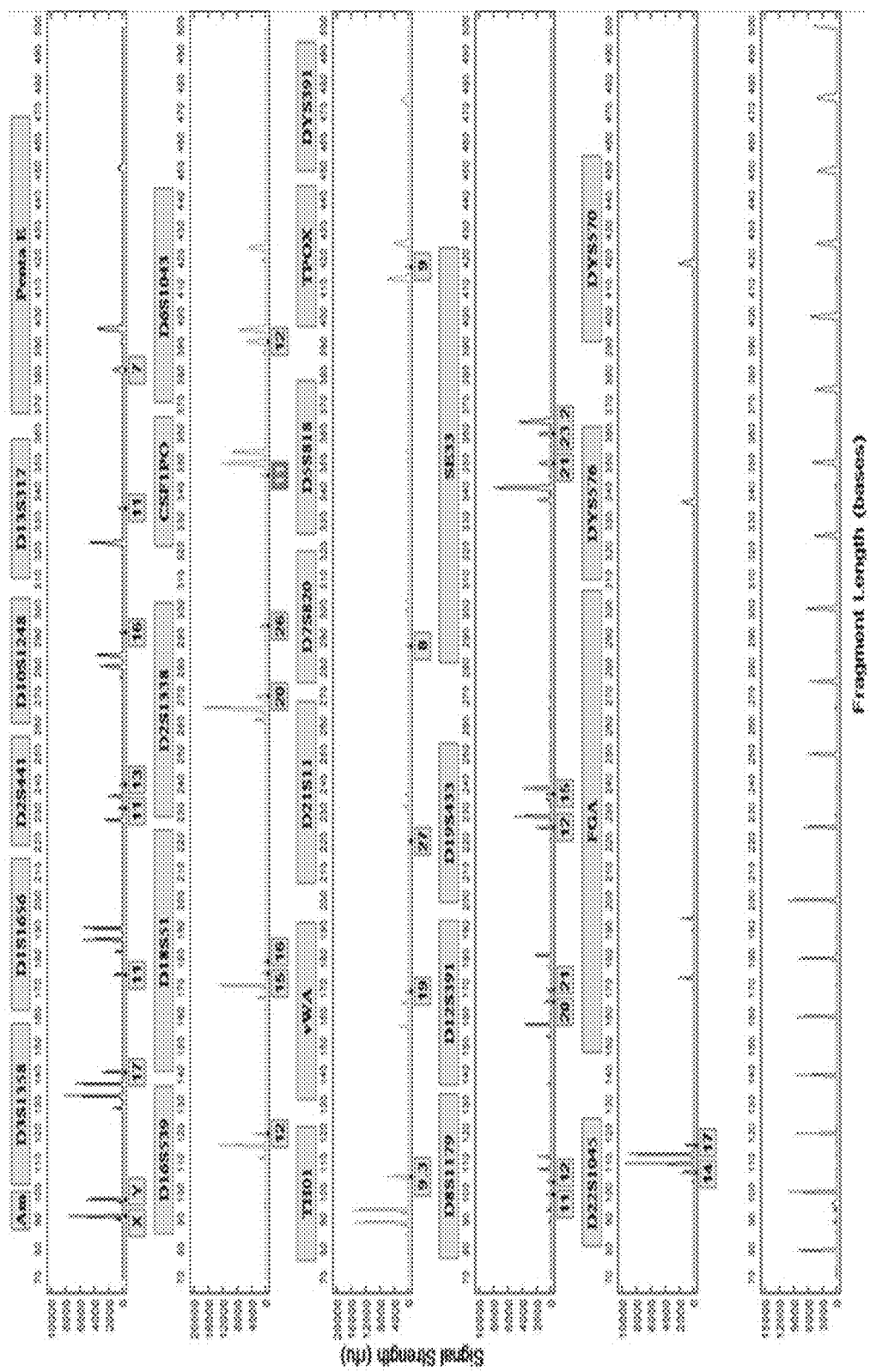

FIGS. 6 and 7 show the resultant DNA ID of the primary donor and of the secondary donor respectively, when the sample data is processed with the Adaptive Expert System. A detailed discussion of this process is discussed in Example 13. The Adaptive Expert System applied a locus specific parameter adjustments to generate the DNA ID of the primary donor. The DNA ID from the primary component was subtracted from the sample data and this data was reprocessed by the AES. The AES classified the modified sample data as that of low DNA content, and processed this sample data with a Low DNA content ES parameter set to generate the DNA ID from the secondary component. This approach and variants on this approach are utilized when a mixture DNA ID has characteristics of low, medium, and high DNA content. In general, once the AES determines the presence of a mixture, it will assess the sample using parameter sets designed to optimize calling of the highest peaks (typically from the major contributor), subtract these peaks, assess using parameter sets designed to optimize intermediate DNA content calling, subtract intermediate peaks, and assess using parameter sets designed to optimize calling of the lowest signal peaks (typically from minor contributors). Frequently, a given peak may be derived from two or more underlying STR features. For example, the stutter peak derived from a given STR allele may fall in the identical position as the peak from a second allele. The AES may be configured to apply mixture deconvolution algorithms to assign relative portions of such peaks and most are either binary or probablilistic. Mixture deconvolution algorithms are, broadly speaking, based on identifying each contributor by the relative peak heights across all loci for that contributor (e.g. in a two-person mixture, the highest peaks across are loci are likely to be derived from the major contributor and the lower peaks from the minor contributor). [Gill P., Sparkes R. L., Pinchin R., Clayton T., Whitaker J. P., and Buckleton J. S.: Interpreting simple STR mixtures using allelic peak areas. *Forensic Sci. Int.* 1998; 91: pp. 41-53; D. A. Taylor, J.-A. Bright, J. S. Buckleton, The interpretation of single source and mixed DNA profiles, *Forensic Science International: Genetics.* 7(5) (2013) 516-528; J.-A. Bright, I. W. Evett, D. A. Taylor, J. M. Curran and J. S. Buckleton, A series of recommended tests when validating probabilistic DNA profile interpretation software. *Forensic Science International: Genetics,* 2015. 14: 125-131; T. W. Bille, S. M. Weitz, M. D. Coble, J. S. Buckleton and J.-A. Bright, Comparison of the performance of different models for the interpretation of low level mixed DNA profiles. *Electrophoresis,* 2014. 35:3125-33; S. J. Cooper, C. E. McGovern, J.-A. Bright, D. A. Taylor and J. S. Buckleton, Investigating a common approach to DNA profile interpretation using probabilistic software. *Forensic Science International: Genetics,* 2015. 16:121-131; T. R. Moretti, R. S. Just, S. C. Kehl, L. E. Willis, J. S. Buckleton, J.-A. Bright, D. A. Taylor, Internal validation of STRmix™ for the interpretation of single source and mixed DNA profiles. *Forensic Science International: Genetics,* 2017. 29:126-144.]

D. Degraded and/or Inhibited Samples

Samples with DNA inhibition may include certain SSE samples collected from substrates that contain PCR inhibiting substances like Heme (from blood), Humic Acids (from soil samples), Tanins and Indigo Dyes (from cloth), and EDTA (from reagents). Furthermore, degradation can result from exposure to environmental factors (e.g. heat, light, humidity, and salt water). When such a sample is processed, the signal strengths of one or more loci will exhibit imbalance in signal strength relative to the average signals strength of the sample. The standard expert system parameters, result in loci that are inhibited from being called and, hence, a loss of information.

Samples with inhibitors/degradation are first classified as one with low, intermediate or high signals DNA content following the characteristics above.

Figure 8:
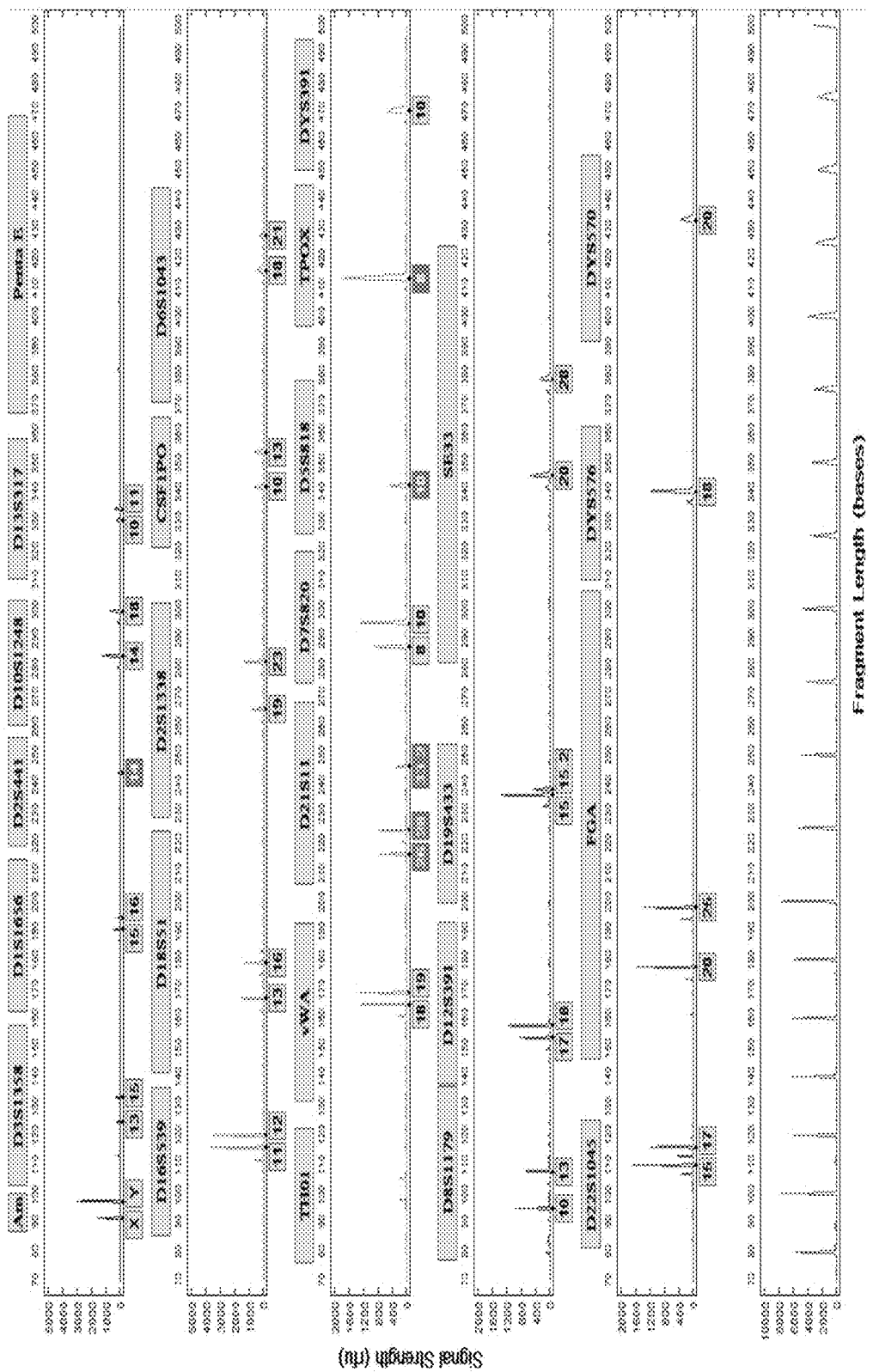
FIG. 8 shows a representative DNA ID having DNA inhibition.

Following this classification, the sample is further classified as being inhibited if the relative signal strength of one or more locus, compared to the average signal strength of the locus is out of range. The specific loci that are inhibited/degraded are identified by the AES. In some cases of inhibition/degradation, the signal strength of the large fragments are significantly lower than that of the smaller fragments. In other cases, specific loci may be inhibited and demonstrate a much lower or much higher signal strength. In FIG. 8, the sample has the following characteristics:

Average heterozygote peak height (RFU) less 3000 RFU.

Loci with peak heights below a standard (buccal) Expert System calling threshold that are not labeled. See D6S1043.

Multiple homozygote loci labeled in red warning boxes. See Am, D135317, D18551, CSF1PO, D7S820.

All iNTA peaks are at levels that are within the standard levels and are not labeled by the expert system.

All Alleles have peak widths that are within the standard levels.

Relative signal strength of one (or more) loci is significantly lower or higher than the average signal strength of the loci in the color. In FIG. 8, Th01 is significantly low.

Figure 9:
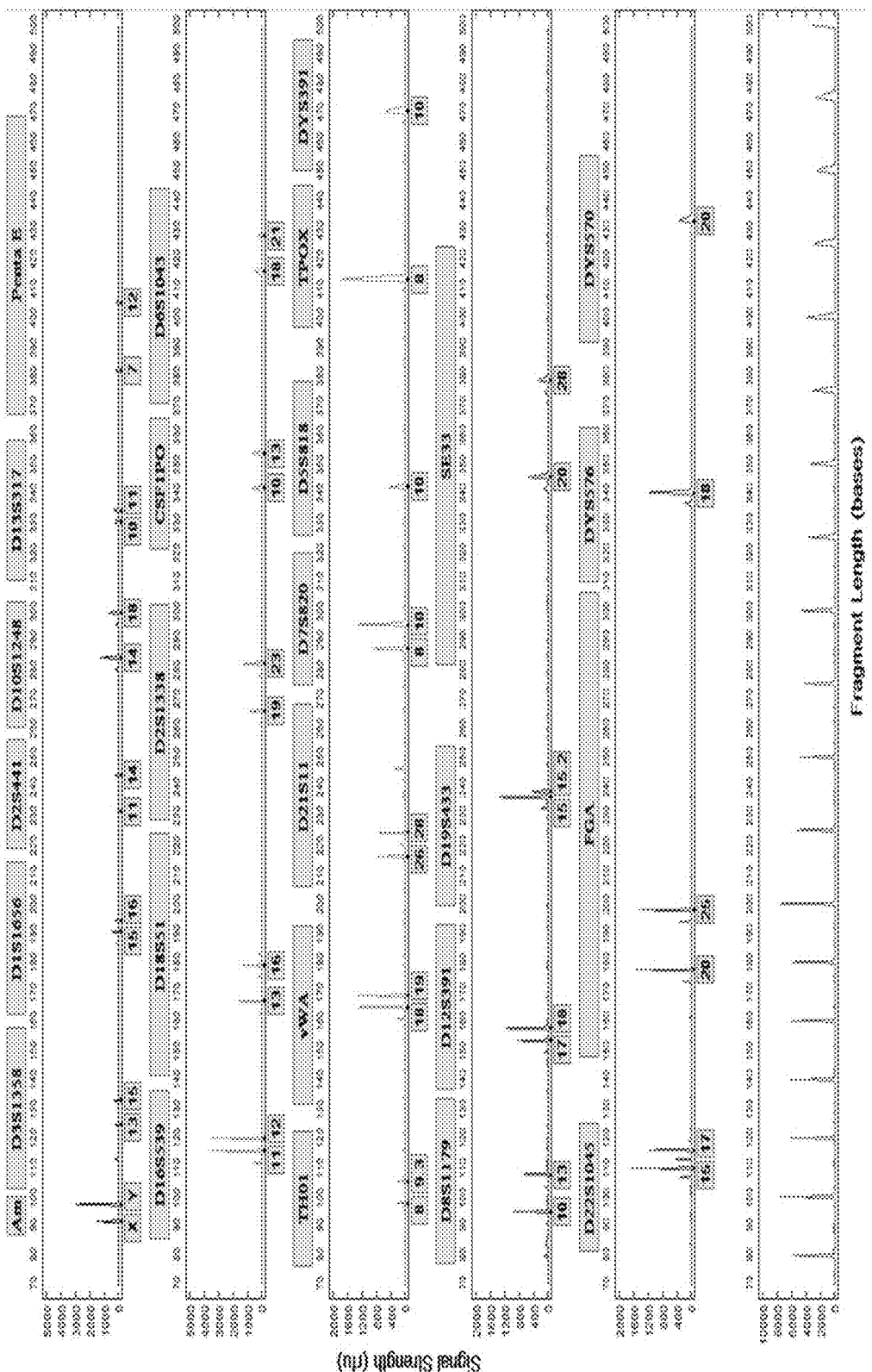
FIG. 9 shows the resultant DNA ID of the sample data of FIG. 8 when processed with the Adaptive Expert System.

FIG. 9 shows the resultant DNA ID of the sample data of FIG. 8 when processed with the Adaptive Expert System. The Low DNA Content parameter set is applied to the sample data, followed by a locus specific adjustment to the Th01 locus. The Peak height thresholds and peak height ratio for the inhibited locus were selected such that the maximal number of alleles are called, with the minimum number of dropouts and dropins to yield a full DNA ID.

Example 1. AES Analysis Workflow

Figure 10:
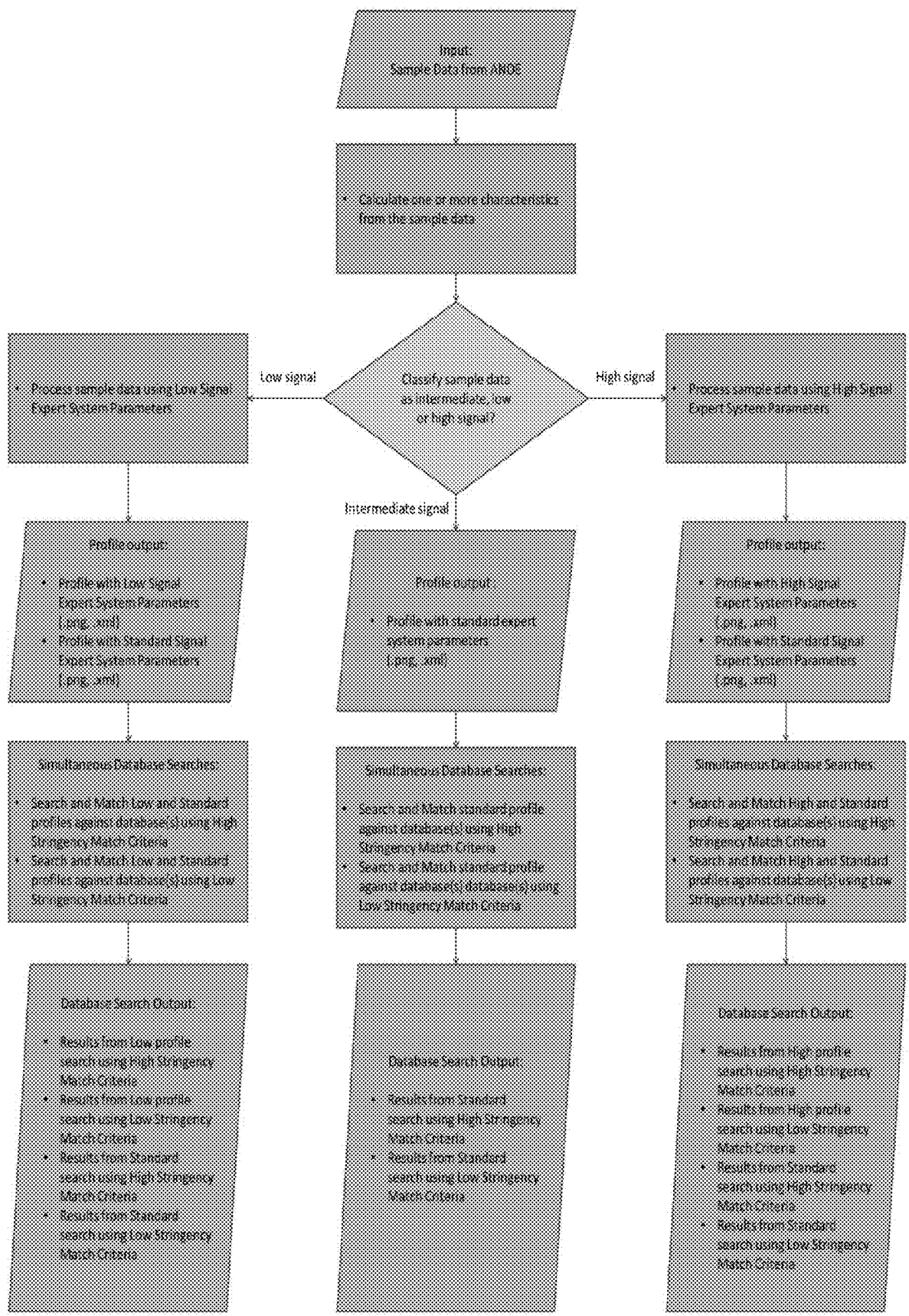
FIG. 10 is a flowchart of AES processing in which a standard/baseline parameter is first performed followed by evaluation of sample characteristics and further AES processing.
Figure 11:
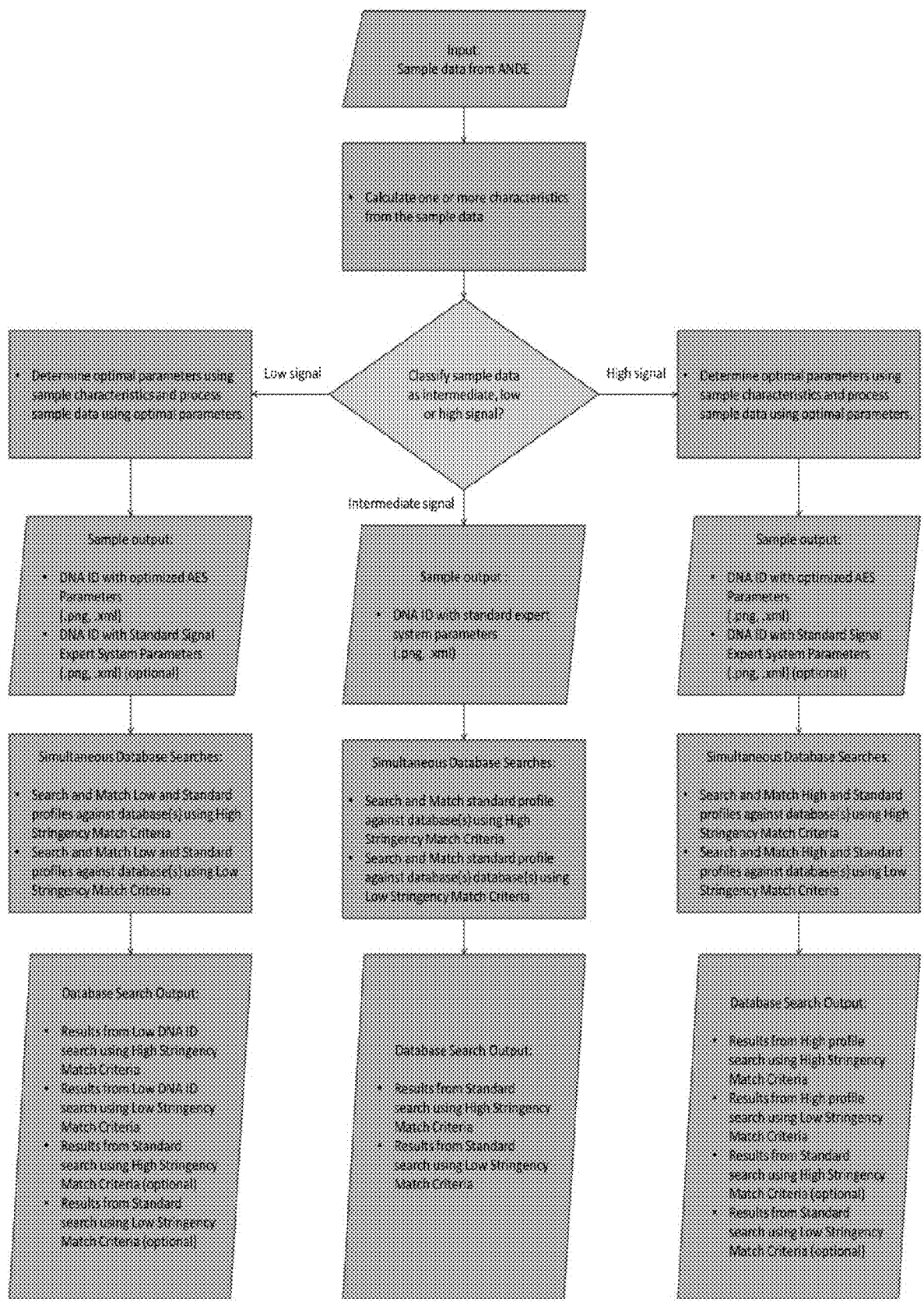
FIG. 11 is a flowchart of AES processing in the absence of the initial application of the standard/baseline parameter set.

FIGS. 10 and 11 are flowcharts that describe how the AES functions:

1. Sample data (optical signals from the detectors stored in .csv (comma delimited) format, or .dat, (tab delimited) or other compatible formats) or raw electropherogram data (optical data that has been color corrected and is stored in .nbo, or .FSA, or .HID formats) from the ANDE run is imported into the ANDE Database Management System (ADMS) or the ANDE FAIRS application. For example, the optical data or Electropherogram data is transmitted to and stored on the computing device (e.g., via a communications network such as the Internet, or ethernet, or via a removable disk or USB drive).

ANDE ADMS and ANDE FAIRS are standalone applications that execute on a computing device (e.g., a laptop, or desktop, or server). These applications allow data that is generated on ANDE to be imported, exported, stored, and processed. These applications have instances of the ANDE Expert system and AES and are capable of processing sample data including optical data or electropherogram data. These applications also have databases (e.g. relational and non-relational) to store sample data (including optical data, and electropherogram data), sample metadata, sample allelic data, and DNA ID characteristics. They also allow DNA ID database creation, import, export, and editing (the DNA IDs may be generated from ANDE, other Rapid DNA, or conventional lab systems). These applications have modules for kinship analysis and for familial searching and claimed relationship testing for immigration and disaster victim identification. ADMS and FAIRS software also have modules for mixture analysis including inclusion and exclusion analysis, and mixture deconvolution. They also have modules for DNA ID search and match.

Alternatively, the optical data from the ANDE run can be processed directly on board the instrument by the Expert System or the Adaptive Expert System prior presentation to the user. This configuration integrates the ANDE ES and AES with the instrument.

The examples herein are focused on but not limited to optical data when the analyte is DNA, in this case used to generate DNA IDs. Other analytes that may be analyzed using the instant invention include one or more of proteins, peptides, messenger RNA, copy DNA, methylated or other modified forms of DNA, Single Nucleotide polymorphisms, sequenced DNA, other biomolecules, and inorganic chemicals. The form of detected data includes optical, electrical, thermal, chemical, magnetic, physiochemical, mechanical, and others. In these cases, the Expert System parameter set may be automatically applied based on certain characteristics of the sample data.

The source of the DNA data can be from:
A Rapid DNA instrument,
A modified Rapid DNA instrument,
A capillary electrophoresis instrument,
A microchip electrophoresis instrument,
A Mass spectroscopy instrument,
A DNA sequencing instrument,
A real-time PCR (RT-PCR, qPCR) instrument,
A microfluidic instrument,
Other instruments that detect aspects of DNA.

The AES can function on:
The ANDE Rapid DNA instrument,
Another Rapid DNA instrument,
A modified Rapid DNA instrument,
A microchip electrophoresis instrument,
A Mass spectroscopy instrument,
A DNA sequencing instrument,
A real-time PCR (RT-PCR, qPCR) instrument,
A microfluidic instrument,
A computing device separate from the ANDE Rapid DNA instrument,
A computing device separate from a Rapid DNA instrument,
A computing device separate from a modified Rapid DNA instrument,
A computing device separate from a capillary electrophoresis instrument,
A computing device separate from a microchip electrophoresis instrument,
A computing device separate from a Mass spectroscopy instrument,
A computing device separate from a DNA sequencing instrument,
A computing device separate from a real-time PCR (RT-PCR, qPCR) instrument,
A computing device separate from a microfluidic instrument,
A computing device separate from a microchip electrophoresis instrument,
A computing device separate from other instruments that detect aspects of DNA, In this example, sample data from up to five samples are imported for A-Chips and up to four samples for I-Chips. The following steps follow the ANDE AES processing of sample data from a single sample.

2. Process sample data using Standard Expert System parameters. Parameters include heterozygous peak height ratio, heterozygous peak height threshold, signal to noise ratio, iNTA candidate peak height ratio, stutter candidate peak height ratio, triallele peak height, triallele peak height ratio, mixture peak height threshold, homozygous peak height ratio, homozygous peak height threshold, hemizygous peak height ratio, hemizygous peak height threshold, peak width threshold, and peak shape. Application of this parameter set generates a DNA ID. The following characteristics on the DNA ID are also quantified and made available for subsequent processing: signal strength of each allele, iNTA peak height and Peak Height ratio for each locus, peak heights ratios of the heterozygote peaks, number of peaks in each locus, width and shape of each allelic peak, signal to noise ratio of each dye channel, stutter ratio of each allele.

Note that processing of a DNA ID with Standard (or baseline) Expert System parameters is optional. If such processing is not desired, the sample data can be utilized to directly generate one or more characteristics including but not limited to: signal strength of each allele, iNTA peak height and Peak Height ratio for each locus, peak heights ratios of the heterozygote peaks, number of peaks in each locus, width and shape of each allelic peak, signal to noise ratio of each dye channel, stutter ratio of each allele. This data can then be used directly to generate DNA IDs using one or a plurality of AES parameter sets. Furthermore, the AES of the invention may utilize different baseline parameter sets based on chip type and meta-information about the sample.

3. Based on one or a plurality of the characteristics of the sample data or DNA ID (including but not limited to: signal strength of each allele, total number of alleles, number of alleles per locus, relative signal strength of alleles within loci, relative signal strength of alleles as compared to allele size (e.g. bases), iNTA peak height and Peak Height ratio for each locus, peak heights ratios of the heterozygote peaks, number of peaks in each locus, width and shape of each allelic peak, signal to noise ratio of each dye channel, stutter ratio of each allele) categorize the sample as within typical range, high, low, mixture, degraded, inhibited, or others. The number of characteristics utilized for categorization may be 1, 2, 3, 4, 5, more than 5, more than 10, more than 25, more than 50, more than 100, more than 200, more than 500, or more than 1000 categories can be utilized based on the sample type, sample data, and operation value of the sample.

4A. For standard category DNA IDs, prepare the .xml file for database search, kinship analysis, or other evaluation.

FIG. 12 shows a portion of an .xml file. The .xml file follows the CODIS CMF file format and contains metadata for the sample, locus, and allele calls. The file is formatted to allow searching of databases including the NDIS, SDIS, LDIS and many international DNA databases. The ANDE Expert System and Adaptive Expert System lists all called alleles in the XML file. In the ANDE system, .XML files for samples that pass criteria (defined by the agency and consisting of the number of called loci) are available for export to the user. This practice is specific to ANDE. Other systems may allow the XML files to be generated for samples that pass or fail the agency criteria (and the ANDE System can be configured to do the same).

4B. For High DNA content category DNA IDs, apply High Signal Expert System parameters and, independently (and optionally), apply standard Expert System parameters. Prepare both .xml files for database search (or other use). In this example, the process workflow is designed to generate calls using the High Signal Expert System parameters and, optionally, standard Expert System parameters. Alternatively, a workflow that only includes the generation of DNA IDs with only the High Signal Expert system parameter set can also be applied. Furthermore, multiple sets of High Expert System parameters may be applied in parallel 4C. For Low DNA content category DNA IDs, apply Low Signal Expert System parameters and, independently (and optionally), apply Standard Expert System parameters. Prepare both .xml files for database search (or other use). In this example, the process workflow is designed to generate calls using the standard Expert System parameters and, optionally, Low Signal Expert System parameters. Alternatively a workflows that only includes the generation of DNA IDs with only the Low Signal Expert system parameter set can also be applied. Furthermore, multiple sets of Low Expert System parameters may be applied in parallel. Furthermore, when the AES is integrated with the instrument, the Agency or an individual superadmin user may desire only one .XML output to be generated for the user. This XML output is generated by the AES parameters.

5. Simultaneously search and match all generated .xml files (two if standard signal, four if either low or high signal). Searching can be performed can be done using a DNA ID database and search functionality or the ANDE Data Management System database and search functionality. Each .xml file is searched twice, once with high stringency search criteria and the other with low stringency search criteria.

XML files generated by the ANDE Expert System or the ANDE AES can be used for simple search and matching, familial search and matching, and mixture search and matches on the ANDE ADMS and ANDE FAIRS applications. When searching a DNA ID against a database, the search may be performed by first identifying loci that overlap. An overlapping locus is defined as a locus that is present in both the DNA ID being searched and a DNA ID in the database and one where there is at least one identical allele call present in the locus. For each overlapping locus, the following is determined:

the number of alleles within the locus of the samples being compared,
the number of alleles that match within the locus of the samples being compared,
the number of alleles that do not match within the locus of the samples being compared.

A locus of samples being compared in which all the alleles match is classified as a perfect match, a locus in which one of the alleles matches (and at least one allele does not match) is classified as a partial match, and a locus in which no alleles match is classified as a mismatch. This analysis is performed on all loci shared by the sample being searched and each individual DNA ID in the database, and the software determines the number of overlapping loci, number of loci with perfect matches, number of loci with partial matches, and number of mismatched loci. Based on this data, a wide variety of search criteria with varying stringencies may be applied:

An example of low stringency search criteria for the FlexPlex system, with 27 loci, is as follows:
Minimum number of overlapping loci is 8,
Minimum number of matching loci is 8.
An example of a high stringency search criteria is as follows:
Minimum number of overlapping loci is 20 CODIS loci,
Minimum number of matching loci is 19 CODIS loci,
Maximum number of mismatch loci is 1 CODIS locus.
An example of a familial search criteria is as follows:
Minimum number of overlapping loci is 8,
Minimum number of partially matching loci is 8.
An example of a mixture search criteria is as follows:
Minimum number of overlapping loci is 8,
Minimum number of partially matching loci is 8.

FIG. 10 shows AES processing in which a standard/baseline parameter is first performed followed by evaluation of sample characteristics and further AES processing. FIG. 11 shows AES processing in the absence of the initial application of the standard/baseline parameter set. Furthermore in FIG. 11, the standard DNA ID is optionally generated. The flowcharts show steps in the ANDE Adaptive Expert System followed by database searches. In the case of DNA ID with standard signal (central path), two search outputs are generated, one based on a high stringency search and the other on a low stringency search. In the case of a DNA ID with high or low signal (left or right path), a total of four database search outputs are generated. DNA ID database searching, kinship evaluation (including familial searching and claimed relationship evaluation), DVI searching, mixture searching, probabilistic genotyping, and various forms of mixture deconvolution, can be performed with the DNA IDs resulting from the AES. For simplicity, DNA database searching is illustrated herein.

In this example, the process workflow is designed to generate calls using the standard Expert System parameters and the Adaptive Expert System parameters. Alternatively a workflows that only includes the generation of DNA IDs with only the Low Signal Expert system parameter can also be applied.

In this example, an instance of the AES resides on a standalone ANDE ADMS or ANDE FAIRS application that executes on a laptop computer or desktop computer or server. Alternatively, AES can be incorporated with the ANDE system and be integrated with the instrument.

In this example, the process workflow is designed to generate a low stringency search and a high stringency search for the DNA ID generated with standard parameters. In addition a low stringency search and a high stringency search is also performed for the DNA ID generated with the AES parameters. Alternatively work flows which include the search using only the low or high stringency searches can be applied. Alternatively work flows which include the search using the familial search criterial (low or high stringency) or the mixture search criteria (with low or high stringency) can also be applied. One that is knowledgeable (such as a system administrator) will be able to reconfigure the processing parameters and the search type and search stringency, preferably using a GUI-based User Configuration screen.

The searching engine may be contained within or apart from the AES application. In either case, the AES calling functionality and the searching engine can be used interactively. For example, the AES can use a series of progressively less stringent parameter sets. Each time a DNA ID (and XML output) is generated from a parameter set, that DNA ID can be utilized to search the database. That search can also use a series of progressively less conservative match criteria, generating and scoring a number of matches (a match score may be defined by random match probability, or totals of matching alleles and loci, or other ways as defined by the agency). If the match score does not reach a desired level, the next parameter set is applied, again searched against the database using a series of search criteria. This process can continue automatically until a desired match score is achieved (or can be conducted manually for the same purpose). This arrayed searching approach may be conducted within that AES if desired and configured with simple GUI screens. AES reports, AES/ Search reports, and Arrayed Search reports can be generated for export (e.g. as pdf files) and presented on the instrument or computer screen.

Example 2. Generation of Sample Data for AES Analysis

Separation and detection of the DNA is carried out on in a chips and instruments in the following U.S. patents herein incorporated by reference: U.S. Pat. Nos. 8,018,593; 8,173, 417; 8,206; 974; 9,523,656; 9,606,083; "Ruggedized apparatus for analysis of nucleic acid and proteins," 9,366,631 "Integrated systems for the multiplexed amplification and detection of six and greater dye labeled fragments," 8,858, 770; 8,961,765; 9,994,895 "Plastic microfluidic separation and detection platforms."

The separation and detection instrument comprise an excitation and detection subsystems for interrogating the DNA sample. Although DNA samples are described in the examples, the sample can include one or more biological molecules including but not limited to DNA, RNA, and proteins that are labeled with one or more fluorescent dyes.

The excitation subsystem comprises and excitation source or sources and an excitation beam path with optical elements including lenses pinholes, mirrors, and objectives, to condition and focus the excitation source in an excitation/ detection window. Optical excitation of a sample can be accomplished by a series of laser types, with emission wavelengths in the visible region between 400 and 650 nm.

The detection subsystem comprises one or more optical detectors, a wavelength dispersion device (which performs wavelength separation), and a set of optical elements including but not limited to lenses, pinholes, mirrors, and objectives to collect emitted fluorescence from fluorophore-labeled DNA fragments that are present at the excitation/ detection window. The fluorescence emitted can be from a single dye or a combination of dyes. In order to discriminate the signal to determine its contribution from the emitting dye wavelength, the fluorescence wavelength is separated and subsequently detected by the optical detectors. The fluorescence excitation and detection excites the components separated by electrophoresis of DNA sample by scanning an energy source (e.g. a laser beam) through a portion of each of the microchannels, and while collecting and transmitting the induced fluorescence from the dye to one or more light detectors.

In a first embodiment, the wavelength components are separated by the use of dichroic mirrors and bandpass filters and these wavelength components are detected with Photomultiplier tube (PMT) detectors (H7732-10, Hammamatsu). The dichroic mirrors and bandpass components can be selected such that incident light on each of the PMTs consist of a narrow wavelength band corresponding to the emission wavelength be centered about the fluorescent emission peak with a band pass of wavelength range of between 1 and 50 nm. The system is capable of eight color detection can be designed with up to 8 PMTs and a corresponding set of dichroic mirrors and filters to divide the emitted fluorescence into either distinct colors. More than eight dyes can be detected by applying additional dichroic mirrors and PMT detectors.

In a second embodiment, a spectrograph is used in place of the dichroic and bandpass filters to separate the wavelength components from the excited fluorescence. Collected fluorescence is imaged on the pinhole and reflected, dispersed, and imaged by the concave holographic grating onto the linear array PMT detector that is mounted at the output port of the spectrograph. The optical detection system comprising of a linear array PMT detector with at least 2, 4, 5, 6, 16, 32, 64, 128, or 256 detector elements.

In a third embodiments, the system allows for the simultaneous detection of multiple lanes and multi dye colors using a CCD camera. In this embodiment, all of the lanes in the capillary or microfluidic chip are illuminated simultaneously, and the light that is emitted from the fluorescence is passed through a wavelength dispersive element (e.g. prism) and onto a CCD.

The first two embodiments described above use optical separation and detection systems that were developed and are in use at ANDE. In these systems, the optical detection is performed by photodetectors (PMT detectors) that are in communication with the processor to provide optical data.

The optical data, which can be for a single dye to many number of dyes, is used by the processor as input to the AES.

In fact, the input to AES is either the optical data, raw electropherogram data (color corrected) or DNA ID. These forms of data can be acquired from instruments other than those manufactured by ANDE, including commercially available ones like the ABI prism 3100 genetic analyzer, ABI prism 3130XL genetic analyzer, Thermo Fisher Scientific 3500 genetic analyzer, and Promega Spectrum CE systems. In fact, the data for analysis is not restricted to those from capillary or microchip electrophoresis systems that are used to generate examples here.

Example 3. Characterize DNA IDs and Generate Working AES Dataset

In building an AES, an initial step is to establish a dataset from which real world DNA IDs from a wide range of sample types with known DNA ID (truth) can be generated and specific characteristics of the DNA IDs can be quantified. Furthermore, from these datasets, quantitative AES rules can be derived and back tested. In other words, for whatever DNA processing system and data collection system to be adapted, it is important to quantify characteristics such as heterozygote signal strength and peak height ratios, homozyote peak heights, iNTA peak height and peak Height ratio for each allele, number of peaks in each locus, width and shape of each allelic peak, signal to noise ratio of each dye channel, stutter ratio of each allele in a wide range of samples. For example, the above quantified characteristics of the DNA ID allow AES parameters to be established, and ultimately allow sample data and DNA IDs to be categorized. Furthermore, these datasets (which may be large and extensive) form the basis for implementing AES using artificial intelligence by allowing AES to learn.

Similarly, it is useful to develop a large dataset of samples, generating a wide range of DNA IDs to ensure a robust set of AES rules is developed. Although signal strength is one important parameter to characterize DNA IDs, it may not be the only or the best characteristic for all sample data and applications. To generate the instant AES dataset, buccal, tissue, and touch sample DNA IDs were processed on the ANDE instrument to generate a wide range of signal strengths.

Greater than 500 low signal samples, 1000 standard samples, 500 high signal samples were processed.

Characteristics calculated included: average heterozygote signal strength, PHR, iNTA, stutter, peak width, number of called alleles, ILS success, number of called alleles, number of alleles below the Standard ES Peak height threshold, and number of loci below the PHR threshold. The parameters selected are of interest for the ANDE AES; for other AES not based on ANDE, these or other parameters may be of interest. For example, if a given data processing/Expert System is characterized by substantial bleed-through in one or more colors, with increasing bleedthrough based on increasing signal strength, bleedthrough peaks might be incorporated in the parameter set described above.

The initial dataset consisted of 2,000 DNA IDs. The number of DNA IDs in a given dataset depends on factors including the variability for a given sample type and the number of desired categories and may be as small as 2, and preferably more than 2, more than 5, more than 10, more than 25, more than 50, more than 100, more than 250 more than 500, more than 1,000, more than 2,000, more than 5,000, more than 10,000, more than 25,000, more than 50,000, more than 100,000, more than 250,000, more than 500,000, more than 1,000,000, more than 5,000,000, more than 10,000,000, and more than 100,000,000.

Example 4. Establishment of DNA ID Categories (or Phenotypes)

Following review of the DNA ID dataset as described in Example 2, it is possible to establish a series of subgroups of DNA IDs classifications; these will form the basis of the AES. The number of subgroups need not be fixed but is instead affected by the DNA processing system, data analysis system, types of samples, and number of samples. In this example, the FlexPlex DNA IDs within the dataset allowed six distinct DNA ID classifications to be created:

1) Intermediate Signal Strength DNA IDs—Samples with a passing ILS and twenty CODIS 20 core loci called. These are successful samples using ANDE's Standard ES parameter set and do not require further AES processing. Again, the number of called loci or specific loci used for a "successful" DNA ID is established by the agency or user. Note that although a set of 7 characteristics are used to categorize the sample data this list of characteristics can be modified (e.g. more added or some can be removed). For example, the characteristic of "number of CODIS20 loci called" described here can be changed to "number of CODIS 18 loci called" or "number of Autosomal loci called" or "number of flex plex loci called."

Figure 13:
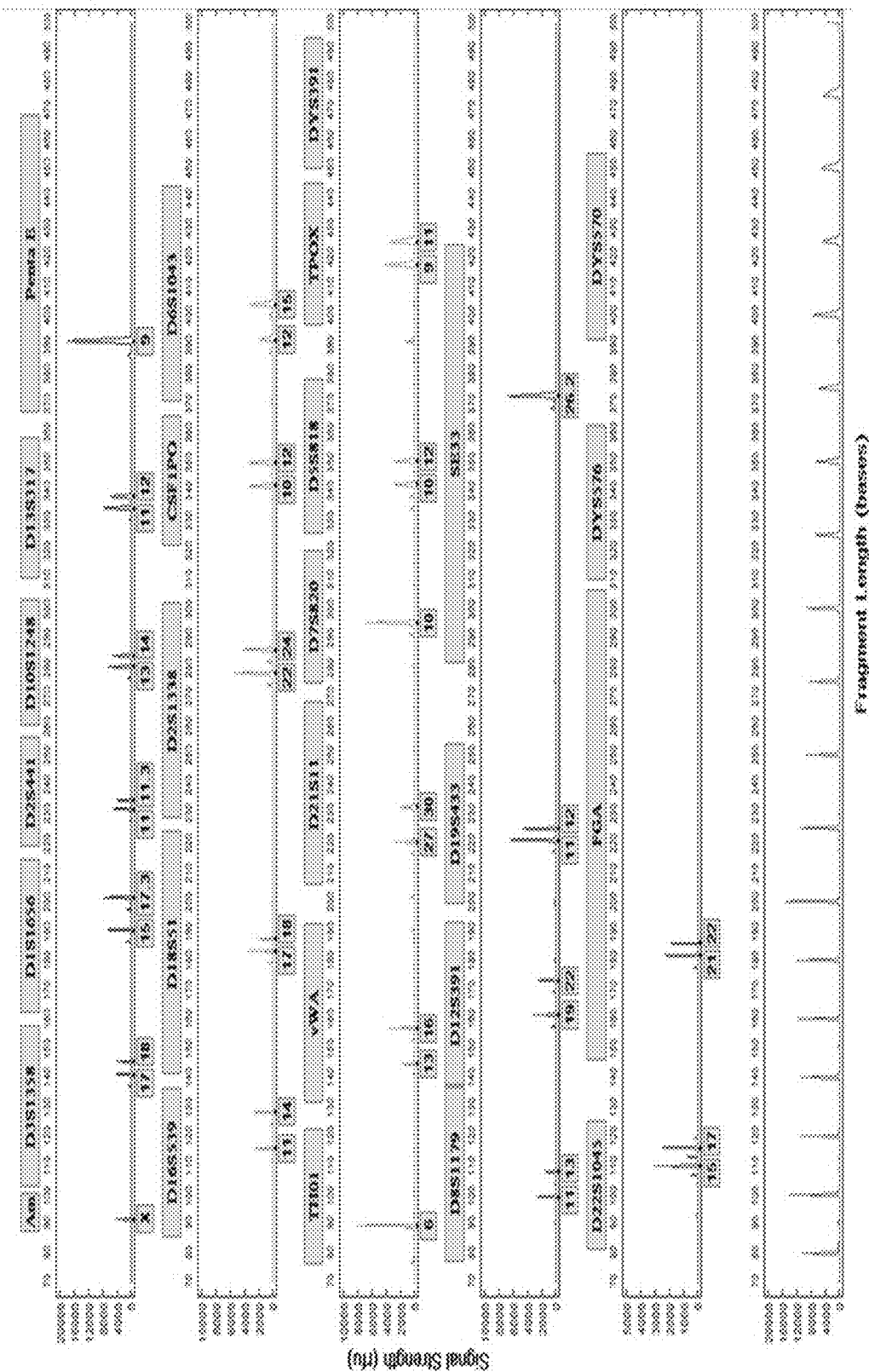
FIGS. 13 to 16 show DNA IDs of samples with intermediate signal strengths from A-Chips.
Figure 14:
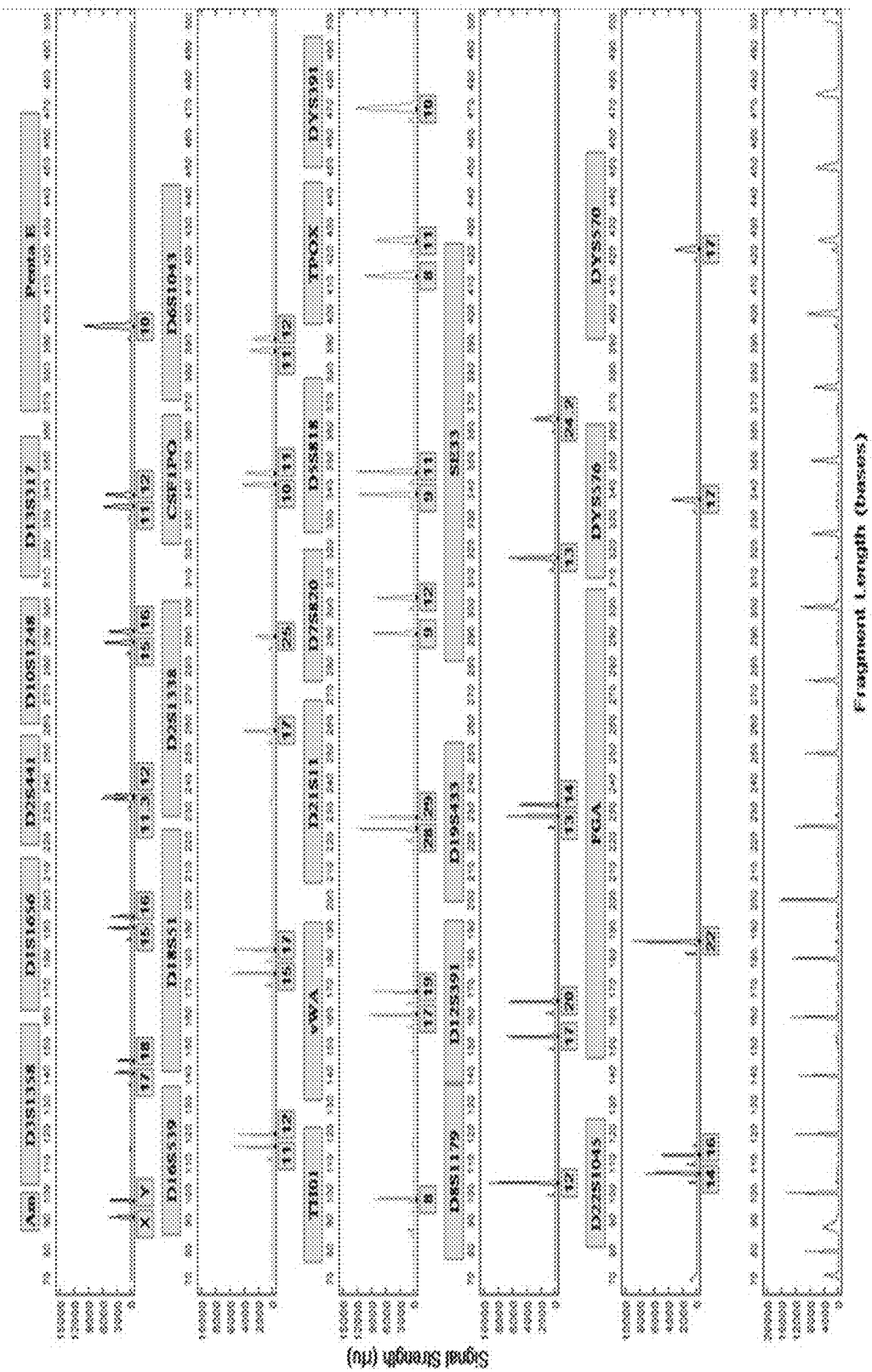
Figure 15:
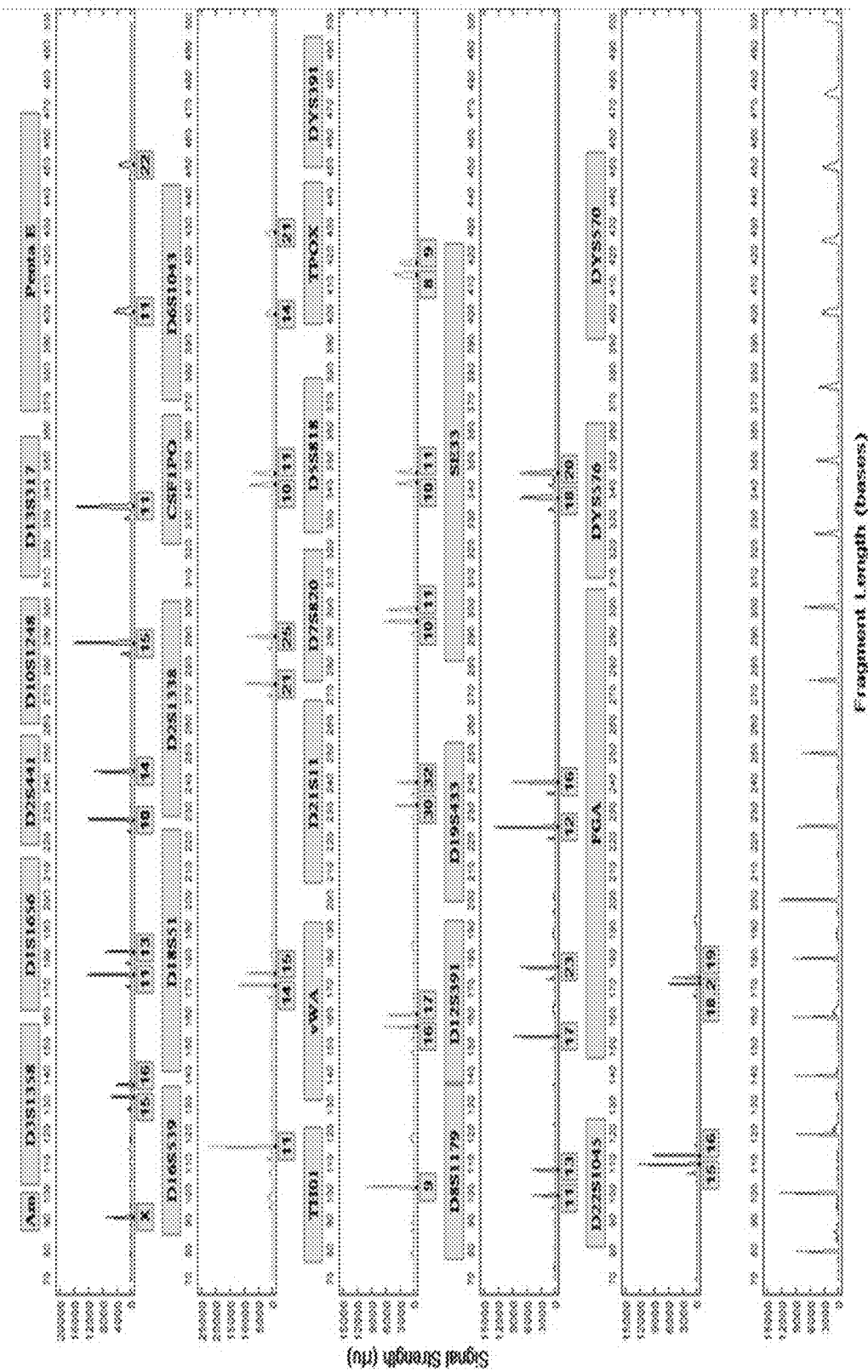
Figure 16:
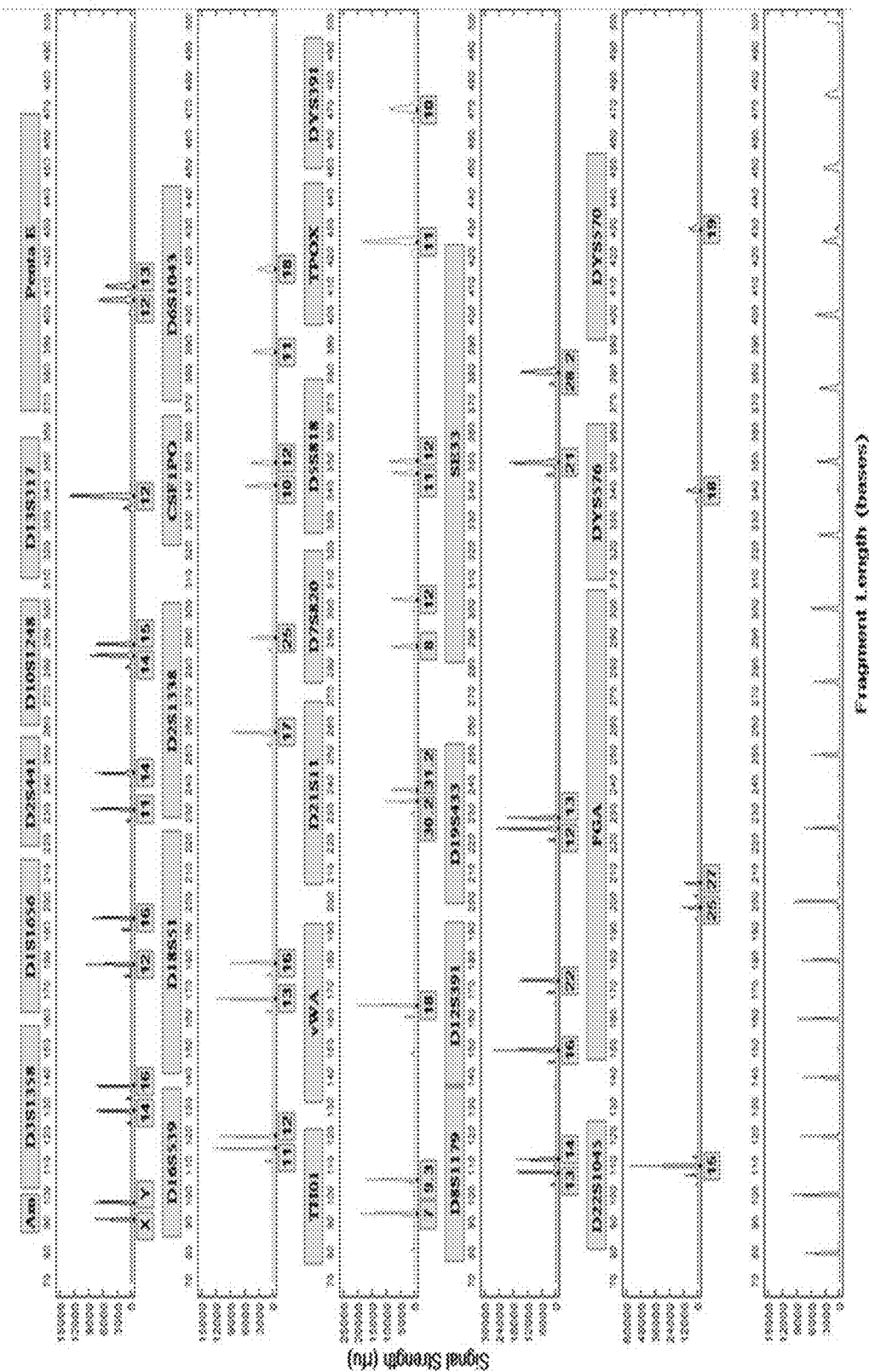
Figure 17A:
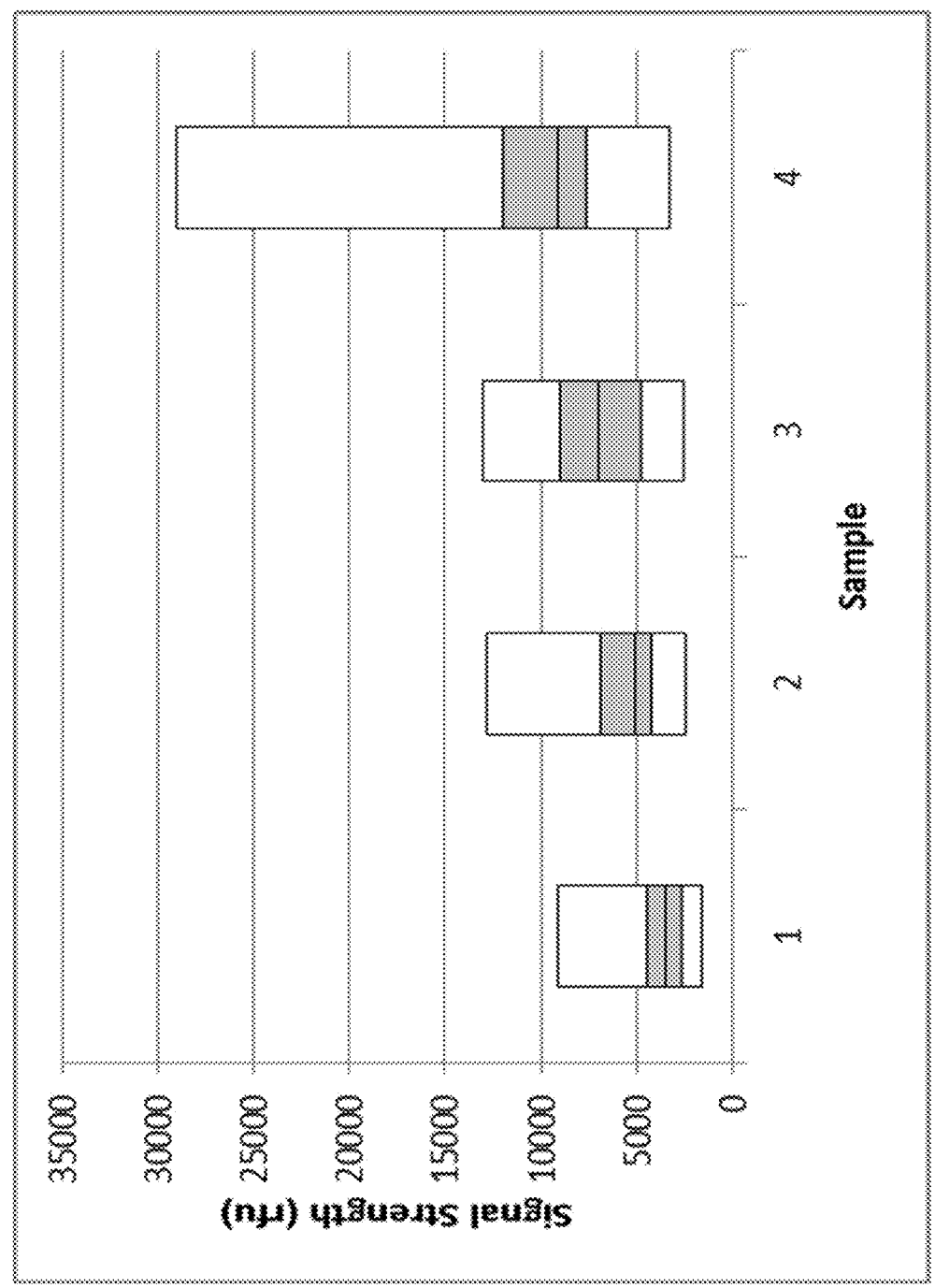
FIG. 17*a* shows the distribution of the signal strength of alleles and FIG. 17*b* shows the heterozygote peak height ratios for the loci for the DNA IDs of FIGS. 13 to 16.
Figure 17B:
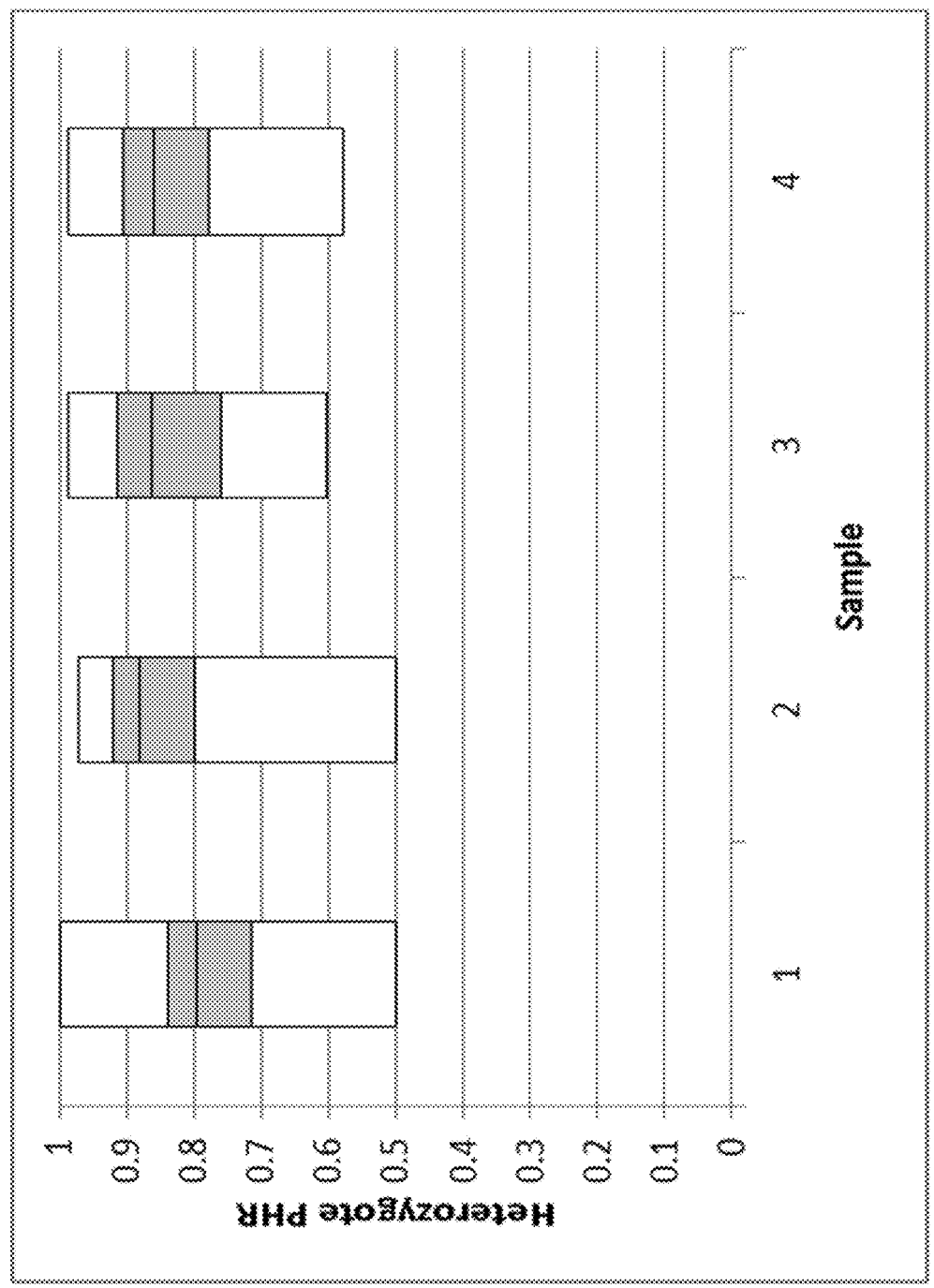

FIGS. 13 to 16 show DNA IDs of samples with intermediate signal strengths from A-Chips. FIG. 13 shows an intermediate signal strength sample generated with an A-Chip. This sample has all CODIS 20 loci and all FlexPlex 27 loci called (three of the loci have no alleles as this DNA sample is from a female). FIG. 14 shows an intermediate signal strength sample generated with a A-Chip. This sample has all CODIS 20 loci and all FlexPlex 27 loci called. FIG. 15 shows an intermediate signal strength sample generated with an A-Chip. This sample has all CODIS 20 loci and all FlexPlex 27 loci called (three of the loci have no alleles as this DNA sample is from a female). FIG. 16 shows an intermediate signal strength sample generated with an A-Chip. This sample has all CODIS 20 loci and all FlexPlex 27 loci called. FIG. 17a shows the distribution of the signal strength of alleles and FIG. 17b shows the heterozygote peak height ratios for the loci.

Figure 18:
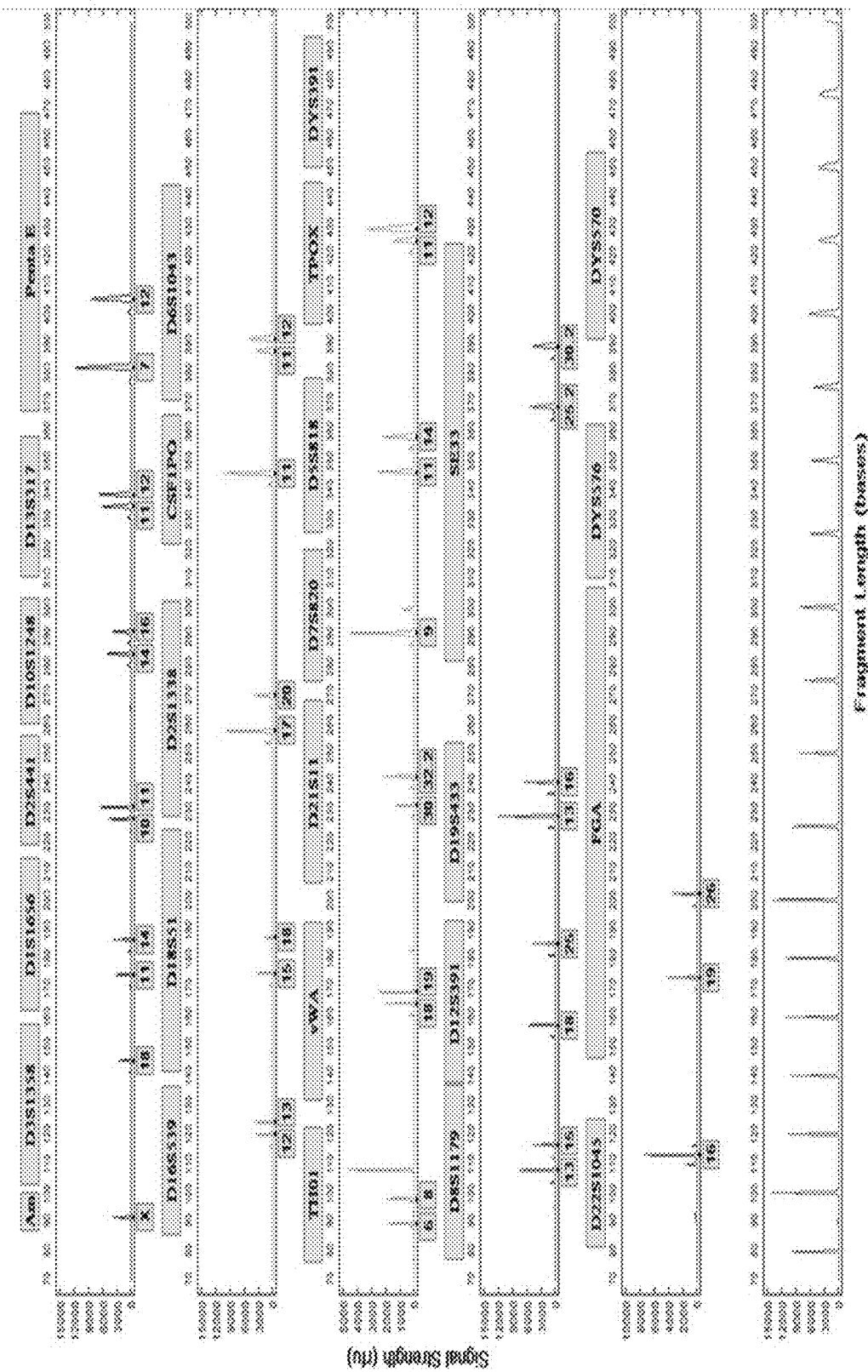
FIGS. 18 to 21 show DNA IDs of samples with intermediate signal strengths from I-Chips.
Figure 19:
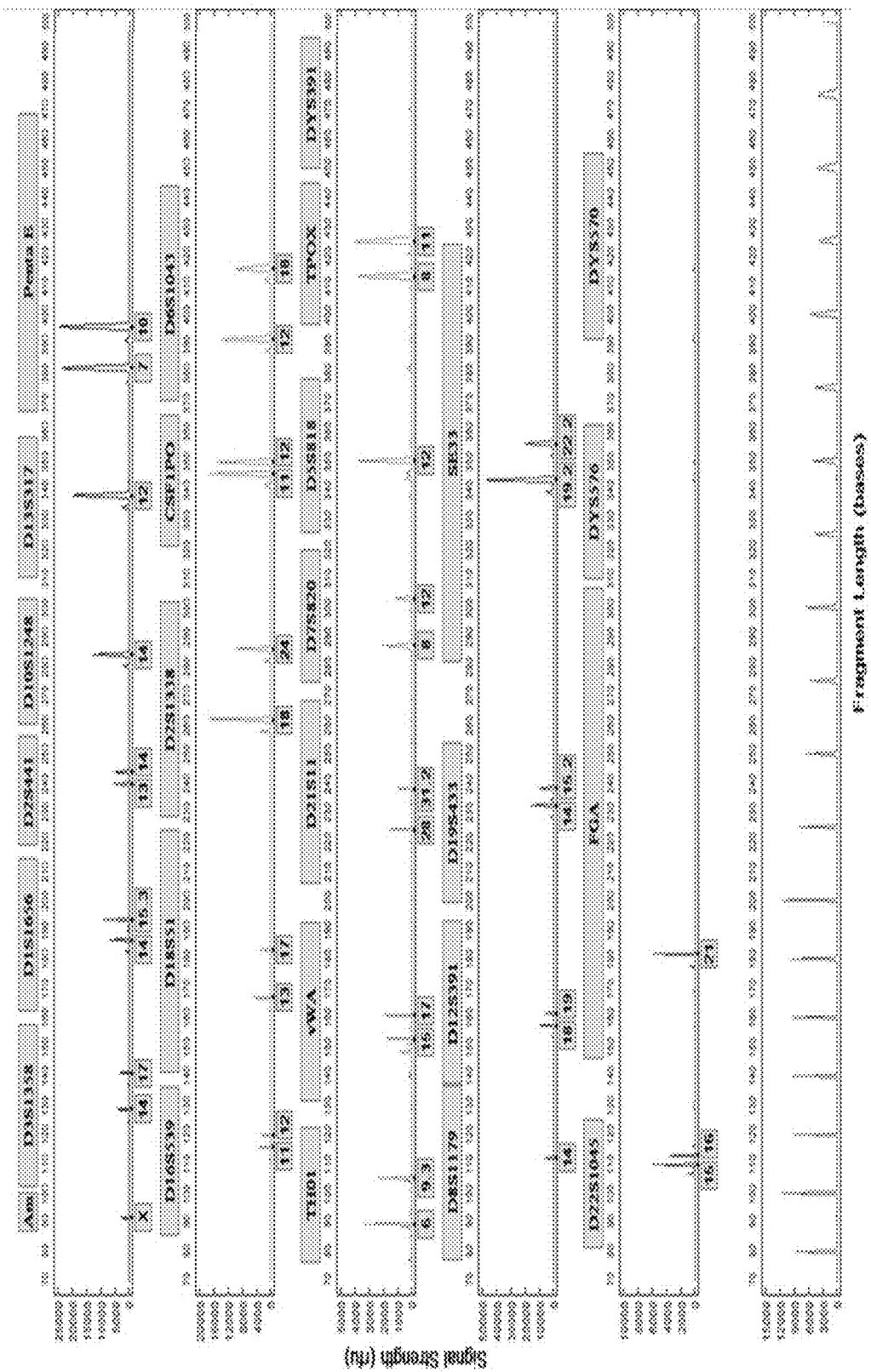
Figure 20:
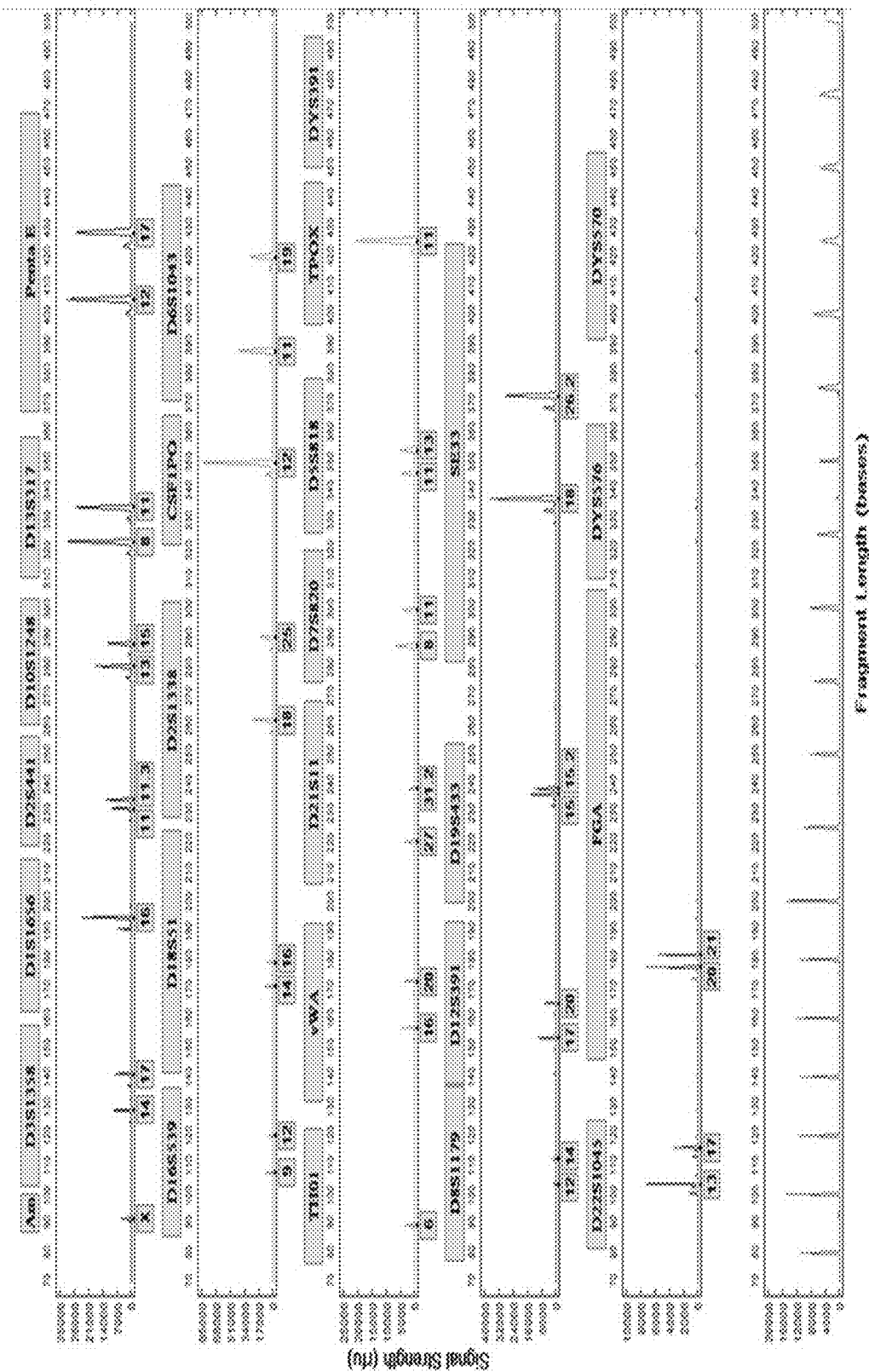
Figure 21:
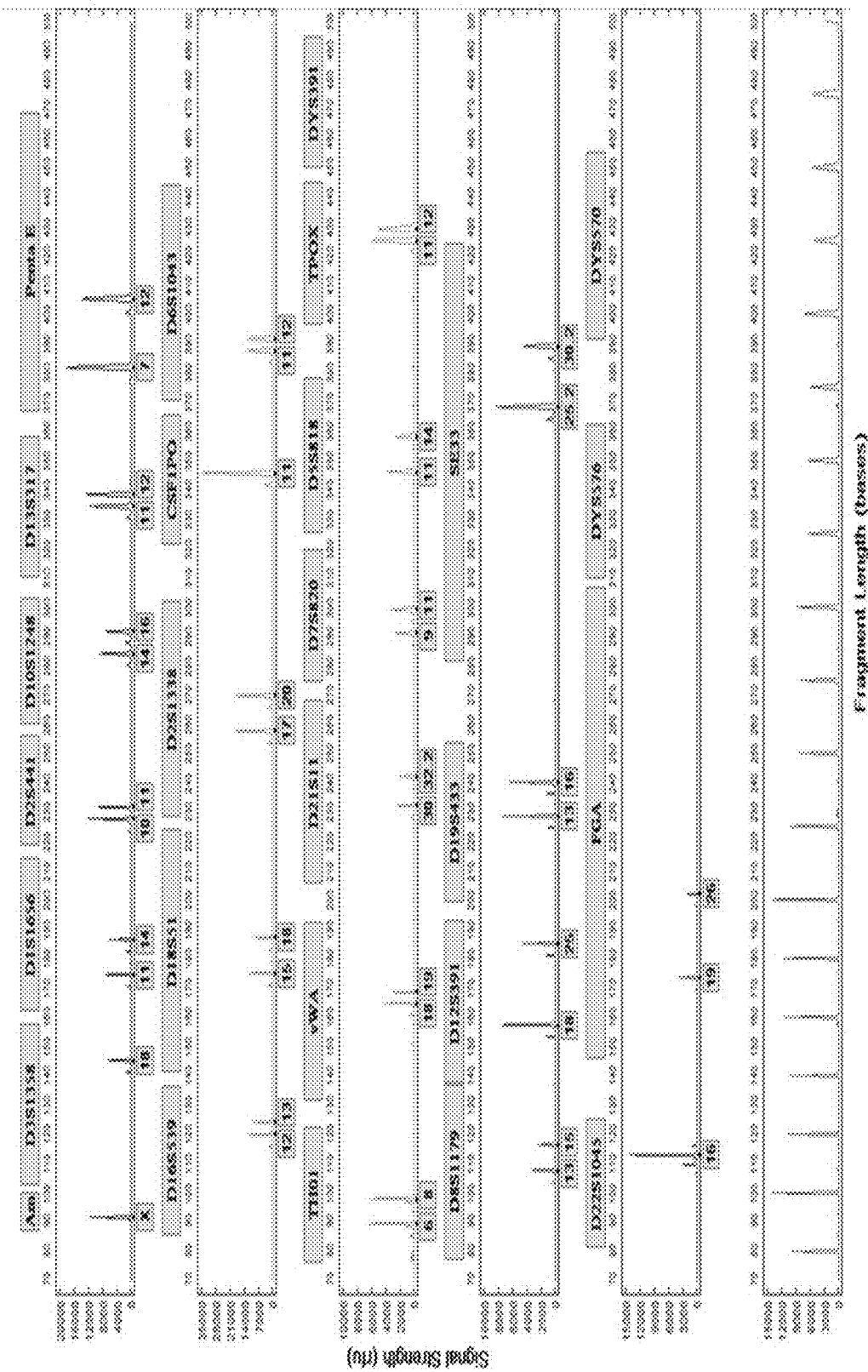
Figure 22A:
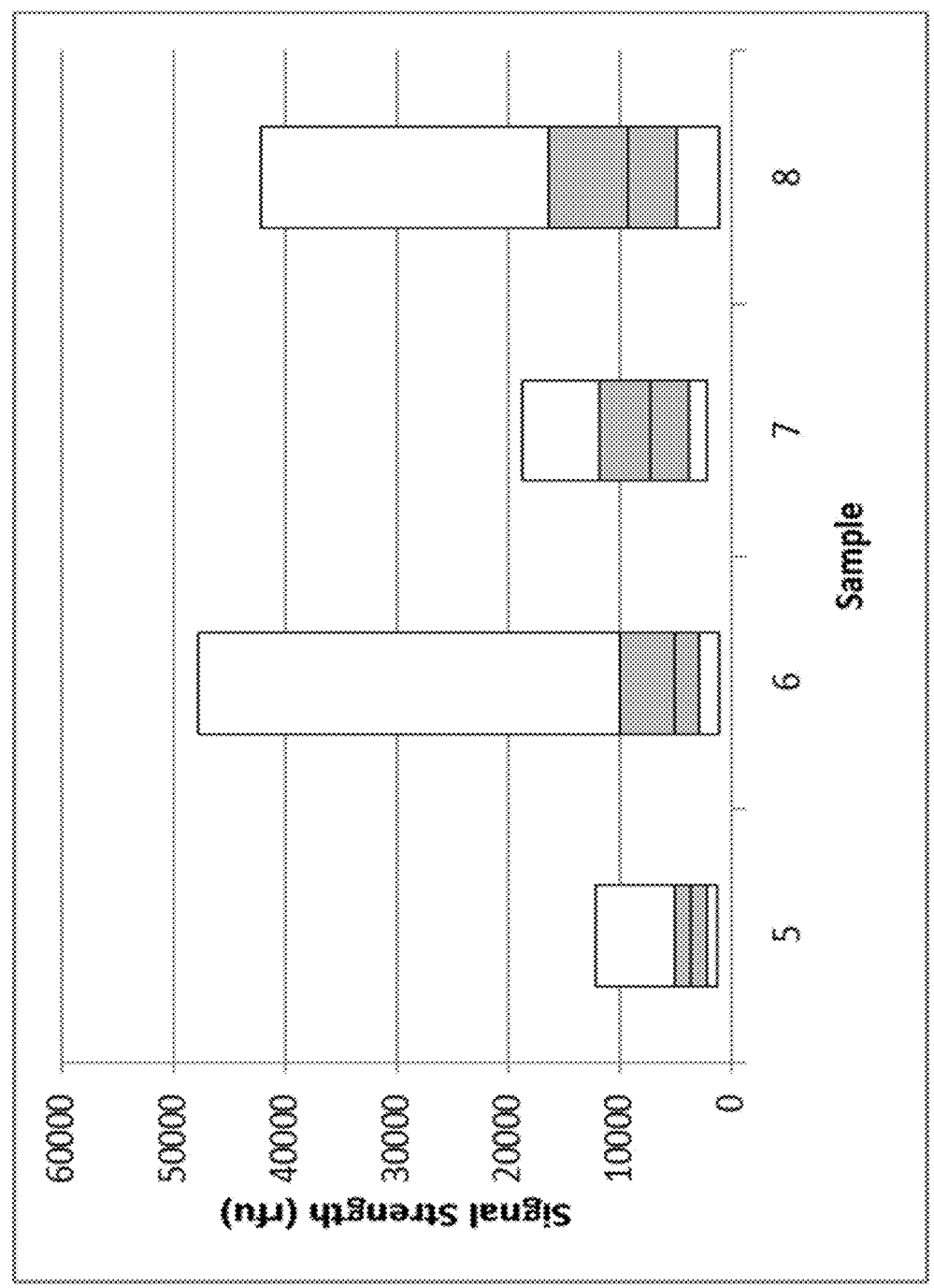
FIG. 22*a* shows the distribution of the signal strength of alleles and FIG. 22*b* shows the heterozygote peak height ratios for the loci for the DNA IDs of FIGS. 18 to 21.
Figure 22B:
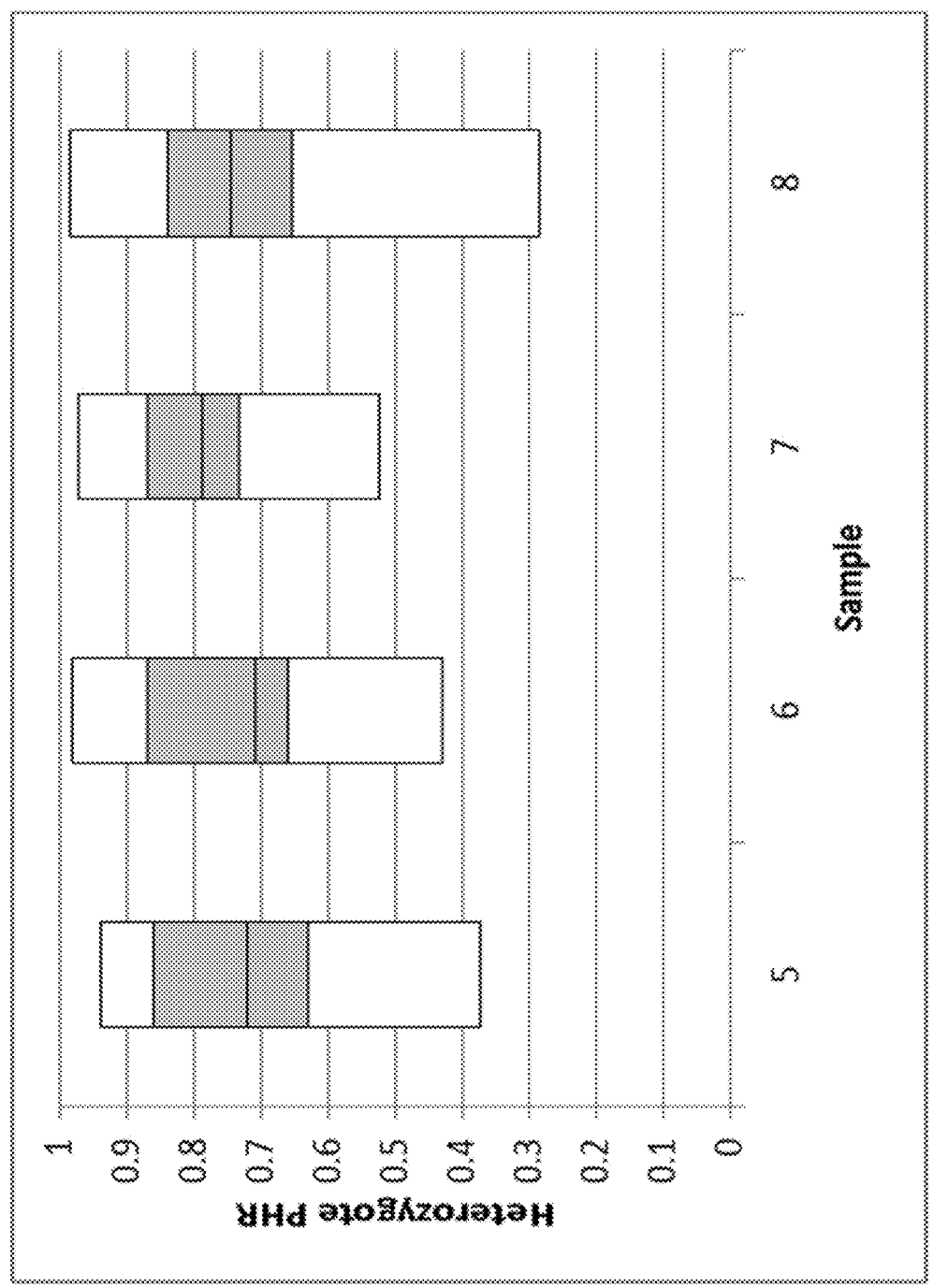

FIGS. 18 to 21 show DNA IDs of samples with intermediate signal strengths from I-Chips. FIG. 18 shows the intermediate signal strength sample generated with a I-Chip. This sample has all CODIS 20 loci and all FlexPlex 27 loci called. FIG. 19 shows the intermediate signal strength sample generated with an I-Chip. This sample has all CODIS 20 loci and all FlexPlex 27 loci called. FIG. 20 shows the intermediate signal strength sample generated with an I-Chip. This sample has all CODIS 20 loci and all FlexPlex 27 loci called. FIG. 21 shows the Intermediate signal strength sample generated with an I-Chip. This sample has all CODIS 20 loci and all FlexPlex 27 loci called. FIG. 22a shows the distribution of the signal strength of alleles and FIG. 22b shows the heterozygote peak height ratios for the loci.

The median heterozygote peak height from both A-Chips and I-Chips for all the intermediate signal strength samples in the dataset ranges from 1580 rfu to 49220 rfu, with a median of 8180 rfu. The median signal strength of 8180 rfu is used to separate the low signal strength and high signal strength samples. Again, these values are characteristic of the ANDE Rapid DNA System; other Rapid DNA Systems or conventional STR processing systems (or, indeed, other analytic systems quite apart from STR analysis) will have characteristic values for a "successful" result).

The median heterozygote peak height ratio from both A-Chip and I-Chip for all the intermediate signal strength samples in the dataset ranges from 0.614 to 0.931, with a median of 0.840.

Criteria defining Intermediate Signal Strength DNA IDs are listed in the following Table 1:

TABLE 1

| | Parameter | Criteria |
|---|---|---|
| 1 | ILS condition | Pass |
| 2 | Number of CODIS 20 Loci called | 20 |
| 3 | Signal Strength | Intermediate |
| 4 | Number of Loci with alleles with PH less than the PH threshold | 0 |
| 5 | Number of Loci with alleles with PH greater than PH min | ≥6 (≥20) |
| 6 | Number of Loci with PHR of less than PHR threshold | 0 |
| 7 | Number of Loci with wide peaks and iNTAp | 0 |

2) High Signal Strength DNA IDs—These are samples with passing ILS but have less than twenty of the CODIS 20 core loci called. Loci are labeled in red warning boxes or are unlabeled because:
  alleles are too wide, fail the peak morphology criteria of the ES, and are unlabeled;
  iNTA peaks have peak heights and peak height ratios that are too high, causing the locus to be identified as a mixture and labeled in red warning boxes.

As noted above, allele dimensions, peak morphology, iNTA peak heights and morphology, mixture criteria, and essentially all other DNA ID features are characteristic of the DNA processing system, data analysis system, types of samples, and number of samples. Type of sample may also have characteristic signatures. For example, a clinical sample characterized by a malignancy-related duplication or deletion may have a given peak or peaks that are particularly high, low, or otherwise characteristic of the sample type. In this Example, all dimensions and morphologies are characteristic of the ANDE system.

Figure 23:
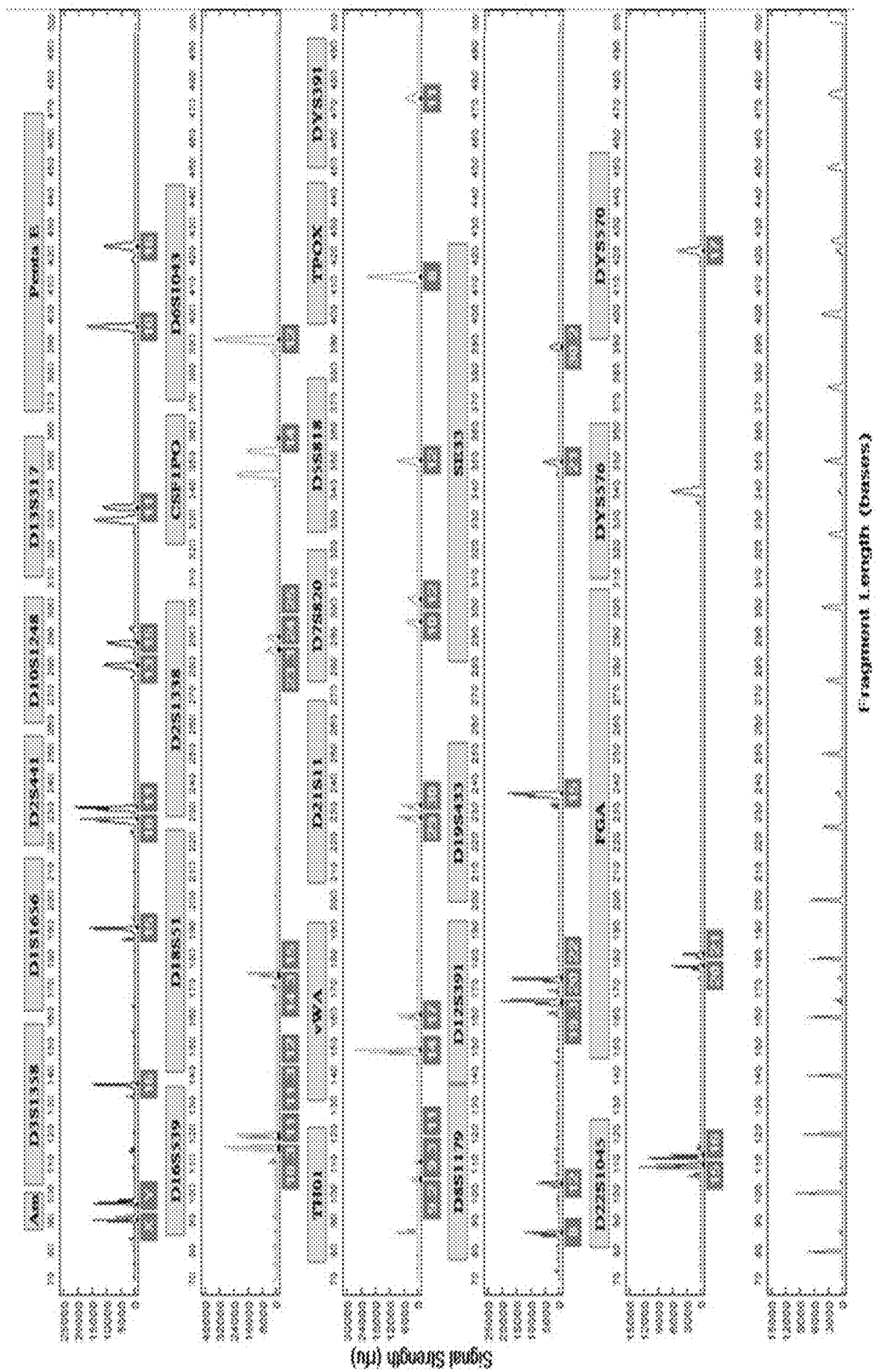
FIGS. 23 to 26 show DNA IDs of samples with high signal strengths.
Figure 24:
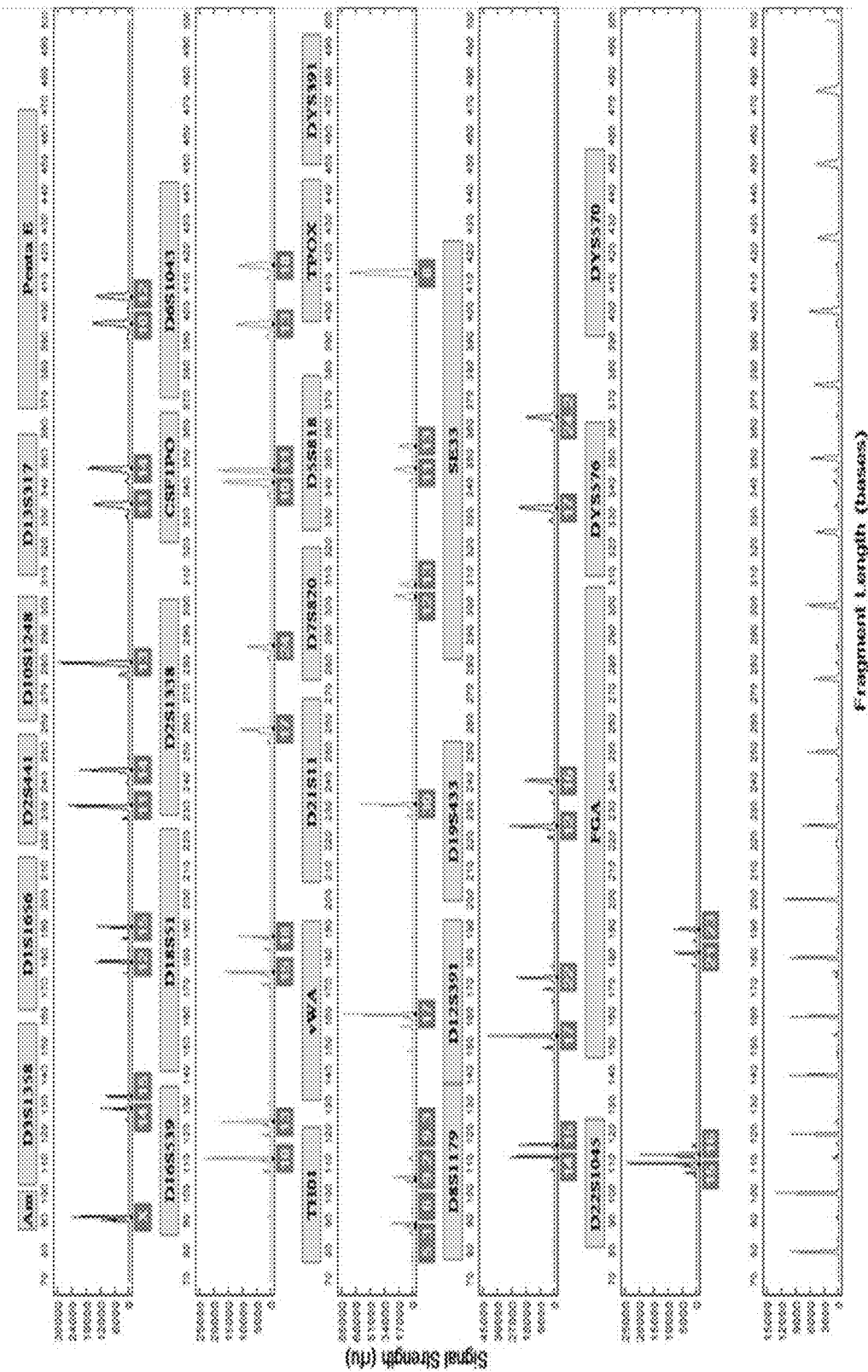
Figure 25:
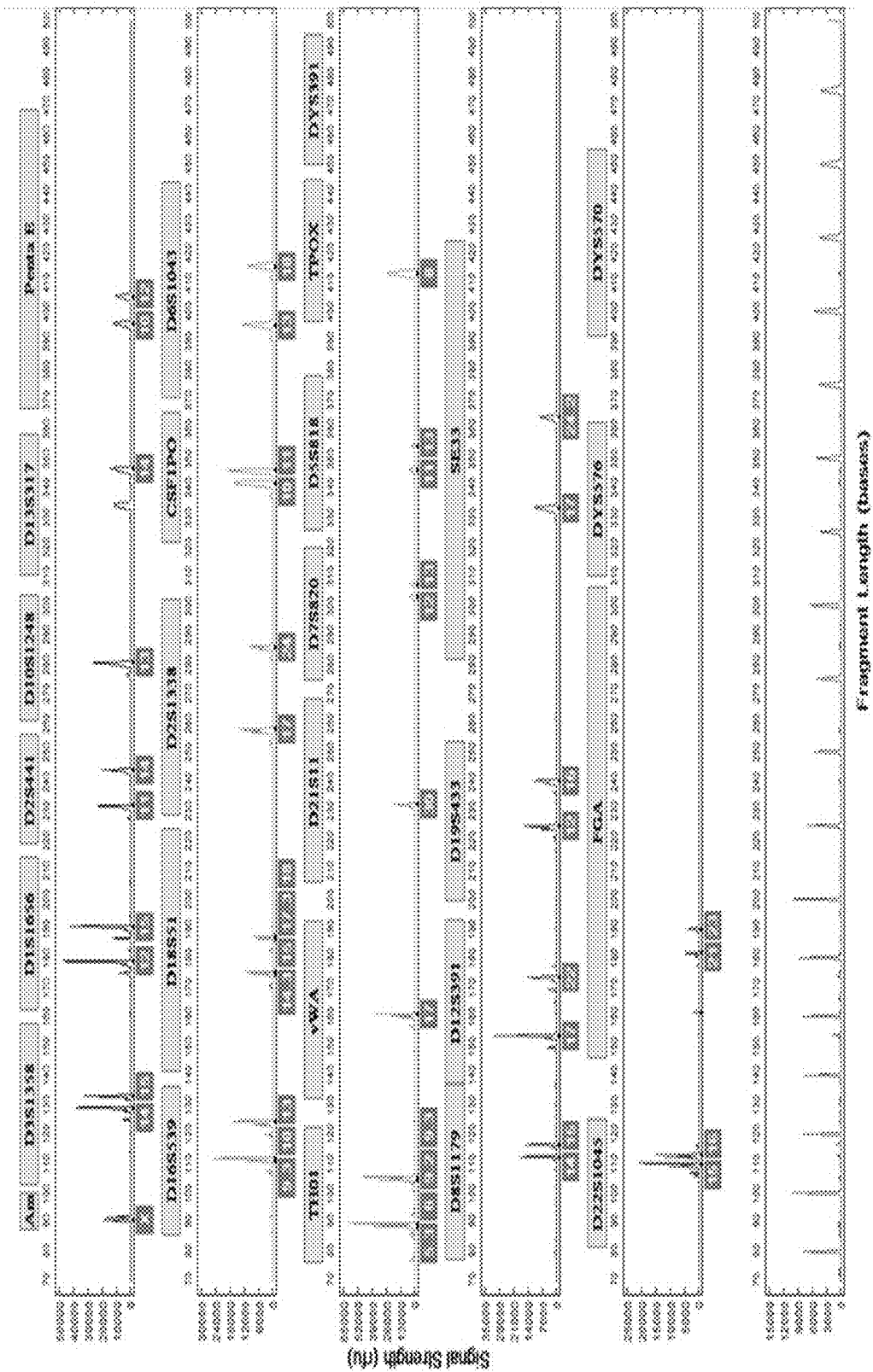
Figure 26:
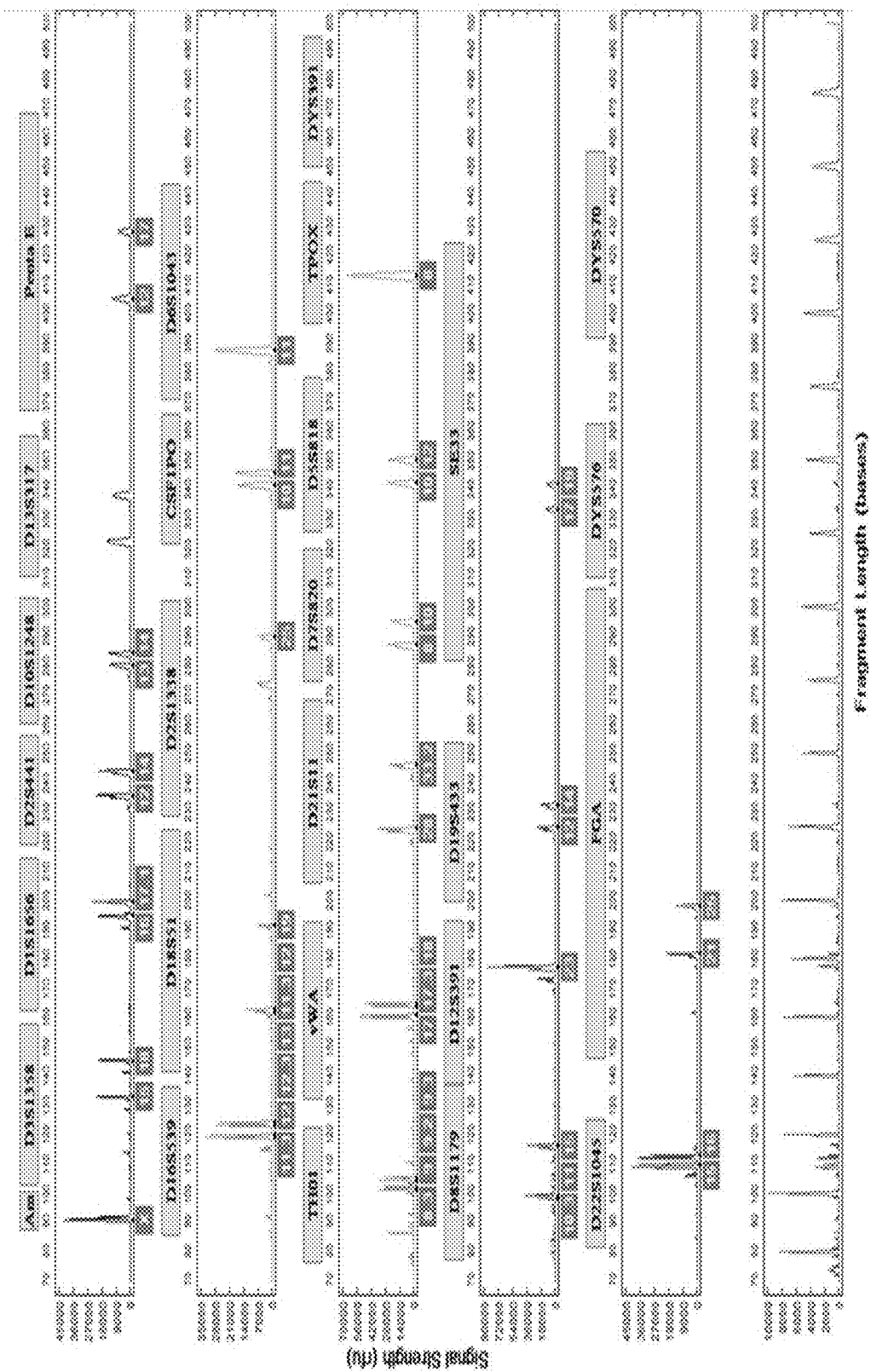
Figure 27A:
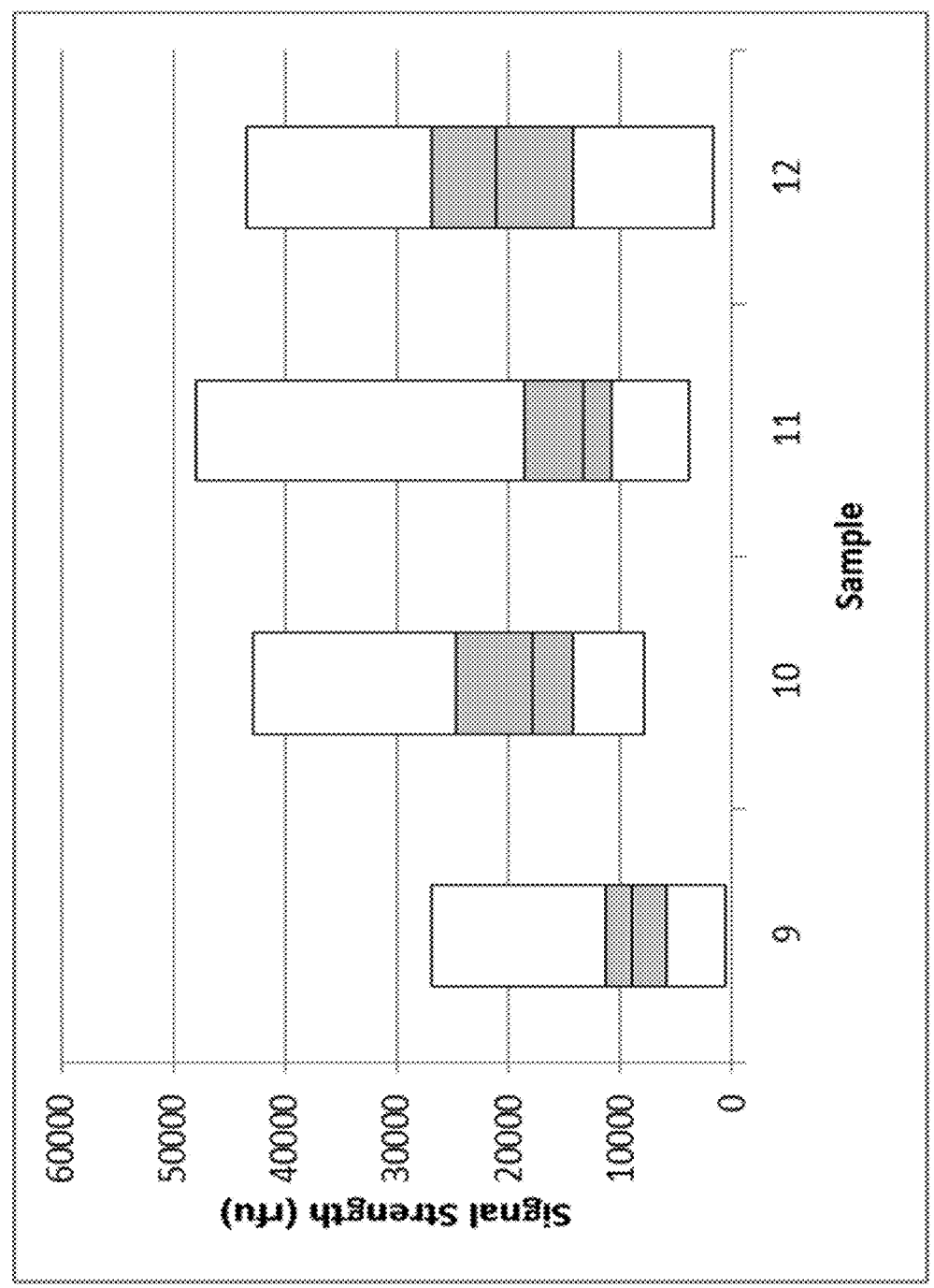
FIG. 27*a* shows the distribution of the signal strength of alleles and FIG. 27*b* shows the heterozygote peak height ratios for the loci for the DNA IDs of FIGS. 23-26.
Figure 27B:
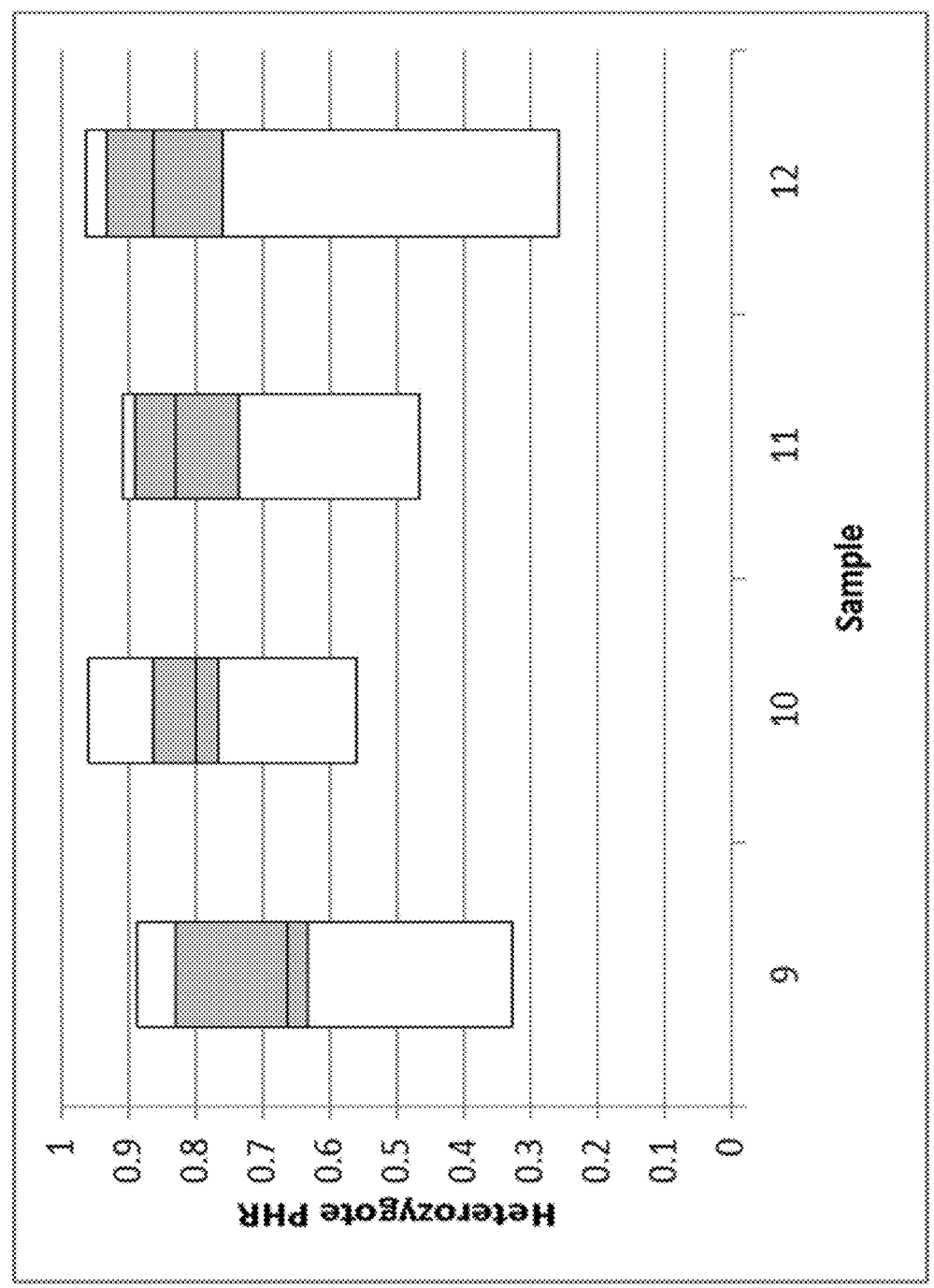
Figure 28:
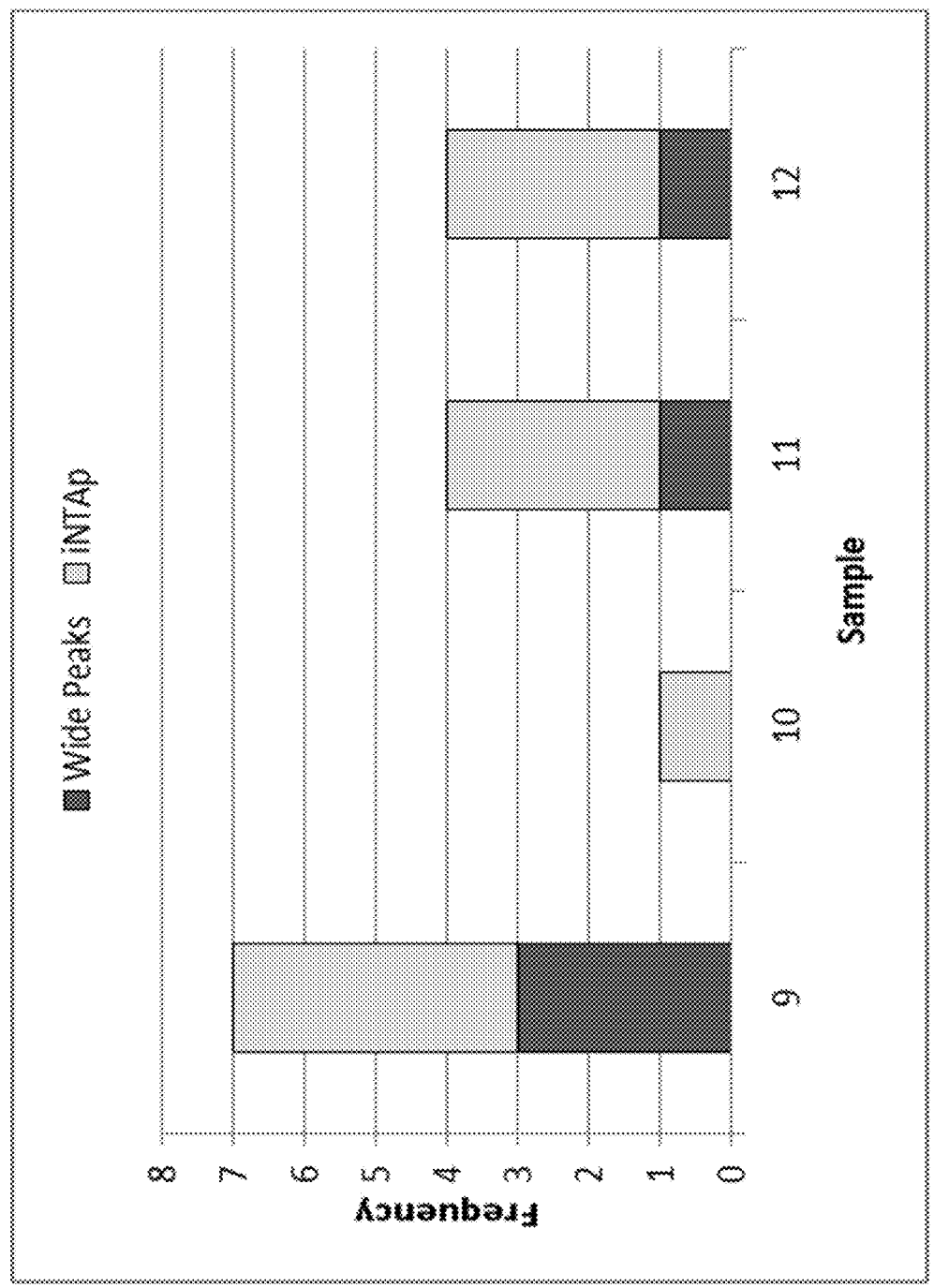
FIG. 28 shows the number of loci with either Wide Peaks or iNTAp in samples of FIGS. 23 to 26.

FIGS. 23 to 26 show DNA IDs of samples with this classification. FIG. 23 shows a High signal strength sample with all alleles labeled in red or unlabeled. FIG. 24 shows a High signal strength sample with all alleles labeled in red. FIG. 25 shows a High signal strength sample with all alleles labeled in red. FIG. 26 shows a High signal strength sample with all alleles labeled in red or unlabeled. FIG. 27a and FIG. 27b shows the distribution of the signal strength of alleles and heterozygote peak height ratios for the loci. A parameter defined as the number of loci with wide peaks and iNTA was defined to uniquely describe this classification. FIG. 28 shows the Number of loci with either Wide Peaks or iNTAp in samples of FIGS. 23 to 26.

Criteria defining DNA IDs with this classification are listed in the following Table 2:

TABLE 2

| | Parameter | Criteria |
|---|---|---|
| 1 | ILS condition | Pass |
| 2 | Number of CODIS 20 Loci called | <20 |
| 3 | Signal Strength | High |
| 4 | Number of Loci with alleles with PH less than the PH threshold | 0 |
| 5 | Number of Loci with alleles with PH greater than PH min | ≥6 (≥20) |

TABLE 2-continued

| | Parameter | Criteria |
|---|---|---|
| 6 | Number of Loci with PHR of less than PHR threshold | 0 |
| 7 | Number of Loci with wide peaks and iNTAp | >0 |

3) Intermediate signal strength DNA IDs, PHR—These are samples with passing ILS but less than twenty of the CODIS 20 core loci are called. Loci are labeled in red warning boxes because:
  alleles within the locus have a peak height ratio that is less than the peak height ratio threshold. The number of loci with a peak height ratio below threshold is greater than 0.
  none of the alleles within the locus have a peak height that is less than the peak height calling threshold.

Note that a passing ILS is a surrogate for a successful ANDE run (meaning that the instrument and chip functioned as designed). Many other criteria can be used for ANDE, other Rapid DNA systems, or conventional processes.

Figure 29:
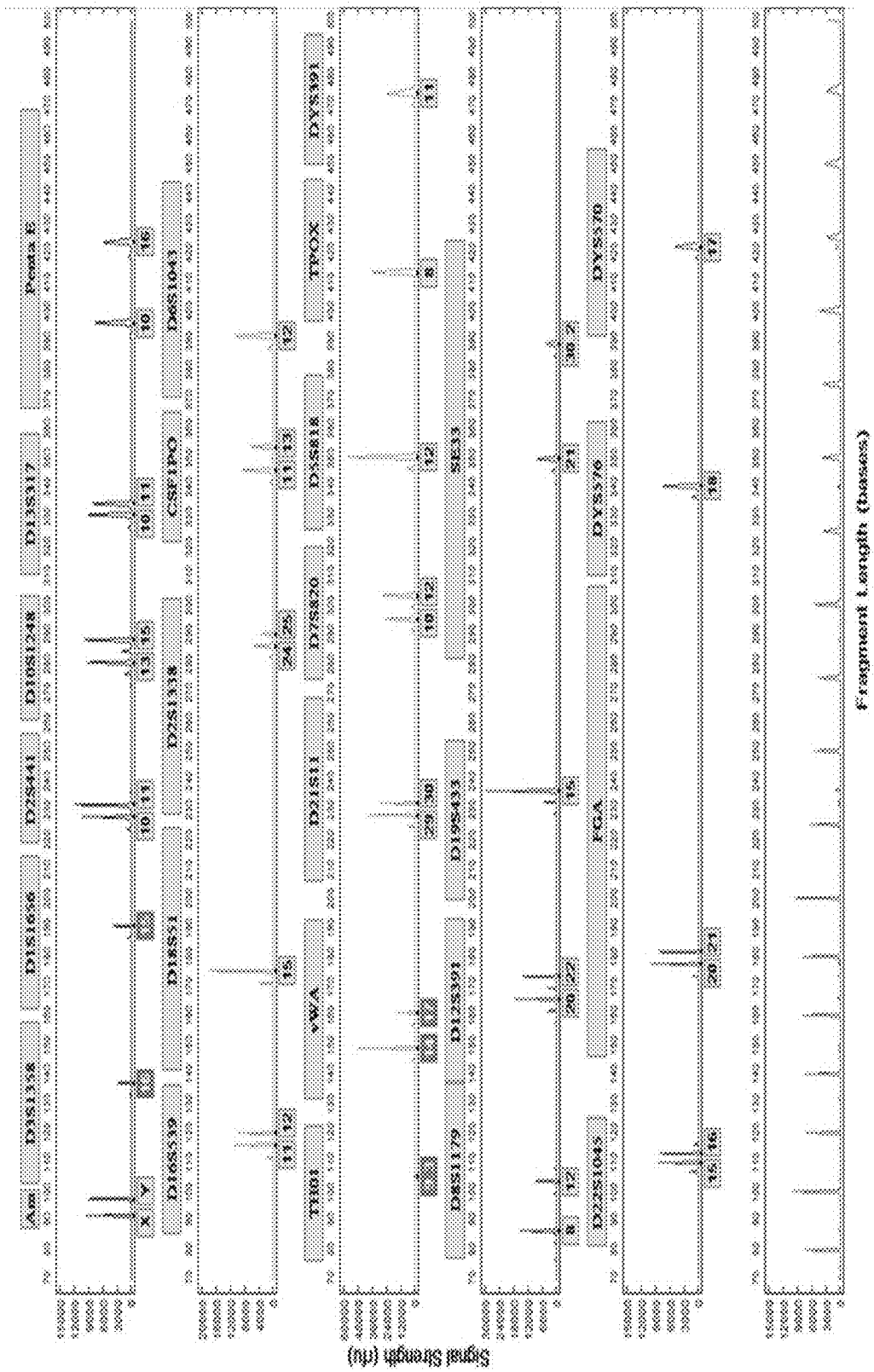
FIGS. 29 and 30 show this classification of samples with intermediate signal strength and with several alleles labeled in red.
Figure 30:
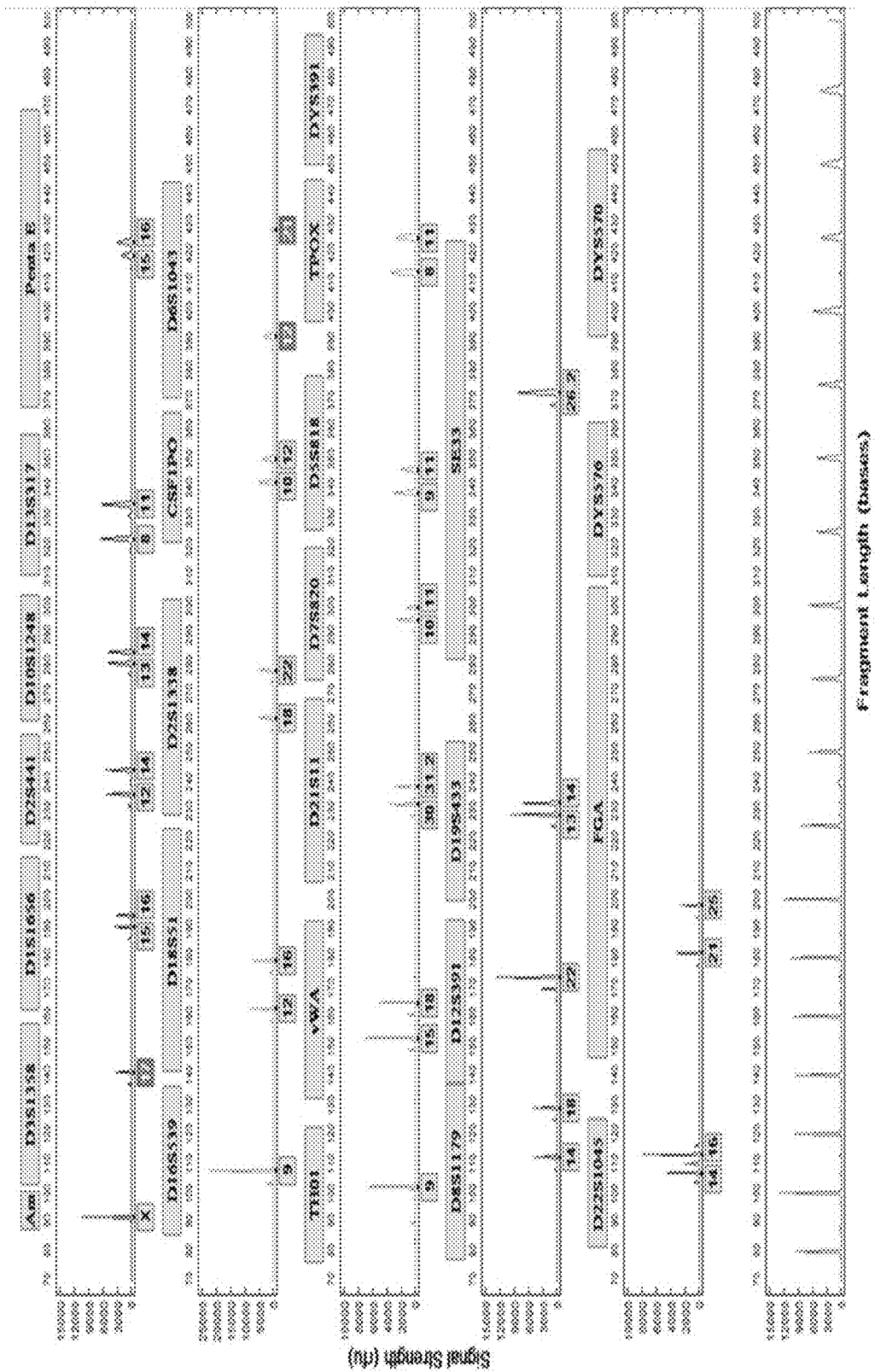
Figure 31A:
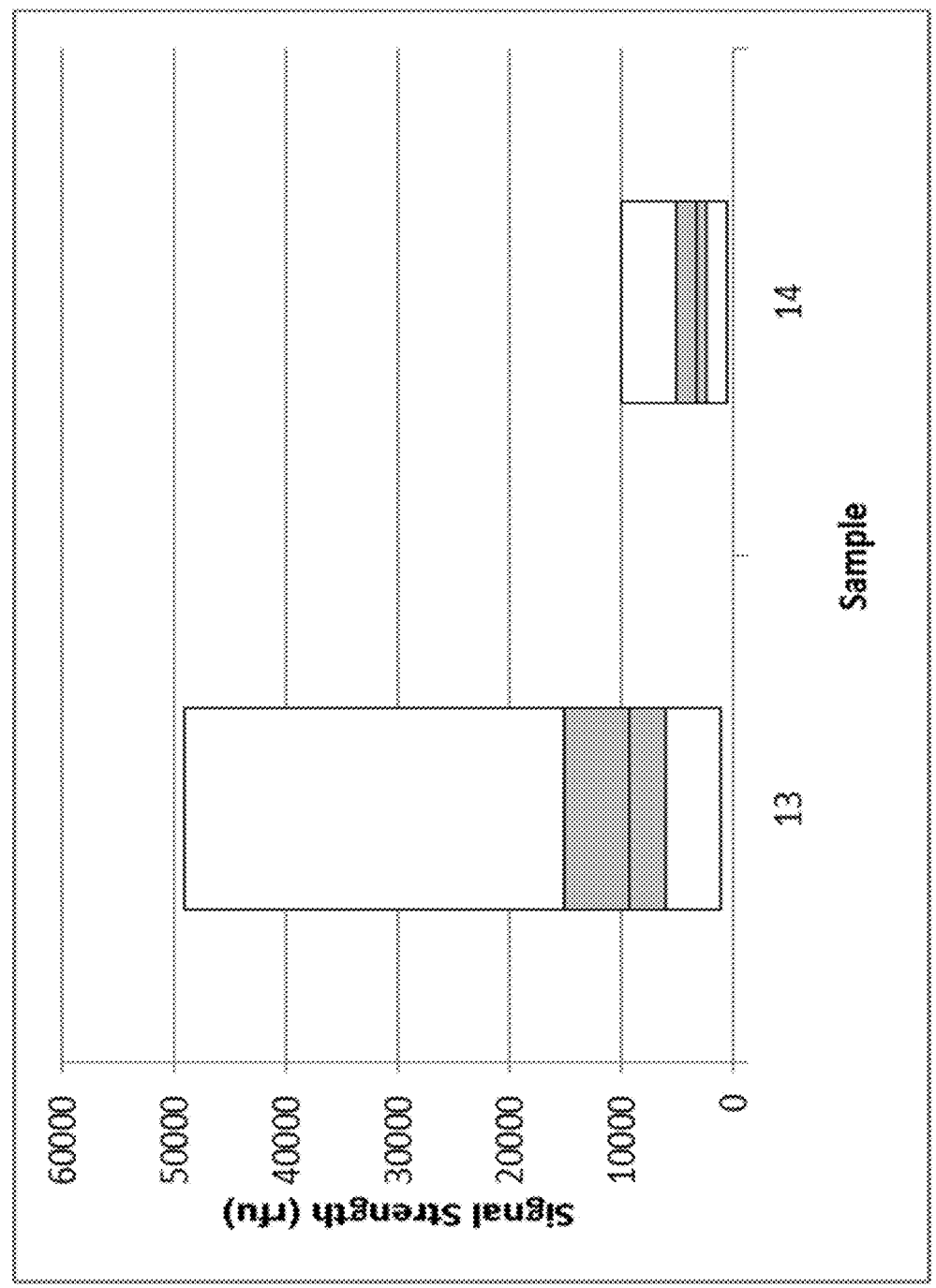
FIG. 31*a* shows the distribution of the signal strength of alleles and FIG. 31*b* shows the heterozygote peak height ratios for the loci for the DNA IDs of FIGS. 29 and 30.
Figure 31B:
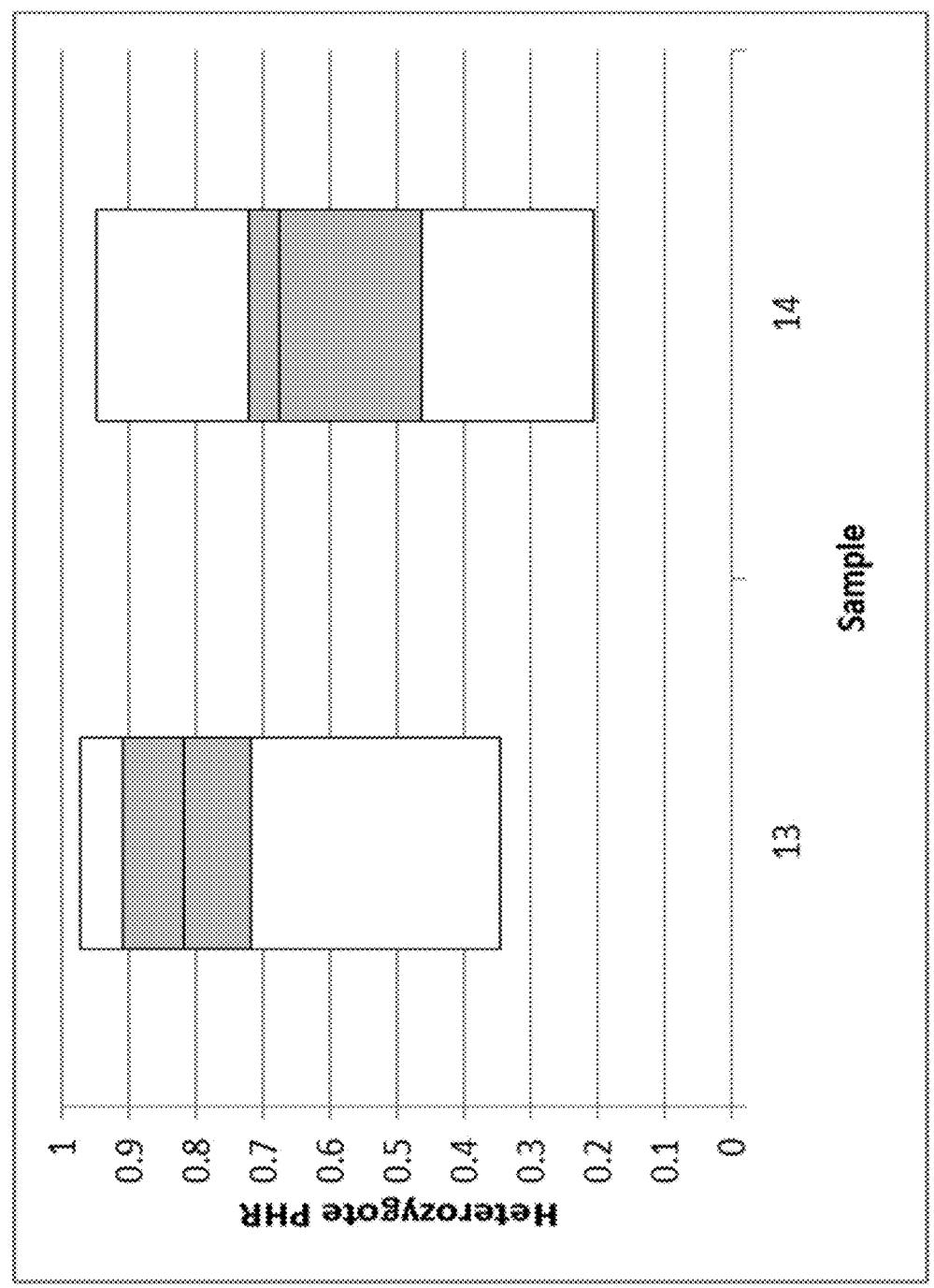

FIGS. 29 and 30 show this classification of samples with Intermediate signal strength and with several alleles labeled in red. FIG. 31a and FIG. 31b shows the distribution of the signal strength of alleles and heterozygote peak height ratios for the loci for the DNA IDs of FIGS. 29 and 30.

Criteria defining DNA IDs with this classification are listed in the following Table 3:

TABLE 3

| | Parameter | Criteria |
|---|---|---|
| 1 | ILS condition | Pass |
| 2 | Number of CODIS 20 Loci called | <20 |
| 3 | Signal Strength | Intermediate |
| 4 | Number of Loci with alleles with PH less than the PH threshold | 0 |
| 5 | Number of Loci with alleles with PH greater than PH min | ≥6 (≥20) |
| 6 | Number of Loci with PHR of less than PHR threshold | >0 |
| 7 | Number of Loci with wide peaks and iNTAp | 0 |

4) Low signal strength DNA IDs with low peak heights—These are samples with passing ILS but have less than twenty of the CODIS 20 core loci called. Loci are labeled in red warning boxes or are unlabeled because:
  alleles within the locus have a peak height that is less than the peak height calling threshold are unlabeled;
  alleles within the locus have a peak height ratio that is less than the peak height ratio threshold are labeled in red.

Figure 32:
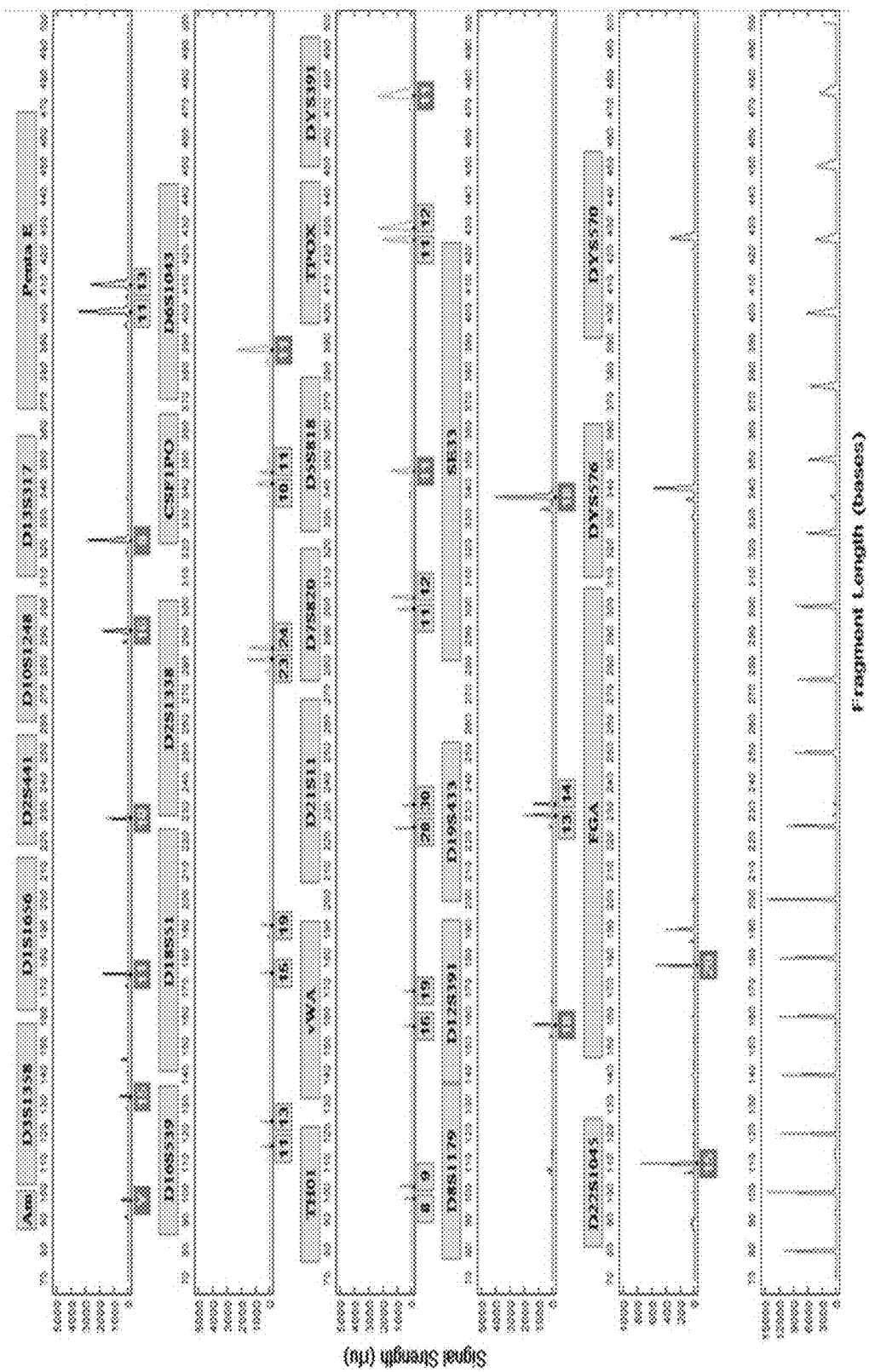
FIGS. 32 to 34 show DNA IDs of samples with low signal strengths with several alleles labeled in red and unlabeled alleles.
Figure 33:
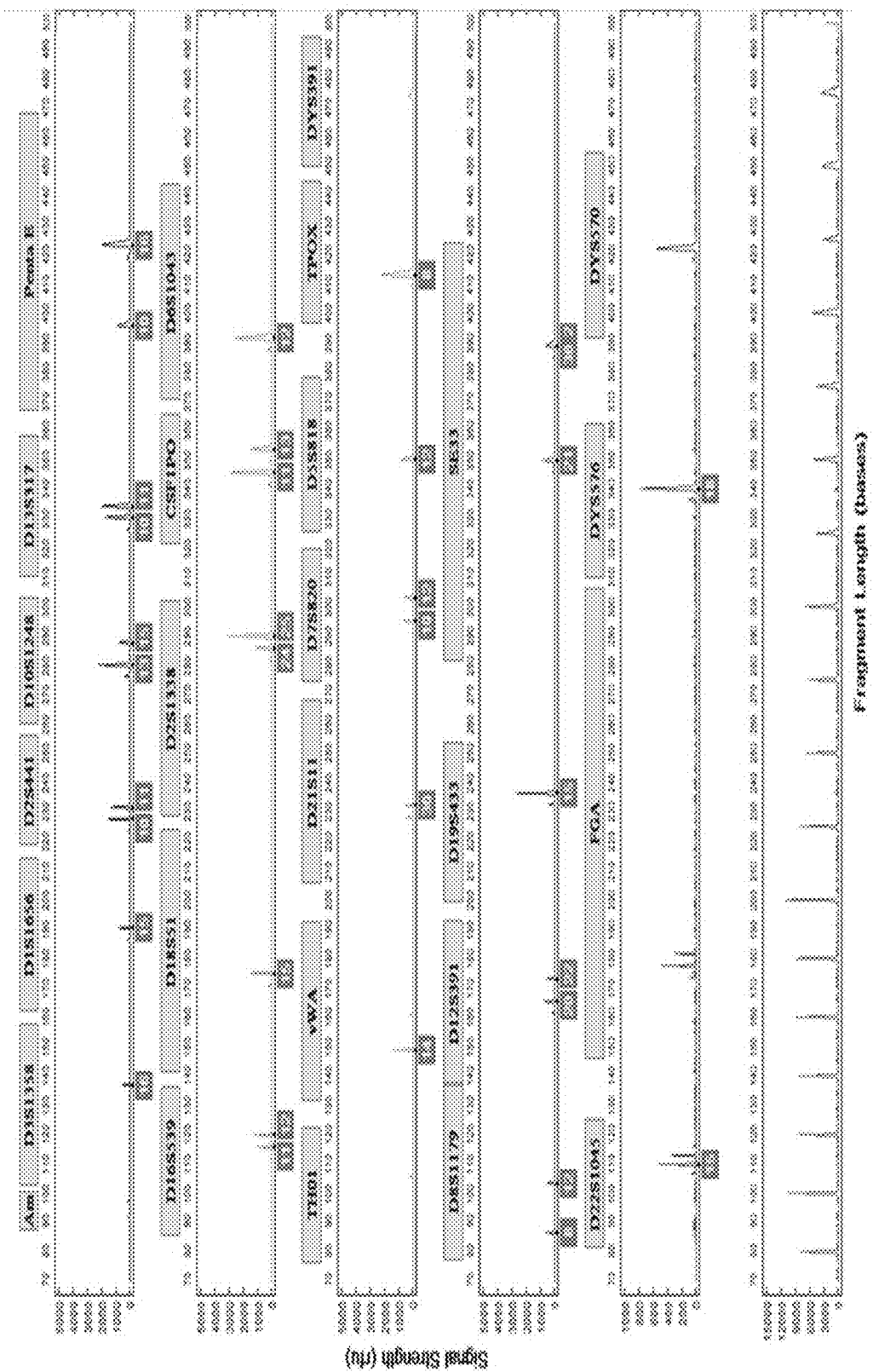
Figure 34:
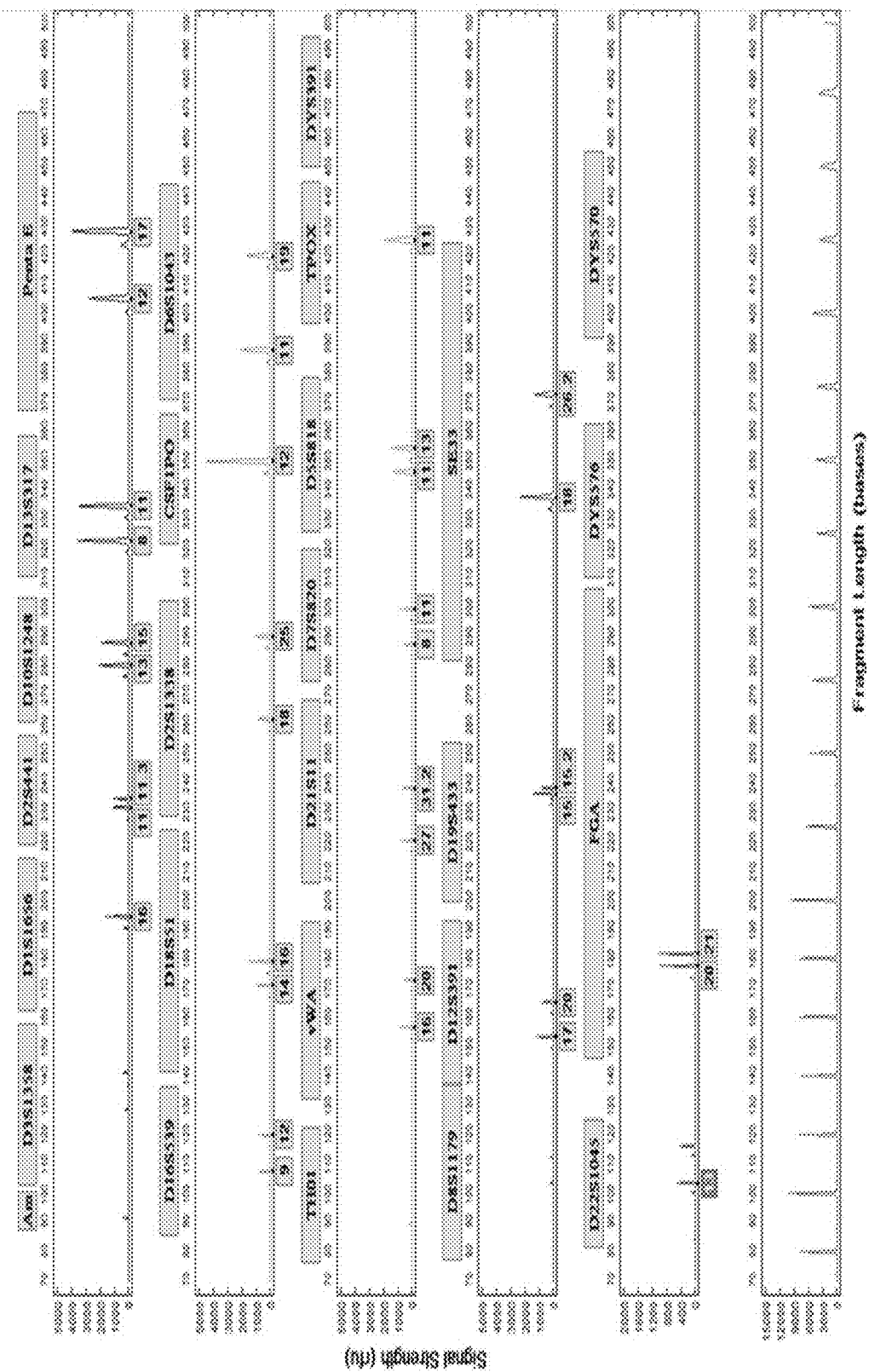
Figure 35A:
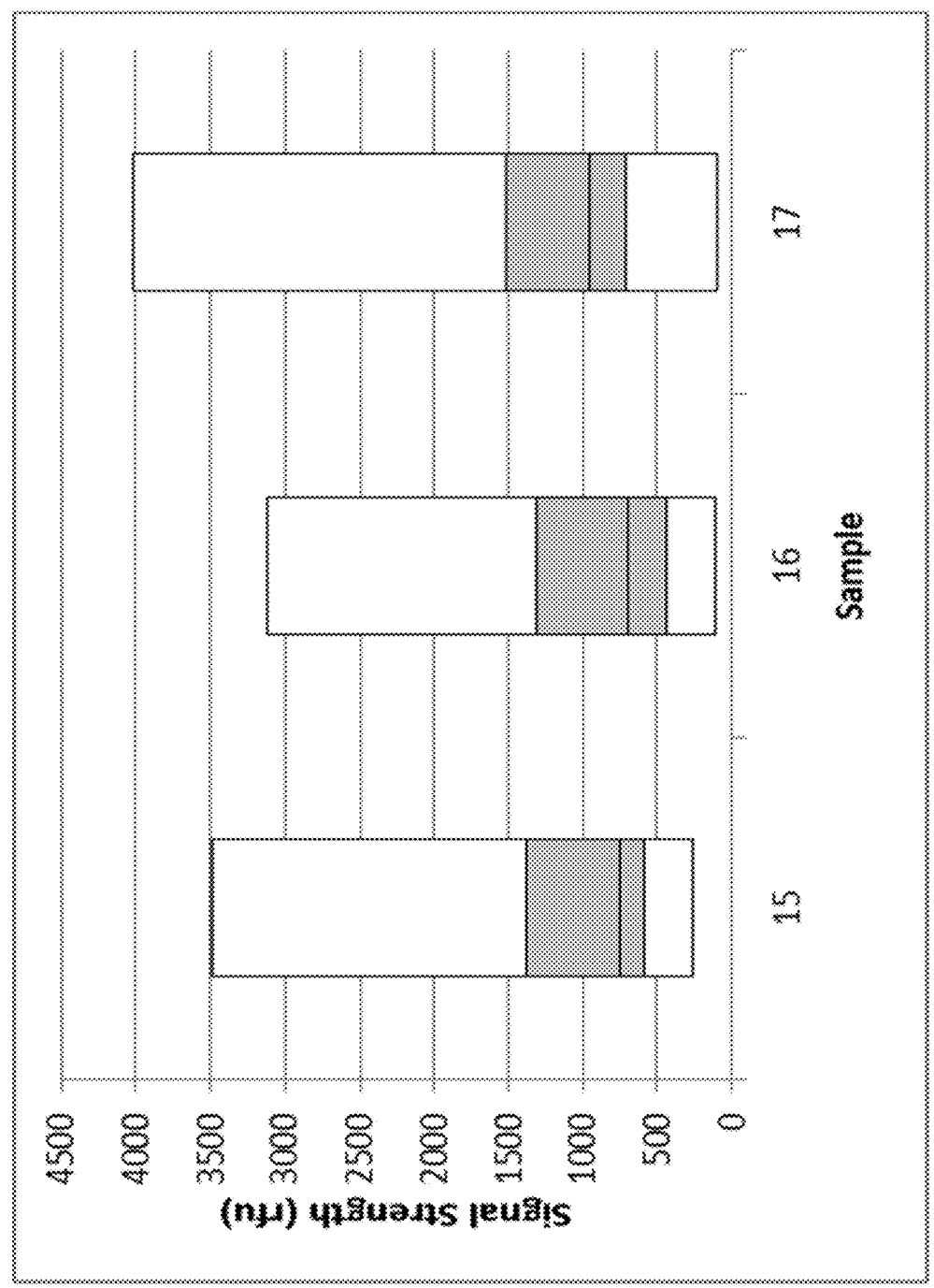
FIG. 35a shows the distribution of the signal strength of alleles and FIG. 35b shows the heterozygote peak height ratios for the loci for the DNA IDs of FIGS. 32 to 34.
Figure 35B:
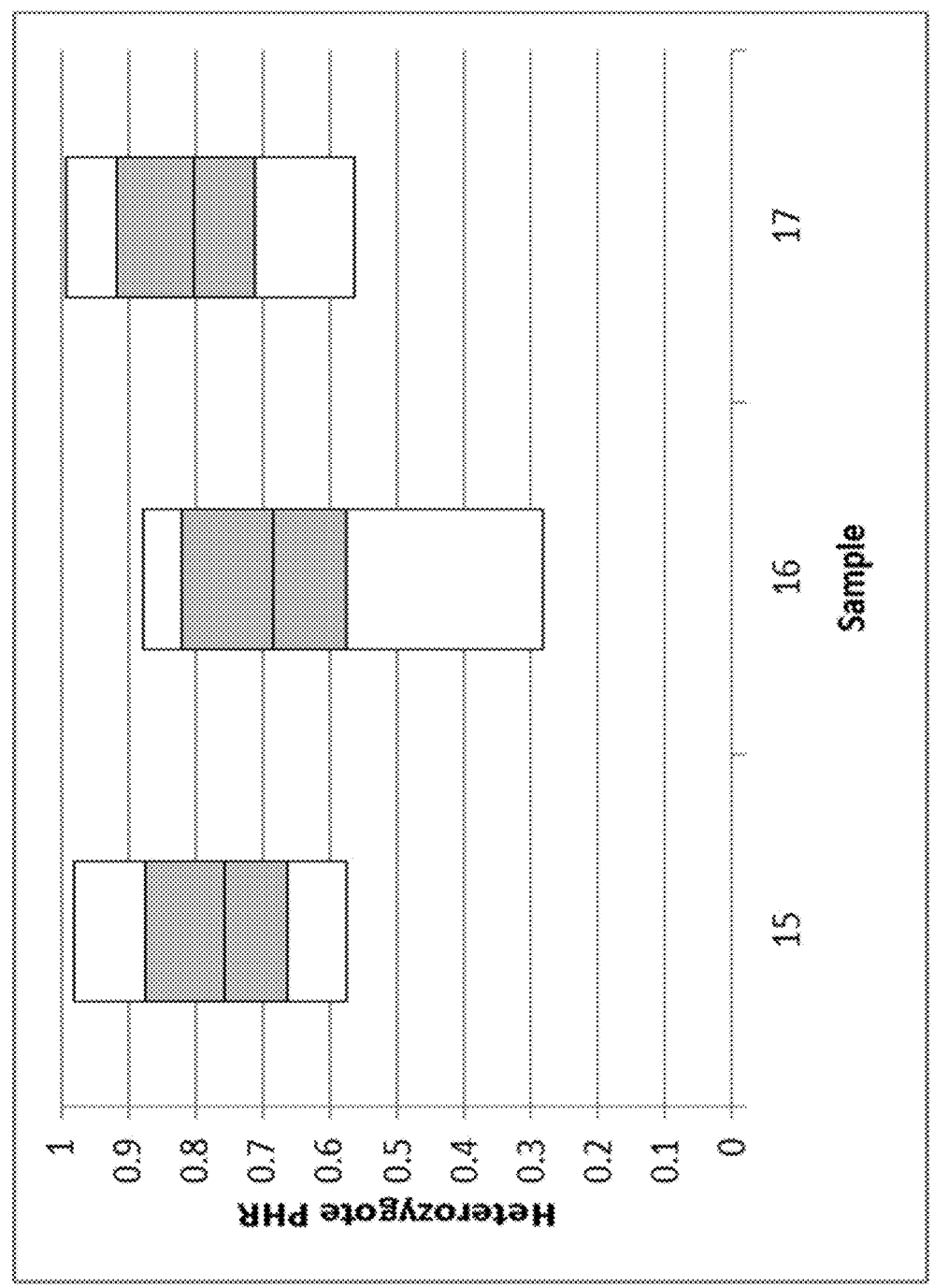

FIGS. 32 to 34 show DNA IDs of samples with low signal strengths with several alleles labeled in red and unlabeled alleles. FIG. 35a and FIG. 35b shows the distribution of the signal strength of alleles and heterozygote peak height ratios for the loci for the DNA IDs of FIGS. 32 to 34.

Criteria defining DNA IDs with this classification are listed in the following Table 4:

TABLE 4

| | Parameter | Criteria |
|---|---|---|
| 1 | ILS condition | Pass |
| 2 | Number of CODIS 20 Loci called | <20 |
| 3 | Signal Strength | Low |
| 4 | Number of Loci with alleles with PH less than the PH threshold | >0 |

TABLE 4-continued

| | Parameter | Criteria |
|---|---|---|
| 5 | Number of Loci with alleles with PH greater than PH min | ≥6 |
| 6 | Number of Loci with PHR of less than PHR threshold | ≥0 |
| 7 | Number of Loci with wide peaks and iNTAp | 0 |

5) Very Low Signal DNA IDs—These are samples with passing ILS but have less than twenty of the CODIS 20 core loci called. Very few loci are labeled in red warning boxes and many loci are unlabeled because:
- alleles within the locus have a peak height that is less than the peak height calling threshold,
- alleles within the locus have a peak height ratio that is less than the peak height ratio threshold,
- less than 6 loci have alleles with peak heights greater than the minimum peak height calling threshold. This threshold is defined as the minimum peak height threshold to of the AES, lowered from the standard Expert System's PH threshold.

As with all the DNA ID types, these criteria may be varied; for example, the number of loci with alleles with peak heights greater than the minimum peak height may be increased or decreased.

Criteria defining DNA IDs with this classification are listed in the following Table 5:

TABLE 5

| | Parameter | Criteria |
|---|---|---|
| 1 | ILS condition | Pass |
| 2 | Number of CODIS 20 Loci called | <20 |
| 3 | Signal Strength | Low |
| 4 | Number of Loci with alleles with PH less than the PH threshold | >0 |
| 5 | Number of Loci with alleles with PH greater than PH min | <6 |
| 6 | Number of Loci with PHR of less than PHR threshold | ≥0 |
| 7 | Number of Loci with wide peaks and iNTAp | 0 |

6) Failed DNA IDs—In these samples, the ILS was failed by the Adaptive Expert System and no peaks were called. These samples are not processed further. The samples can fail for a variety of reasons, including:
- A bubble in the separation channel. The ANDE Expert System failed the sample because it could not size the ILS.
- The sample was not injected during separation and detection. The ANDE Expert System failed the sample because it could not detect the ILS.
- A microfluidic channel was blocked, preventing DNA processing.
- A DNA binding filter was torn, preventing DNA purification.
- Such failure modes are characteristic of the DNA processing system under study.

Figure 36:
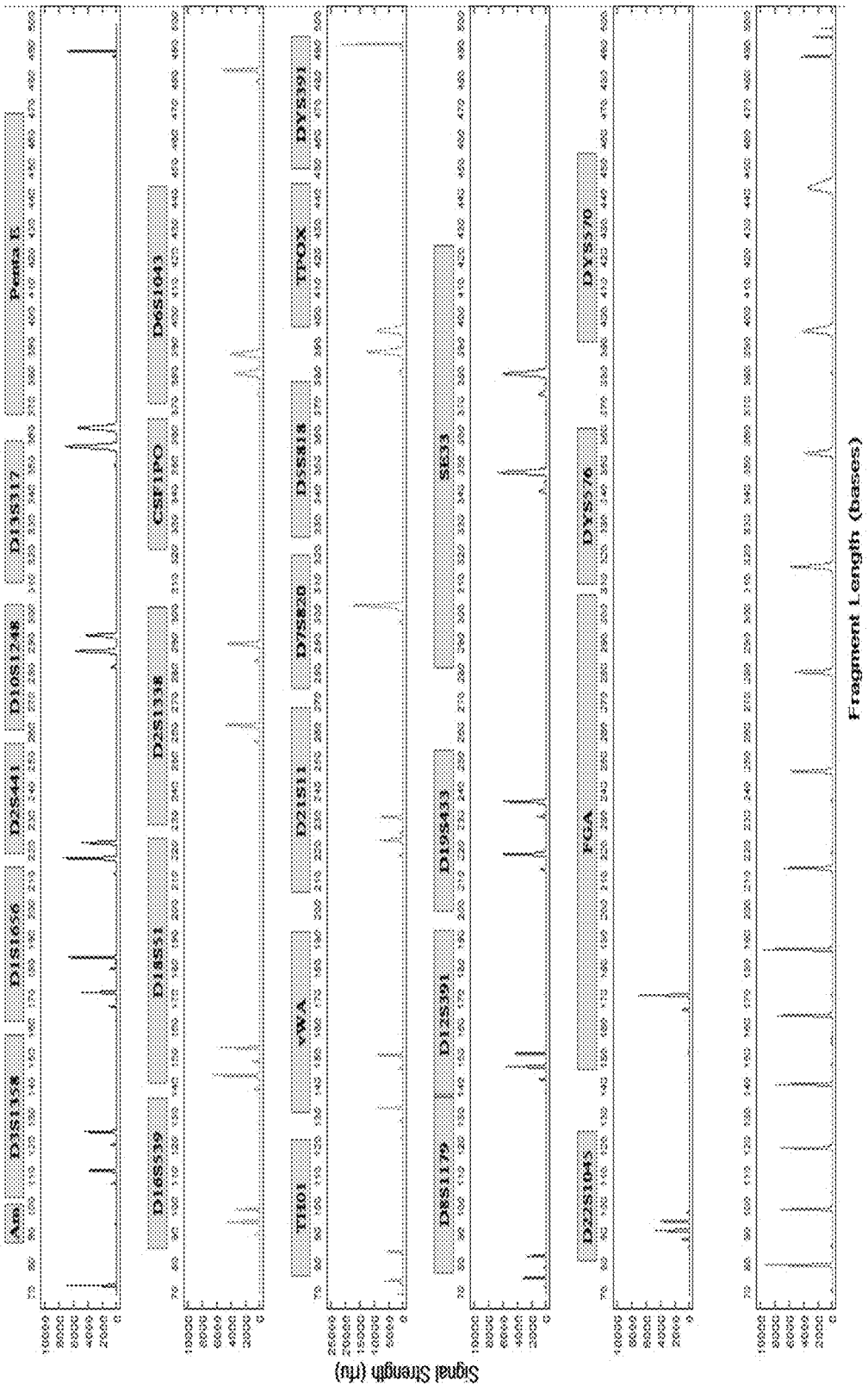
FIGS. 36 and 37 show example DNA IDs of failed samples.
Figure 37:
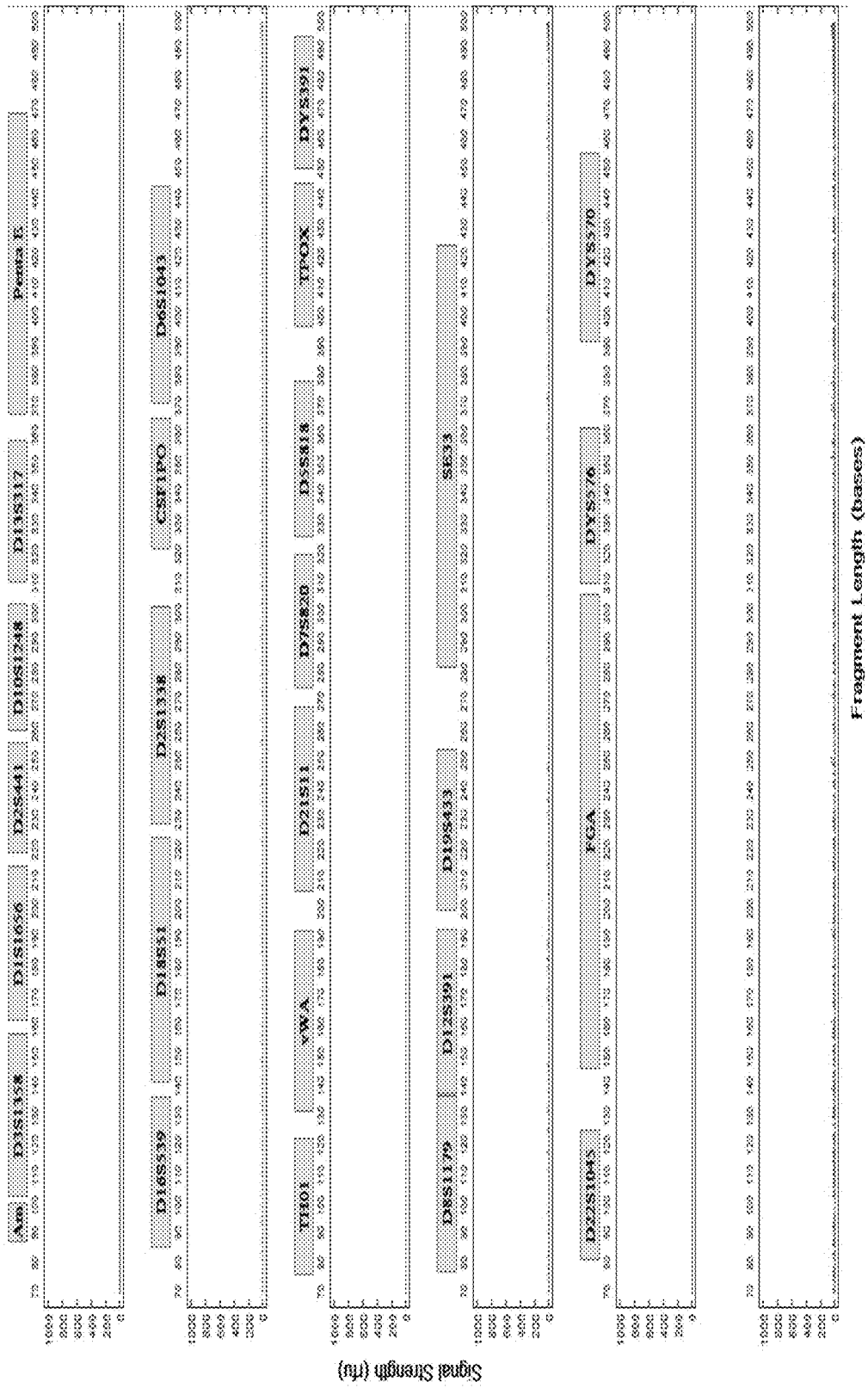

FIGS. 36 and 37 show example DNA IDs of failed samples of this classification.

Criteria defining DNA IDs with this classification are listed in the following Table 6:

TABLE 6

| | Parameter | Criteria |
|---|---|---|
| 1 | ILS condition | Fail |
| 2 | Number of CODIS 20 Loci called | N/A |
| 3 | Signal Strength | N/A |

TABLE 6-continued

| | Parameter | Criteria |
|---|---|---|
| 4 | Number of Loci with alleles with PH less than the PH threshold | N/A |
| 5 | Number of Loci with alleles with PH greater than PH min | N/A |
| 6 | Number of Loci with PHR of less than PHR threshold | N/A |
| 7 | Number of Loci with wide peaks and iNTAp | N/A |

In summary, DNA IDs generated by ANDE have been categorized into 6 classification and criteria for each classification has been defined. The definition of the phenotypical DNA ID categories above allows an AES parameter set to be used for each. These parameters have been established based on the dataset generated and tested by measuring alleles called and dropout/dropin appearance. The final parameter set selected generates the greatest number of called alleles while minimizing dropins and dropouts. This maximizes the utility of the DNA ID data, a major benefit of the instant invention.

A summary table of the DNA ID classification is shown in FIG. 38.

Figure 39:
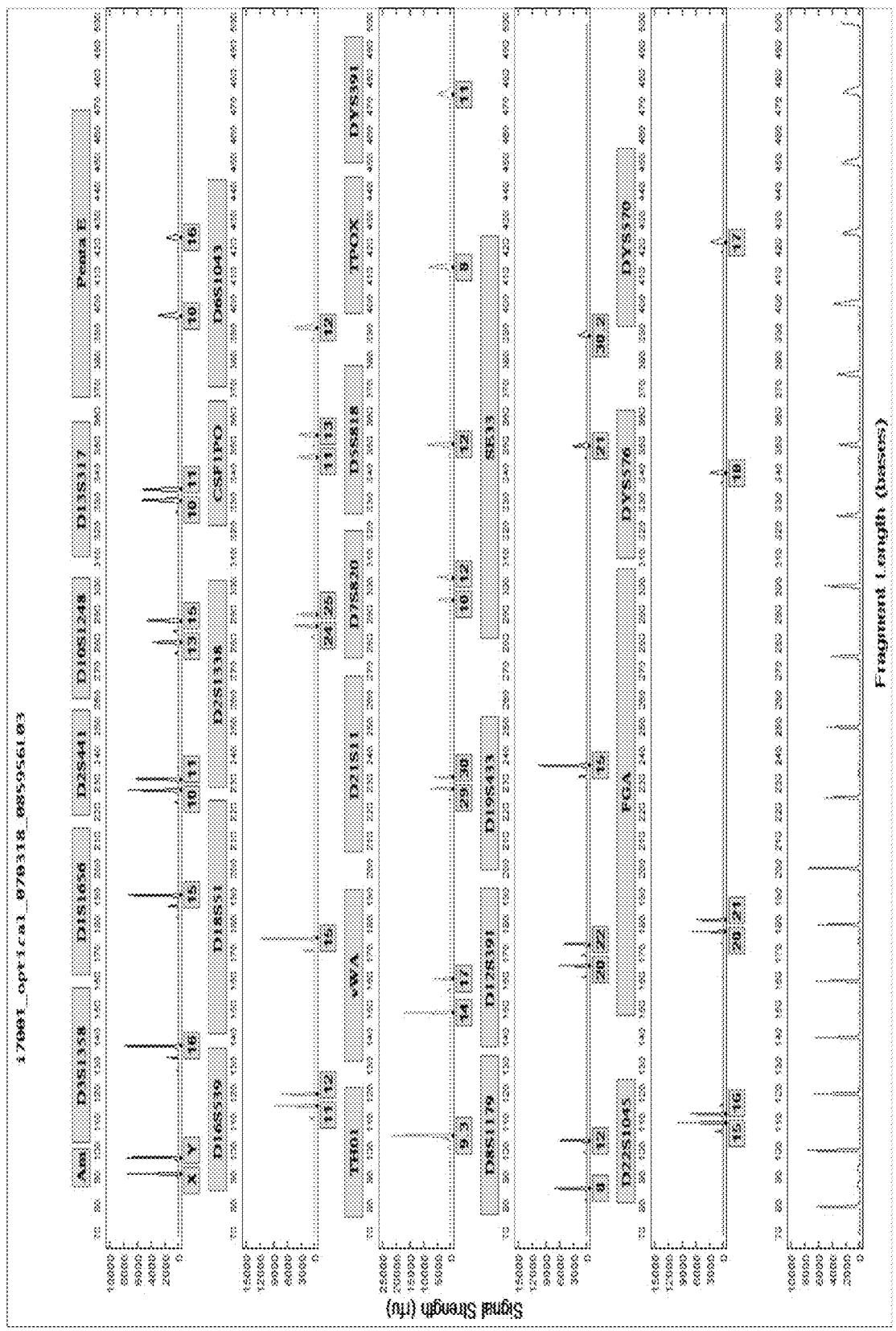
FIG. 39 shows the DNA ID of a passing sample.

The ANDE Expert system characterizes sample data to classify samples. These sample classifications can be helpful in providing feedback to the user. In many cases the user will not have a technical background or the ability to interpret an electropherogram, and providing these users with feedback based on AES analysis may be desirable. This feedback may be as simple as noting that processing is successfully completed, be related to a detain/release or match/no match finding, or be geared toward alerting the user to an issue with the results and contain instructions on recollecting a sample for another run. These classifications may be displayed to the user after a run has completed. The screen lists the samples that were processed including the sample ID, another sample identifier, and/or a chip lane number, and an icon or message representing the classification of the sample. Several icons and a description of each is as follows:

Green Checkmark Icon/description—This icon represents a passing sample was successfully processed. The condition for success is an agency or user defined number of called loci. When a sample meets or exceeds this threshold, the sample is considered a pass. The DNA ID of a passing sample is shown in FIG. 39. A measure of DNA ID quality may be incorporated in the feedback of this or any other icon/description. For example, the number of called loci, the presence of a rare allele, or the presence of a tri-allele may be indicated. Based on jurisdictional policies and the operational value of the sample, this feedback may lead to a repeat run of the sample, the collection of other samples, or other actions.

Figure 40:
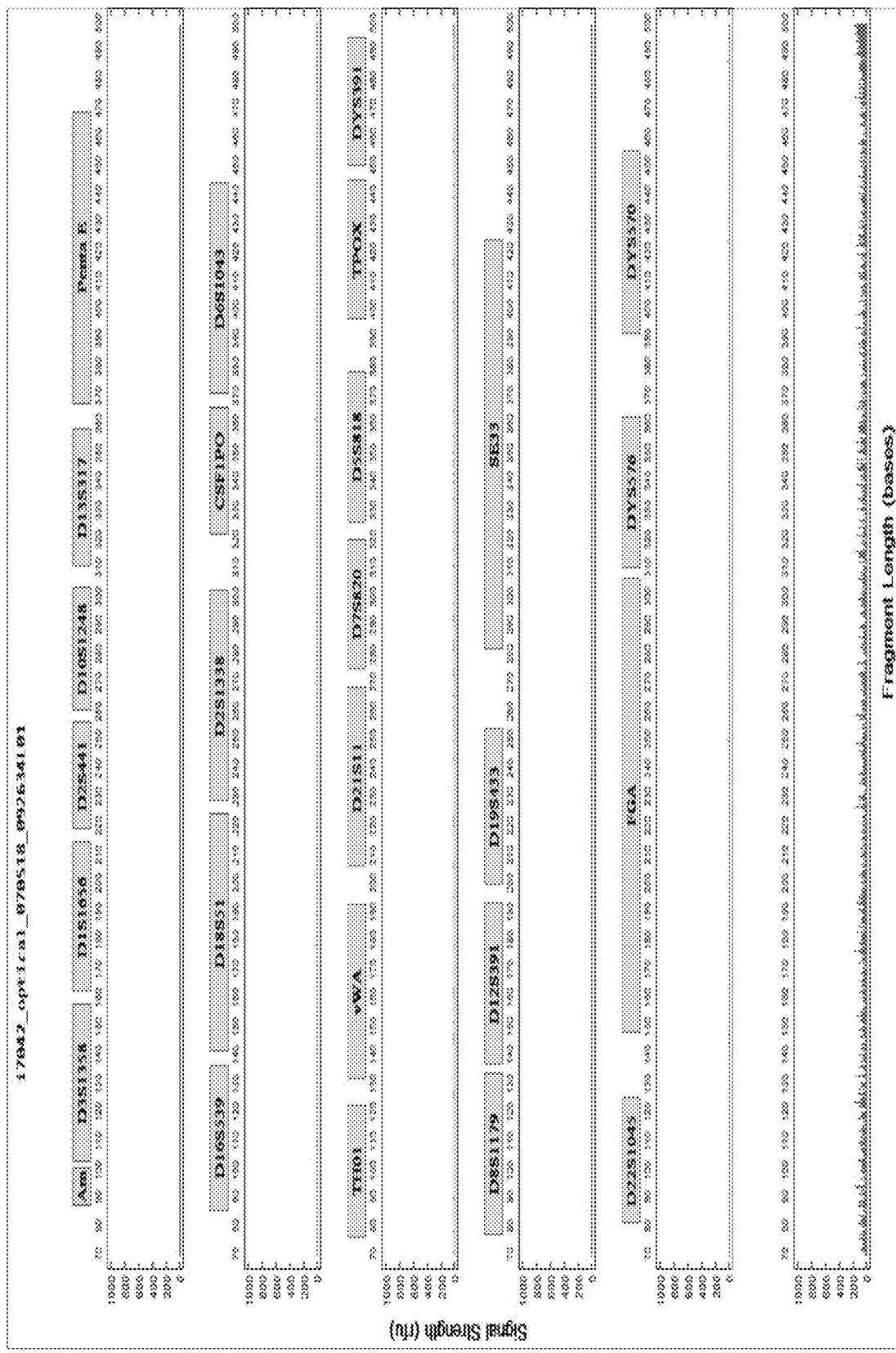
FIG. 40 shows the DNA ID of a sample that suffered from fluidic failure.

Fluidic Failure Icon/description—On occasions, a sample will fail because of microfluidic chip or lane failure. The ES identifies this class of sample data by the absence of a good set of ILS peaks. This feedback directs the user to recollect and reprocess this sample if possible. The DNA ID of a sample that suffered from fluidic failure is shown in FIG. 40.

Figure 41:
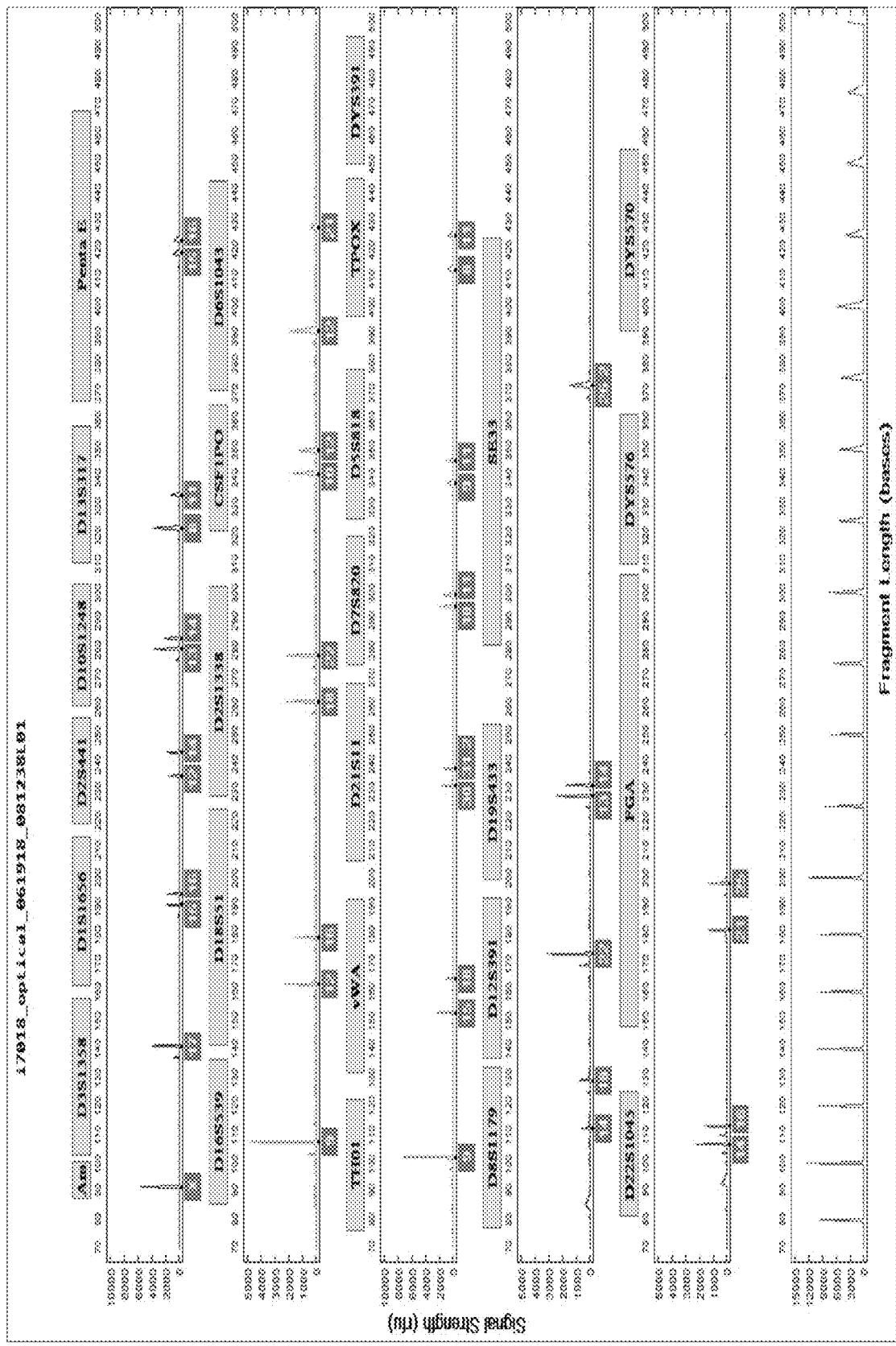
FIG. 41 shows the DNA ID of a low DNA content sample.

Low Sample Icon—A low signal sample is classified by having low signal strength, low peak height ratios, and all alleles that are labeled in red warning boxes. This feedback directs the user to recollect the sample (ideally obtaining a larger volume) and reprocess on the system. The DNA ID of a low DNA content sample is shown in FIG. 41.

Figure 42:
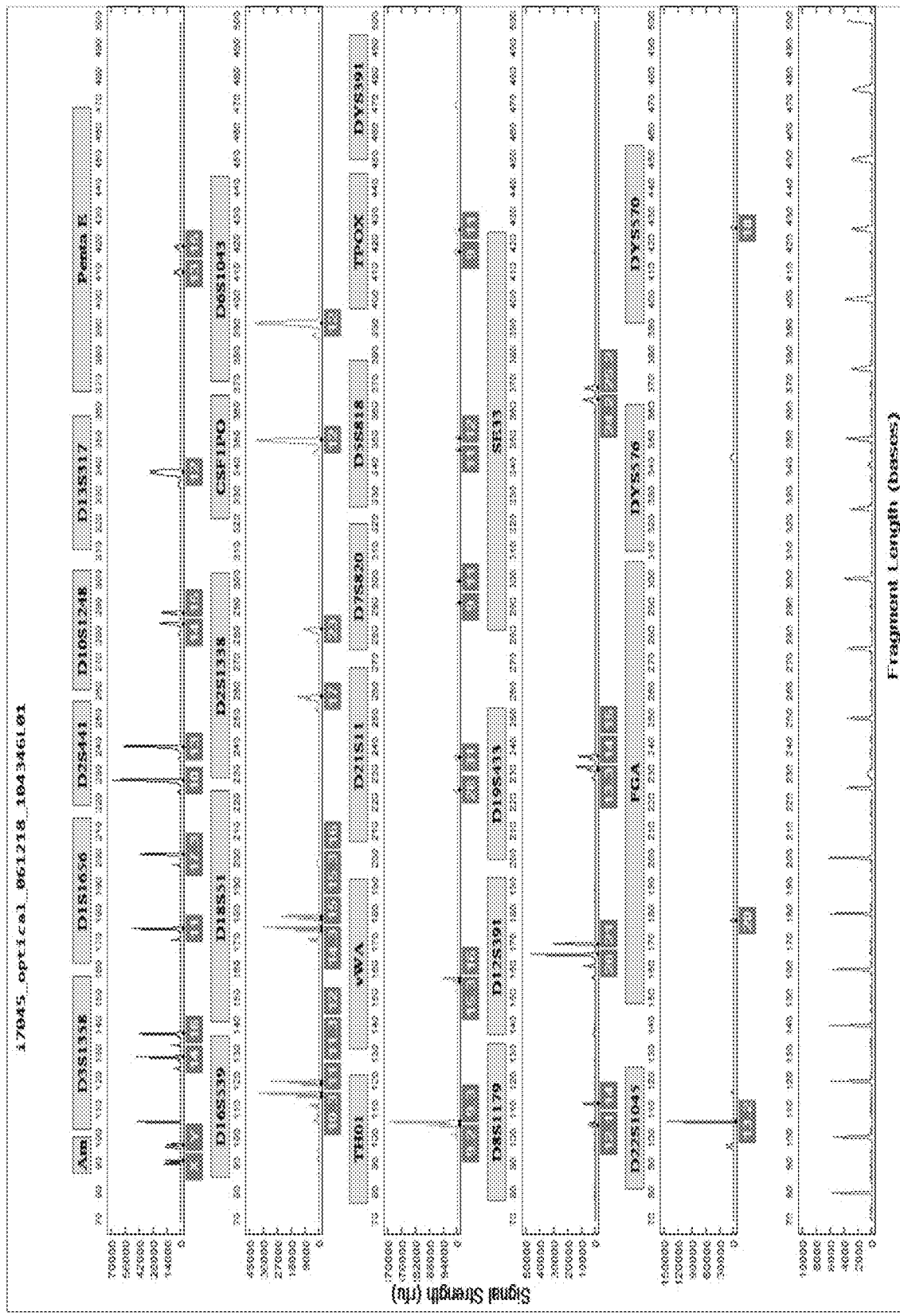
FIG. 42 shows the DNA ID of a high DNA content sample.

High Sample Icon/description—A high signal sample is classified by having signal strengths greater than 10,000 RFU, alleles with wide peaks, iNTA, and all alleles that are labeled in red warning boxes. This feedback directs the user to recollect the sample (preferably obtaining a smaller volume) and reprocess on the system. The DNA ID of a high DNA content sample is shown in FIG. 42.

Figure 43:
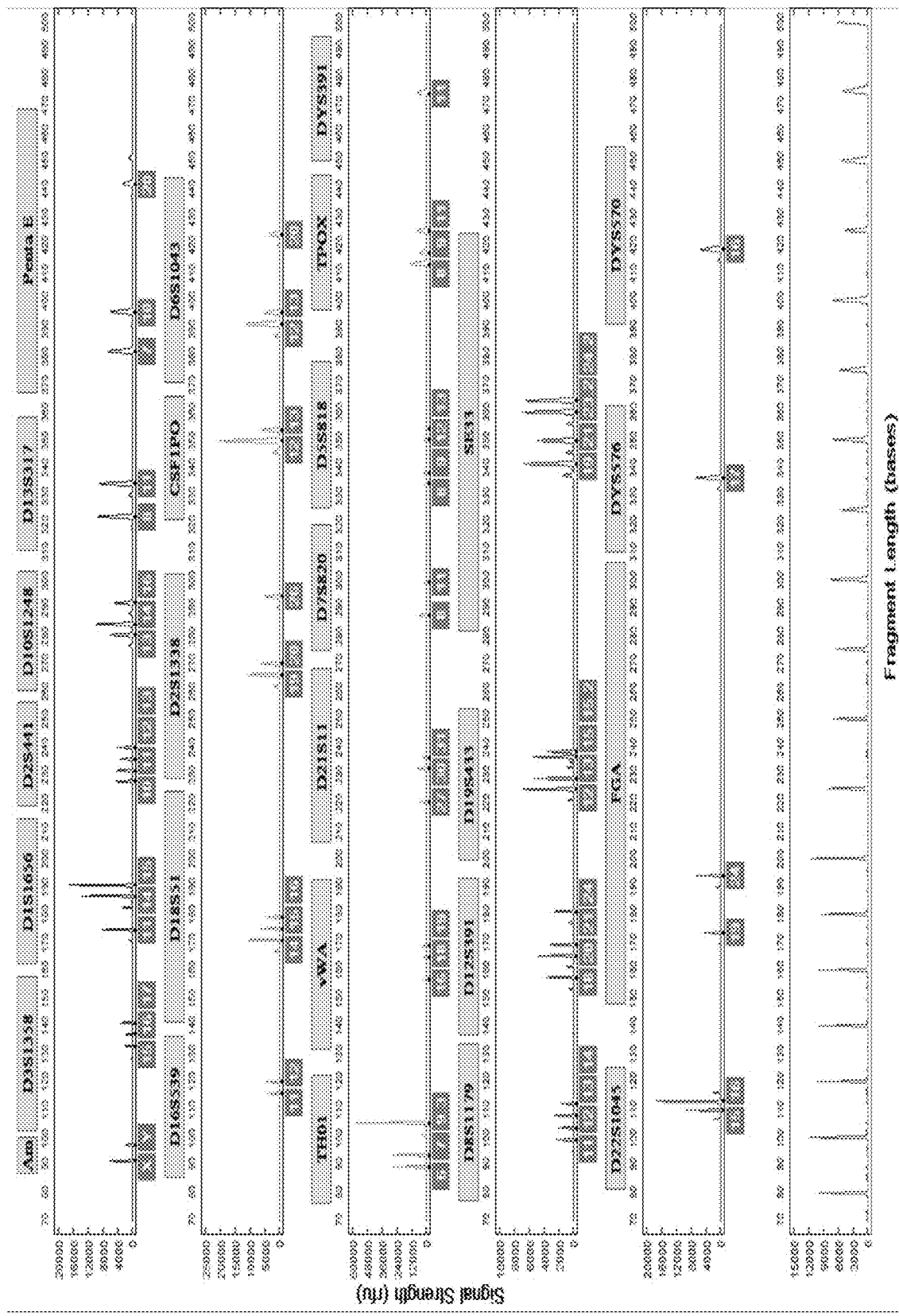
FIG. 43 shows the DNA ID of a mixture sample.

Mixture Icon/description—A mixture is classified by having more than one locus with four alleles in the locus or more than two loci with more than three alleles in the locus. This feedback directs the user to recollect the sample (preferably obtaining it from a smaller area than before to reduce the possibility of generating a mixture) and reprocess on the system. The DNA ID of a mixture sample is shown in FIG. 43.

Displaying the classification of samples to a user provides useful direction and feedback on the sample that has been processed. A major advantage of such feedback (preferably on a GUI screen) is that a non-technical user that cannot interpret DNA IDs is given clear direction on how to proceed. The number of sample classifications is not limited to the ones shown above. Additional sample classifications can be defined and new icons can be associated with each of these classifications. As an example, for a Claimed relationship application or DNA ID matching application, classes that can be displayed to the user include:

Relative—to indicate that the claimed relationship of the sample donors has been confirmed based on agency-defined limits, Match—to indicate that the sample matches with another sample in the database, No Match—to indicate that the sample does not match with another sample in the database.

Example 5. Establishing the AES Parameter Sets

Figure 44:
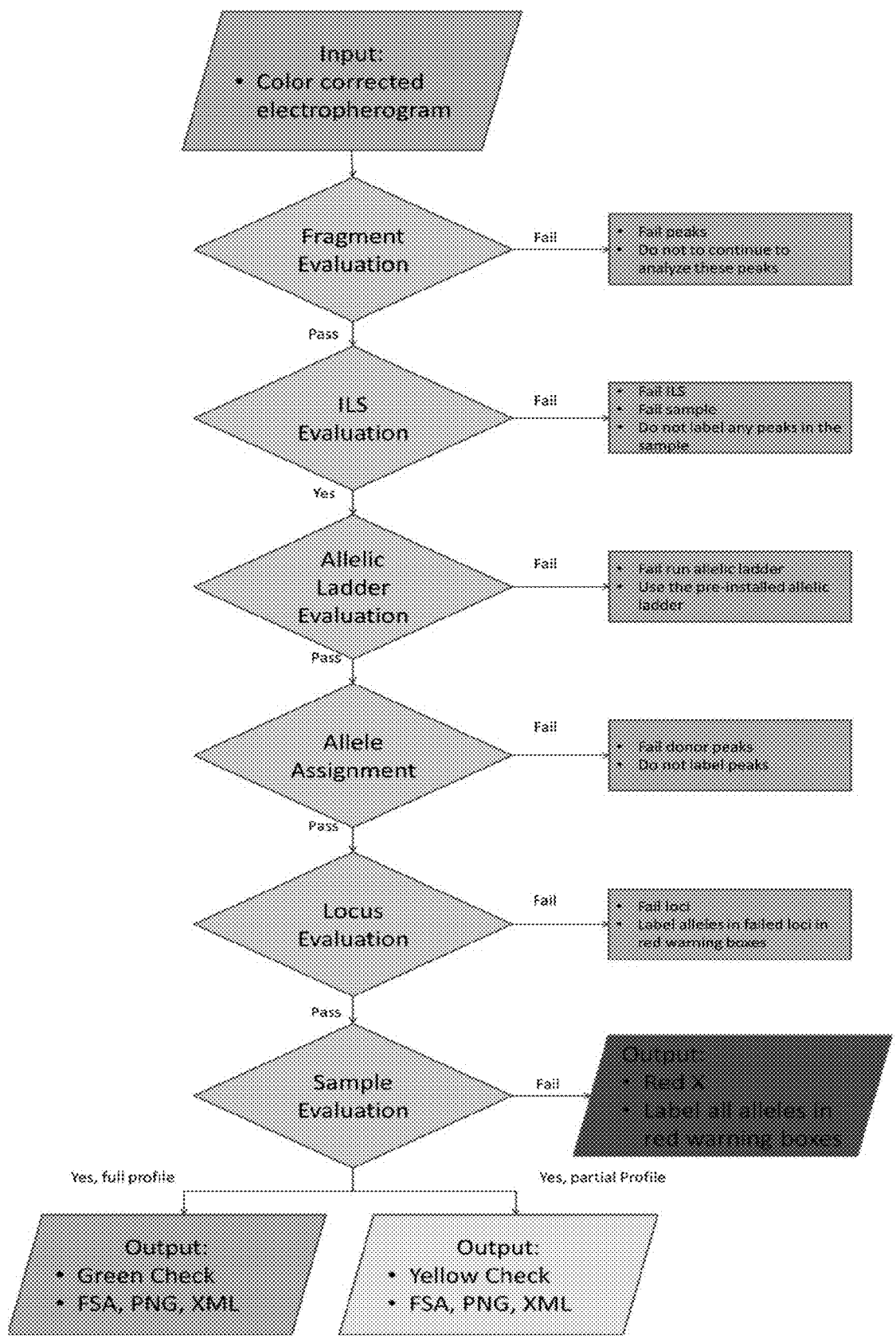
FIG. 44 is a flowchart showing how the ANDE Expert System processes raw data stepwise through a series of modules to generate a DNA ID.

In order to design the AES properly, it was important to take the ANDE Standard Expert System rules into account. The ANDE Expert System is integrated with the instrument and automatically processes raw data that is generated during separation and detection. In ANDE, optical data is automatically transferred to the onboard Expert System Software (which is housed within the onboard ANDE CPU; note that the Expert System Software need not reside onboard). For passing samples, the Standard Expert System will generate an electropherogram, .xml file, allele table, and an .FSA file. For failing samples, the Standard Expert system will only generate an electropherogram and an .FSA file. The ANDE Expert System processes raw data stepwise through a series of modules to generate a DNA ID (FIG. 44):

1) Fragment evaluation Rules—This module identifies peaks in the electropherogram that meet the minimum requirements for processing.

Peaks must have a height greater than the peak height minimum ($PH_{min}$).

Peaks must have signal to noise ratios greater than the threshold.

Peaks must have widths greater than 2 points.

Peaks that meet the minimum requirement are sorted into three candidate classes: ILS, allelelic ladder, and alleles based on color.

2) ILS evaluation—This module identifies and evaluates ILS peaks. ILS that pass the minimum requirements are used for sizing donor peaks with the Local Southern method. Samples with failed ILS peaks are rejected and not subjected to further analysis.

3) Allelic ladder evaluation—This module identifies and evaluates allelic ladder peaks. Run allelic ladders that meet the minimum requirements are used to define calling bins for designating donor alleles. An instrument specific pre-installed ladder is used to define calling bins when the run allelic ladder fails.

4) Allele Assignment—This module assigns peaks to a locus and alleles.

Figure 45:
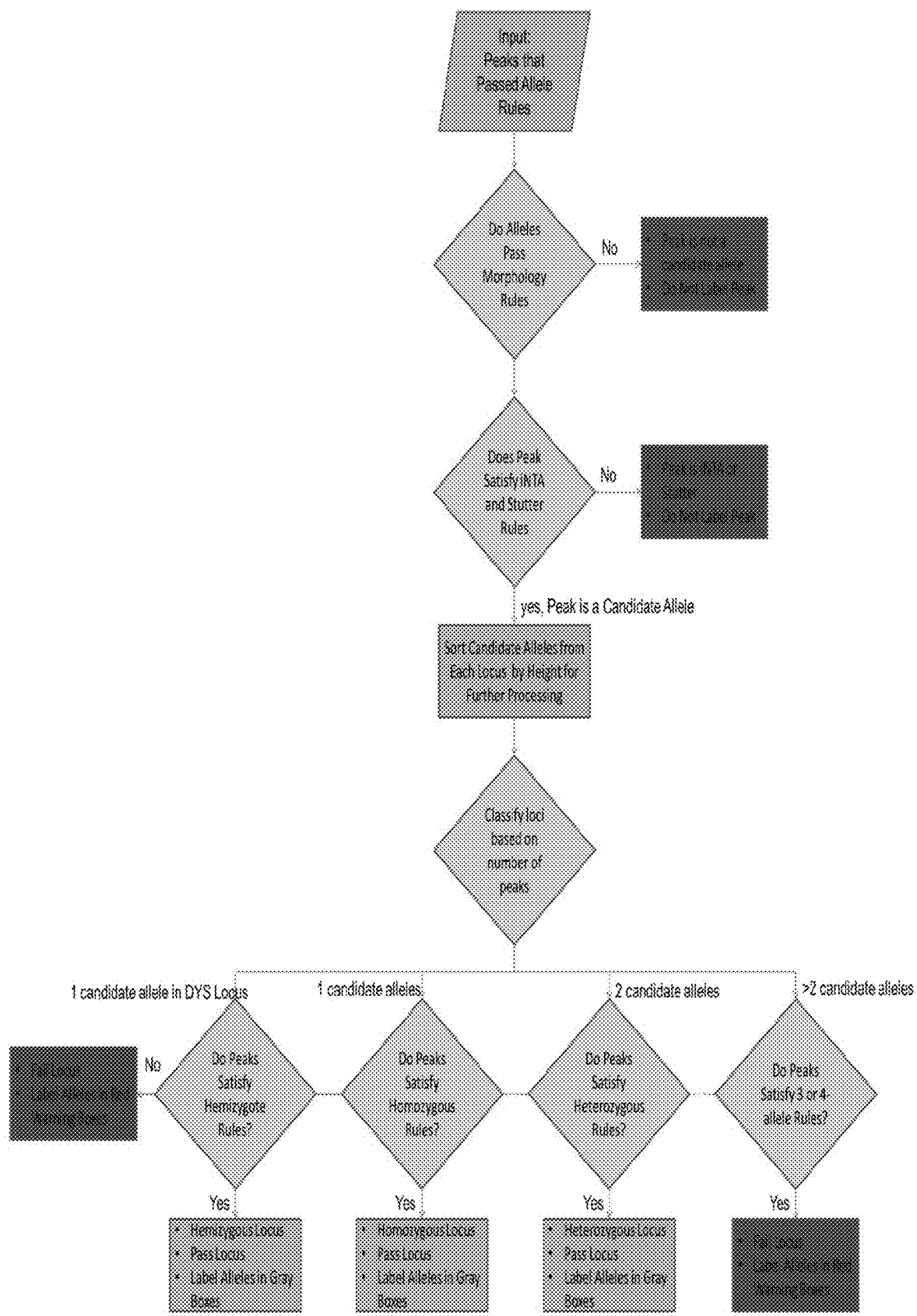
FIG. 45 is a flowchart of the locus evaluation module processes.

5) Locus Evaluation Rules—This module evaluates loci for the Hemizygote, Homozygote, or Homozygote requirements. Loci that meet the requirements are called. Loci that fail, including ones with three or more alleles, are labeled in red warning boxes. FIG. 45 shows the locus evaluation module processes as follows:

Assess peaks meet the requirements for morphology. Peaks that pass are subjected to further analysis. Peaks that failed are not labeled.

Identify and classify peaks as iNTA and stutter peaks using fragment size, and peak height ratios. Stutter and iNTA peaks are not labeled or further processed.

Identify and classify hemizygous loci as DYS loci with one peak with peak height greater than the calling threshold. In these loci, the peak is called and labeled with a gray box.

Identify and classify homozygous loci as loci with a main peak with a peak height that exceeds the calling threshold, and all other peaks within the loci having a peak height ratio less than the threshold.

Heterozygote loci as loci with two peaks with peak heights that are greater than the calling threshold, and a peak height ratio greater than the threshold.

All loci that do not pass the Hemizygote, Homozygote, and Heterozygote rules are labeled in red.

Figure 46:
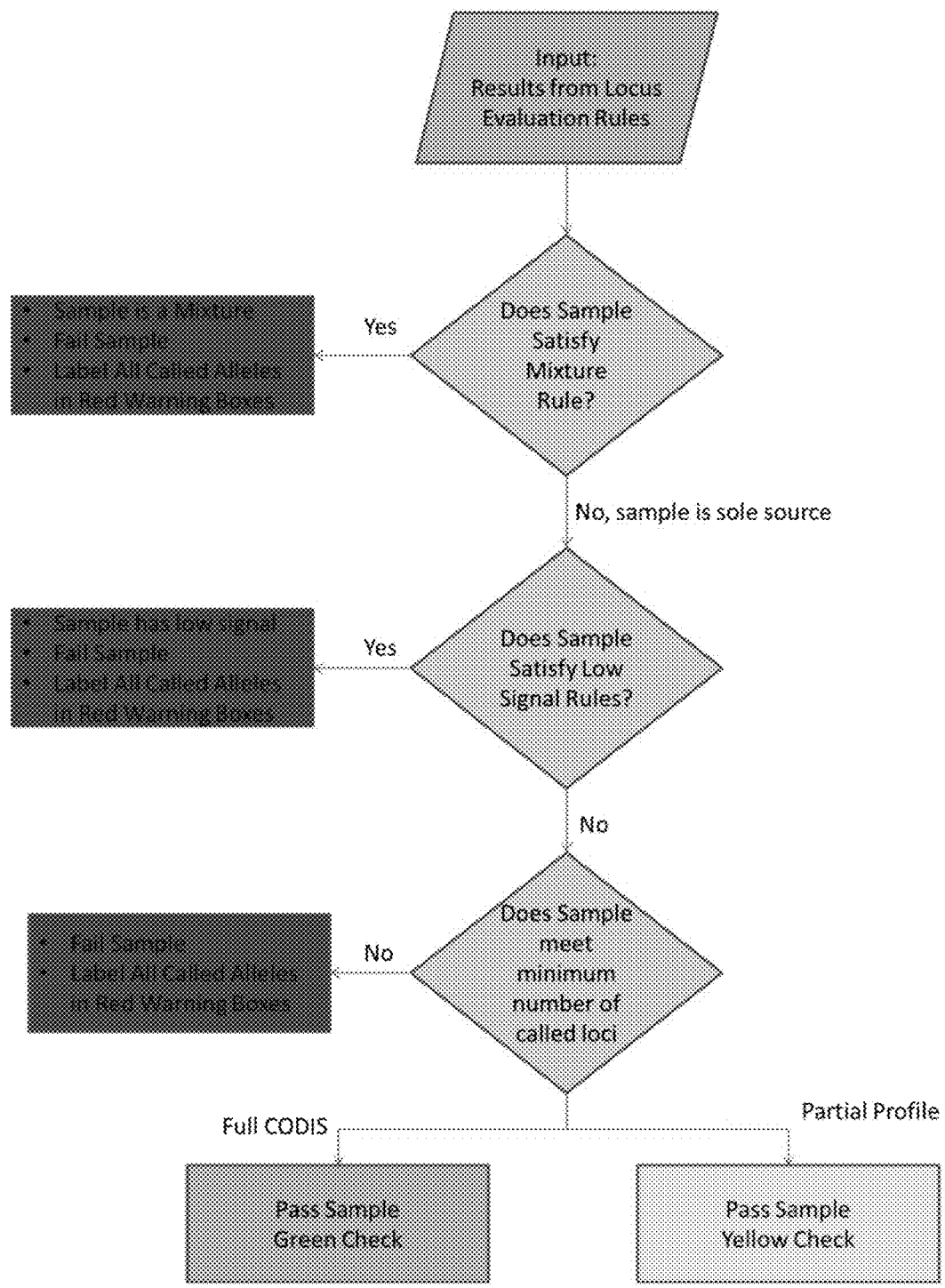
FIG. 46 is a flowchart of the sample protection rules.

6) Sample Evaluation Rules—This module evaluates samples for mixtures, low signal, and minimum number of CODIS loci. The sample protection rules were developed to conservatively call single source buccal samples and are applied as follows (FIG. 46):

The low signal protection rule is applied to samples run with the HDC BioChipSet. For these samples, homozygote loci are labeled in red warning boxes when the peak heights of less than the protection peak height threshold.

The mixture protection rule identifies mixtures as ones with least two loci with three alleles or at least one locus with one allele is identified. Samples identified as mixtures will have all loci labeled in red warning boxes.

The minimum number of CODIS loci rule will fail a sample and label all loci in red warning boxes if the number of CODIS loci is less than the minimum required.

Figure 47C:
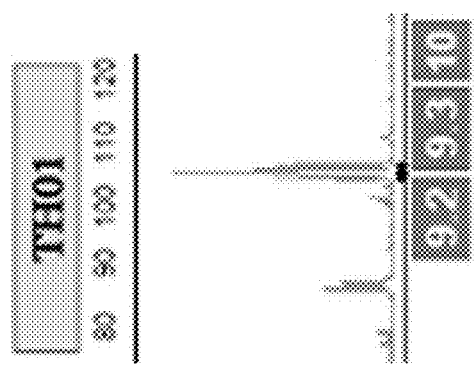
FIG. 47c shows for heterozygous loci where the two alleles are 1 base apart, the high iNTA results in three peaks being identified as alleles.
Figure 47B:
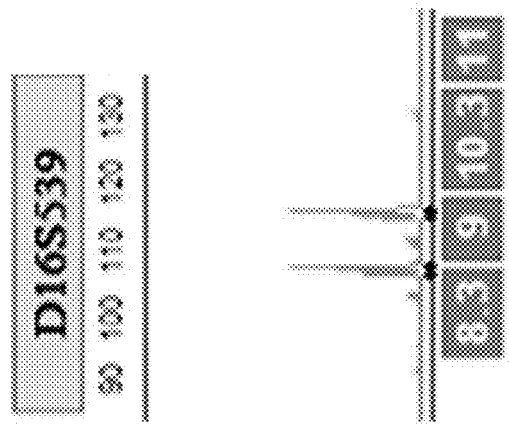
FIG. 47b shows for heterozygous loci where the two alleles are separated by more than 1 base apart, the high iNTA results in the four peaks being identified as alleles.
Figure 47A:
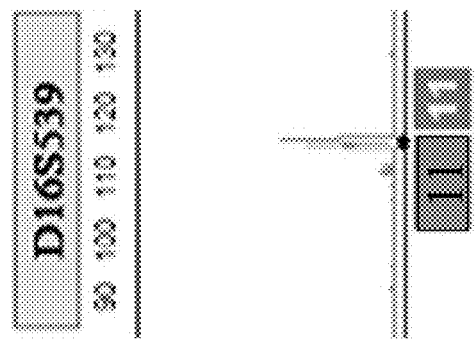
FIG. 47a shows for homozygous loci, the high iNTA results in two peaks that are separated by 1 base as being identified as alleles.

When samples with DNA content above the dynamic range of the system are processed, the iNTA peaks for the allele can have iNTA peak height ratios greater than the threshold. The Standard Expert System treats these cases as follows:

For homozygous loci—the high iNTA results in two peaks that are separated by 1 base as being identified as alleles. The alleles are labeled in red warning boxes and the locus fails. (see FIG. 47a).

For heterozygous loci where the two alleles are separated by more than 1 base apart—the high iNTA results in the four peaks being identified as alleles. The alleles are labeled in red warning boxes and the locus fails. (see FIG. 47b).

For heterozygous loci where the two alleles are 1 base apart—the high iNTA results in three peaks being identified as alleles. The alleles are labeled in red warning boxes and the locus fails. (see FIG. 47c).

High DNA content samples are also optionally processed with a "peak quantification module." In this scenario, the primary detector signals for peak are saturated and a flat top is observed. This module uses unsaturated optical data of the peak (from a secondary detector) to generate the signals of the primary detector in the saturated portion of the peak. This module works with the following algorithm:

Detect and store the signal strengths and positions of the saturated and unsaturated portions of the optical detector signals (the optical signal is saturated when it the signals returned a value is the maximum for the detector (in the ANDE system, this value is 262,144) for the primary detector.

Detect and store the signal strengths and positions of the secondary detector signals for the peak. The secondary detectors for this peak are maximized for detection at a different fluorescent wavelength, and do not saturate.

Calculate the "Primary/Secondary detector signal strength ratio" defined as the ratio of the primary peak over the secondary peak across the entire peak and store this value in the portions of the peak where the primary detector is not saturated.

In the region where the peak is saturated, use the calculated "Primary/Secondary detector signal strength ratio" to calculate the signal strength of the primary. This is done by dividing the signal strength of the secondary peak by the "Primary/secondary detector signal strength ratio."

The use of this module will result in the optical signal of the primary detector that is no longer saturated and are quantified at the signal levels as if the optical signals of the primary detector were not saturated. This approach can be utilized with two or more, 4 or more, 5 or more, 6 or more, 8 or more, 12 or more, 16 or more, 32 or more, 64 or more, 128 or more, or 256 or more detectors. Linear array detectors consisting of two or more, 4 or more, 5 or more, 6 or more, 8 or more, 12 or more, 16 or more, 32 or more, 64 or more, 128 or more, or 256 or more detector elements can be used in place of discreet detectors.

A "high iNTA module" was developed to accommodate cases when the DNA content of the sample exceeds the dynamic range of the system and iNTA levels above the threshold are observed. One approach to identifying the presence of a high iNTA sample is the use of the iNTA Peak Height Ratio in AM. The extensive dataset that was generated allowed us to observe that the iNTA ration of AM is a strong and reliable indicator for samples with potentially high iNTA. Although AM is used, other loci and alternative conditions can also be applied to identify potentially high iNTA samples.

Figure 48D:
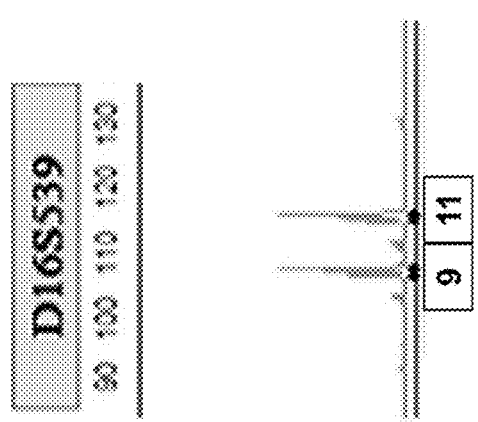
FIG. 48d shows four peaks spaced one base apart with Peak heights greater than the calling threshold, and the second and fourth peaks have a PHR greater than the iNTA threshold.
Figure 48C:
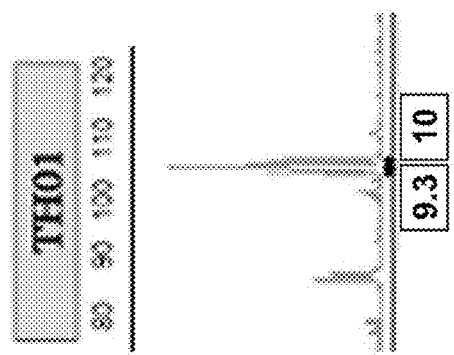
FIG. 48c shows three peaks spaced one base apart with Peak heights greater than the calling threshold and the peaks are separated by 1 base.
Figure 48B:
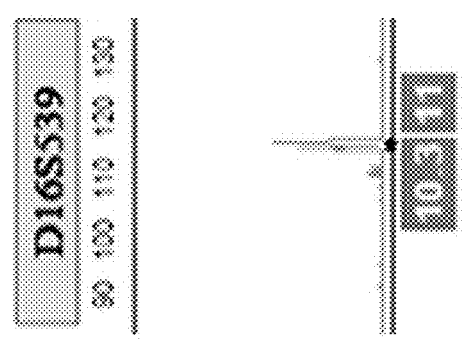
FIG. 48b shows two peaks spaced one base apart with peak heights greater than the calling threshold, and the second peak has a PHR greater than the iNTA threshold.
Figure 48A:
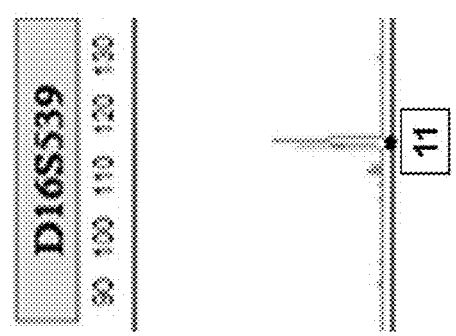
FIG. 48a shows two peaks spaced one base apart with peak heights greater than the calling threshold, and the second peak has a PHR greater than the iNTA threshold.

When this module is turned on and when samples with potentially high iNTA are identified (for example using the iNTA PHR of AM), iNTA that is observed in a locus is treated as follows (FIGS. 48a to 48d):

When two peaks spaced one base apart with peak heights greater than the calling threshold are observed, and the second peak has a PHR greater than the iNTA threshold, do not label the second peak (see FIG. 48a).

An alternative and more conservative treatment of the two peak scenario (above) is applied as follows: When two peaks spaced one base apart with peak heights greater than the calling threshold are observed, and the second peak has a PHR greater than the iNTA threshold, label both peaks in red warning boxes. This treatment is applied to prevent the dropout of the small fragment size of two alleles that are separated by 1 base (see FIG. 48b).

When three peaks spaced one base apart with Peak heights greater than the calling threshold and the peaks are separated by 1 base are observed, and the third peak has a PHR greater than the iNTA threshold, do not label the third peak (see FIG. 48c).

When four peaks spaced one base apart with Peak heights greater than the calling threshold are observed, and the second and fourth peaks have a PHR greater than the iNTA threshold, do not label the second and fourth peaks. (see FIG. 48d).

Figure 49:
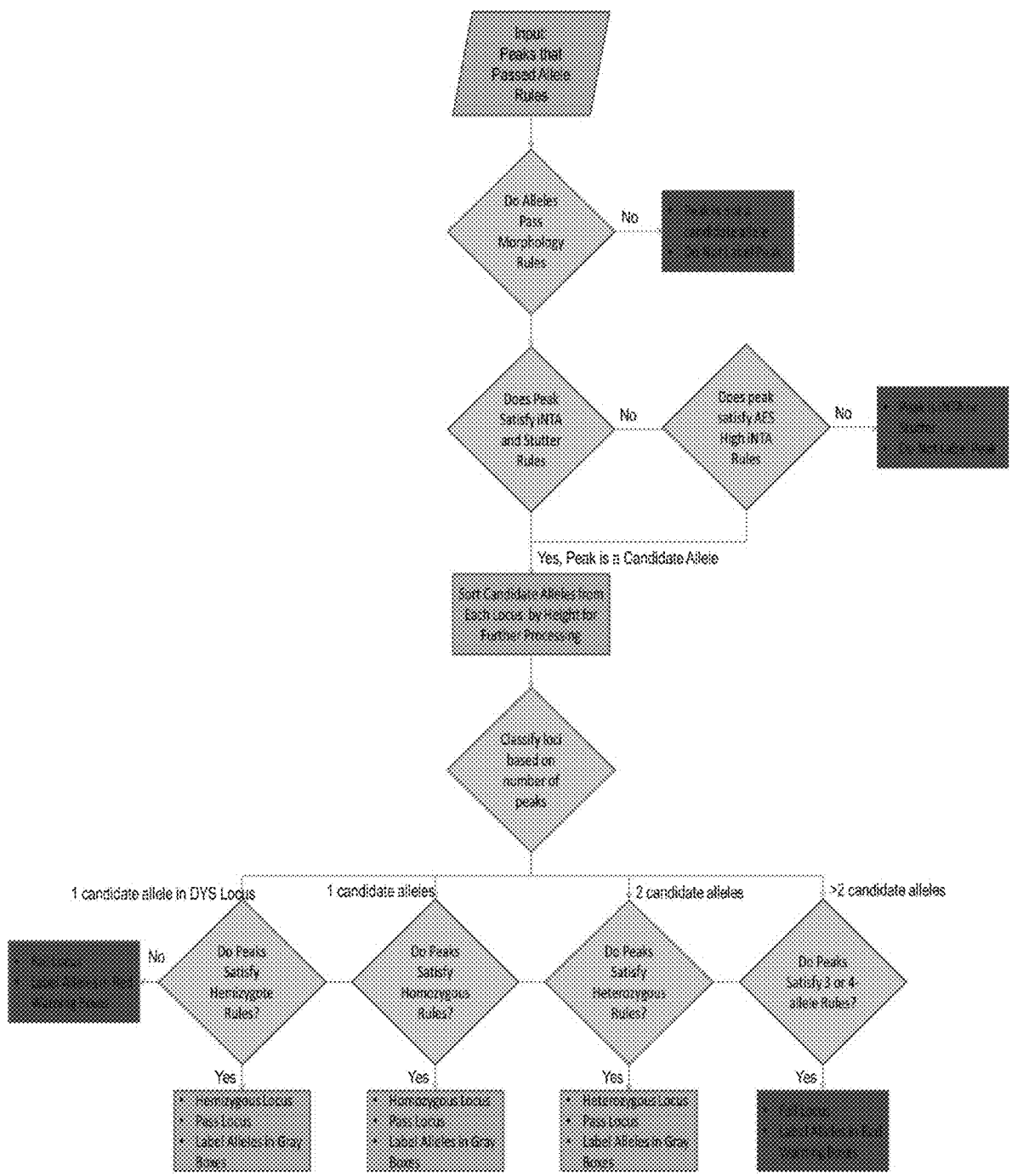
FIG. 49 is a flowchart for the iNTA module.

This flowchart for the iNTA module is shown in FIG. 49. Application of AES Parameters Sets to Various Classes of Sample Data.

Several AES parameter sets were developed for each of the DNA ID classes listed above. These parameter sets were developed by testing the effect of each change to the number of alleles called and the number of drop-outs and drop-in observed. An optimal parameter set is established when the number of alleles called is maximized and drop-outs and drop-ins are minimized. Drop-outs are heterozygote loci where only one of the two alleles is called and the other is unlabeled. Drop-ins are loci where an allele not belonging to a single-source donor is called. The AES parameters for each of the DNA ID classifications is as follows:

Intermediate Signal Strength Samples—These samples have a passing ILS and twenty CODIS 20 core loci called. These are successful samples using a standard expert system parameter set and do not require further processed with the AES. The ES parameter set shown below is for the standard A-Chip and I-Chip process. Rows 10 and 11 show the difference between the standard A-Chip ES parameter set (Table 7) compared with the standard I-Chip parameter set (Table 8):

TABLE 7

Standard A-Chip calling parameter set.

| | Parameter | Value |
|---|---|---|
| 1 | Peak height minimum threshold | 150 |
| 2 | Peak width parameter threshold | 0.044 |
| 3 | Heterozygote peak height threshold | 500 |
| 4 | Heterozygote peak height ratio | 0.35 |
| 5 | Homozygote peak height threshold | 600 |
| 6 | Homozygote peak height ratio threshold | 0.24 |
| 7 | Hemizygote peak height threshold | 650 |
| 8 | High iNTA rule | Off |
| 9 | Mixture sample protection rule | On |
| 10 | Low signal sample protection rule | On |
| 11 | Minimum number of called loci to generate a CMF file | 10 |

TABLE 8

Standard I-Chip calling parameter set.

| | Parameter | Value |
|---|---|---|
| 1 | Peak height minimum threshold | 150 |
| 2 | Peak width parameter threshold | 0.044 |
| 3 | Heterozygote peak height threshold | 500 |
| 4 | Heterozygote peak height ratio | 0.35 |
| 5 | Homozygote peak height threshold | 600 |
| 6 | Homozygote peak height ratio threshold | 0.24 |
| 7 | Hemizygote peak height threshold | 650 |
| 8 | High iNTA rule | Off |
| 9 | Mixture sample protection rule | On |
| 10 | Low signal sample protection rule | Off |
| 11 | Minimum number of called loci to generate a CMF file | 2 |

High Signal Strength Samples with wide peaks and iNTA—These samples have a passing ILS but have less than twenty of the CODIS 20 core loci called. Alleles are unlabeled because they fail for peak morphology or are labeled in red because high iNTA peaks are called as alleles. Additional alleles will be called when these samples are processed with the AES parameter set shown in Table 9 below.

Figure 50:
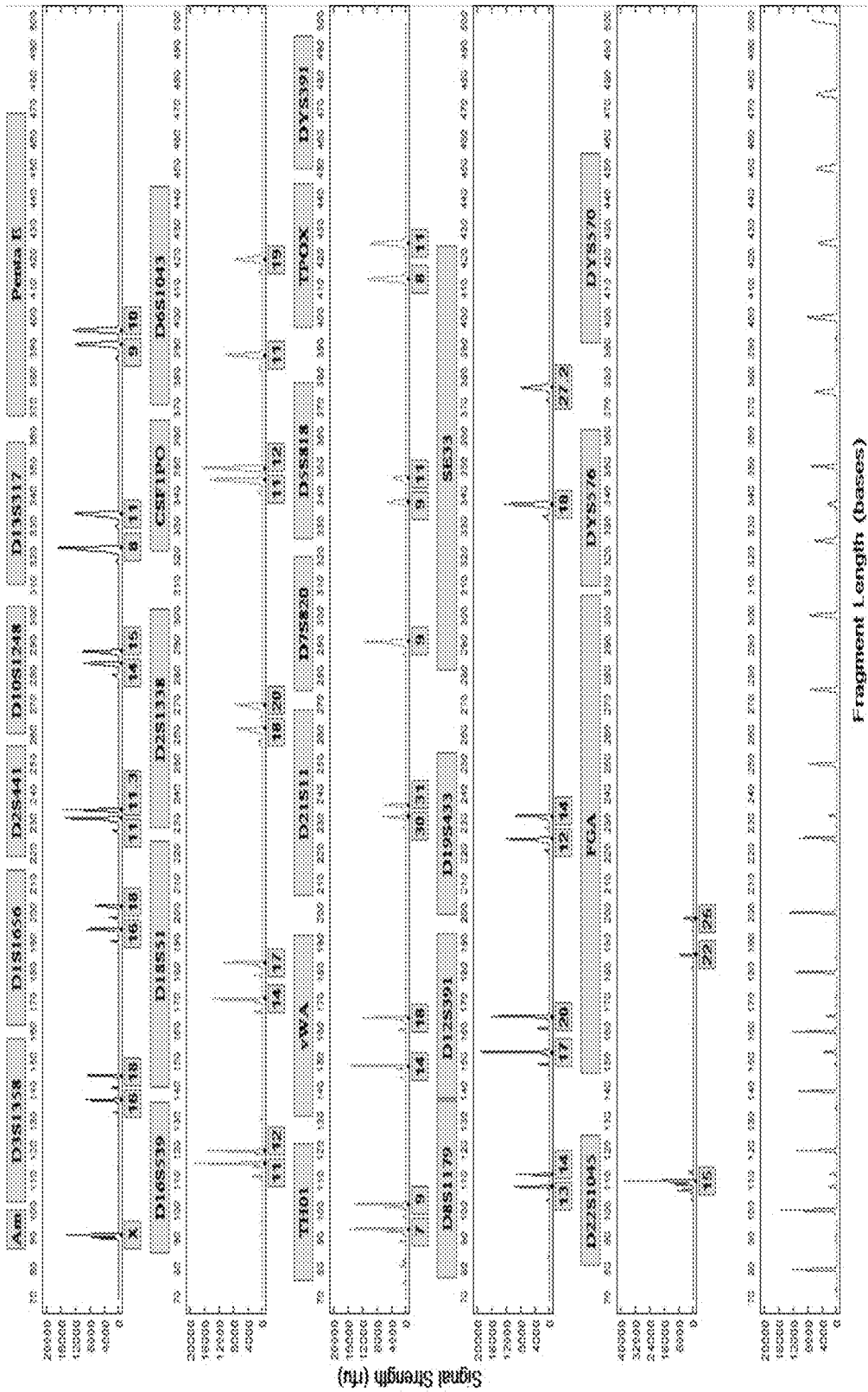
FIGS. 50 and 51 show DNA IDs for a sample with high signal strength called with standard A-Chip and AES parameter sets.
Figure 51:
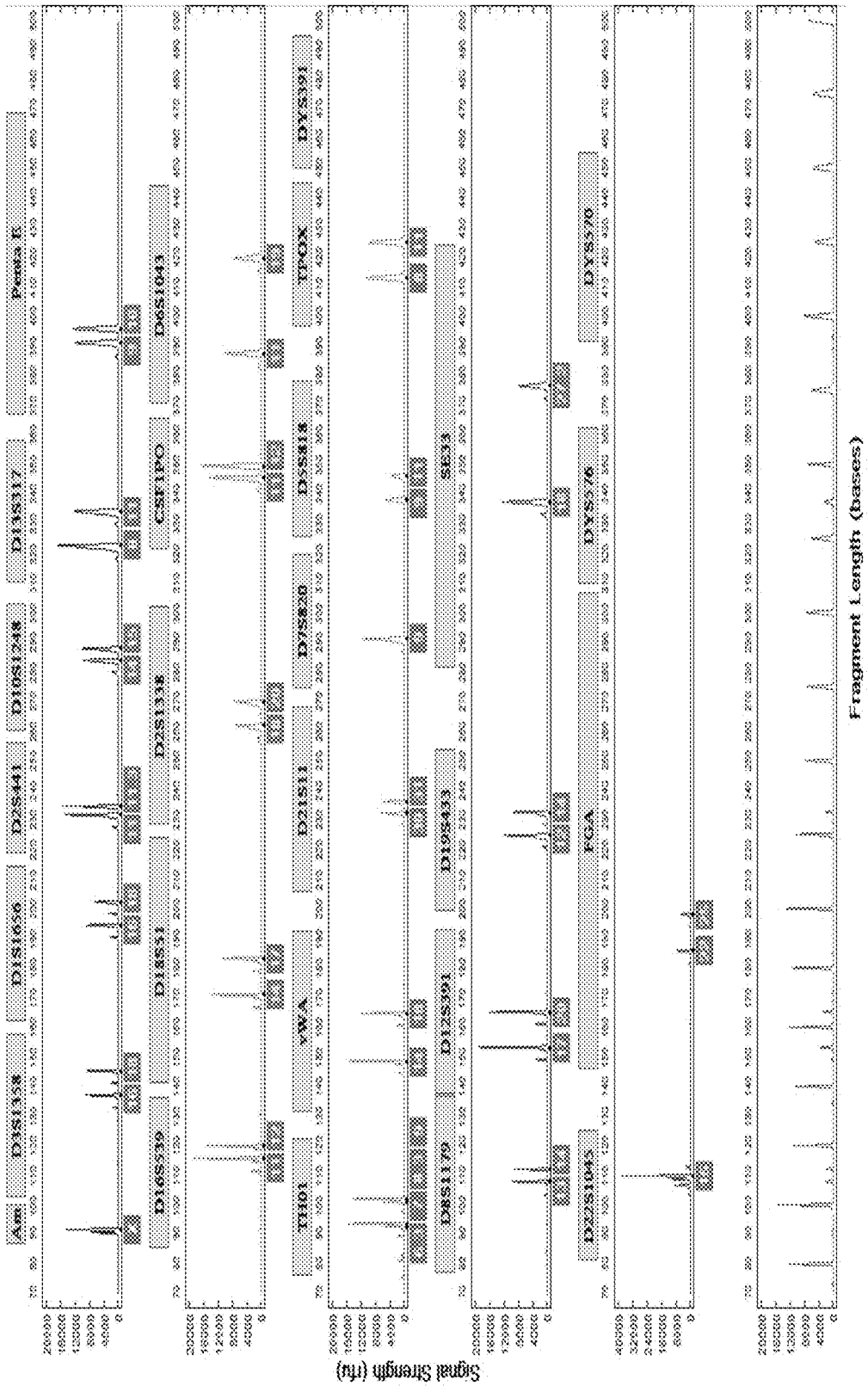

DNA IDs for a sample with high signal strength called with standard A-Chip and AES parameter sets are shown in FIGS. 50 and 51. The AES parameters allow alleles in Th01, with high iNTA, to be called properly. A full DNA ID is generated. Note that the identical raw data is utilized—the application of the appropriate parameter set extracts much more data from the data, a major benefit of the instant invention.

Figure 52:
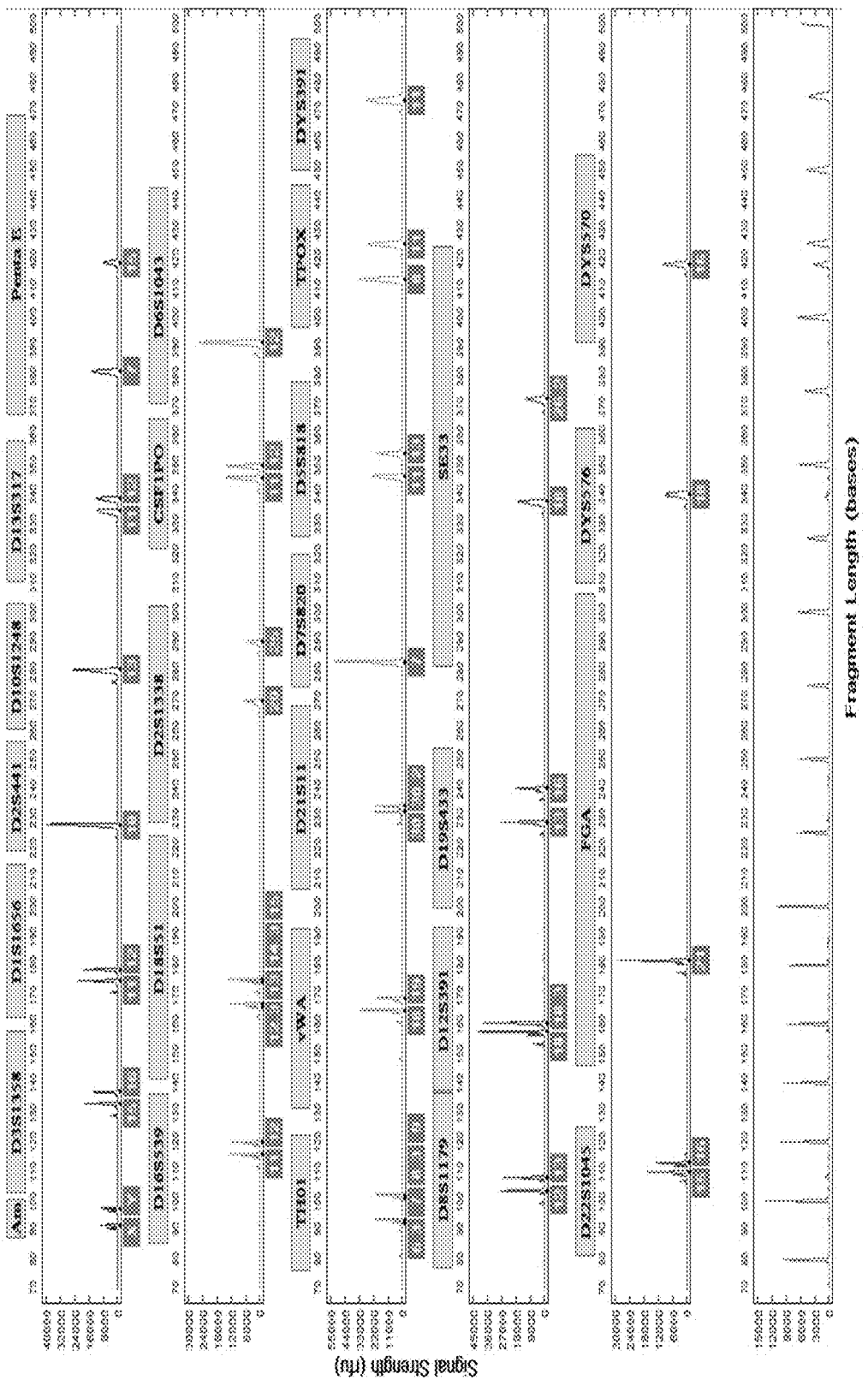
FIGS. 52 and 53 show DNA IDs for another sample with high signal strength called with standard A-Chip and AES parameter sets.
Figure 53:
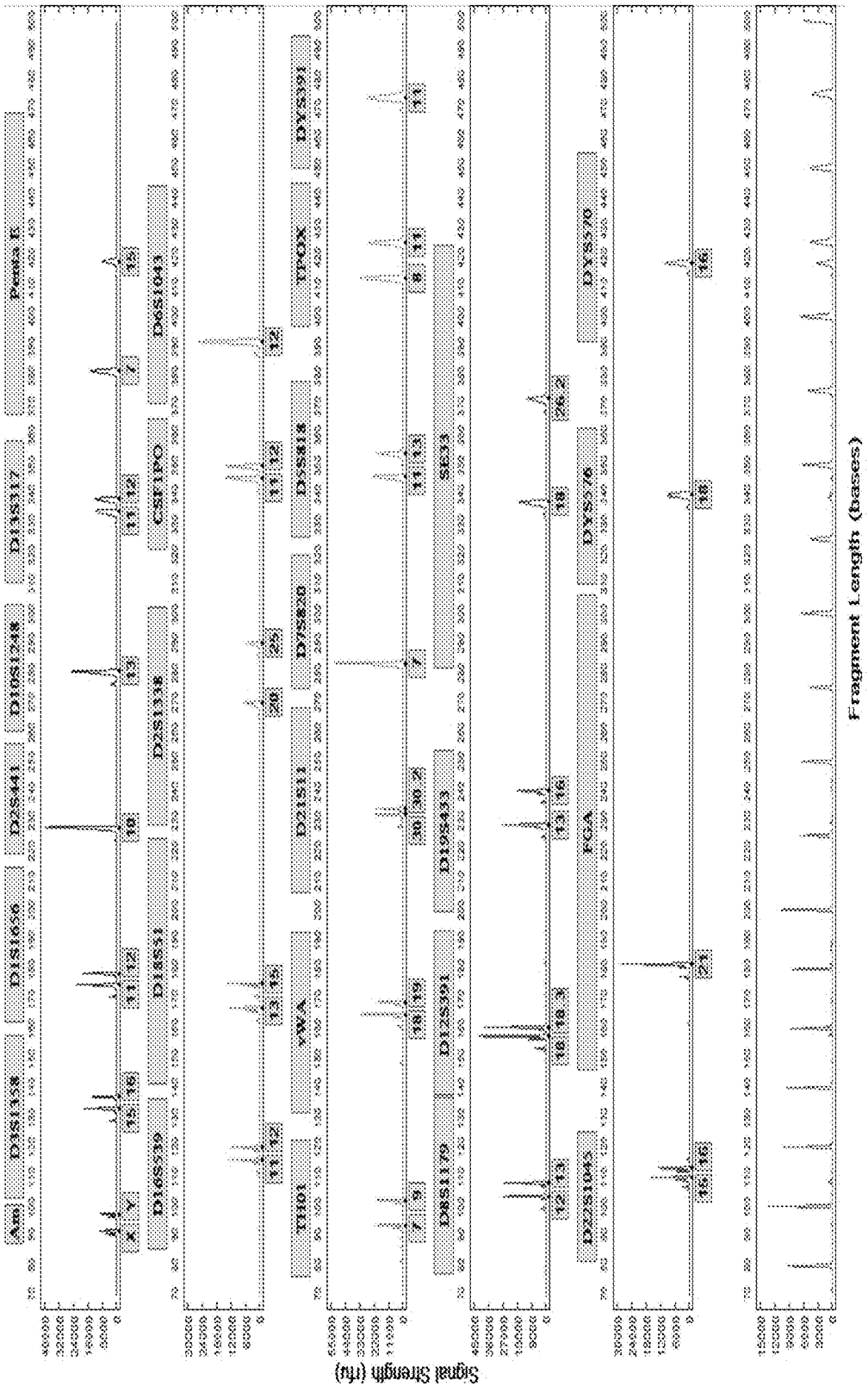

DNA IDs for another sample with high signal strength called with standard A-Chip and AES parameter sets are shown in FIGS. 52 and 53. The AES parameter set (Table 9) allows alleles in D18 and Th01, which have high iNTA, to be called properly. A full DNA ID is generated.

TABLE 9

High Signal Strength Sample calling parameter set.

| | Parameter | Value |
|---|---|---|
| 1 | Peak height minimum threshold | 150 |
| 2 | Peak width parameter threshold | 0.055 |
| 3 | Heterozygote peak height threshold | 500 |
| 4 | Heterozygote peak height ratio | 0.35 |
| 5 | Homozygote peak height threshold | 600 |
| 6 | Homozygote peak height ratio threshold | 0.24 |
| 7 | Hemizygote peak height threshold | 650 |
| 8 | High iNTA rule | On |
| 9 | Mixture sample protection rule | Off |
| 10 | Low signal sample protection rule | Off |
| 11 | Minimum number of called loci to generate a CMF file | 2 |

Intermediate signal strength samples with low peak height ratios—These samples have a passing ILS but have less than twenty of the CODIS 20 core loci are called. One or more loci are labeled in red because of poor peak height ratio. Additional alleles are called when these samples are processed with AES parameters (shown in the table below).

Figure 54:
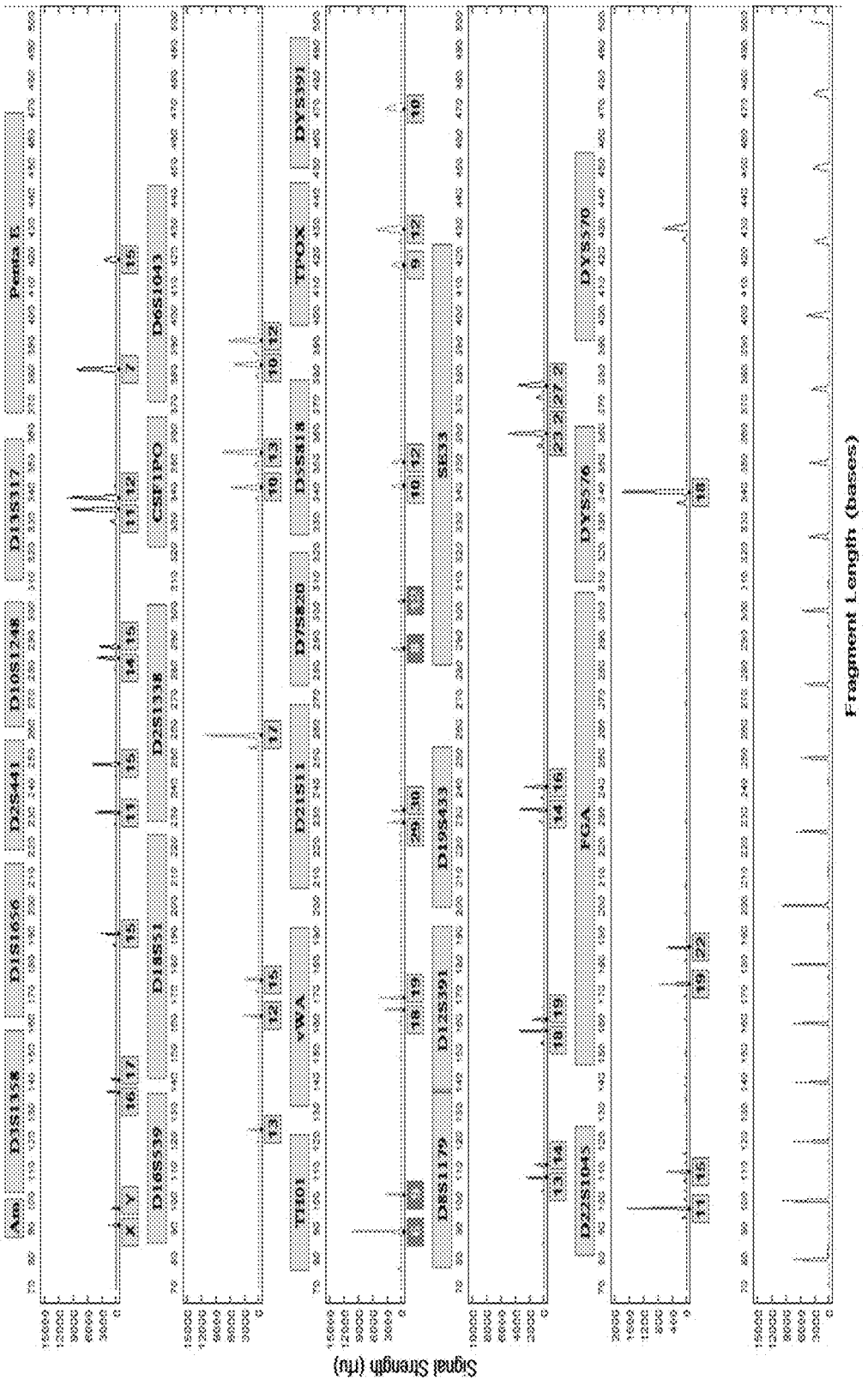
FIGS. 54 and 55 show DNA IDs for a sample with low peak height ratio called with standard A-Chip and AES parameter sets.
Figure 55:
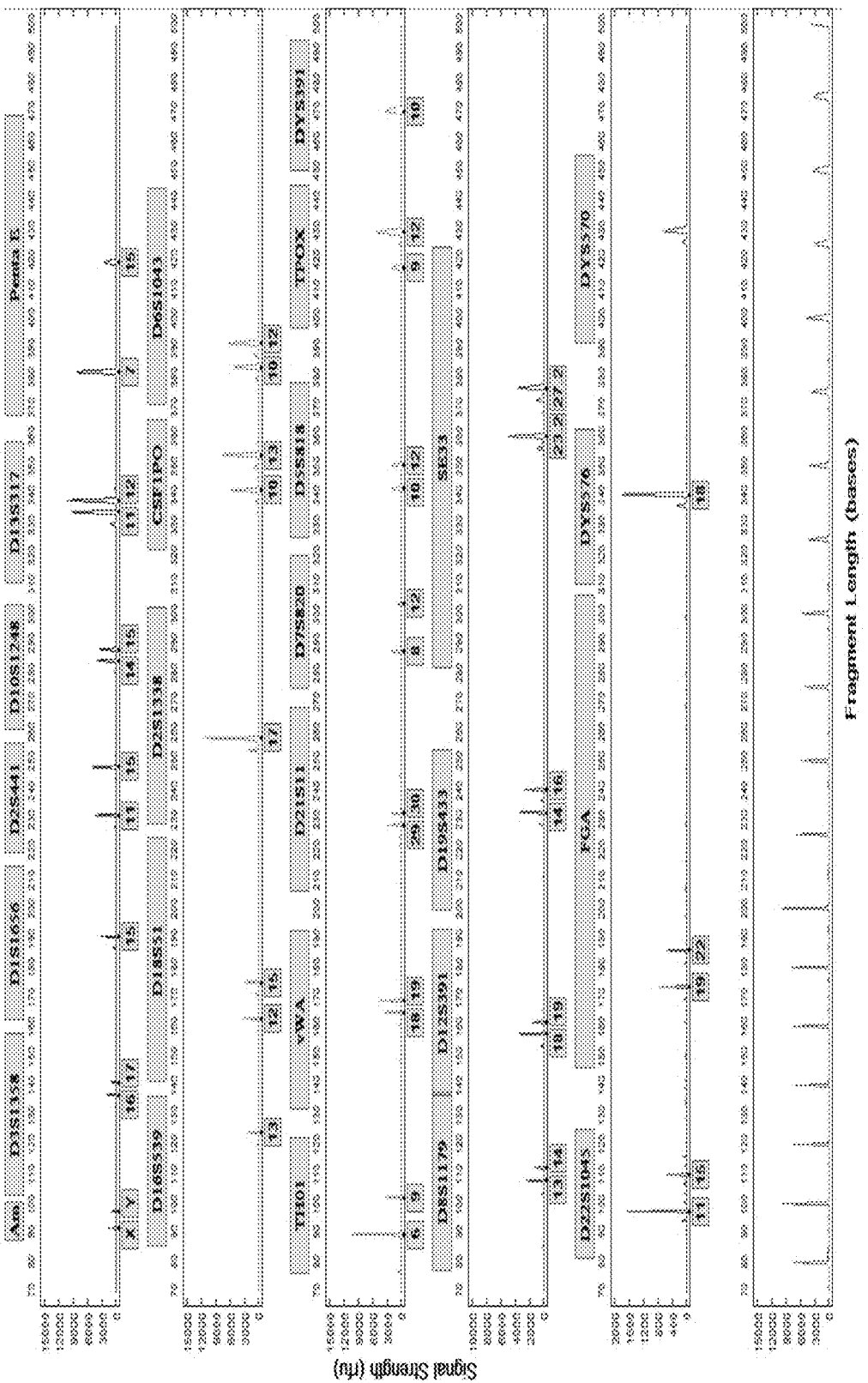

DNA ID for a sample with low peak height ratio called with standard A-Chip and AES parameter sets are shown in FIGS. 54 and 55. The AES parameter set (Table 10) allows alleles in Th01 and D7, with high iNTA, to be called properly. A full DNA ID is generated.

TABLE 10

Intermediate Signal Strength Samples with low PHR.

| | Parameter | Value |
|---|---|---|
| 1 | Peak height minimum threshold | 150 |
| 2 | Peak width parameter threshold | 0.055 |
| 3 | Heterozygote peak height threshold | 500 |
| 4 | Heterozygote peak height ratio | 0.24 |
| 5 | Homozygote peak height threshold | 600 |
| 6 | Homozygote peak height ratio threshold | 0.24 |
| 7 | Hemizygote peak height threshold | 650 |
| 8 | High iNTA rule | Off |
| 9 | Mixture sample protection rule | Off |
| 10 | Low signal sample protection rule | Off |
| 11 | Minimum number of called loci to generate a CMF file | 2 |

Figure 56:
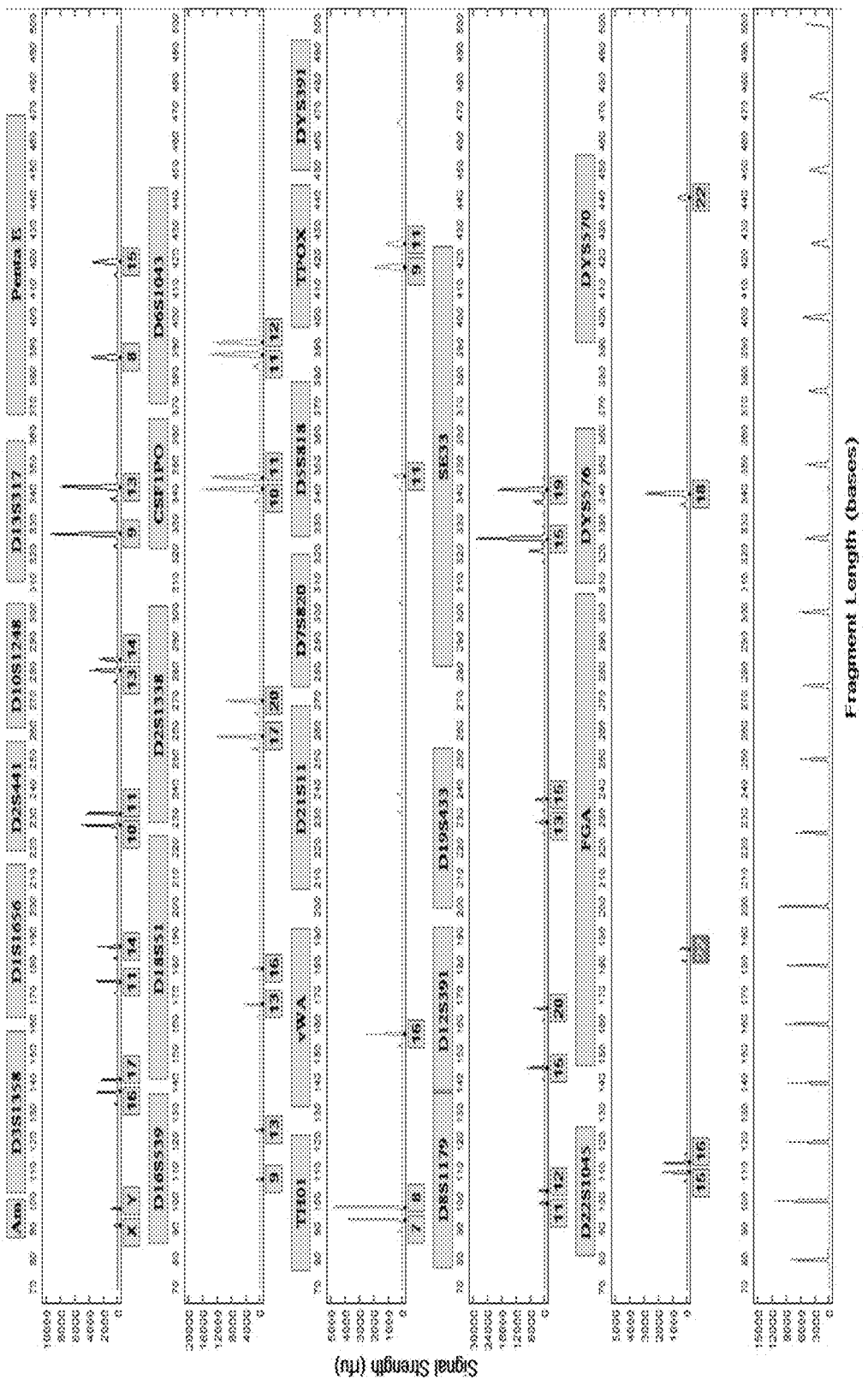
FIG. 56 shows a Low signal sample with standard I-Chip ES parameter set and FIG. 57 shows a sample of Low signal strength processed with AES parameter set.
Figure 57:
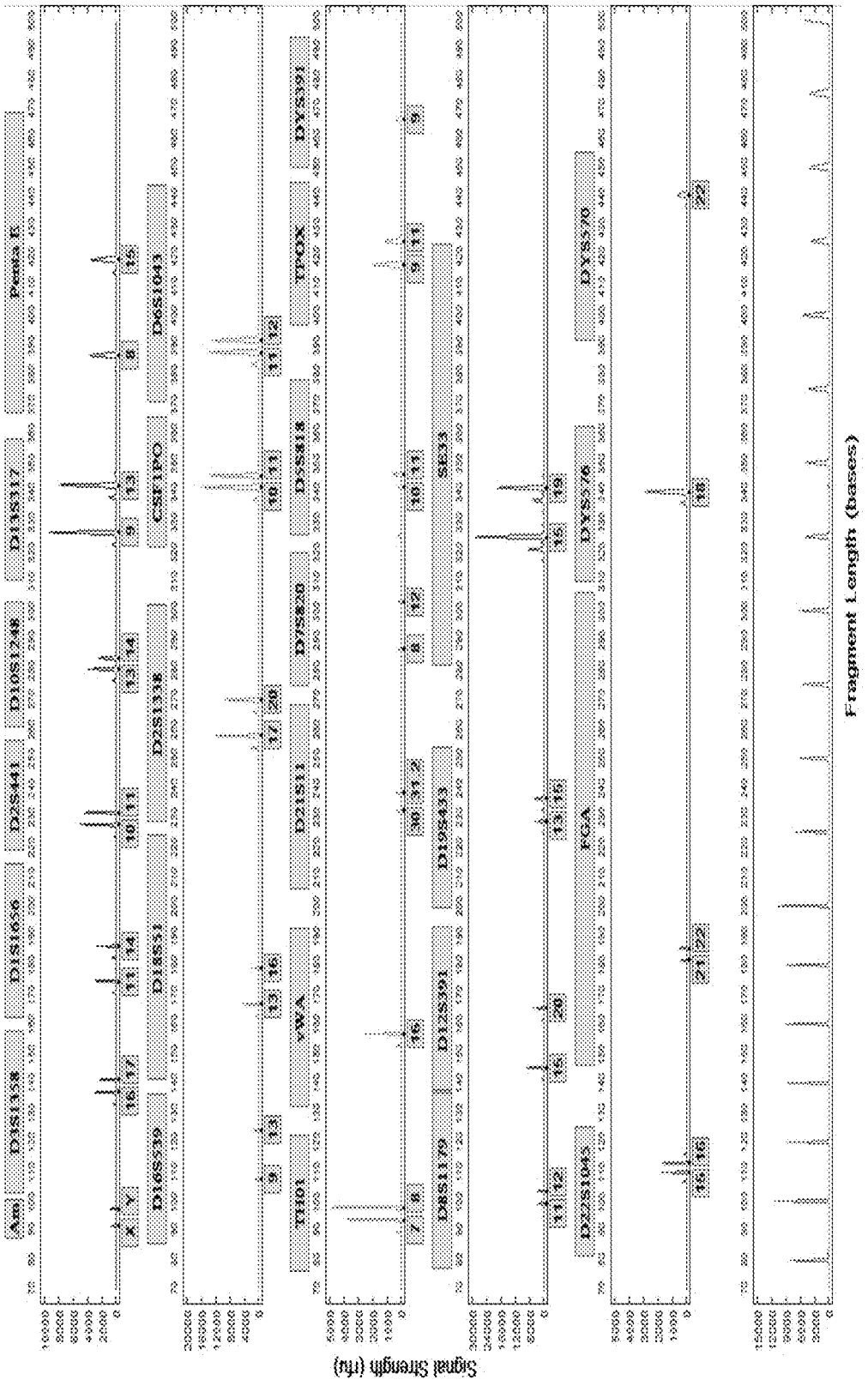

Low signal strength samples with low peak heights and low peak height ratios—These samples have a passing ILS but less than twenty of the CODIS 20 core loci called. Loci are labeled in red because of low peak heights and low peak height ratios. Additional alleles will be called when these samples are processed with AES parameters (Table 11). FIG. 56 shows a Low signal sample with standard I-Chip ES parameter set and FIG. 57 shows a sample of Low signal strength processed with AES parameter set.

TABLE 11

Low Signal Strength Sample parameter set.

| | Parameter | Value |
|---|---|---|
| 1 | Peak height minimum threshold | 150 |
| 2 | Peak width parameter threshold | 0.055 |
| 3 | Heterozygote peak height threshold | 200 |
| 4 | Heterozygote peak height ratio | 0.24 |
| 5 | Homozygote peak height threshold | 200 |
| 6 | Homozygote peak height ratio threshold | 0.224 |
| 7 | Hemizygote peak height threshold | 250 |
| 8 | High iNTA rule | Off |
| 9 | Mixture sample protection rule | Off |
| 10 | Low signal sample protection rule | Off |
| 11 | Minimum number of called loci to generate a CMF file | 2 |

Very Low Signal Content Samples—These samples have a passing ILS but have less than twenty of the CODIS 20 core loci called. Peak with very low peak heights are observed. Very few loci are labeled in red warning boxes and others are unlabeled. These samples are identified as very low signal samples but are not processed further. Alternatively, a parameter set can be developed to yield allele calls from this very low signal sample data Failed samples—In these samples, the ILS was failed by the Expert System and no peaks were called. These samples are not processed further.

In summary, a greater than 2,000 sample dataset has been generated, quantitative parameters were defined to categorize DNA IDs into 6 classifications, and AES parameters for recalling of the DNA ID classifications was developed.

Example 6. Data Flow for an AES Run with Standalone Software (FIG. 58)

Figure 58:
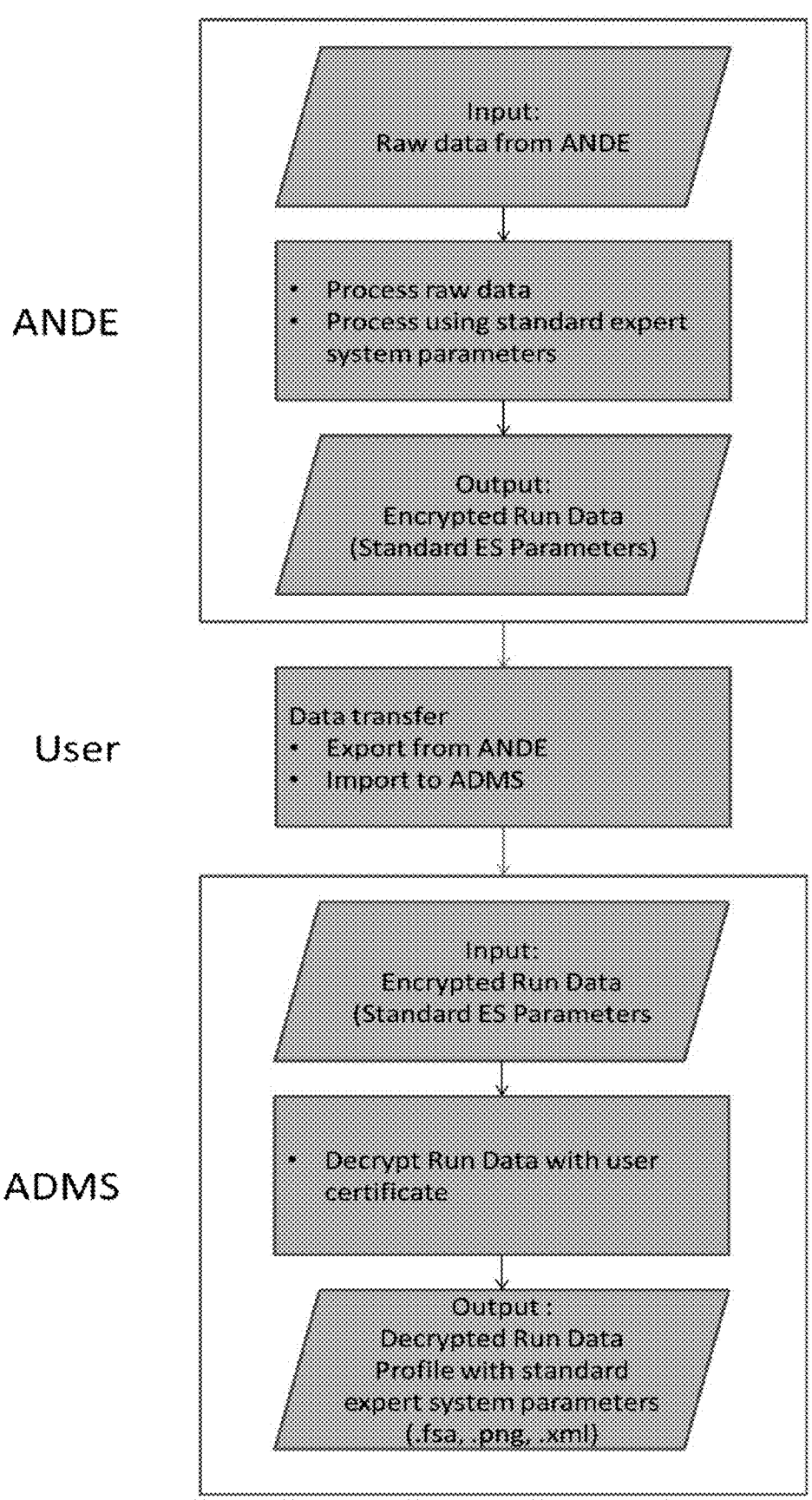
FIG. 58 shows the data flow for an ANDE run.

FIG. 58 shows the data flow for an ANDE run.

The ANDE system generates and automatically processes optical data with the integrated-on board expert system. The on-board expert system is configured to process data using Standard Expert System parameters. Output from the expert system (Run Data) is encrypted and stored in an ANDE database.

A user exports the encrypted Run Data using a USB stick or Ethernet connection with ADMS or FAIRS and imports this data into ADMS or FAIRS.

ADMS or FAIRS imports the encrypted Run Data and using a user generated certificate and stores the decrypted run data in a folder on the ADMS or FAIRS computer. The decrypted run data consists of an .fsa, .png, and .xml file for each of the samples.

Figure 59:
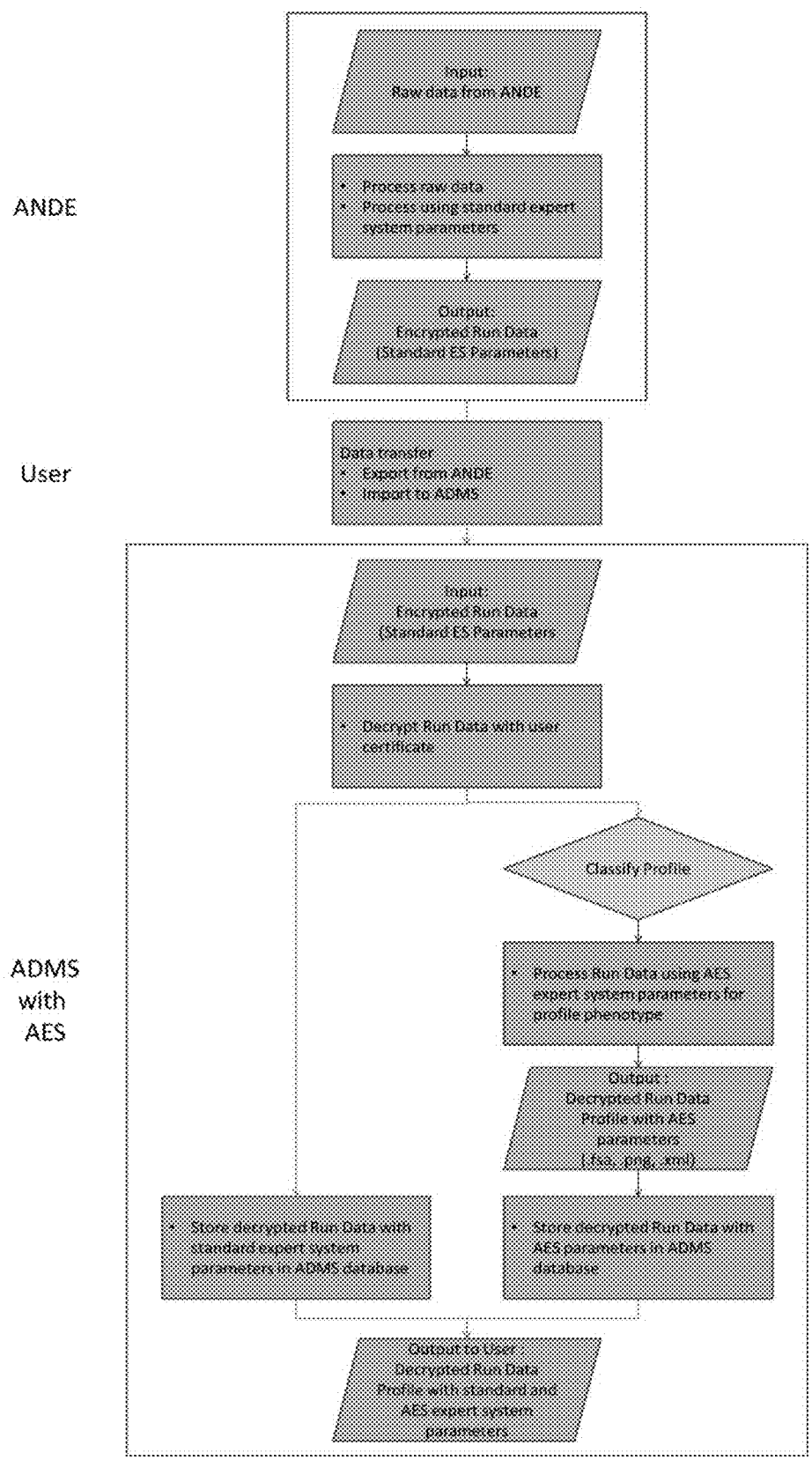
FIG. 59 is a flowchart showing the data flow with the Adaptive Expert System incorporated into ADMS or FAIRS and the data flow for a run with ANDE and AES.

The Adaptive Expert System can be incorporated into ADMS or FAIRS, another Expert System, or can function as a stand-alone application. The data flow with the Adaptive Expert System incorporated into ADMS or FAIRS and the data flow for a run with ANDE and AES is shown in FIG. 59.

ANDE generates and automatically processes raw data with the integrated-on board expert system. The on-board expert system is configured to process data using standard expert system parameters. Output from the expert system (Run Data) is encrypted and stored in an ANDE database.

The User exports the encrypted Run Data using a USB stick or Ethernet connection with ADMS and imports this data into ADMS.

ADMS imports the encrypted Run Data and using a user generated certificate and decrypts the run data.

Decrypted run data with standard parameters is stored in a database on the ADMS computer.

Decrypted run data is also processed by AES. The AES classifies the DNA ID and applies the optimal AES parameters based on the DNA ID classification. The decrypted run data with AES parameters is stored in a database on the ADMS computer.

The decrypted run data with standard parameters and with AES parameters is displayed to the user through a graphic user interface (GUI). The decrypted run data with standard parameters and with AES parameters is displayed to the user. The GUI may take many forms:
 A simple interface that merely reports success or failure of the samples under study,
 A simple interface that provides the number of called STR alleles (e.g. based on whichever provides more called alleles, Standard or AES),
 A more complex interface that, for example, indicates the number of alleles and loci called in one or both Expert Systems and provides one or both DNA IDs.
 These and many other configurations can be hard-coded or user configurable.

Example 7. Data Flow for an AES Run with Software that is Integrated with the Instrument The ANDE system generates and automatically processes optical data with the integrated-on board expert system. The on-board expert system is configured to process data using Standard Expert System parameters. The AES can be integrated with the ANDE instrument by installing the software on the instrument and allowing it to receive sample data directly from the instrument. In this configuration, both the output of run data from the standard expert system and the AES is stored in a database on the instrument. The instrument system software is configured to allow the user to export encrypted standard run data and or AES run data using a USB stick or Ethernet connection with ADMS or FAIRS and imports this data into ADMS or FAIRS. The exported data consists of encrypted Run Data that is generated by the standard expert system or by the AES or both. The option to export the desired run data is configurable based on agency/jurisdictional policies and implemented by configuration options selected using simple GUI screens.

Example 8: AES with a Discrete Set of Input Parameters that for Very Low DNA to Very High DNA Content Samples. An Algorithm is Used to Iterate the Input Parameter Set to Derive the Optimal One to be Used for Calling the Sample Example 4 separates samples into six DNA ID classifications and their characteristics. Example 5 defines sets of Adaptive Expert System parameters for the High Signal Strength samples (Table 4), Intermediate Signal Strength samples with low PHR (Table 5), and Low signal strength sample (Table 6). In this example, nineteen parameter sets for Low Signal Strength samples are generated based on the parameter set of Table 6 and 3 parameter sets were generated for High Signal Strength samples based on the parameter set of Table 4. Additionally, a rule for samples with high iNTA was defined. These parameter sets were generated by defining parameter sets with intermediate parameter values.

The nineteen parameter sets for the Low Signal condition (L01 to L19) were generated by varying the following parameters across the defined range:
 Heterozygote Peak Height Threshold—250 to 100 RFU,
 Heterozygote Peak Height Ratio—0.35 to 0.15,
 Homozygote Peak Height Threshold—300 to 120 RFU,
 Heterozygote Peak Height Threshold for $2^{nd}$ peak—100 to 50,
 Homozygote Peak Height Ratio—0.15 to 0.10,
 Hemizygote Peak Height Minimum—200 to 80 RFU.

These parameter sets L01 to L19 were designed by reducing the calling thresholds to allow increasingly more peaks to be called. L01 is the most conservative parameter set and L19 is the most aggressive parameter set.

The three parameter sets for High Signal condition (H01 to H03) were generated by of varying the following parameters across the defined range:
 Allele PH/PA in Zone 1—0.08 to 0.07,
 Allele PH/PA in Zone 2—0.079 to 0.049,
 Allele PH/PA in Zone 3—0.044 to 0.030,
 Allele PH/PA in Zone 4-0.03 to 0.025.

These parameter sets H01 to H03 were designed to allow peaks with increasingly wider widths and to allow increasing more peaks to be called. H01 is the most conservative parameter set and H03 is the most aggressive parameter set.

When samples with high levels of iNTA are observed, the iNTA ratio at the Amelogenin locus is above 0.4. As a result, when the iNTA ratio for either of the X and Y alleles is 0.4 or greater, the iNTA rule will be invoked. In this rule, the iNTA peak of loci with 2, 3, and 4 alleles are not called.

The optimal parameter set is determined by the following algorithm:
1) Calculate the number of called loci, and the number of homozygote and number of heterozygote loci for each sample using the as-called I-Chip or A-Chip criteria.
2) If all of the CODIS20 loci are called, the as called parameter sets are acceptable and no recall is performed. The as-called parameter set is the optimal parameter set.
3) Iterate through the 19 Low Signal parameter sets (L01 to L19). For each of the parameter sets used, calculate the number of called loci, and the number of homozygote and number of heterozygote loci.
4) Determine the best Low signal parameter set as the parameter set that meets the following criteria:
   a. Most number of called loci CODIS20.
   b. No change in any called locus from homozygote to heterozygote.
5) Iterate through the 3 High Signal parameter sets (H01 to H03). For each of the parameters sets used, calculate the number of called loci, and the number of homozygote and number of heterozygote loci.
6) Determine the best High signal parameter set as the parameter set that meets the following criteria:
   a. Most number of called loci CODIS20.
   b. No change in any called locus from homozygote to heterozygote.
7) Compare the number of called loci between the best Low Signal parameter set and best High Signal parameter set. Select the best Low or High.
8) Calculate the ratio of the iNTA for Amelogenin alleles. If this value is equal or greater than 0.40, apply the iNTA rule.

The algorithm above allows determines the optimal parameter set with the following criteria:

Maximize the number of called CODIS20 loci in the sample—to yield the most information content available from the sample.

Apply least aggressive parameter sets—to yield the most information content while avoiding unnecessary risk of using aggressive parameter sets.

Avoid drop-ins—When the calling thresholds are reduced, the likelihood of a noise peak being called as an allele increases. When a noise peak is mistakenly called as an allele, this allele has a miscall and this condition is called a drop-in. Drop-in loci can be avoided by identifying parameter sets that result in a locus that is initially called as a homozygote changes to a heterozygote.

Figure 60:
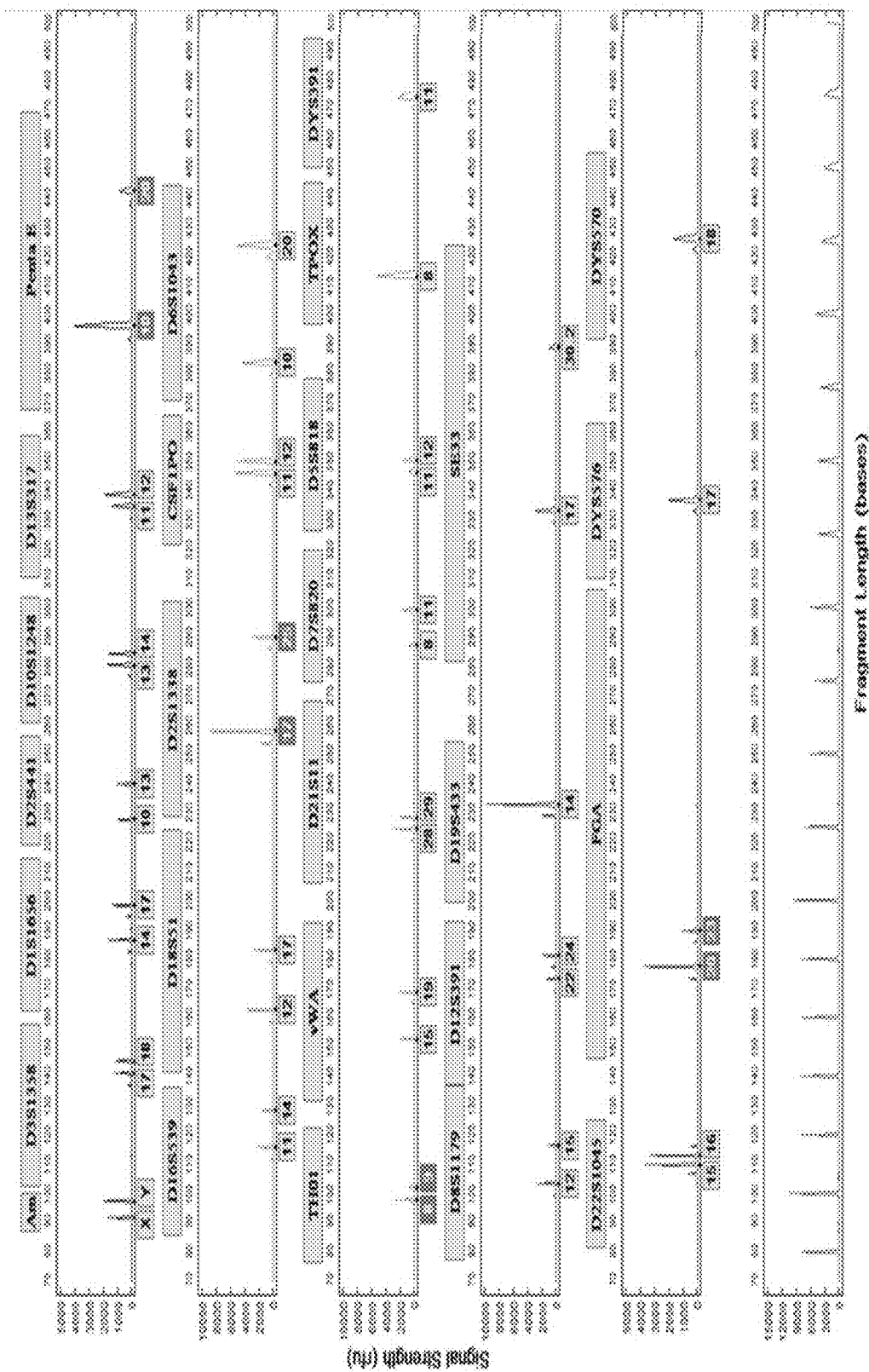
FIG. 60 shows a DNA ID generated from 0.5 µl of blood and which is of intermediate to low signal strength.
Figure 61:
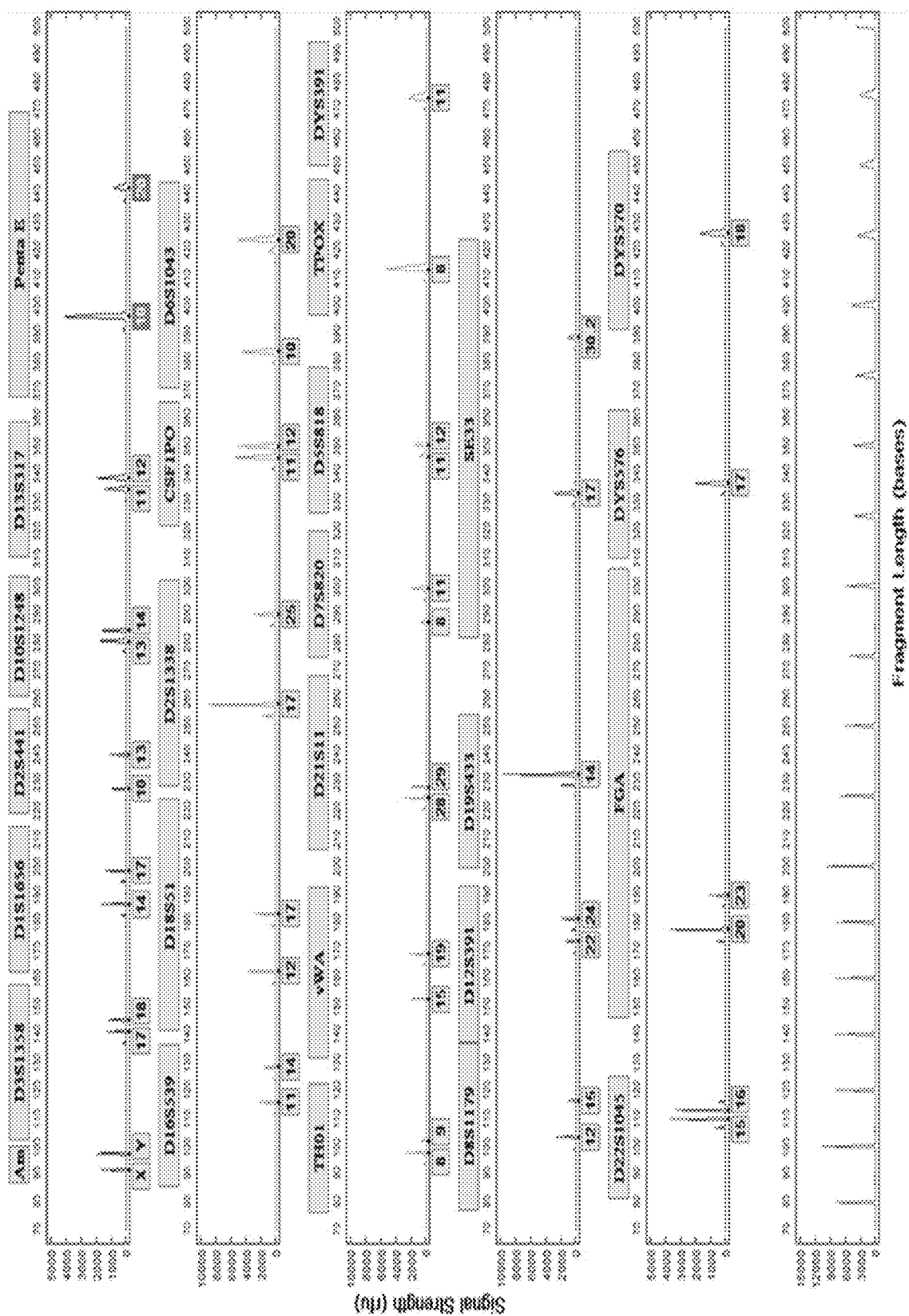
FIG. 61 shows a DNA ID resulting from processing the raw data with AES with parameter set of L02.

The DNA ID of FIG. 60 was generated from 0.5 µl of blood. This DNA ID is of intermediate to low signal strength where 4 loci with peaks that are labeled in red warning boxes (Penta E, D2S1338, Th01, and FGA). Processing the raw data with AES with parameter set of L02 results in the DNA ID of FIG. 61. The above algorithm determined that the parameter set of L02 was optimal for recalling this DNA ID.

Figure 62:
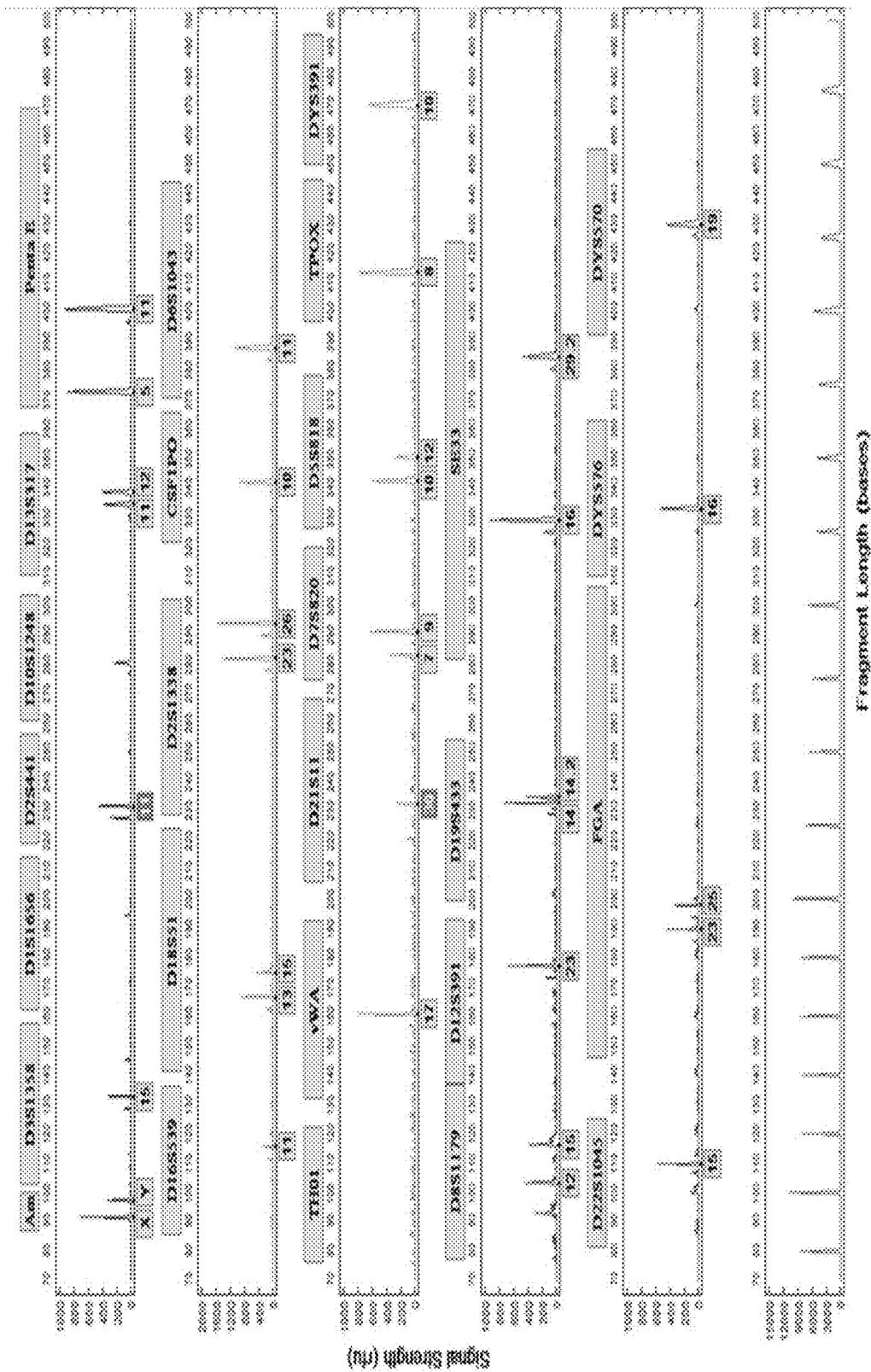
FIG. 62 shows a DNA ID generated from 0.1 µl of blood and which is of low signal strength.
Figure 63:
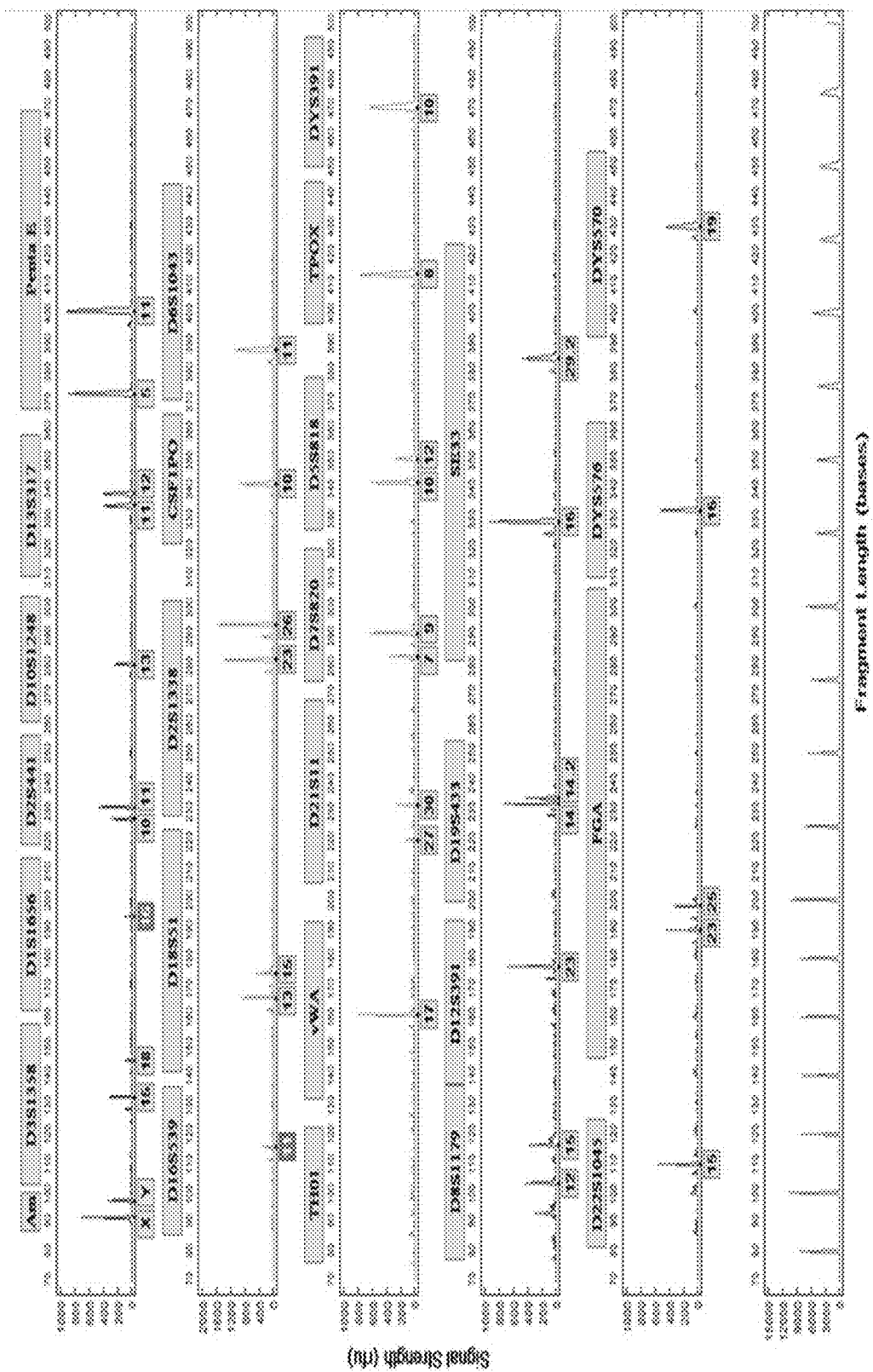
FIG. 63 shows a DNA ID resulting from processing the raw data with AES using parameter set L16.

The DNA ID of FIG. 62 was generated from 0.1 µl of blood. This DNA ID is of low signal strength where 2 loci with peaks that are labeled in red warning boxes (D2S441 and D21S11) and 3 loci with no labeled peaks (D1S1656, D10S1248, and Th01). Processing the raw data with AES using parameter set L16 results in the DNA ID of FIG. 63. The above algorithm determined that the parameter set of L16 was optimal for recalling this DNA ID. The L16 is a relatively aggressive parameter set compared to the L02 of the previous figures.

Although this example varies values for six ES parameters (Heterozygote Peak Height Threshold, Heterozygote Peak Height Ratio, Homozygote Peak Height Threshold, Heterozygote Peak Height Threshold for 2nd peak, Homozygote Peak Height Ratio threshold, and Hemizygote Peak Height Minimum) for the Low Signal parameters sets, four parameters for the High Signal parameter set, and one test for iNTA; any parameter in the expert system can be included for optimization. The Adaptive Expert System has over 334 parameters and any or all of these parameters can be varied for generating an optimized AES DNA ID. At least one, more than 2, 3, 4, 5, 6, 7, 8, 9, 10, 15, 20, 25, 50, 100, 200, 300, 500, or 1,000 parameters may be utilized in a given parameter set.

Although this example uses 19 Low Signal parameters and 3 High Signal parameters, the number of parameter sets can be increased in many ways, including (1) by reducing the step size between parameter sets to allow for increasing more optimized parameter and (2) by expanding the upper and lower ranges to allow for a wider range of samples that can be processed. Instead of using preprogrammed number of discrete parameter sets, a continuous set of parameters can automatically be generated and applied by using a loop. This will result in the ability to achieve finer steps and a more optimal parameter set for each sample.

Although this example uses 3 criteria (maximizing the number of Maximize the number of called CODIS20 loci, applying the least aggressive parameter set to yield the most information content, and avoid drop-ins and drop-outs) for determining the optimal parameter set, additional criteria can be added to further optimize the result.

Although this example shows the recalculating of all parameters sets, more efficient numerical optimization techniques can be applied to determine the optimal parameter set. By using these techniques, the number of recalls is minimized and results can be achieved more rapidly.

The total number of parameter sets and hence the total number of recalls required to generate optimal results can be determined by tradeoff between the number of parameter sets and hence a more optimal result and the total processing time required to achieve a result. This number will increase as compute power increases and more efficient numerical methods for solution finding are applied.

The AES can be incorporated into mixture deconvolution software and database search and match software.

Example 9: AES with a Continuous Set of Input Parameters that for Very Low DNA to Very High DNA Content Samples. An Algorithm is Used to Iterate the Input Parameter Set to Derive the Optimal One to be Used for Calling the Sample In Example 8, nineteen parameter sets for Low Signal Strength samples were generated based on the parameter set of Table 6 and 3 parameter sets were generated for High Signal Strength samples based on the parameter set of Table 4. Additionally, a rule for samples with high iNTA was defined. In this example, instead of defining discrete parameter sets for Low Signal Strength and High Signal Strength samples, each parameter that is to be adjusted is assigned a minimum and maximum value and a step. The Low Signal condition parameters are refactored as follows:

Heterozygote Peak Height Threshold—max value 250, min value 100, step 10 RFU,

Heterozygote Peak Height Ratio—max value 0.35, min value 0.15, step 0.5,

Homozygote Peak Height Threshold—max value 300, min value 120, step 10 RFU,

Heterozygote Peak Height Threshold for 2nd peak—max value 100, min value 50, step 10 RFU, Homozygote Peak Height Ratio—max value 0.15, min value 0.10, step 0.05, Hemizygote Peak Height Minimum—max value 200, min value 80, step 10 RFU.

In this approach, each parameter is iterated starting from the maximum value to the minimum value in the defined step. The iteration from the maximum value to the minimum value represents a flow from the most conservative parameter value (e.g. generating relatively less called alleles) to the most aggressive parameter values (e.g. generating relatively more called alleles).

The parameters for High Signal condition are refactored as follows.

Allele PH/PA in Zone 1—max value 0.08, min value 0.07, step 0.01,

Allele PH/PA in Zone 2—max value 0.079, min value 0.049, step 0.001,

Allele PH/PA in Zone 3—max value 0.044, min value 0.030, step 0.001,

Allele PH/PA in Zone 4—max value 0.03, min value 0.025, step 0.001.

In this approach, each parameter is iterated starting from the maximum value to the minimum value in the defined step. The iteration from the maximum value to the minimum value represents a flow from the most conservative parameter value to the most aggressive parameter values.

When samples with high levels of iNTA are observed, the iNTA ratio at the Amelogenin locus is above 0.4. As a result, when the iNTA ratio for either of the X and Y alleles is 0.4 or greater, the iNTA rule will be invoked. In this rule, the iNTA peak of loci with 2, 3, and 4 alleles are not called.

The optimal parameter set is determined as follows:
1) Calculate the number of called loci, and the number of homozygote and number of heterozygote loci for each sample using the as-called I-Chip or A-Chip criteria.
2) If all of the CODIS20 loci are called, the as-called parameter sets are acceptable and no recall is performed. The as-called parameter set is the optimal parameter set.
3) Iterate through the Low Signal parameters starting from the max value to the min value and stepping at the give step value. For each of the parameter value used, calculate the number of called loci, and the number of homozygote and number of heterozygote loci.
4) Determine the best Low signal parameter set as the parameter set that meets the following criteria:
   a. Most number of called loci CODIS20.
   b. No change in any called locus from homozygote to heterozygote.
5) Iterate through the High Signal parameters starting from the max value to the min value and stepping at the given step values. For each of the parameters sets used, calculate the number of called loci, and the number of homozygote and number of heterozygote loci.
6) Determine the best High signal parameter set as the parameter set that meets the following criteria:
   a. Most number of called loci CODIS20.
   b. No change in any called locus from homozygote to heterozygote.
7) Compare the number of called loci between the best Low Signal parameter set and best High Signal parameter set. Select the best Low or High.
8) Calculate the ratio of the iNTA for Amelogenin alleles. If this value is equal or greater than 0.40, apply the iNTA rule.

The algorithm above allows determines the optimal parameter set with the following criteria:
   Maximize the number of called CODIS20 loci in the sample—to yield the most information content available from the sample.
   Apply least aggressive parameter sets—to yield the most information content while avoiding unnecessary risk of using aggressive parameter sets.
   Avoid drop-ins—When the calling thresholds are reduced, the likelihood of a noise peak being called as an allele increases. When a noise peak is mistakenly called as an allele, this allele has a miscall and this condition is called a drop-in. Drop-in loci can be avoided by identifying parameter sets that result in a locus that is initially called as a homozygote changes to a heterozygote.

The use of this algorithm allows more discrete stepping of the parameter values and the achievement of a more optimal set of parameters for AES compared the discrete parameter sets of Example 8.

The following adaptions to the above approach can be made:
1) Allow the software to iterate outside of the initial limits provided. This adaptation allows the AES parameter values to be effectively unlimited in range, and outside of the initial limits that were initially set. This adaptation is particularly effective when additional data sets are generated for test. The limits that were initially set typically represent ranges that have been observed, however, with additional testing, sample data that exceed the limits may be encountered. The ability of the algorithm to iterate outside the initial limits will allow new data sets to be processed without having to readjust the initial input parameters.
2) Allow the step size to vary. It is inefficient to select a fixed step size to iterate over a range of parameter values. To maximize the speed of operation, a variable step size can be adopted. The step size can be determined by the rate of change of the output with step size. When the rate of change is high, a smaller step size will ensure that the optimal values are not missed. When the rate of change is small, a larger step size will ensure efficient iteration to the optimal value.
3) Include the search and match results as an objective of the iteration toward an optimal solution. In the example above, the resultant DNA ID that is generated from the optimized parameter set will be used to search and match against DNA IDs in a database. A quality of match is generated for each match that is made. The quality of match includes the number of overlapping loci, the number of matching loci, the number of partially matching loci, and the number of loci that do not match, number of matches against the database. The quality of search can be included in the optimization criteria for generating the optimal parameter set. The AES parameter sets may vary from more to less conservative, and each DNA ID resulting from each of the parameter sets search parameters may be used to search a database (or perform other analyses). Search/match criteria may also be varied from more to less stringent. Accordingly, each parameter set will give a range or search results based on this stringency, and these search results can be scored. The array of DNA IDs vs search/match criteria may then be assessed for the highest score or scores, and this information can be used to define the parameter set and its companion search stringency that are most effective (which may include the highest quality match as well as the relative number of matching DNA IDs in the database).

Example 10: Artificial Intelligence and Machine Learning is Incorporated into AES. Together with the Large Datasets Allows AES to Self-Learn and Execute The dataset that is generated in Example 5 and the algorithms described in Examples 6, 7, and 8 lend themselves to Machine Learning and Artificial Intelligence. The characteristics of the sample data (optical data, electropherogram, DNA ID) are inputs to the machine and include but not limited to the designation of each allele signal strength of each allele, iNTA peak height and Peak Height ratio for each locus, peak heights ratios of the heterozygote peaks, number of peaks in each locus, width and shape of each allelic peak, signal to noise ratio of each dye channel, stutter ratio of each allele. The known truth of each DNA ID in the provided as the desired result. A set of decision making nodes are incorporated to self-learn and generate an optimal set of ES parameters for a given set of characteristics calculated from the sample dat. Sets of Expert System parameters are definable by the AES and determined through self-learning. Over time, additional inputs or characteristic of the DNA ID are added to further increase the knowledgebase.

Example 11: Dataflow for an AES Run to Classify Data without Generating a Standard or Baseline DNA IDs Some of the Examples in this specification have used the sample data (optical data, electropherogram data, and DNA ID) as the input for the AES. In these Examples, the sample data is processed using a standard (or baseline) set of ES parameters to generate a standard (or baseline) DNA ID. Characteristics of sample data are calculated from the standard DNA ID to classify the sample data. This Example will show that the generation of a standard (or baseline) DNA ID is optional and not a necessary step for AES processing. The characteristics of the sample data can be calculated directly from the optical data without generating a standard DNA ID. The sample type is classified based on the characteristics and an appropriate AES parameter set can be selected for processing the sample data.

Figure 66:
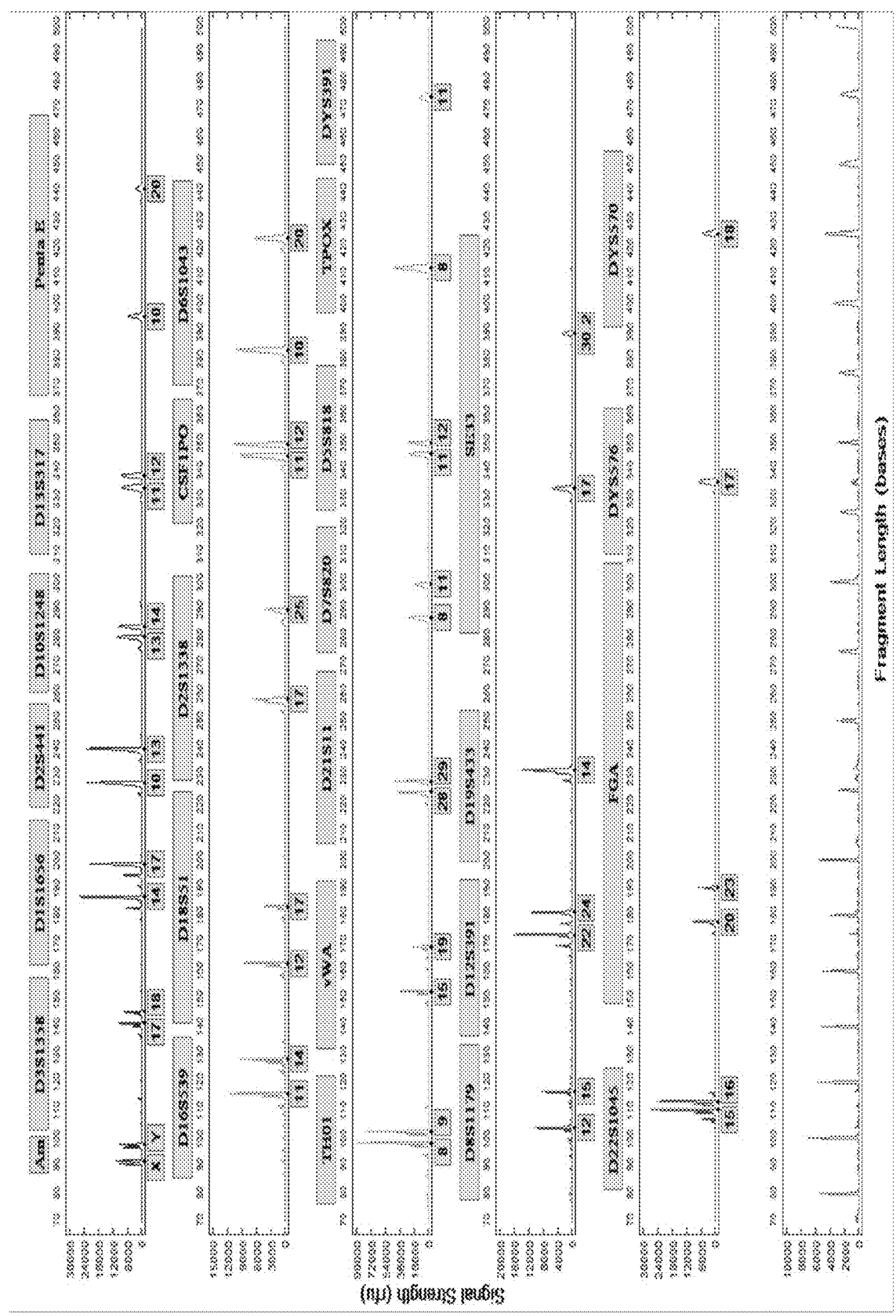
FIG. 66 shows the resultant output of this data set with the selected parameter set.

FIGS. 64a-64c show a segment of the optical data that is generated for a sample by the ANDE instrument. The optical data is in the form of an ASCII file that is comma delimited (.CSV) file) with the rows representing detector sampling points and the columns representing the signal at each of the six detectors. The optical data is processed following a series of steps including baseline subtraction and color correction to generate electropherogram data. The characteristics of each of the peaks of the electropherogram are calculated for following six characteristics are determined for each peak:
Peak color
Peak position
Peak Color
Peak Locus
Peak Allele #
Peak Height
Peak Width
Peak Asymmetry
Peak Width Deviation
Peak Shape Deviation A snapshot of the peak characteristics for all the peaks in the sample data is shown in FIGS. 65a-65c. The table of peaks characteristics were used to classify the optical data into classes. For this example, only peak height and width were used to classify the sample data. Specifically, the average peak height of the data was determined by averaging the peak heights of the highest two peaks across all loci. When the peak height is greater than 8,000 RFU, then the high signal parameters were applied. The class and a high signal strength parameter set was applied to this raw data. The resultant output of this data set with the selected parameter set is shown in FIG. 66. In this case the High signal sample processed by characterizing the optical data to classify the sample data as a high signal sample and applying the high signal AES parameter set.

Figure 67:
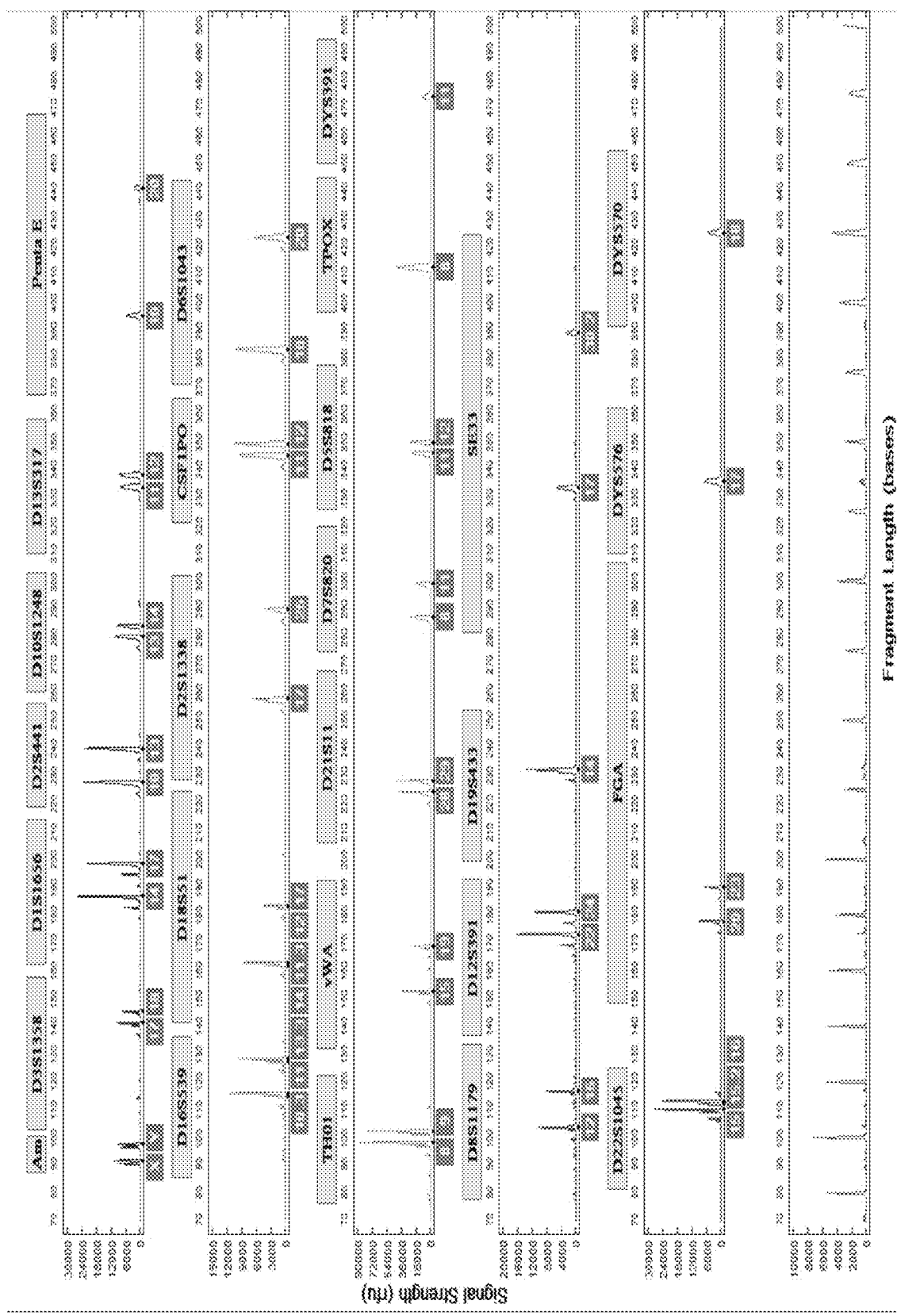
FIG. 67 shows the same data called using the standard parameter set.

As a comparison, FIG. 67 shows the same data called using the standard parameter set. Note that the DNA ID showing the calls when processed using the standard DNA ID was not required for classifying the optical data. This resulting DNA ID of FIG. 67 is an improvement over the standard DNA ID of FIG. 66.

Figure 68:
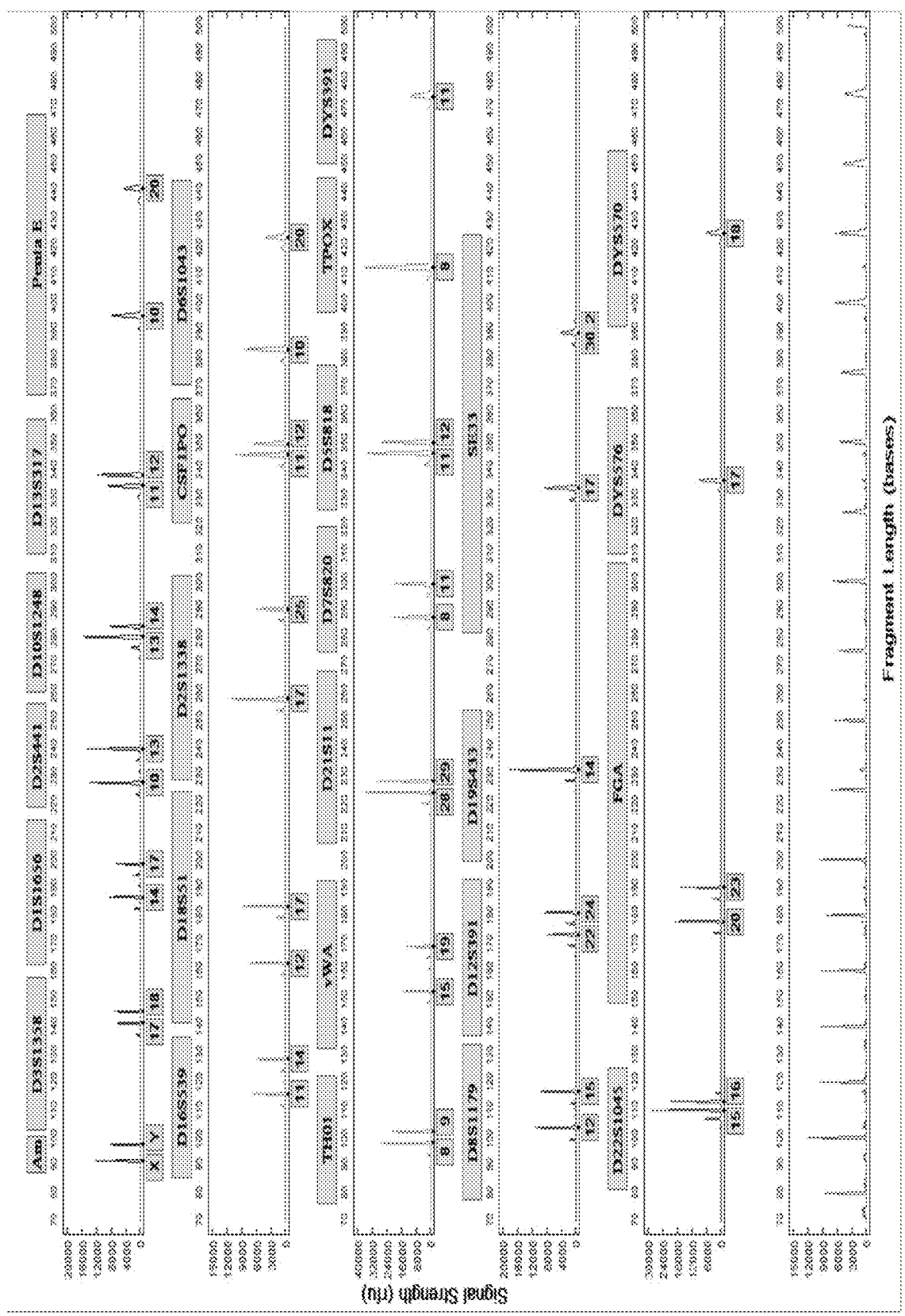
FIG. 68 shows a standard signal strength sample being classified as such because the peak height of the alleles is between 3000 and 8000 RFU.

FIG. 68 shows a standard signal strength sample being classified as such because the peak height of the alleles is between 3000 and 8000 RFU. The standard parameters were applied to generate the output.

Figure 69:
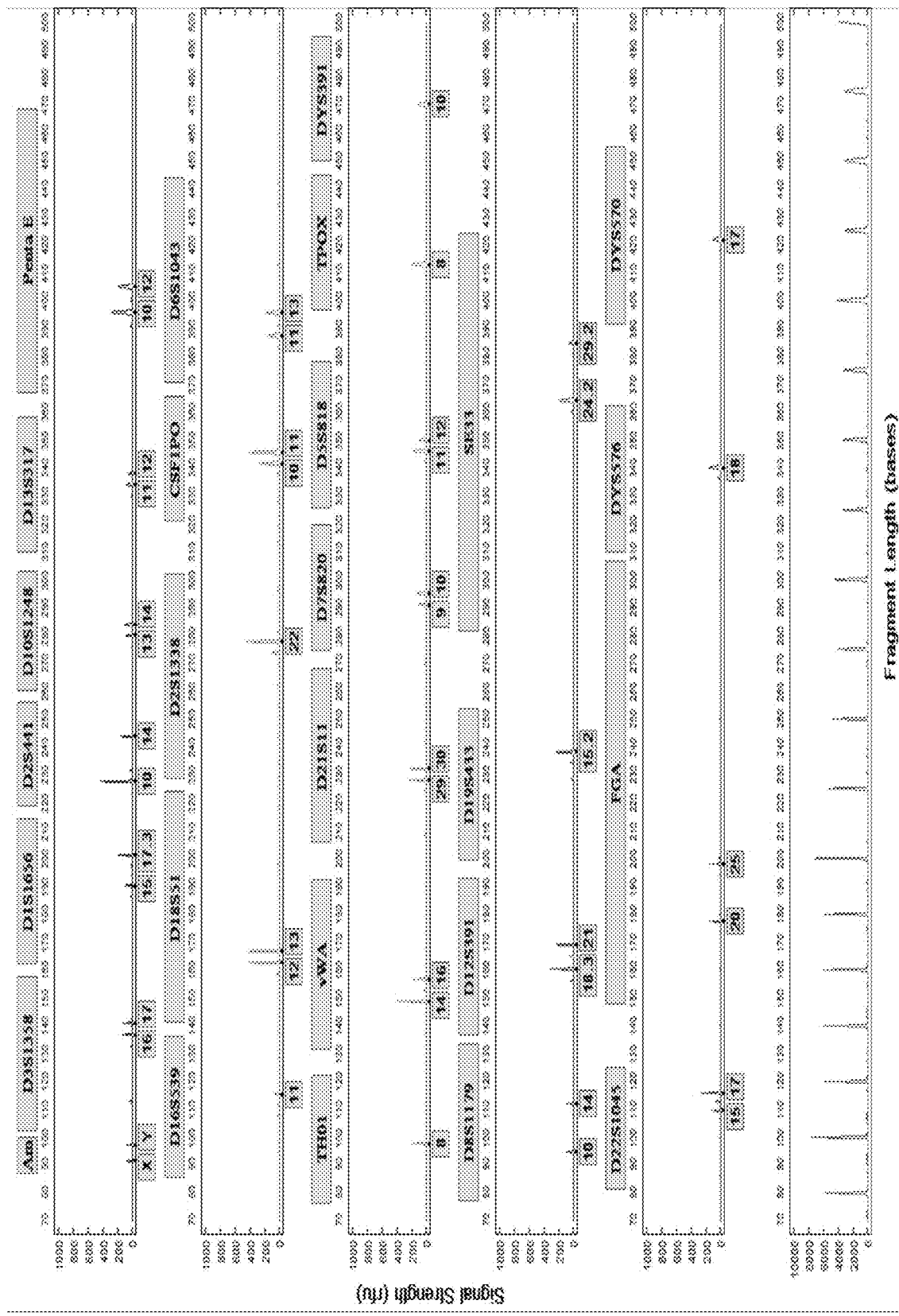
FIG. 69 shows the sample data of a low DNA sample being called using the low DNA parameter set.
Figure 70:
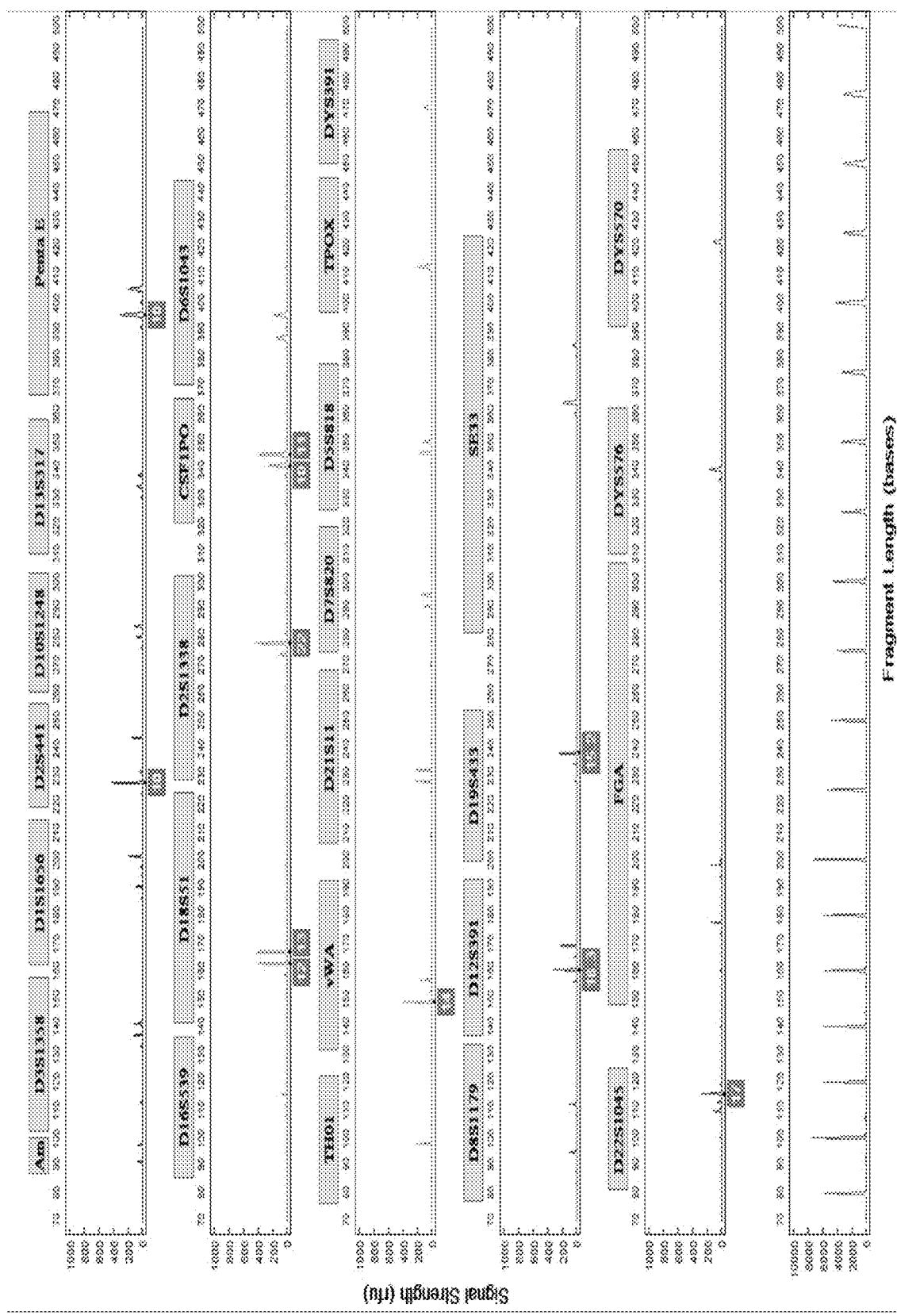
FIG. 70 shows the same data called using the standard parameter set.

As a comparison, FIG. 69 shows the sample data of a low DNA sample being called using the low DNA parameter set. In this case the Low signal sample processed by characterizing the optical data to classify the sample data as a low signal sample and applying the low signal AES parameter set. The sample data was classified as a low DNA sample type because its signal strength was below 3,000 RFU. Note that the DNA ID showing the calls when processed using the standard DNA ID was not required for classifying the optical data. This resulting DNA ID of FIG. 69 is an improvement over the standard DNA ID of FIG. 70.

Six characteristics for each peak were typically calculated, although one knowledgeable in the art can use fewer classification (e.g. only one classification of can be used) or more classification (by adding, for example, the number of loci or using a new or overlapping series of characteristics). Furthermore, one knowledgeable in the art can also define other characteristics to measure. Each classification can be divided into multiple levels. In short, the number of characteristics that can be calculated from the optical data is flexible. Each characteristic can be divided into numerous levels. These characteristics and levels in turn can be applied to classify the sample data and assign an AES parameter set for calling.

Example 12: AES Using Only One Characteristic to Classify the Sample and to Apply an Input Parameter to Call the Data In Example 4, seven characteristics of the sample data, including:
ILS condition
Number of CODIS 20 loci called
Signal strength
Number of loci with alleles with PH less than the PH threshold
Number of Loci with alleles with PH greater than PH min
Number of Loci with PHR of less than pHR threshold
Number of Loci with wide peaks and iNTAp
were used to classify the sample data into the following:
Intermediate signal strength samples
High signal strength samples with wide peaks and iNTA
Intermediate signal strength samples with low peaks height ratios
Low signal strength samples with low peak heughs and low peak height ratios
Very low signal content samples
Failed samples An AES parameter set was associated with each of the classifications (classifications) and applied to the data.

Only one characteristic is required to classify each of the sample data or DNA ID (classifications). Table 12 below shows the DNA ID classification for one characteristic. In this example, signal strength is selected as the characteristic for classification:

TABLE 12

| Classification: | Characteristic: Signal Strength Range |
|---|---|
| High Signal Strength Samples | <2000 RFU |
| Intermediate Signal Strength Samples | 2000 RFU to 10000 RFU |
| Low Signal Strength Samples | >10000 RFU |

Three discrete AES parameter sets were defined with each to be applied to a classification based on the sample data.

Figure 71:
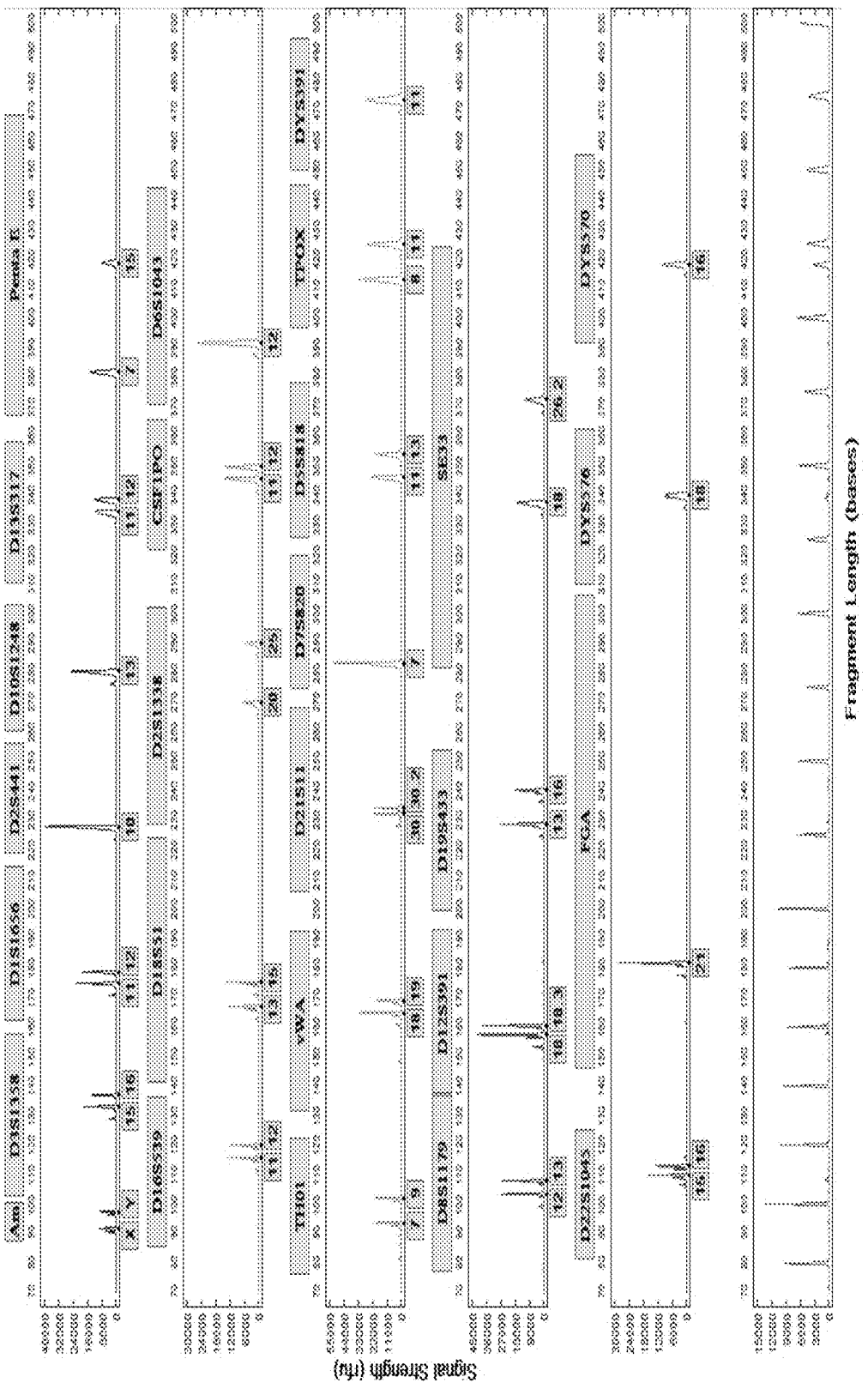
FIG. 71 shows a DNA ID classified as a High Signal Sample as its characteristic, average signal strength of the Alleles is greater than 10,000 RFU.

High Signal Strength Sample—the data set of FIG. 71 is classified as a High Signal Sample as its characteristic, average signal strength of the Alleles is greater than 10,000 RFU. The AES parameter set for High Signal Strength Samples when applied to the dataset generate a resulting DNA ID of FIG. 71. The use of one characteristic to classify the sample data is effective in selecting the proper AES parameter set to improve the calling results compared with the standard parameter set.

Figure 72:
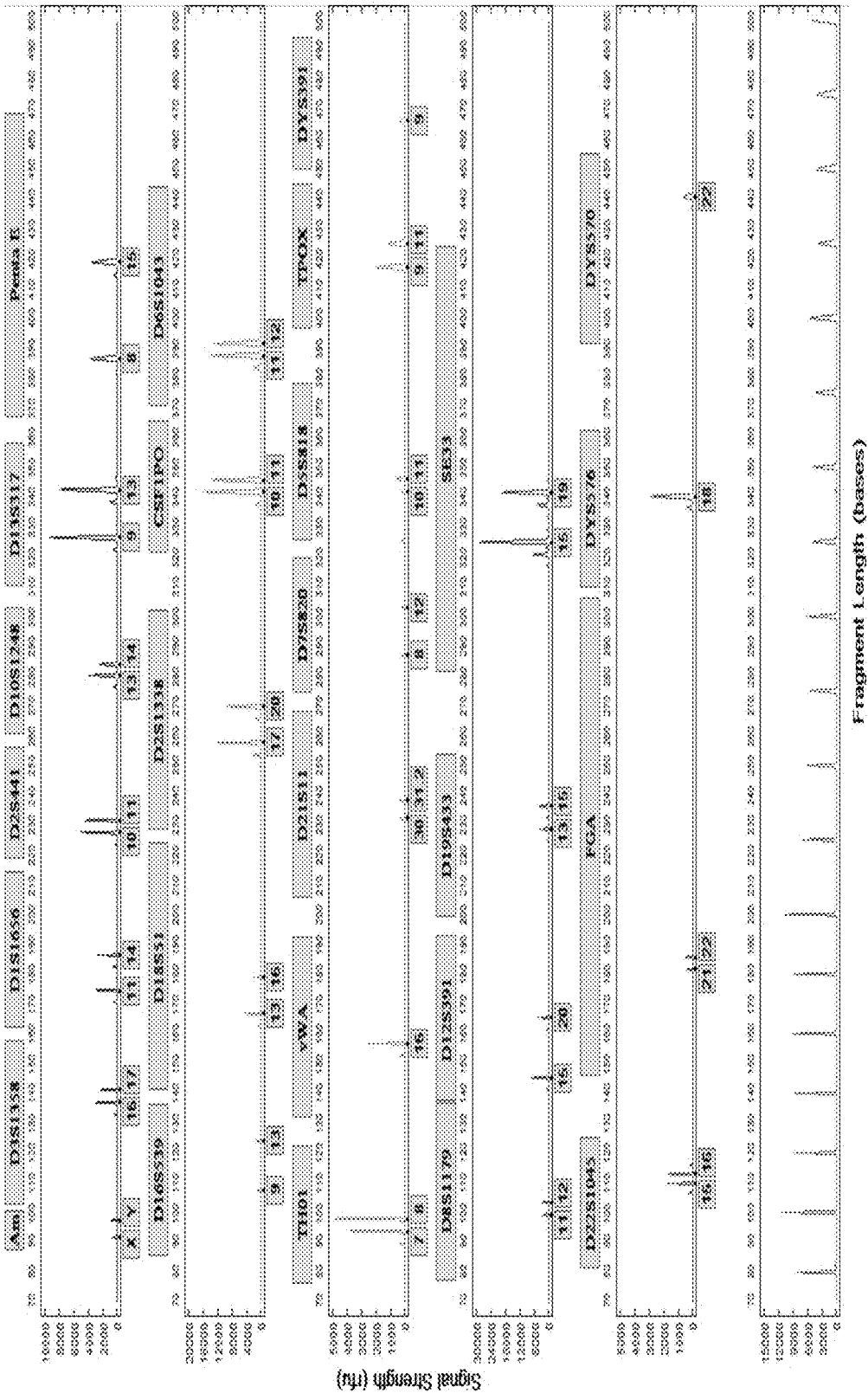
FIG. 72 shows a DNA ID classified as a standard Sample as its characteristic, average signal strength of the Alleles is between 3,000 and 10,000 RFU.

Standard Signal Strength Sample—the data set of FIG. 72 is classified as a standard Sample as its characteristic, average signal strength of the Alleles is between 3,000 and 10,000 RFU. The AES parameter set for Standard Signal Strength Samples when applied to the dataset generate a resulting DNA ID of FIG. 72.

Figure 73:
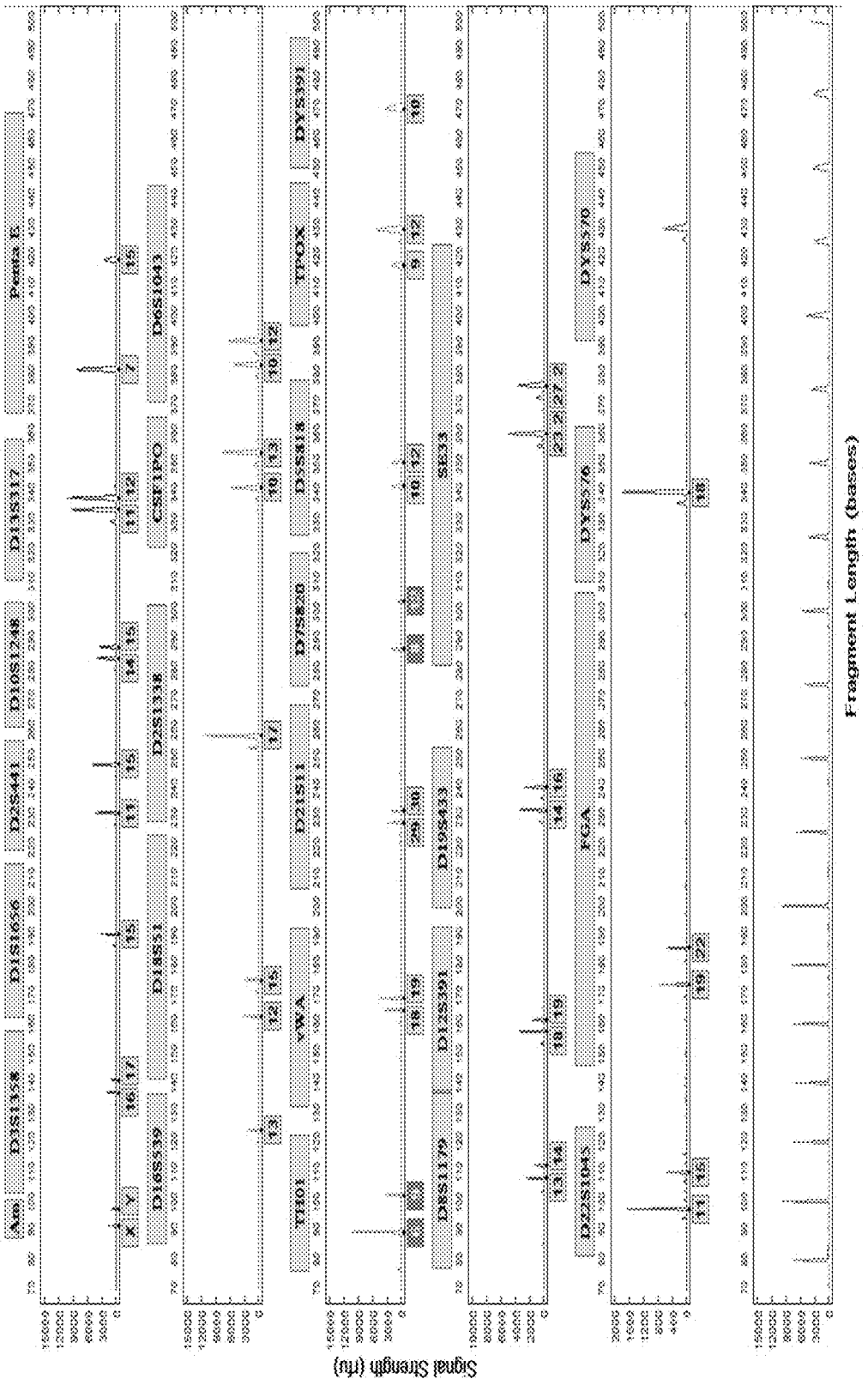
FIG. 73 shows a DNA ID classified as a Low Signal Sample as its characteristic, average signal strength of the Alleles is below 3,000 RFU.

Low Signal Strength Sample—the data set of FIG. 73 is classified as a Low Signal Sample as its characteristic, average signal strength of the Alleles is below 3,000 RFU. The AES parameter set for Standard Signal Strength Samples when applied to the dataset generate a resulting DNA ID of FIG. 73. The use of one characteristic to classify the sample data is effective in selecting the proper AES parameter set to improve the calling results compared with the standard parameter set.

This example shows that one characteristic is effective for classifying sample data and selecting an AES parameter set for calling the sample data. In this example, three classifications were defined using one characteristic. The number of classifications that can be defined for each characteristic can be increased by dividing the range of values into smaller steps.

Example 13: AES to Call a Mixture Sample with Two Donors

Figure 74:
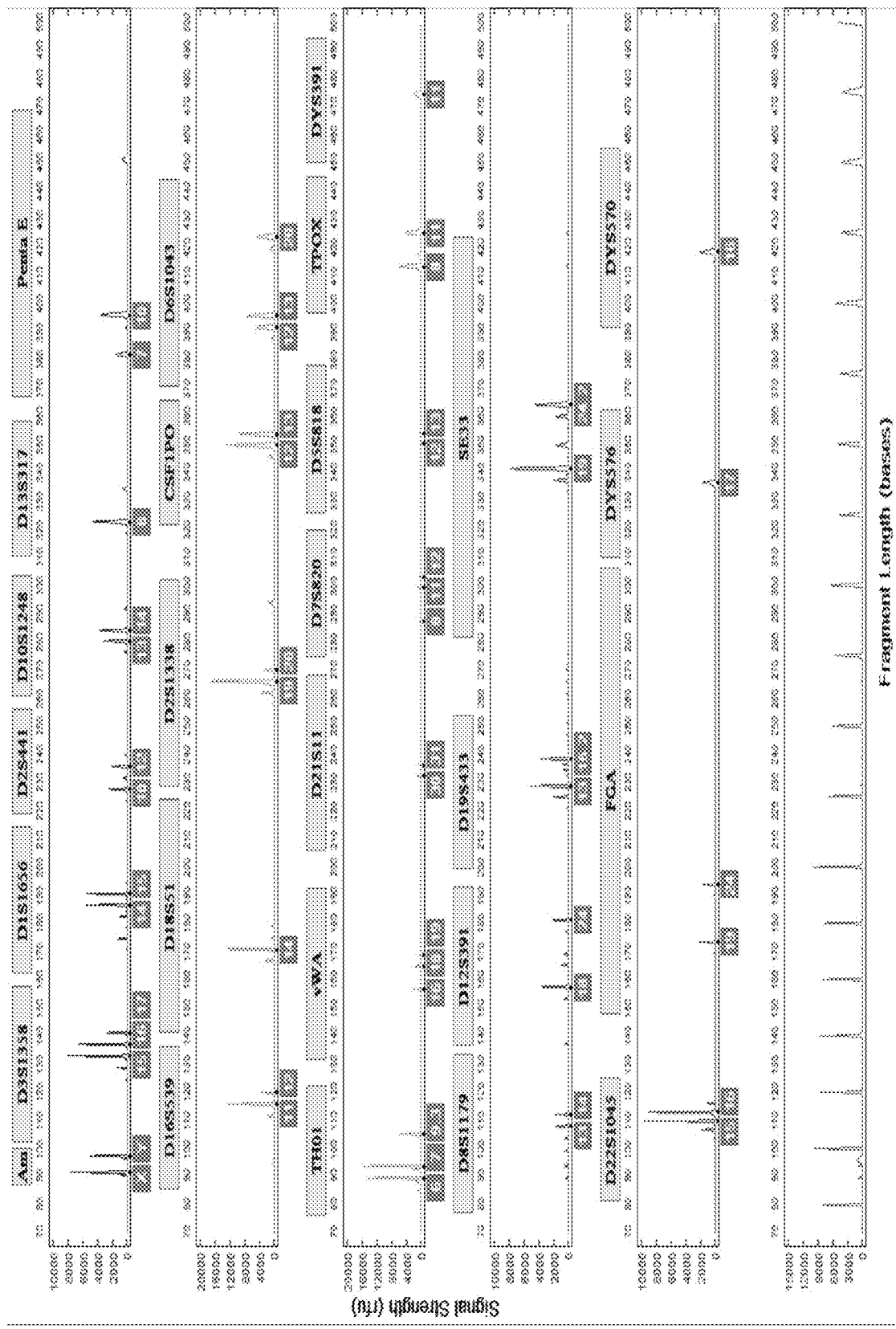
FIG. 74 shows the DNA ID of the sample data processed with the Expert System using the standard Expert System parameters.

In this example, sample data for a two donor sample is processed by the Adaptive Expert System. FIG. 74 shows the DNA ID of the sample data processed with the ES using the standard ES parameters. This DNA ID is presented to illustrate the effect of using standard ES, but is not required for AES processing. This figure shows that the sample has multiple loci three alleles labeled in red warning boxes (e.g. D3S1358, Th01, vWA, D7S820). Many loci are also observed with three or more labeled and unlabeled peaks. This is characteristic is typical of a mixture sample. Also observed in the figure is a major contributor DNA ID and a minor contributor DNA ID. The minor contributor has alleles with signal strengths that are between 0.1 to 0.6 times that of the major contributor. The standard ES failed the DNA ID and labeled all peaks in red warning boxes.

The AES processes the sample data with the following algorithm:

1) Characterize sample data and classify the sample.

The Adaptive Expert System processes the sample data by first characterizing the following sample data:
   Average heterozygote peak height of the alleles are between 200 to 10,000 RFU.
   No alleles with wide peaks are observed.
   No alleles with high levels of iNTA are observed.
   Some alleles with low signal strengths are unlabeled.
   Many loci with three or more peaks.
These characteristics classify the sample data as a mixture with between low to standard DNA content.

2) Determine a set of ES parameters to generate DNA ID of the primary contributor.

The peak height threshold (locus specific) is adjusted for each locus to achieve one of the three following conditions:
   A heterozygote locus—This condition is met when only two peaks with peak heights greater than the peak height threshold are present and the peak height ratio for the peaks is greater than the peak height threshold for a standard DNA content sample. In this case, 0.70.
   A homozygote locus—This condition is met when only one peak with a peak height greater than the peak height threshold (locus specific) and all other peaks in the locus have a peak height ratio of less than 0.70.
   A failed locus—This condition is met when the peaks in the locus do not meet the heterozygote or homozygote conditions above. See Penta E, D6S1043, and D7S820.

The high signal iNTA rules and high signal sample peak width adjustments were not applied to this sample data because it was not classified as a high DNA content sample.

Figure 75:
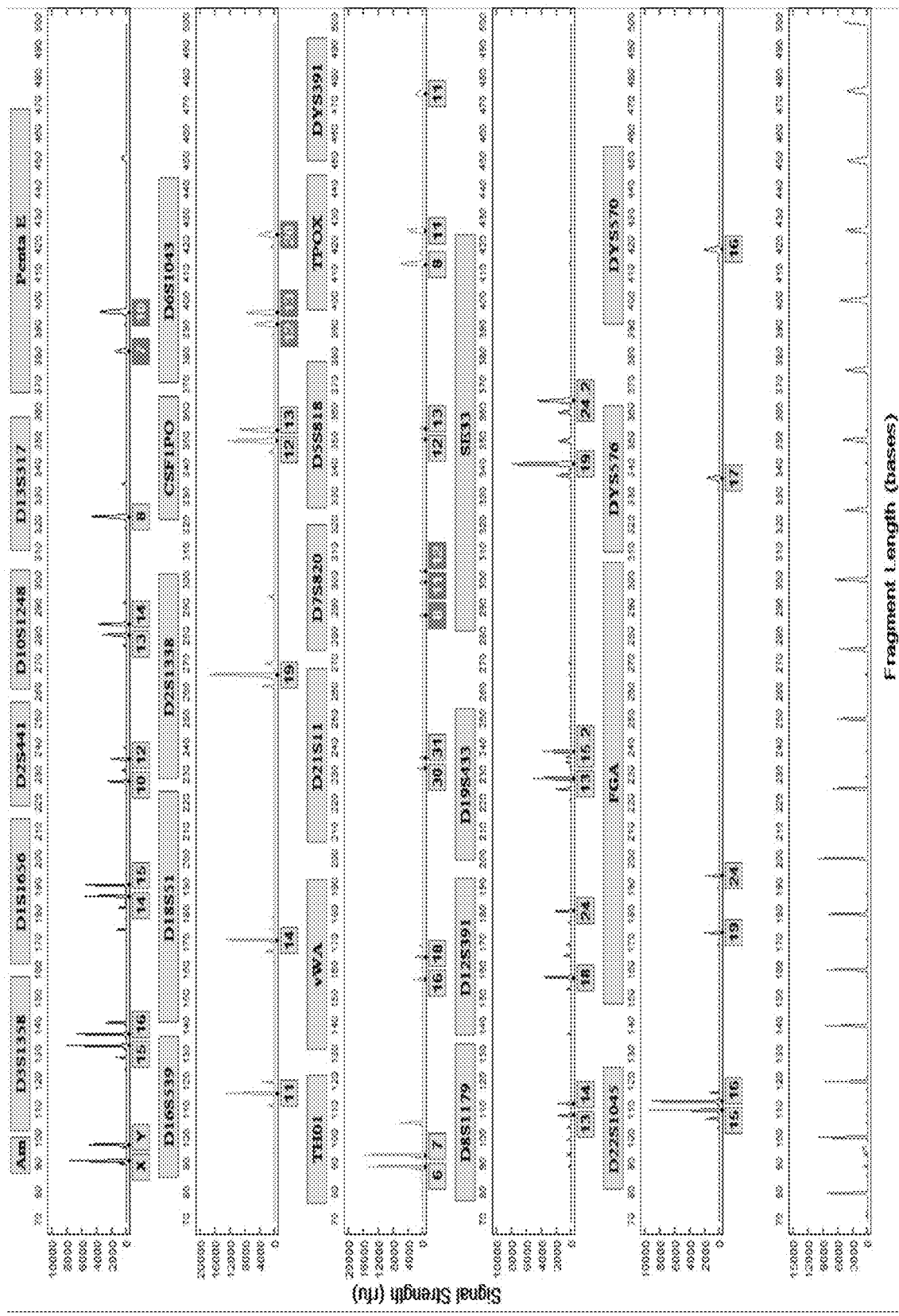
FIG. 75 shows the DNA ID of the primary contributor as generated by the AES.

The DNA ID of the primary contributor is generated by the AES (see gray boxes of the DNA ID of FIG. 75).

3) Subtract the DNA ID of the primary contributor from the sample data.

Alleles in the DNA ID for the primary contributor identified in step 2. These alleles are set to be ignored by the AES when the sample data is processed a second time to generate the DNA ID of the secondary contributor.

4) Characterize the sample data for the secondary contributor.

The Adaptive Expert System characterizes the sample data (after the DNA ID peaks of the primary contributor are ignored) as:
   Average heterozygote peak height of the alleles are between 200 to 3,000 RFU.
   No alleles with wide peaks are observed.
   No alleles with high levels of iNTA are observed.
   Some alleles with low signal strengths are unlabeled.
   These characteristics classify the sample data as a low DNA content sample.

5) Determine a set of ES parameters to generate DNA ID of the secondary contributor.

Figure 76:
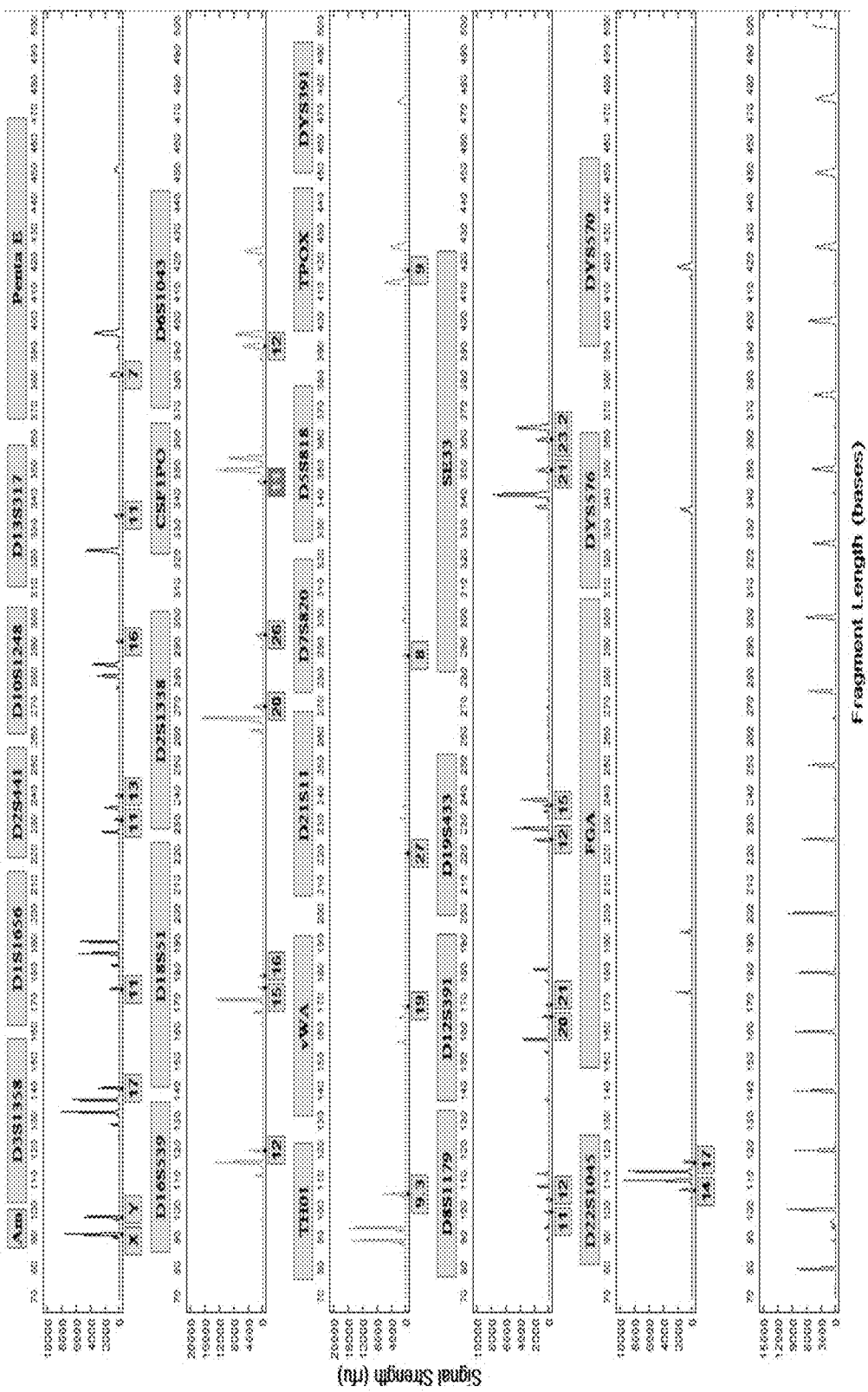
FIG. 76 shows a DNA ID with the maximal number of alleles called, and with the minimum number of dropouts and dropins.

The Peak height thresholds and peak height ratios were selected such that the maximal number of alleles are called, with the minimum number of dropouts and dropins. The resultant DNA ID is shown in FIG. 76.

The AES is able to generate the individual DNA IDs of the primary and secondary contributors. With this method of mixture deconvolution any allele of the secondary contributor that overlaps between the primary contributor will have been subtracted and not be called and the loci will have a drop out. The above algorithm can be adapted to extract the alleles that overlap between the secondary contributor and primary contributor, by applying the signal strength in step 3, when subtracting the primary donor from the sample data.

This example shows that the AES is not only for single source samples and that it is capable of generating the components from a sample with multiple genomic components. Although this example shows the use of AES for multiple component analysis of non-single source samples for human forensic identification, this same algorithm can also be applied to a sample data in clinical setting to identify samples from more than one infectious agent. This is particularly important in dual microbial infections.

SUMMARY

In the examples presented, we have taught and exemplified the approach of how to generate and use sample data to identify other DNA ID characteristics that can be used to classify DNA IDs, and to establish rules and parameters. So now, even if we did not write about a specific characteristic of the DNA ID and a rule, it is easy for the reader to perform the steps described in the examples to generate additional classifications, rules, and parameters for AES.

The above-described method steps can be performed by one or more special-purpose processors executing a computer program to perform functions of the invention by operating on input data and/or generating output data. Method steps can also be performed by, and an apparatus can be implemented as, special-purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, special-purpose microprocessors. Generally, a processor receives instructions and data from a read-only memory or a random access memory or both. The essential elements of a computer are a specialized processor for executing instructions and one or more specifically-allocated memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Computer-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computing device in communication with a display device, e.g., a CRT (cathode ray tube), plasma, or LCD (liquid crystal display) monitor, a mobile device display or screen, a holographic device and/or projector, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above-described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, near field communications (NFC) network, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

A network link typically provides data communication through one or more networks to other data devices. For example, a network link may provide a connection through local network to a host computer or to data equipment operated by an Internet Service Provider or private network service provider ("ISP"). ISP in turn provides data communication services through a packet data communication network such as the worldwide network commonly referred to as the "Internet" or a private network. An example of a private network is a secure data network linking law enforcement agencies and used for transmission of DNA and/or non-DNA information. A local network and the Internet both use electrical, electromagnetic or optical signals that carry digital data streams.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, Universal Mobile Telecommunications System (UMTS), 3GPP Long Term Evolution (LTE) and/or other communication protocols.

Devices of the computing system can include, for example, a computer, a computer with a browser device, a telephone, an IP phone, a mobile device (e.g., cellular phone, personal digital assistant (PDA) device, smart phone, tablet, laptop computer, electronic mail device), and/or other communication devices. The browser device includes, for example, a computer (e.g., desktop computer and/or laptop computer) with a World Wide Web browser (e.g., Chrome™ from Google, Inc., Microsoft® Internet Explorer® available from Microsoft Corporation, and/or Mozilla® Firefox available from Mozilla Corporation). Mobile computing device include, for example, a Blackberry® from Research in Motion, an iPhone® from Apple Corporation, and/or an Android™-based device. IP phones include, for example, a Cisco® Unified IP Phone 7985G and/or a Cisco® Unified Wireless Phone 7920 available from Cisco Systems, Inc.

The computer systems described herein can be configured using the methods of this invention to provide services across a network to forensic personnel having client computers capable of connection to the network. These services can also be provided to other software, located in either the computer system described above or a separate computer system connected by a network, network link, or communication interface to the computer system. The services can be protected using methods of authentication and/or encryption that are known in the fields of computer science and computer security in order to ensure data are neither compromised nor disclosed and to trace all accesses to the data. The computer system and other associated information storage and communication components can be protected using devices and methods that are known in the fields of computer science and computer security, such as with firewalls, physical access controls, power conditioning equipment, and backup or redundant power sources. The information stored by computer system and computer-readable media can be further protected using backup or redundant information storage systems, such as those that are well-known in the art. Examples include tape storage systems and RAID storage arrays.

Comprise, include, and/or plural forms of each are open ended and include the listed parts and can include additional parts that are not listed. And/or is open ended and includes one or more of the listed parts and combinations of the listed parts.

One skilled in the art will realize the subject matter may be embodied in other specific forms without departing from the spirit or essential characteristics thereof. The foregoing embodiments are therefore to be considered in all respects illustrative rather than limiting of the subject matter described herein.

What is claimed is:

1. A system for analysis and classification of DNA sample data using iterative search and matching, the system comprising:
a first computing device having a memory that stores first programmatic instructions and a processor configured to execute the first instructions, the first instructions configured to:
receive sample data comprising at least one of raw data, optical data, and electropherogram data from a DNA analysis device, the DNA analysis device generating the sample data from a sample containing DNA;
determine at least one characteristic of the sample data, the at least one characteristic including a signal strength;
utilize the at least one characteristic to classify the sample data and apply a first predefined parameter set to the sample data to generate as output a plurality of first structured data files comprising a first DNA ID, wherein the number of first structured data files generated is based upon the signal strength; and
transfer the plurality of first structured data files to a second computing device comprising a DNA database;
the second computing device having a memory that stores second programmatic instructions and a processor configured to execute the second instructions, the second instructions configured to:
perform, for each of the plurality of first structured data files, a first series of searches for DNA data matching one or more characteristics of the first DNA ID in the first structured data file using progressively less conservative match criteria in each search, including, for each search: generating a match score, comparing the match score to a predetermined threshold score, and transmitting the match score and the matched DNA data to the first computing device for display when the match score meets or exceeds the predetermined threshold score;
when none of the match scores for the first series of searches meet or exceed the predetermined threshold score:
instruct the first computing device to automatically iterate one or more values in the first predefined parameter set based upon the match scores for the first series of searches to generate a second predefined parameter set,
instruct the first computing device to apply the second predefined parameter set to the sample data to generate a plurality of second structured data files comprising a second DNA ID and transfer the plurality of second structured data files to the second computing device; and
perform, for each of the plurality of second structured data files, a second series of searches for DNA data matching one or more characteristics of the second DNA ID using progressively less conservative match criteria in each search, including, for each search: generating a match score, comparing the match score to a predetermined threshold score, and transmitting the match score and the matched DNA data to the first computing device for display when the match score meets or exceeds the predetermined threshold score.

2. The system of claim 1, wherein the structured data file comprises one or more of: an .xml file, an .fsa file, a .bmp file, or an allele table.

3. The system of claim 1, wherein the second instructions are configured to utilize the plurality of first structured data files and the plurality of second structured data files to compare two or more DNA IDs to assess kinship.

4. The system of claim 1, wherein when the at least one characteristic classifies the sample data as a mixture, the first predefined parameter set applied modifies at least one of the following parameters: Heterozygote Peak Height Threshold, Heterozygote Peak Height Ratio Threshold, Homozygote Peak Height Threshold, Heterozygote Peak Height Threshold for 2nd Peak, Homozygote Peak Height Ratio Threshold, Hemizygote Peak Height Minimum Threshold, Allele PH/PA Threshold in a first Zone, Allele PH/PA Threshold in a second Zone, Allele PH/PA Threshold in a third Zone, Allele PH/PA Threshold in a fourth Zone, Maximum Number of Dropins, Maximum Number of Dropouts, Signal to Noise Ratio Threshold of one or more dye channels, Peak Base Assignment Limits, Peak Fragment Size Threshold, Peak Height Threshold, Peak Width Threshold, Peak Shape Threshold, Peak Morphology Threshold, Peak Asymmetry Threshold, Peak Width Deviation Limit, Peak Shape Deviation Limit, Base Confidences Threshold, Heterozygote Peak Height Threshold, Heterozygote Peak Height Ratio Threshold, Average Heterozygote Peak Height by Color Threshold, Homozygote Peak Height Threshold, Average Homozygote Peak Height by Color Threshold, Relative Signal Strength of Alleles within Loci Threshold, Relative Signal Strength of Alleles as Compared to Allele Size Threshold, iNTA Peak Height Threshold, iNTA Peak Height Ratio Threshold, Stutter Peak Height Threshold, Stutter Ratio Threshold, Triallate Peak Height Threshold, Triallele Peak Height Ratio Threshold, Mixture Peak Height Threshold, ILS Success Limits, High iNTA Rule State, Mixture Sample Protection Rule State, Low Signal Protection Rule State, Maximum Number of Peaks in a Locus, Maximum Number of Called Alleles, Maximum Number of Alleles Labeled in Red Warning Boxes, Maximum Number of Unlabeled Alleles, Maximum Number of Loci with Alleles with PH Less than a PH Threshold, Maximum Number of Loci with Alleles with PH Greater than the PH Threshold, Maximum Number of Loci with PHR Less than a PHR Threshold, Maximum Number of Loci with PHR Greater than the PHR Threshold, Maximum Number of Loci with Wide Peaks, Maximum Number of Loci with iNTA Greater than iNTA Threshold, Maximum Number of Loci with Three or More Peaks that are Labeled in Red Warning Boxes, Maximum Number of Loci with Four or More Peaks that are Labeled in Red Warning Boxes, Maximum Number of Heterozygote Loci Labeled in Red Warning Boxes, Maximum Number of Homozygote Loci Labeled in Red Warning Boxes, Maximum Number of Bleed-through Peaks, Minimum Number of CODIS20 Loci Called, Minimum Number of CODIS18 Loci Called, Minimum Number of Autosomal Loci Called, Minimum Number of Flex Plex Loci Called, Minimum Number of Called Loci to Generate a CMF File, Quality of DNA ID Threshold, or Quality of Search and Match Threshold.

5. The system of claim 4, in which the first instructions are configured to apply the first predefined parameter set to the sample data to generate a first set of called alleles, extract the first set of called alleles from the sample data, and generate modified sample data, wherein the first instructions are configured to utilize the at least one characteristic to classify the modified sample data and apply a third predefined parameter set to said modified sample data to generate a second set of called alleles.

6. The system of claim 1, wherein based upon classifying the sample data and applying the first predefined parameter set, the processor of the computing device executes the instructions to modify one or more other predefined parameter sets that, when applied to a third DNA ID, are utilized by the processor of the first computing device to generate a plurality of third structured data files comprising the third DNA ID.

7. The system of claim 1, wherein the processor of the first computing device executes the first instructions to generate a visualization of the plurality of first structured data files for presentation on a display device.

8. The system of claim 7, wherein the visualization comprises one or more of: a value indicating a number of alleles called for each of one or more other predefined parameter sets, or a visualization of a plurality of alleles called for each of one or more other predefined parameter sets.

9. The system of claim 1, wherein the match score for each of the first series of searches is defined by one or more of: random match probability, or totals of matching alleles and loci.

* * * * *